(12) United States Patent
Kumar et al.

(10) Patent No.: US 10,723,716 B2
(45) Date of Patent: Jul. 28, 2020

(54) ALPHA-HELIX MIMETICS AS MODULATORS OF ABETA SELF-ASSEMBLY

(71) Applicant: New York University, New York, NY (US)

(72) Inventors: Sunil Kumar, New York, NY (US); Andrew D. Hamilton, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/851,367

(22) Filed: Dec. 21, 2017

(65) Prior Publication Data

US 2018/0170910 A1 Jun. 21, 2018

Related U.S. Application Data

(60) Provisional application No. 62/481,485, filed on Apr. 4, 2017, provisional application No. 62/437,354, filed on Dec. 21, 2016.

(51) Int. Cl.
*C07D 401/14* (2006.01)
*A61P 25/28* (2006.01)
*C07D 401/12* (2006.01)

(52) U.S. Cl.
CPC ............ *C07D 401/14* (2013.01); *A61P 25/28* (2018.01); *C07D 401/12* (2013.01)

(58) Field of Classification Search
CPC .................................................. C07D 401/14
See application file for complete search history.

(56) References Cited

U.S. PATENT DOCUMENTS

| | | |
|---|---|---|
| 4,476,116 A | 10/1984 | Anik |
| 4,511,069 A | 4/1985 | Kalat |
| 4,778,810 A | 10/1988 | Wenig et al. |
| 5,203,840 A | 4/1993 | Graf et al. |
| 5,759,565 A | 6/1998 | Azria et al. |
| 5,860,567 A | 1/1999 | Fuchs et al. |
| 5,893,484 A | 4/1999 | Fuchs et al. |
| 5,998,140 A | 12/1999 | Dervan et al. |
| 6,143,901 A | 11/2000 | Dervan |
| 6,227,415 B1 | 5/2001 | Ritsche et al. |
| 6,364,166 B1 | 4/2002 | Ritsche et al. |
| 6,514,496 B1 | 2/2003 | Platz et al. |
| 6,559,125 B1 | 5/2003 | Dervan et al. |
| 6,673,940 B1 | 1/2004 | Dervan et al. |
| 7,087,378 B1 | 8/2006 | Baird et al. |
| 7,312,246 B2 | 12/2007 | Hamilton et al. |
| 7,799,782 B2 | 9/2010 | Munson et al. |
| 8,846,074 B2 | 9/2014 | Bryson et al. |
| 9,453,049 B2 | 9/2016 | Sebti et al. |
| 2006/0270727 A1 | 11/2006 | Melander et al. |
| 2009/0220586 A1 | 9/2009 | Hamilton et al. |
| 2018/0170910 A1 | 6/2018 | Kumar et al. |

FOREIGN PATENT DOCUMENTS

| | | |
|---|---|---|
| EP | 0037943 A2 | 10/1981 |
| EP | 0094157 A1 | 11/1983 |
| EP | 0173990 A2 | 3/1986 |
| EP | 0214898 A2 | 3/1987 |
| EP | 0215697 A2 | 3/1987 |
| EP | 0327756 A2 | 8/1989 |
| EP | 0490806 A2 | 6/1992 |
| WO | 00/15242 A1 | 3/2000 |
| WO | 00/15773 A2 | 3/2000 |
| WO | 2004093917 A2 | 11/2004 |
| WO | 2005/112924 A2 | 12/2005 |
| WO | 2005/120582 A2 | 12/2005 |
| WO | 2005120551 A1 | 12/2005 |

OTHER PUBLICATIONS

Jung, Kwan-Young. J Med. Chem. 2015, 58, 3002-3024.*
Estroff, Laura J. Am. Chem. Soc. 2004, 126, 2-3 (and supplemental material).*
Azzarito, V. et al., "Inhibition of a α-Helix-Mediated Protein-Protein Interactions Using Designed Molecules" Nature Chemistry (2013) vol. 5, pp. 161-173.
Cummings, C.G. et al., "Disrupting Protein-Protein Interactions with Non-Peptidic, Small Molecule α-Helix Mimetics" Current Opinion in Chemical Biology (2010) vol. 14, pp. 341-346.
Hebda, J.A. et al., "A Peptidomimetic Approach to Targeting Pre-Amyloidogenic States in Type II Diabetes" Chemistry & Biology (2009) vol. 16, Issue 9, pp. 943-950.
Kulikov, O.V. et al., "Amphiphilic Oligoamide α-Helix Peptidomimetics Inhibit Islet Amyloid Polypeptide Aggregation" Tetrahedron Letters (2015) vol. 56, pp. 3670-3673.
Kumar, S. et al., "A Foldamer Approach to Targeting Membrane Bound Helical States of Islet Amyloid Polypeptide" Chemical Communications (2013) vol. 49, Issue 42, pp. 4749-4751.
Kumar, S. et al., "Foldamer Scaffolds Suggest Distinct Structures are Associated with Alternative Gains-of-Function in a Preamyloid Toxin" Chemical Communications (2016) vol. 52, pp. 6391-6394.
Kumar, S. et al., "Folded Small Molecule Manipulation of Islet Amyloid Polypeptide" Chemistry & Biology (2014) vol. 21, Issue 6, pp. 775-781.
Kumar, S. et al., "Islet Amyloid-Inducted Cell Death and Bilayer Integrity Loss Share a Molecular Origin Targetable with Oligopyridylamide-Based α-Helical Mimetics" Chemisty & Biology (2015), vol. 22, pp. 369-378.
Orner, B.P. et al., "Toward Proteomimetics: Terphenyl Derivatives as Structural and Functional Mimics of Extended Regions of an α-Helix" Journal of the American Chemical Society (2001) vol. 123, Issue 22, pp. 5382-5383.

(Continued)

*Primary Examiner* — Emily A Bernhardt
*Assistant Examiner* — Laura M Daniel
(74) *Attorney, Agent, or Firm* — Troutman Sanders LLP

(57) ABSTRACT

The invention relates to compounds and pharmaceutical compositions capable of treating amyloid diseases and other diseases characterized by oligomerization and/or fibrillation of amyloidogenic peptides such as amyloid beta peptide (Abeta or Aβ).

2 Claims, 38 Drawing Sheets
(36 of 38 Drawing Sheet(s) Filed in Color)

(56) References Cited

OTHER PUBLICATIONS

Peacock, H. et al., "Non-Covalent S—O Interactions Control Conformation in a Scaffold that Disrupts Islet Amyloid Polypeptide Fibrillation" Chemical Science (2016) vol. 7, pp. 6435-6439.

Saraogi, I. et al., "Controlling Curvature in a Family of Oligoamide α-Helix Mimetic" Angewandte Chemie (2008) 5 pages total.

Saraogi, I. et al., "Synthetic α-Helix Mimetics as Agonists and Antagonists of IAPP Amyloid Formation" Angewandte Chemie (2010) vol. 49, Issue 4, pp. 736-739.

Yin, H. et al., "Strategies for Targeting Protein-Protein Interactions with Synthetic Agents" Angewandte Chemie (2005) vol. 44, pp. 4130-4163.

Davis, S.S. et al., "Absorption Enhancers for Nasal Drug Delivery" Clinical Pharmacokinetics (2003) vol. 42, Issue 13, pp. 1107-1128.

Gannon, J.V. et al., "Activating Mutations in p53 Produce a Common Conformational Effect: A Monoclonal Antibody Specific for the Mutant Form" EMBO Journal (1990) vol. 9, No. 5, pp. 1595-1602.

García-Arieta, A. et al., "Spray-Dried Powders as Nasal Absorption Enhancers of Cyanocobalamin" Biol. Pharm. Bull. (2001) vol. 24, No. 12, pp. 1411-1416.

Gong, H. et al., "Amyloidogencity of p53: A Hidden Link Between Protein Misfolding and Cancer" Curr Protein Pept Sci (2014) Abstract.

Gura, T., "Hope in Alzheimer's Fight Emerges from Unexpected Places" Nature Medicine (2008) vol. 14, No. 9, pp. 894-894.

Jayatunga, M.K.P, et al., "α-Helix Mimetics: Outwards and Upwards" Bioorganic & Medicinal Chemistry Letters (2014) vol. 24, No. 3, pp. 717-724.

Kumar, S. et al., "α-Helix Mimetics as Modulators of Aβ Self-Assembly" Journal of the American Chemical Society (2017) vol. 139, No. 16, pp. 5744-5755.

Landers, J.E. et al., "Translational Enhancement of mdm2 Oncogene Expression in Human Tumor Cells Containing a Stabilized Wild-Type p53 Protein" Cancer Research (1997) vol. 57, No. 16, pp. 3562-3568.

Lindberg, D.J. et al., "Binding of Thioflavin-T to Amyloid Fibrils Leads to Fluorescence Self-Quenching and Fibril Compaction" Biochemistry (2017).

Love, I. et al., "p53 Ubiquitination and Proteasomal Degradation" p53 Protocols (2013) pp. 63-73.

Martinez-Zapien, D., "Structure of the E6/E6AP/p53 Complex Required for HPV-Mediated Degradation of p53" Nature (2016) vol. 529, No. 7587, pp. 541-545.

Maslon, M.M et al., "Drug Discovery and Mutant p53" Trends Cell Biology (2010) vol. 20, Issue 9, pp. 542-555.

O'Hagan, DT et al., "Nasal Absorption Enhancers for Biosynthetic Human Growth Hormone in Rats" Pharm. Res. (1990) vol. 7, No. 7, pp. 772-776.

Oda, K. et al., "p53AIPI, A Potential Mediator of p53-Dependent Apoptosis, and its Regulation by Ser-46-Phosphorylated p53" Cell (2000) vol. 102, No. 6, pp. 849-862.

Qin, Y. et al., "Effect of Resveratrol on Proliferation and Apoptosis of Human Pancreatic Cancer MIA PaCa-2 Cells May Involve Inhibition of the Hedgehog Signaling Pathway" Molecular Medicine Reports (2014) vol. 10, No. 5, pp. 2563-2567.

Rahib, L. et al., "Projecting Cancer Incidence and Deaths to 2030: The Unexpected Burden of Thyroid, Liver, and Pancreas Cancers in the United States" Cancer Research (2014) vol. 74, No. 11, pp. 2913-2921.

Rangel, L.P. et al., "The Aggregation of Mutant p53 Produces Prion-Like Properties in Cancer" Prion (2014) vol. 8, No. 1, pp. 75-84.

Rieger, A.M. et al., "Accurate Assessment of Cell Death by Imaging Flow Cytometry" Imaging Flow Cytometry: Methods and Protocols (2016) pp. 209-220.

Riss, T.L. et al., "Cell Viability Assays" Assay Guidance Manual (2016) 31 pages total.

Schlapschy, M. et al., "PASylation: A Biological Alternative to PEGylation for Extending the Plasma Half-Life of Pharmaceutically Active Proteins" Protein Engineering Design and Selection (2013) vol. 26, No. 8, pp. 489-501.

Sidhar, H. et al., "Induction of Bex Genes by Curcumin is Associated with Apoptosis and Activation of p53 in N2a Neuroblastoma Cells" Scientific Reports (2017) vol. 7, No. 41420, 19 pages total.

Soragni, A. et al., "A Designed Inhibitor of p53 Aggregation Rescues p53 Tumor Suppression in Ovarian Carcinomas" Cancer Cell (2016) vol. 29, No. 1, pp. 90-103.

Svensen, N. et al., "Peptides for Cell-Selective Drug Delivery" Trends in Pharmacological Sciences (2012) vol. 33, No. 4, pp. 186-192.

Villa, LL., "Human Papillomaviruses and Cervical Cancer" Advances in Cancer Research (1997) vol. 71, pp. 321-341.

Vogiatzi, F. et al., "Mutant p53 Promotes Tumor Progression and Metastasis by the Endoplasmic Reticulum UDPase ENTPD5" Proceedings of the National Academy of Sciences (2016) vol. 113, No. 52, pp. E8433-E8442.

Wade, M. et al., "MDMZ, MDMX and p53 in Oncogenesis and Cancer Therapy" Nature Reviews Cancer (2013) vol. 13, No. 2, p. 83.

Wang, G. et al., "Multisite Aggregation of p53 and Implications for Drug Rescue" Proceedings of the National Academy of Sciences (2017) pp. E2634-E2643.

Willis, A. et al., "Mutant p53 Exerts a Dominant Negative Effect by Preventing Wild-Type p53 From Binding to the Promoter of its target genes" Oncogene (2004) vol. 23, No. 13, pp. 2330-2338.

Xu, J. et al., "Gain of Function of Mutant p53 by Coaggregation with multiple Tumor Suppressors" Nature Chemical Biology (2011) vol. 7, pp. 285-295.

Zhao, CY et al., "Rescue of p53 Function by Small-Molecule RITA in Cervical Carcinoma by Blocking E6-Mediated Degradation" Cancer Research (2010) vol. 70, No. 8, pp. 3372-3381.

\* cited by examiner

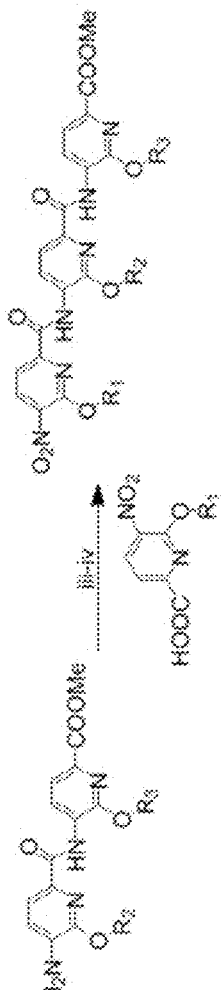
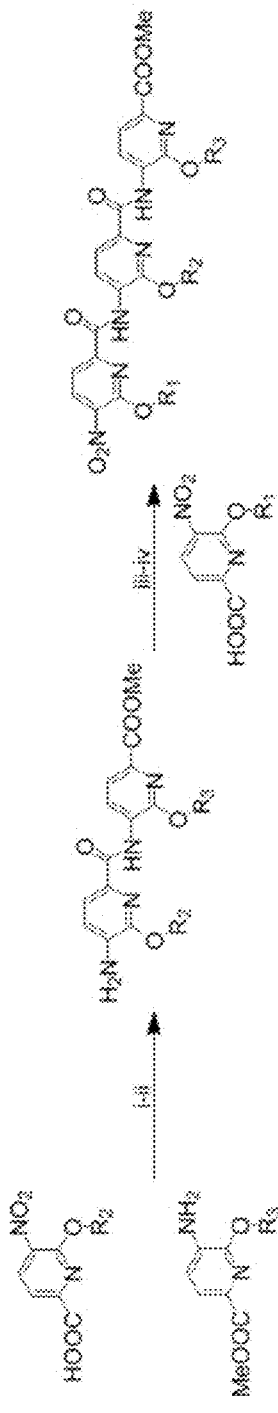
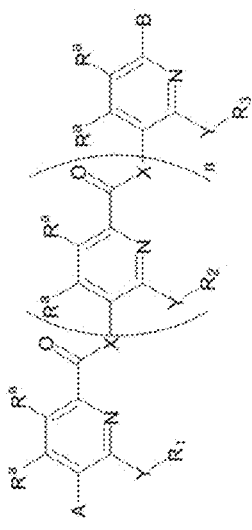
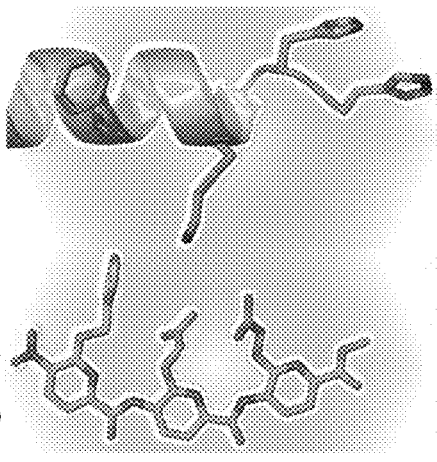
Fig. 1A  Fig. 1B  Fig. 1C  Fig. 1D  Fig. 1E

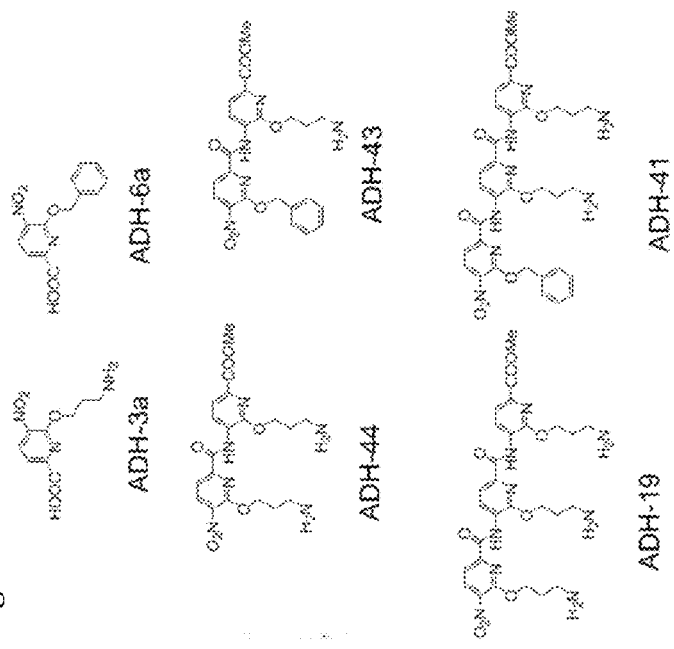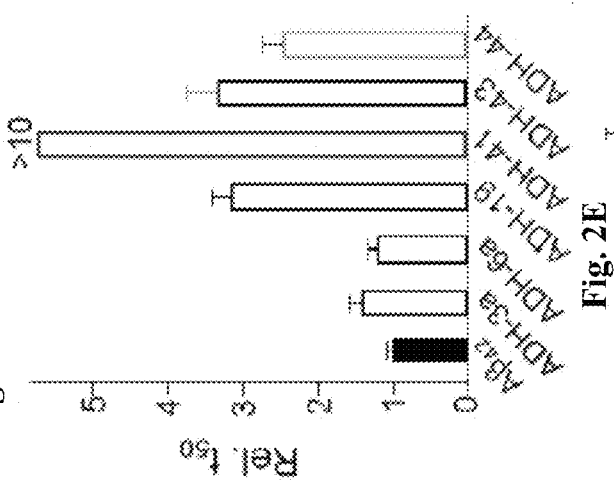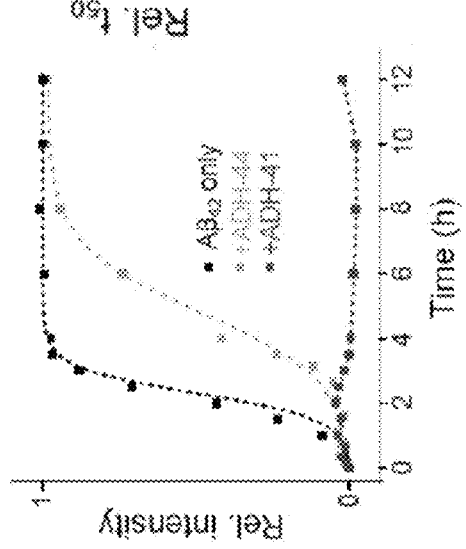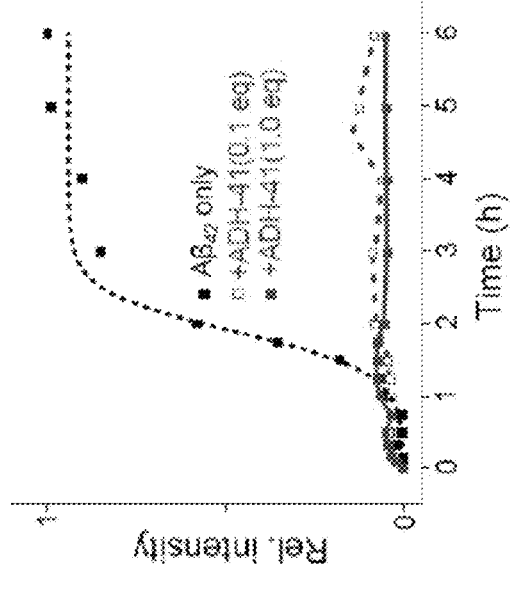

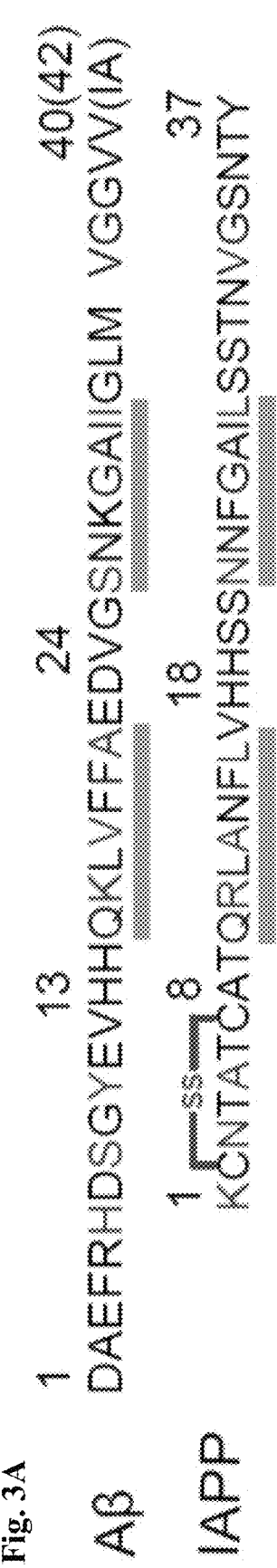
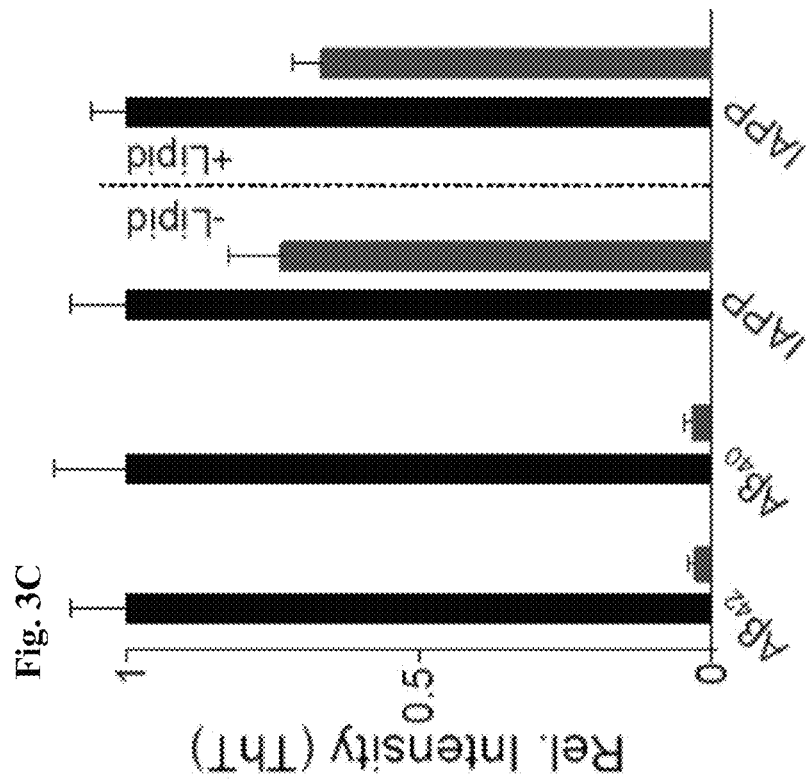
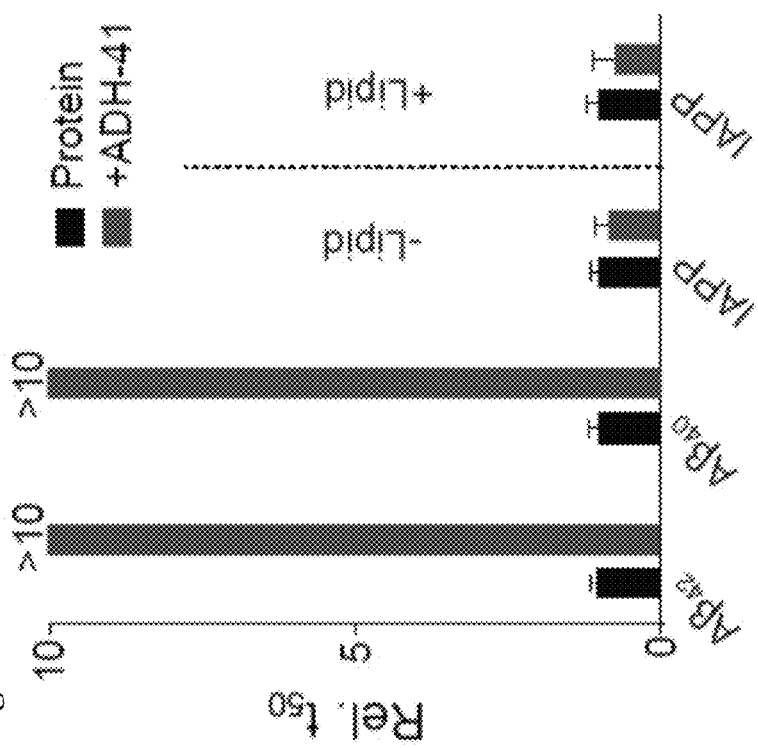
Fig. 3A
Fig. 3B
Fig. 3C

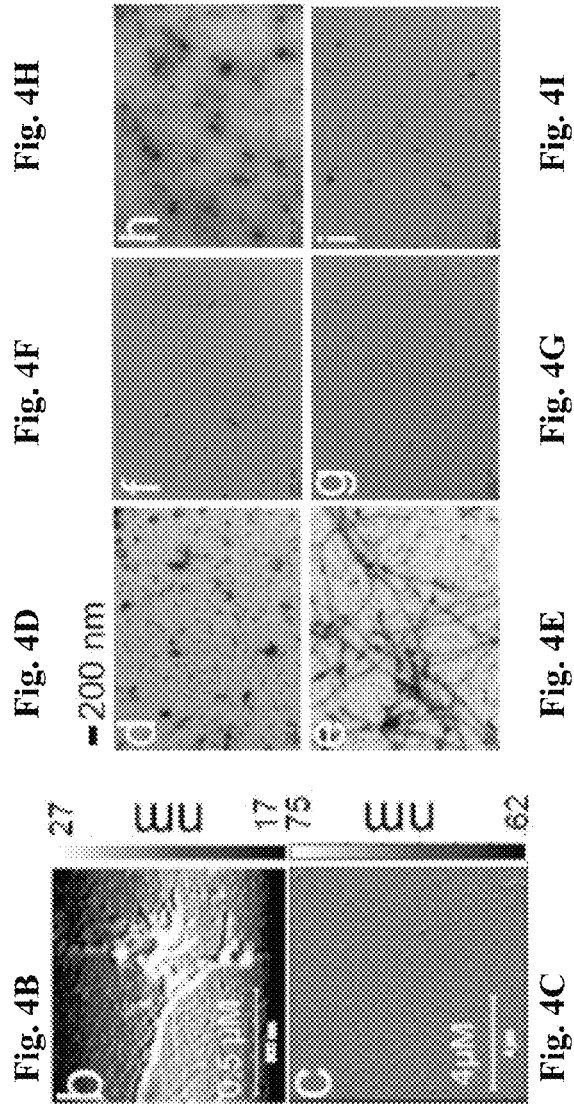
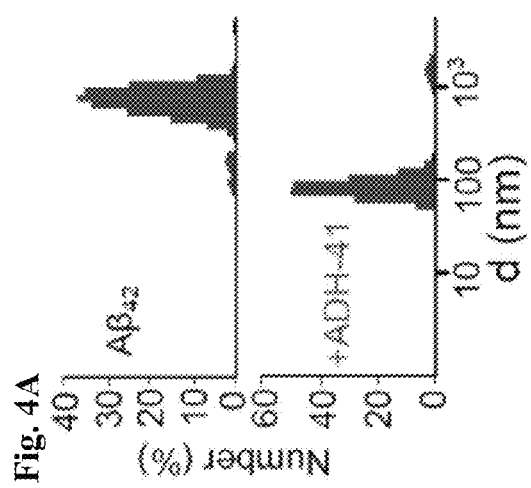
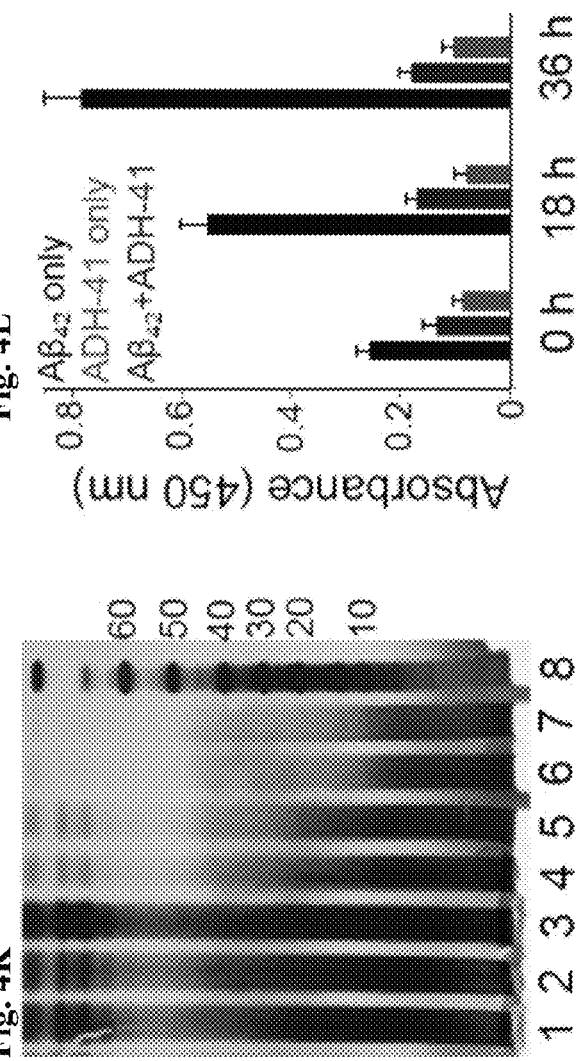
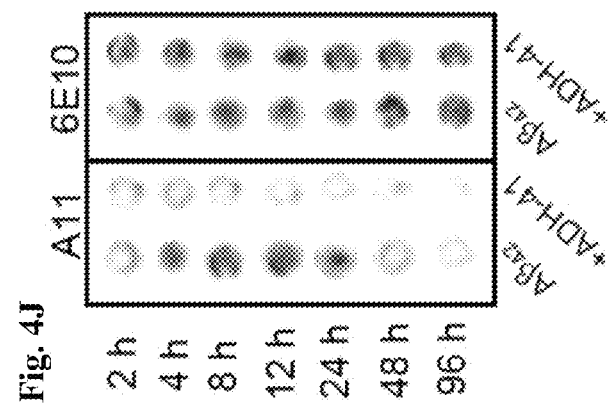

Fig. 5A
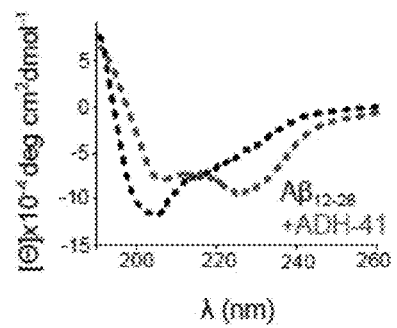
Fig. 5B
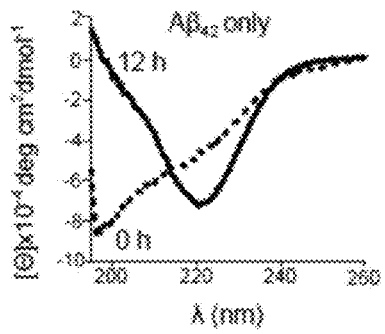
Fig. 5C
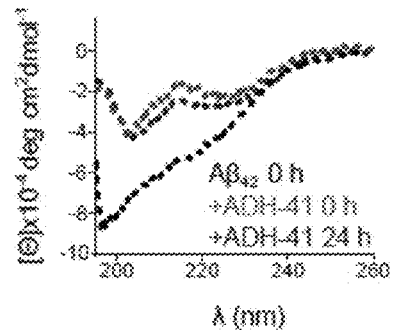
Fig. 5D
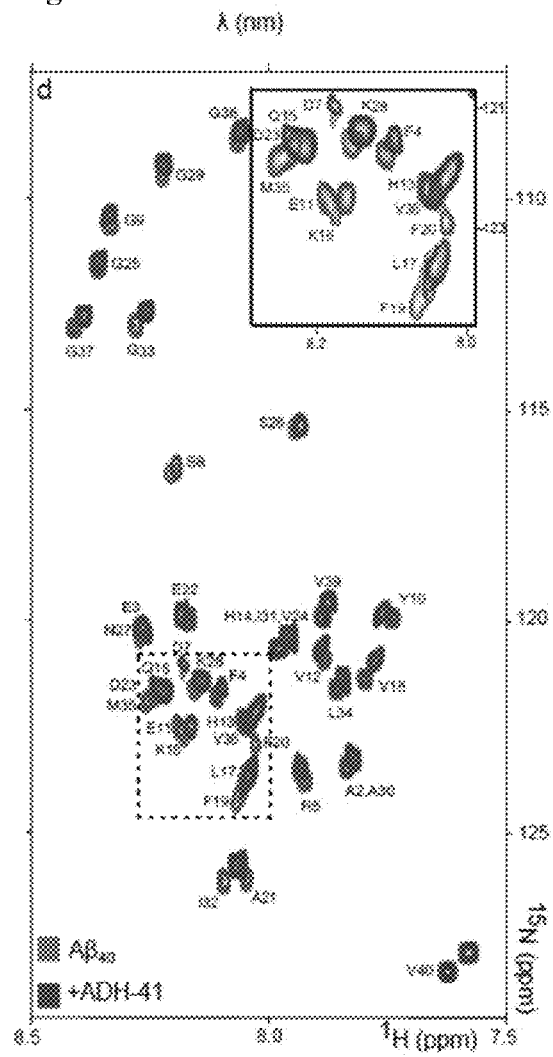
Fig. 5E
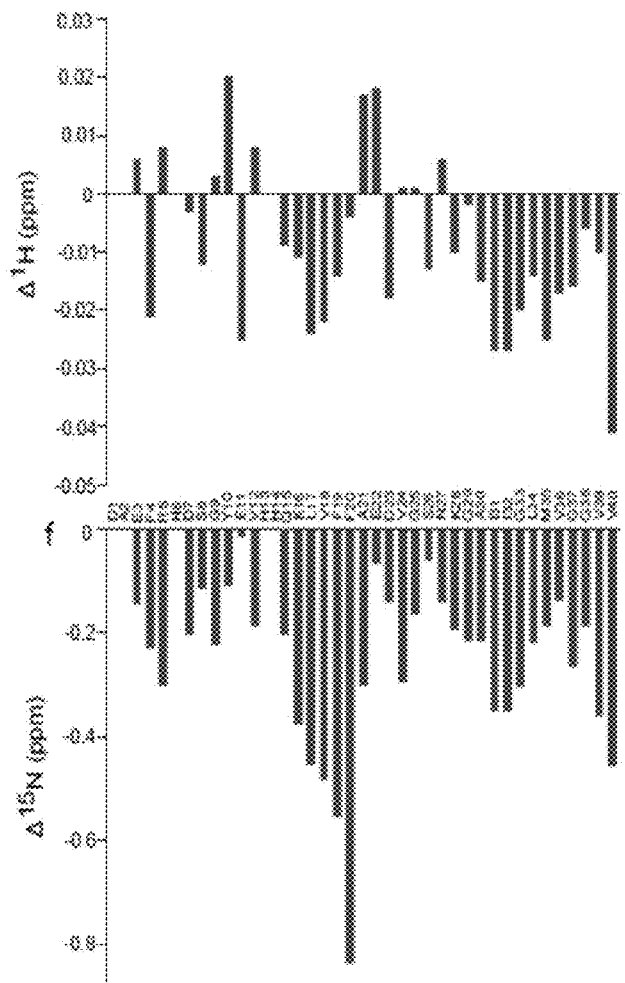
Fig. 5F Aβ$_{42}$ + seeds Aβ$_{42}$ + seeds + ADH-41

[Aβ42:ADH-41] = 5 μM

Aβ42  DAEFRHDSGYEVHHQKLVFFAEDVGSNKGAIIGLM VGGVVIA

IAPP  KCNTATCATQRLANFLVHSSNNFGAILSSTNVGSNTY

Fig. 27A
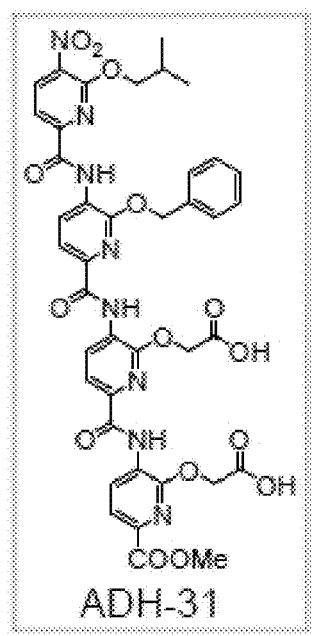
ADH-31
Fig. 27C
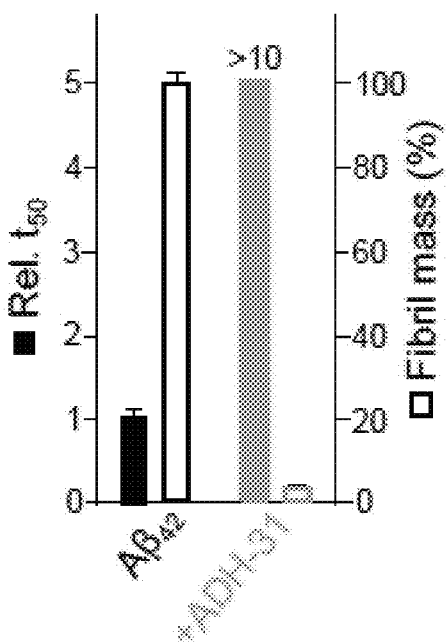
Fig. 27D
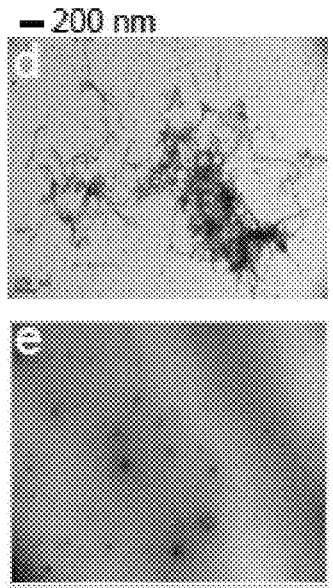
Fig. 27E
Fig. 27B
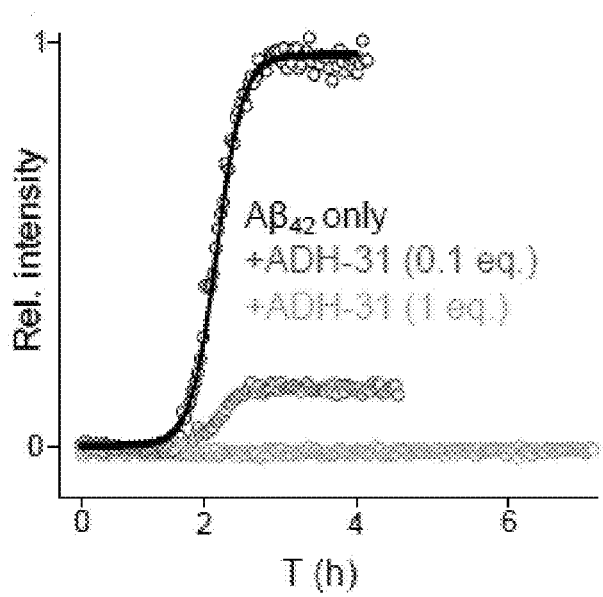
Fig. 27F
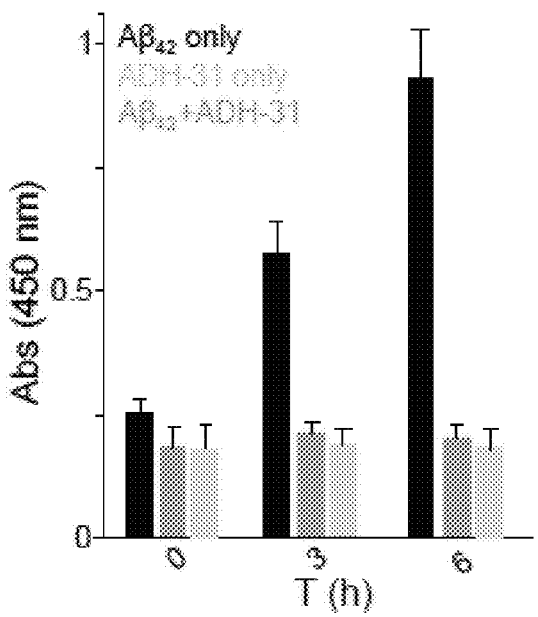

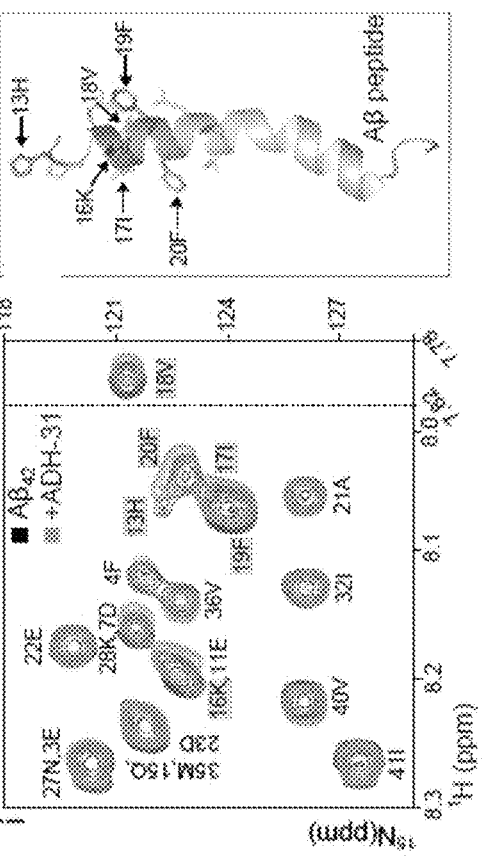
Fig. 27G
Fig. 27H
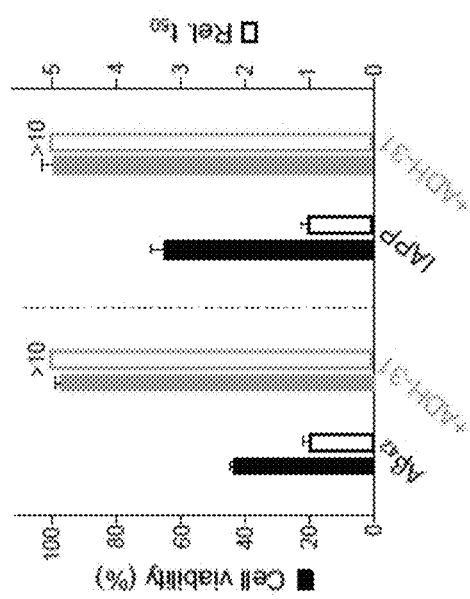
Fig. 27I
Fig. 27J
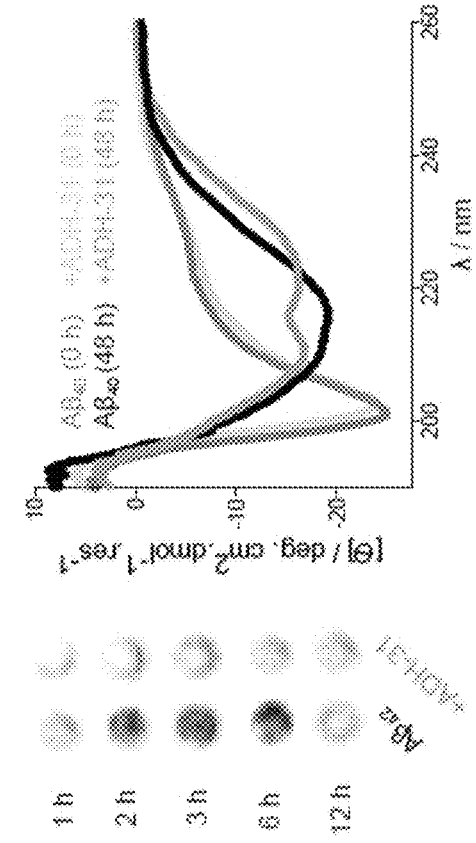
Fig. 27K
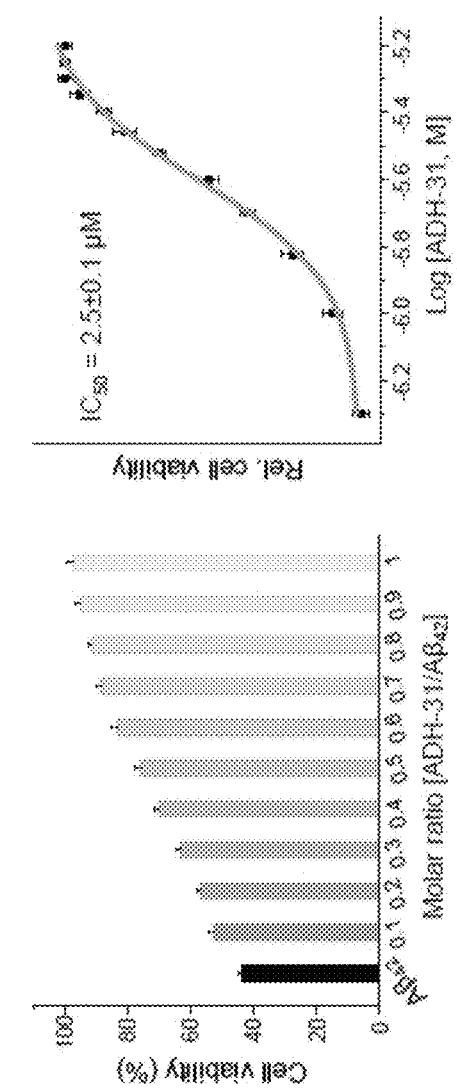
Fig. 27L
Fig. 27M

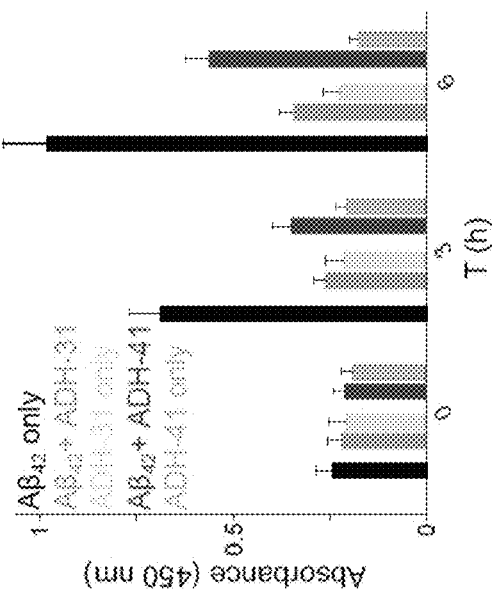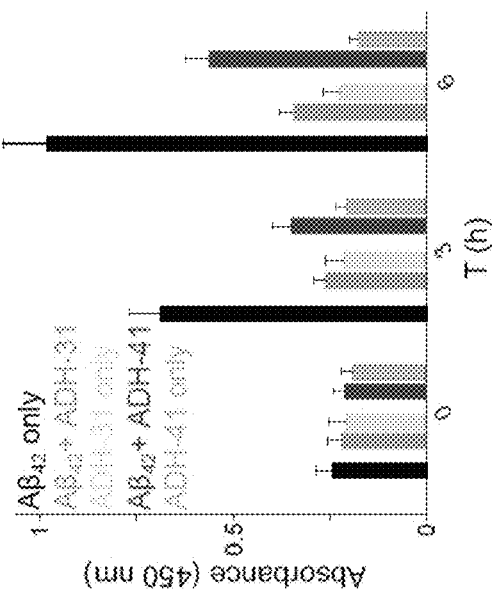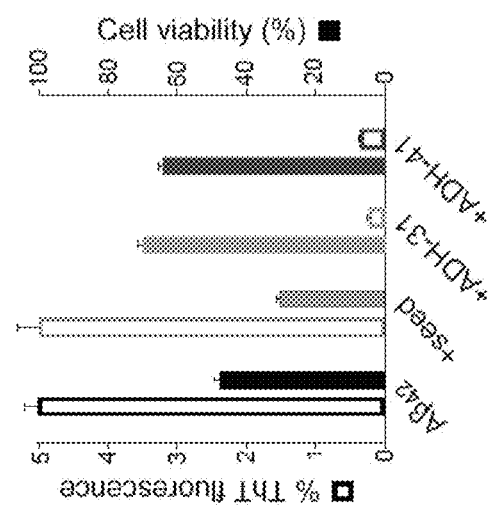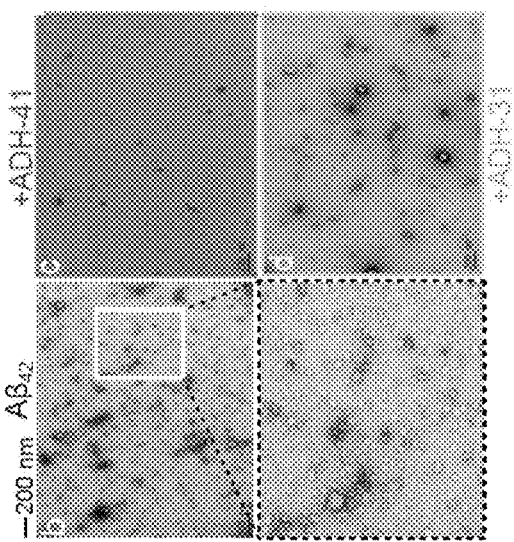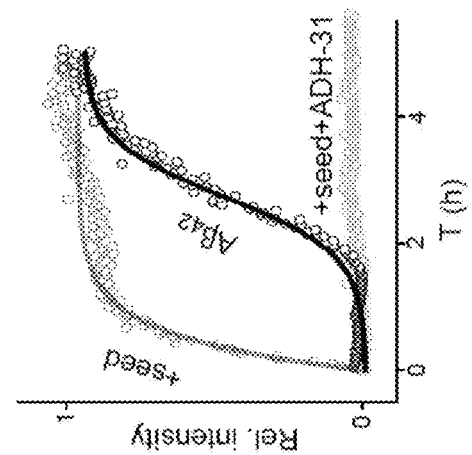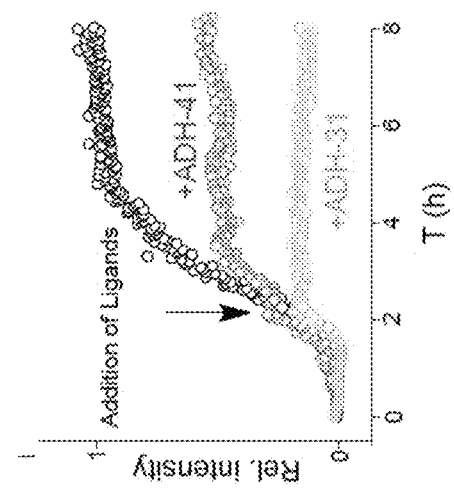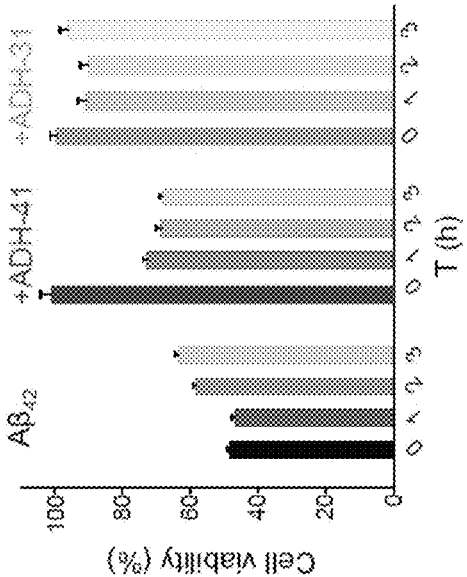

Fig. 29A 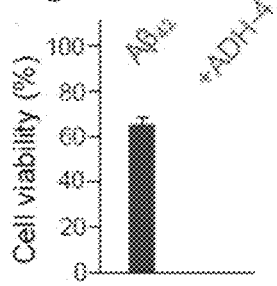 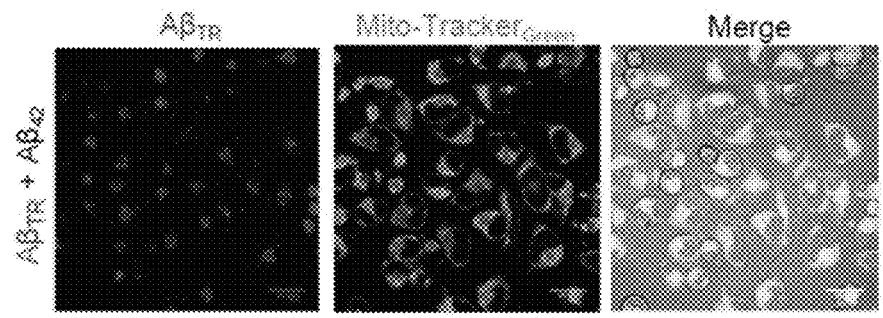
Fig. 29B 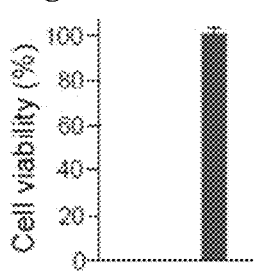 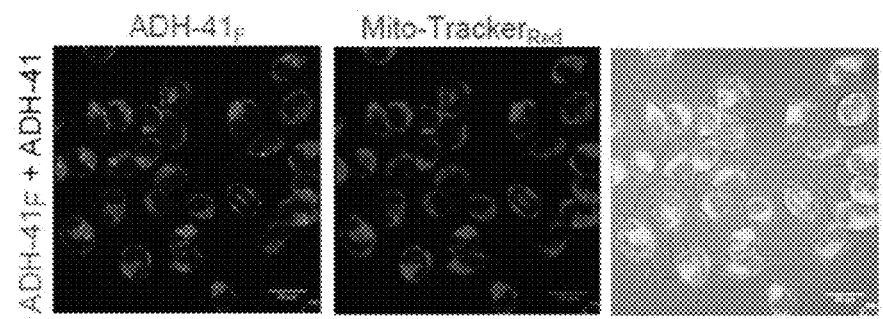
Fig. 29C 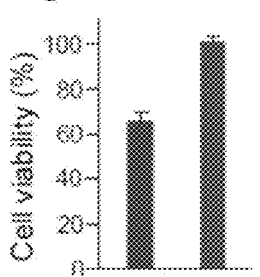 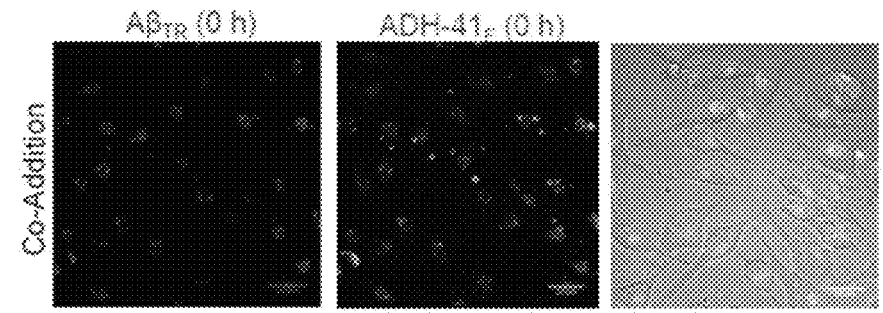
Fig. 29D 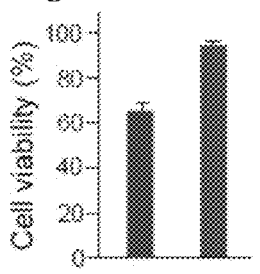 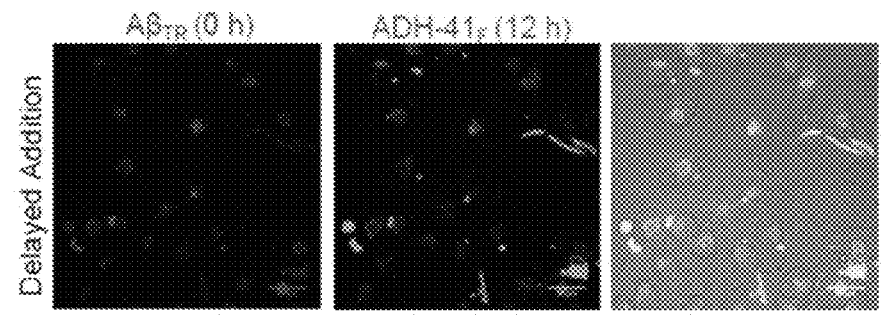

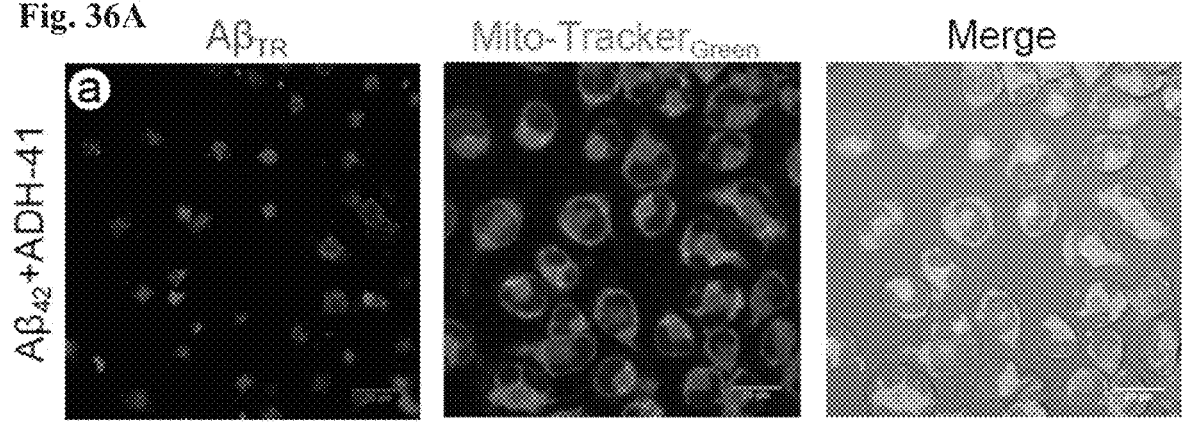
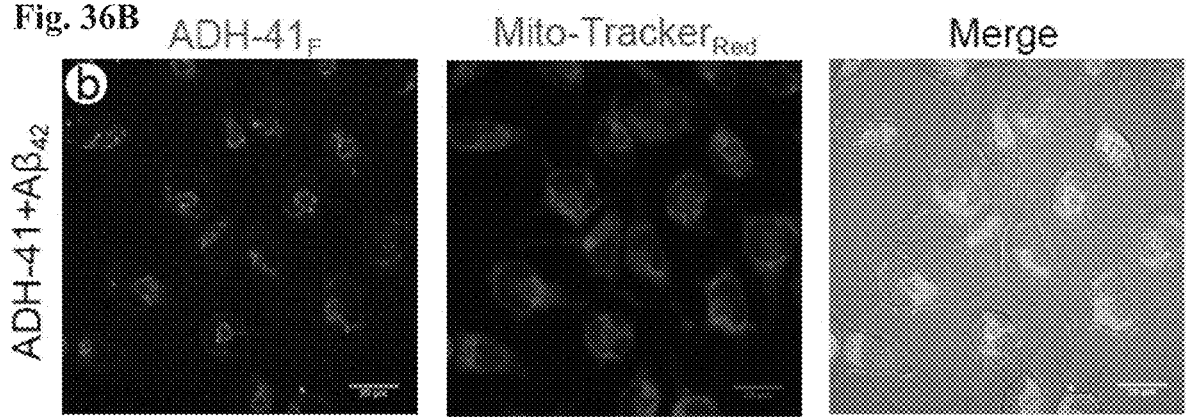

ALPHA-HELIX MIMETICS AS MODULATORS OF ABETA SELF-ASSEMBLY

CROSS-REFERENCE TO RELATED APPLICATIONS

This application claims priority to U.S. Provisional Applications Ser. No. 62/437,354, filed on Dec. 21, 2016, and 62/481,485, filed on Apr. 4, 2017, the contents of which are incorporated herein by reference in their entirety.

FIELD OF THE INVENTION

The present invention relates to compounds and pharmaceutical compositions capable of treating amyloid diseases and other diseases characterized by oligomerization and/or fibrillation of amyloidogenic peptides such as amyloid beta peptide (Abeta or Aβ)

BACKGROUND

Neurodegenerative diseases (NDs) are a large group of pathologies caused by metabolic changes in brain cells, loss of synapses and other compartments of neurons, and finally neuronal death (*Neurodegenerative diseases: From Molecular Concepts to Therapeutic Targets*. Editors: R. von Bernhardi, N. C. Inestrosa, Nova Publishers, 2008; *Neurodegenerative diseases: Clinical aspects, Molecular Genetics and Biomarkers*. Editors: D. Galimberti, E. Scarpini, Springer, 2014). This group of diseases includes Mild Cognitive Impairment (MCI), Alzheimer's disease (AD), Lewy Body dementia, Parkinson's disease (PD), Huntington's disease (HD), frontotemporal dementia (FTD), progressive supranuclear palsy (PSP), vascular dementia, multiple sclerosis (MS), amyotrophic lateral sclerosis (ALS), prion diseases, different ataxias, and others. Due to the increased lifespan, NDs become very common in developed countries. There are about 65 million people living with AD and PD, respectively, and in the U.S. alone, 70-80 million people are at risk of developing one of these conditions.

NDs, and AD specifically, are characterized by neuronal death in different disease-specific areas of the brain. The accumulation of proteinaceous amyloid fiber plaques in the central nervous system initiates and regulates the pathogenic cascade of AD (Hardy, J.; Selkoe, D. J. *Science* 2002, 297, 353-356; Hardy, J. A.; Higgins, G. A. *Science* 1992, 256, 184-185). A central event associated with the progression of AD is the oligomerization and subsequent aggregation of amyloid beta (Abeta or Aβ) peptide and its subsequent conversion into β-sheet rich fibers en route to the formation of amyloid plaques (Haass, C.; Selkoe, D. J. *Nat. Rev. Mol. Cell Biol.* 2007, 8, 101-112).

Aβ is derived from the transmembrane portion of the secreted protein, amyloid precursor protein (APP). Cleavage of APP results in several Aβ isoforms. The predominant species are $A\beta_{42}$ and $A\beta_{40}$. The longer variant of Aβ, $A\beta_{42}$ is the main constituent of amyloid plaques and is far more neurotoxic than $A\beta_{40}$ (Iwatsubo, T.; Odaka, A.; Suzuki, N.; Mizusawa, H.; Nukina, N.; Ihara, Y. *Neuron* 1994, 13, 45-53). Previously, according to the amyloid cascade hypothesis, it was believed that plaques resulting from β-sheet formation are responsible for AD onset. However, in recent years, it has been established that the prefibrillar soluble oligomers of Aβ, and not the fibers themselves, are the key neurotoxic species. The accumulation of these oligomeric intermediates leads to presynaptic loss and eventual neuronal cell death. The implication of Aβ oligomeric intermediates in cellular dysfunction and AD make them an important target for therapeutic intervention. However, the dearth of structural information about the soluble oligomers of Aβ presents a challenging task in identifying suitable strategies to modulate Aβ structure and function.

$A\beta_{40}$ and $A\beta_{42}$ exist predominantly as random coils in aqueous solution, and are known to sample a range of secondary structures under specific conditions (Riek, R.; Güntert, P.; Döbeli, H.; Wipf, B.; Wüthrich, K. *Eur. J. Biochem.* 2001, 268, 5930-5936). Under matched conditions, the aggregation of $A\beta_{42}$ is more aggressive than $A\beta_{40}$ (Yan, Y.; Wang, C. *J. Mol. Biol.* 2006, 364, 853-862). The secondary structures of both peptides are almost identical except that $A\beta_{42}$ adopts a more rigid structure at its C-terminus. In the presence of sodium dodecyl sulfate (SDS) micelles and 1,1,1,3,3,3-hexafluoro-2-propanol (HFIP), both peptides adopt α-helical conformations from residues 15-24 and 29-35 with residues 16, 20, 22, and 23 exposed to solvent (Jarvet, J.; Danielsson, J.; Damberg, P.; Oleszczuk, M.; GrÃslund, A. *J. Biomol. NMR* 2007, 39, 63-72; Coles, M.; Bicknell, W.; Watson, A. A.; Fairlie, D. P.; Craik, D. J. *Biochemistry* 1998, 37, 11064-11077; Serpell, L. C. *Biochim. Biophys. Acta* 2000, 1502, 16-30).

Numerous small molecules have been identified that modulate the kinetic pathways of Aβ oligomerization. These molecules were principally discovered via high throughput screening (HTS), rational design based on the β-sheet structure of Aβ, and mimicry of short Aβ segments. Some effective modulators of Aβ assembly include the polyphenols (−) epigallocatechin-3-gallate (EGCG) and resveratrol, the sugar derivative scyllo-inositol, molecular tweezers (MTs), Methylene Blue, ligand D-737 and its analogs, cucurbit[7]uril, β-cyclodextrins, cyclic D,L-α-peptides, a C-terminal Aβ peptide fragment, cyclic-KLVFF (D and L) and its analogues, congo red, curcumin, trimeric aminopyrazole carboxylic acid derivatives, affibody proteins, and peptoids. (Ehrnhoefer, D. E.; Bieschke, J.; Boeddrich, A.; Herbst, M.; Masino, L.; Lurz, R.; Engemann, S.; Pastore, A.; Wanker, E. E. *Nat Struct Mot Blot* 2008, 15, 558-566; Palhano, F. L.; Lee, J.; Grimster, N. P.; Kelly, J. W. *J. Am. Chem. Soc.* 2013, 135, 7503-7510; Ladiwala, A. R. A.; Lin, J. C.; Bale, S. S.; Marcelino-Cruz, A. M.; Bhattacharya, M.; Dordick, J. S.; Tessier, P. M. *J. Biol. Chem.* 2010, 285, 24228-24237; McLaurin, J.; Golomb, R.; Jurewicz, A.; Antel, J. P.; Fraser, P. E. *J. Biol. Chem.* 2000, 275, 18495-18502; Sinha, S.; Lopes, D. H. J.; Du, Z.; Pang, E. S.; Shanmugam, A.; Lomakin, A.; Talbiersky, P.; Tennstaedt, A.; McDaniel, K.; Bakshi, R.; Kuo, P.; Ehrmann, M.; Benedek, G. B.; Loo, J. A.; KlÃrner, F.; Schrader, T.; Wang, C.; Bitan, G. *J. Am. Chem. Soc.* 2011, 133, 16958-16969; Necula, M.; Breydo, L.; Milton, S.; Kayed, R.; van, d. V.; Tone, P.; Glabe, C. G. *Biochemistry* 2007, 46, 8850-8860; McKoy, A. F.; Chen, J.; Schupbach, T.; Hecht, M. H. *Chem. Biol. Drug Des.* 2014, 84, 505-512; McKoy, A. F.; Chen, J.; Schupbach, T.; Hecht, M. H. *J. Biol. Chem.* 2012, 287, 38992-39000; Lee, H. H.; Choi, T. S.; Lee, S. J. C.; Lee, J. W.; Park, J.; Ko, Y. H.; Kim, W. J.; Kim, K.; Kim, H. I. *Angew. Chem. Int. Ed.* 2014, 53, 7461-7465; WahlstrÃm, A.; Cukalevski, R.; Danielsson, J.; Jarvet, J.; Onagi, H.; Rebek, J.; Linse, S.; GrÃslund, A. *Biochemistry* 2012, 51, 4280-4289; Richman, M.; Wilk, S.; Chemerovski, M.; WÃ○rmlÃ○nder, Sebastian K. T. S.; WahlstrÃm, A.; GrÃslund, A.; Rahimipour, S. *J. Am. Chem. Soc.* 2013, 135, 3474-348; Fradinger, E. A.; Monien, B. H.; Urbanc, B.; Lomakin, A.; Tan, M.; Li, H.; Spring, S. M.; Condron, M. M.; Cruz, L.; Xie, C.; Benedek, G. B.; Bitan, G. *Proc. Natl. Acad. Sci. U.S.A.* 2008, 105, 14175-14180; Arai, T.; Araya, T.; Sasaki, D.; Taniguchi, A.;

Sato, T.; Sohma, Y.; Kanai, M. *Angew. Chem. Int. Ed.* 2014, 53, 8236-8239; Arai, T.; Sasaki, D.; Araya, T.; Sato, T.; Sohma, Y.; Kanai, M. *ChemBioChem* 2014, 15, 2577-2583; Yang, F.; Lim, G. P.; Begum, A. N.; Ubeda, O. J.; Simmons, M. R.; Ambegaokar, S. S.; Chen, P. P.; Kayed, R.; Glabe, C. G.; Frautschy, S. A.; Cole, G. M. *J. Biol. Chem.* 2005, 280, 5892-5901; HochdÃrffer, K.; MÃrz-Berberich, J.; Nagel-Steger, L.; Epple, M.; Meyer-Zaika, W.; Horn, A. H. C.; Sticht, H.; Sinha, S.; Bitan, G.; Schrader, T. *J. Am. Chem. Soc.* 2011, 133, 4348-4358).

Some Aβ modulators act as ligands to induce or stabilize a secondary structure in Aβ, and thus alter its function. For example, a peptoid and an affibody protein were shown to trap Aβ into the central discordant α-helical structure and a β-hairpin conformation, reminiscent of membrane-bound Aβ and Aβ fibril structure, respectively. The interaction of the peptoid with Aβ induced an α-helical structure, which altered the aggregation kinetics of Aβ and rescued PC12 cells from cytotoxicity mediated by Aβ. (See Nerelius, C.; Sandegren, A.; Sargsyan, H.; Raunak, R.; Leijonmarck, H.; Chatterjee, U.; Fisahn, A.; Imarisio, S.; Lomas, D. A.; Crowther, D. C.; Stromberg, R.; Johansson, J. *Proc. Natl. Acad. Sci. U.S.A.* 2009, 106, 9191-9196 and Hoyer, W.; Grönwall, C.; Jonsson, A.; Ståhl, S.; Härd, T. *Proc. Natl. Acad. Sci. U.S.A.* 2008, 105, 5099-5104, respectively). Despite these advances in the art, to date, there is no cure or effective therapy for reducing a patient's amyloid burden or preventing amyloid deposition in AD and other amyloid diseases.

Alpha-helical mimetics are organic scaffolds that imitate the topography of an α-helix, such as those present at protein-protein interfaces. On a molecular level, the surface functionalities of α-helical mimetics are spatially oriented in a well-defined order to mimic the side chain residues of one helical surface at positions i, i+3/i+4, and i+7. α-helical mimetics have previously been shown to act as antagonists of numerous protein-protein interactions, including HIV gp41 oligomerization, Bak BH3/Bcl-xL, p53/HDM2, HIF1α/p300, and membrane-bound α-helical intermediates of islet amyloid polypeptide (IAPP) (Saraogi, I.; Hebda, J.; Becerril, J.; Estroff, L.; Miranker, A.; Hamilton, A. *Angew. Chem. Int. Ed.* 2010, 49, 736-739; Kulikov, O. V.; Kumar, S.; Magzoub, M.; Knipe, P. C.; Saraogi, I.; Thompson, S.; Miranker, A. D.; Hamilton, A. D. *Tet. Lett.* 2015, 56, 3670-3673; Kumar, S.; Birol, M.; Miranker, A. D. *Chem. Comm.* 2016, 52, 6391-6394).

Previously, certain oligopyridylamide-based α-helical mimetics have been used to target the membrane-associated α-helical conformation of IAPP and were found to be strong antagonists of membrane-catalyzed IAPP aggregation. Structure-activity relationship studies were conducted to optimize the inhibitory activity against IAPP self-assembly via charge complementarity and hydrophobic interactions. In addition to in vitro solution biophysical assays confirming the inhibition of self assembly, these α-helical mimetics were shown to be effective in rescuing an insulin secreting cell line from IAPP-mediated cytotoxicity. (Kumar, S.; Schlamadinger, D.; Brown, M.; Dunn, J.; Mercado, B.; Hebda, J.; Saraogi, I.; Rhoades, E.; Hamilton, A.; Miranker, A. *Chem. Biol.* 2015, 22, 369-378; Hebda, J. A.; Saraogi, I.; Magzoub, M.; Hamilton, A. D.; Miranker, A. D. *Chem. Biol.* 2009, 16, 943-950).

IAPP and Aβ share ~50% sequence similarity, with the Aβ(15-21) and Aβ(26-32) sequences sharing particular commonality with those of IAPP(10-16) and IAPP(21-27), respectively. These regions are further thought to participate in amyloidogenesis. These similarities likely account for the observation that many Aβ antagonists also inhibit IAPP amyloid formation and vice versa. Yet, despite certain similarities, IAPP and Aβ are implicated in vastly different diseases and conditions. Accordingly, there exists a need in the art for developing compounds that would exhibit specificity and/or selectivity for Aβ versus IAPP, As discussed herein, several disease-specific amyloidogenic proteins share similar structural and functional properties. These proteins are believed to proceed through a series of conformation switches starting from the native disordered state to soluble oligomeric intermediates which eventually terminate into highly ordered intractable fiber aggregates. An increasing body of evidence suggests that soluble oligomers of the amyloidogenic proteins are the predominant cytotoxic species associated with various amyloid-related diseases. Therefore, elucidation of the structural details of these oligomeric intermediates may provide mechanistic insight for the development of effective therapeutics. Enormous efforts have been directed to identify and characterize these oligomers with limited success because of their complex and dynamic nature. Study of Aβ oligomerization processes by Teplow et al suggested two strategies that could fit the portrait of an ideal therapeutic agent (Ono, K.; Condron, M. M.; Teplow, D. B. *Proc. Natl. Acad. Sci. U.S.A.* 2009, 106, 14745-14750). (1) Conformational organization of the native monomeric state of Aβ which could potentially alter the oligomerization and other downstream functions of Aβ. (2) Destabilization of the oligomeric states to block further oligomerization and fibril formation.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

As discussed herein, there is a great need in the art to develop effective treatments for amyloid diseases and other diseases and conditions characterized by oligomerization and/or fibrillation of an amyloidogenic peptide. The present invention addresses these and other needs by providing new compounds, pharmaceutical compositions, and methods of treatment based on such compounds and pharmaceutical compositons. The compounds of the present invention are useful for altering the structure and/or inhibiting the self-assembly of one or more amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. Some of the compounds of the invention which are useful for altering the structure and/or inhibitng the self-assembly of Aβ, or its $Aβ_{42}$ alloform, display specificity and/or selectivity for Aβ as compared to structurally related amyloidogenic peptides, such as, e.g., IAPP, and decreasing the chances of undesirable side-effects upon their use in vivo.

Various non-limiting embodiments of the invention are described below.

In one embodiment, the compounds of the invention (e.g., the modulators of oligomerization of amyloidogenic peptides, such as Aβ and/or IAPP) have the structure of formula (I):

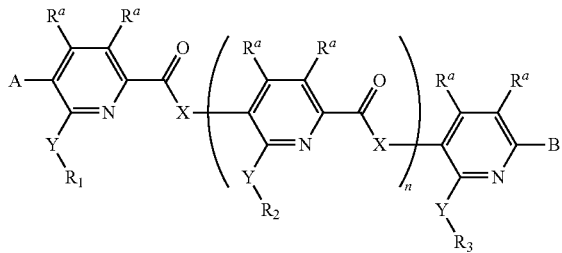

(I)

and pharmaceutically acceptable salts thereof.

In formula (I), IV is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$.

In some embodiments, $R^a$ is present at 0, 1, or 2 different positions on the ring.

In some embodiments, $R^a$ is hydrogen at all occurrences.

X is independently at each occurrence selected from —O—; —S—; —NH—; —NR*—; and —C(R*)$_2$.

In some embodiments X is —NH— or —NR*—, such that —(C=O)—X— is an amide bond, at all occurrences. In some embodiments X is NH—.

In some embodiments X is not —O—. In some embodiments X is not —S—. In some embodiments X is not C(R*)$_2$.

Y is independently at each occurrence selected from —O—; —S—; —NH—; and —NR*—.

In some embodiments Y is —O— at all occurrences.

In some embodiments Y is not —S—. In some embodiments Y is not —NH— or —NR*—.

$R_1$, $R_2$, and/or $R_3$ are independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof.

In some embodiments $R_1$, $R_2$, and/or $R_3$ are independently at each occurrence selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof.

In some embodiments $R_1$, $R_2$, and/or $R_3$ are independently at each occurrence a straight chained, branched or cyclic aliphatic $C_1$-$C_{20}$ hydrocarbon, optionally substituted with one or more of —NH$_2$; —NHR*; —N(R*)$_2$; —N(R*)$_3^+$; —(C=O)—R*; —CO$_2$H; or —CO$_2$R*; and combinations thereof.

In some embodiments $R_1$, $R_2$, and/or $R_3$ are independently at each occurrence a straight chained, branched or cyclic $C_1$-$C_{20}$ hydrocarbon, optionally substituted with one or more of —NH$_2$; —NHR*; —N(R*)$_2$.

In some embodiments $R_1$, $R_2$, and/or $R_3$ are independently at each occurrence a straight chained, branched or cyclic aliphatic $C_1$-$C_{20}$ hydrocarbon, optionally substituted with —CO$_2$H. In some embodiments $R_1$, $R_2$, and/or $R_3$ may independently at each occurrence be —CH$_2$CO$_2$H.

In some embodiments $R_1$, $R_2$, and/or $R_3$ at all occurrences do not contain —CO$_2$H. In some embodiments $R_1$, $R_2$, and/or $R_3$ are not —CH$_2$CO$_2$H at all occurrences.

In some embodiments $R_1$, $R_2$, and/or $R_3$ are independently at each occurrence selected from an aromatic $C_6$-$C_{20}$ hydrocarbon; a heteroaromatic $C_1$-$C_{20}$ hydrocarbon; an aryl $C_6$-$C_{20}$ hydrocarbon; or a heteroaryl $C_1$-$C_{20}$ hydrocarbon optionally containing 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*.

In some embodiments, $R_1$, $R_2$, and/or $R_3$ are independently at each occurrence selected from a substituted or unsubstituted phenyl, benzyl, naphthyl, indolyl, pyrrolidinyl, pyrrolyl, imidazolyl, pyrazolyl, oxazolyl, isoxazolyl, thiazolyl, isothiazolyl, histidinyl (i.e., —CH$_2$-imidazole), triazolyl, pyridyl, pyranyl, diazinyl, oxazinyl, thiazinyl, or triazinyl.

A and B are independently selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl.

In some embodiments A is selected from —NO$_2$; —NH$_2$; —NHR*; —N(R*)—(C=O)—R*, —N(R*)$_2$. In some embodiments A is —NO$_2$. In some embodiments A is NH$_2$; —NHR*; or —N(R*)$_2$.

In some embodiments A is not —N(R*)—(C=O)—R*. In some embodiments A is not NH$_2$; —NHR*; or —N(R*)$_2$.

In some embodiments B is selected from —(C=O)—R*; —CO$_2$H; —CO$_2$R*. In some embodiments B may be —CO$_2$R*, where R* is a $C_1$-$C_{12}$ hydrocarbon. In some embodiments B is —CO$_2$R* and R* is selected from methyl, ethyl, propyl, or butyl groups. In some embodiments A is —CO$_2$R* and R* is methyl.

In some embodiments B is not —CO$_2$H. In some embodiments B is not —(C=O)—R*.

R* is independently selected at each occurrence from hydrogen or $C_1$-$C_{12}$ hydrocarbons each of which optionally contains 1-8 heteroatoms selected from halogen, O, N, and S and combinations thereof.

n is an integer from 0 to 2.

In some embodiments, n is 0, i.e., the compound of formula (I) is a dipyridyl. In other embodiments n is 1, i.e., the compound of formula (I) is a tripyridyl. In yet other embodiments, n is 2, i.e., the compound of formula (I) may be a tetrapyridyl.

In some embodiments, n is 0, and X is —NH—, i.e., the compound of formula (I) is a dipyridylamide. In other embodiments n is 1, and X is —NH—, i.e., the compound of formula (I) is a tripyridylamide. In yet other embodiments, n is 2, and X is —NH—, i.e., the compound of formula (I) is a tetrapyridylamide.

In some embodiments, when n is 0, and Y is O, $R_1$ and $R_3$ are not both —$CH_2CO_2H$.

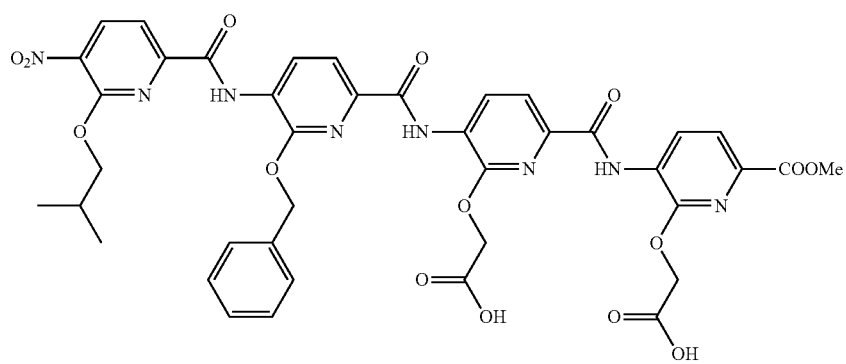

(ADH-31)

In some embodiments, when n is 1, Y is O, and $R_1$ and $R_3$ are both —$CH_2CO_2H$, $R_2$ is not —$CH_2CO_2H$ or a straight chained, branched or cyclic aliphatic or aryl $C_1$-$C_{12}$ hydrocarbon, or $R_2$ does not have the structure —$C(CH_2CO_2H)_3$.

In some embodiments, when n is 1, and Y is O, $R_1$ through $R_3$ are not each an unsubstituted $C_1$-$C_8$ hydrocarbon.

In some embodiments, when n is 2, and Y is O, $R_1$ through $R_3$ are not —$CH_2CO_2H$ at all occurrences.

In another embodiment, a compound of the invention has the following structural formula:

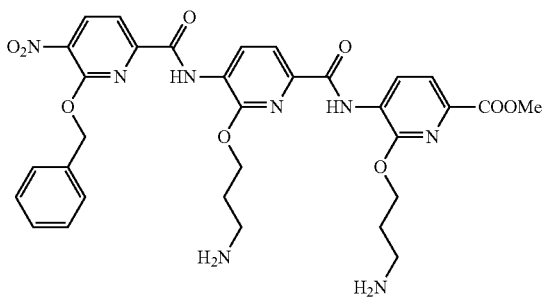

(ADH-41)

or a pharmaceutically acceptable salt thereof.

In yet another embodiment, a compound of the invention has the following structural formula:

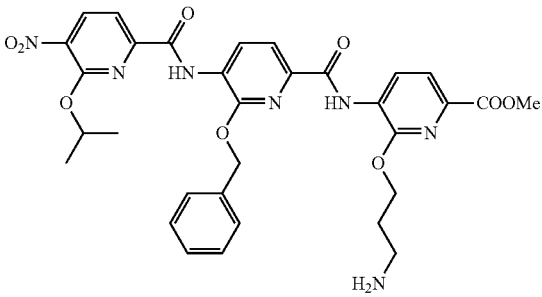

(ADH-39)

or a pharmaceutically acceptable salt thereof.

In yet another embodiment, a compound of the invention has the following structural formula:

or a pharmaceutically acceptable salt thereof.

In one aspect of the invention, pharmaceutical compositions comprising the above compounds as active agents optionally in combination with a pharmaceutically acceptable carrier, additive or excipient are provided. In one embodiment, the pharmaceutical compositions may comprise an effective amount of ADH-41, and/or ADH-31. The pharmaceutical compositions comprising an effective amount of one or more of the compounds of the invention may be formulated as a pharmaceutical dosage form for administration to a subject.

In one aspect, compounds and/or pharmaceutical compositions of the invention may be used for altering the structure of an amyloidogenic peptide. In some embodiments, compounds and/or pharmaceutical compositions according to the invention may be useful for altering structures of amyloidogenic peptides including, without limitation, Aβ, islet amyloid polypeptide (IAPP), α-synuclein, AA amyloid, PrP, β₂-microglobulin amyloid, transthyretin, prealbumin, and procalcitonin. In some embodiments compounds and/or pharmaceutical compositions according to the invention may be useful for altering the structure of Aβ, or its Aβ₄₂ alloform.

In one aspect, compounds and/or pharmaceutical compositions of the invention may be used for modulating oligomerization of an amyloidogenic peptide. In some embodiments, compounds and/or pharmaceutical compositions according to the invention may be useful for modulating oligomerization of amyloidogenic peptides including, without limitation, Aβ, islet amyloid polypeptide (IAPP), α-synuclein, AA amyloid, PrP, β₂-microglobulin amyloid, transthyretin, prealbumin, and procalcitonin. In some embodiments compounds and/or pharmaceutical compositions according to the invention may be useful for modulating oligomerization of Aβ, or its Aβ$_{42}$ alloform.

In one aspect, compounds and/or pharmaceutical compositions of the invention may be used for inhibiting oligomerization of an amyloidogenic peptide. In some embodiments, compounds and/or pharmaceutical compositions according to the invention may be useful for inhibiting oligomerization of amyloidogenic peptides including, without limitation, Aβ, islet amyloid polypeptide (IAPP), α-synuclein, AA amyloid, PrP, β$_2$-microglobulin amyloid, transthyretin, prealbumin, and procalcitonin. In some embodiments compounds and/or pharmaceutical compositions according to the invention may be useful for inhibiting oligomerization of Aβ, or its Aβ$_{42}$ alloform.

In one aspect, compounds and/or pharmaceutical compositions of the invention may be used for inhibiting (i.e., reducing, diminishing, or decreasing) cytotoxicity of an amyloidogenic peptide. In some embodiments, compounds and/or pharmaceutical compositions according to the invention may be useful for inhibiting cytotoxicity of amyloidogenic peptides including, without limitation, Aβ, islet amyloid polypeptide (TAPP), α-synuclein, AA amyloid, PrP, β$_2$-microglobulin amyloid, transthyretin, prealbumin, and procalcitonin. In some embodiments compounds and/or pharmaceutical compositions according to the invention may be useful for inhibiting cytotoxicity of Aβ, or its Aβ$_{42}$ alloform.

In one aspect, compounds and/or pharmaceutical compositions of the invention may be used for treating diseases and/or conditions characterized by a formation of oligomers or fibers of amyloidogenic peptides. In some embodiments, compounds and/or pharmaceutical compositions according to the invention may be useful for treating diseases and/or conditions characterized by a formation of oligomers or fibers of amyloidogenic peptides including, without limitation, Aβ, islet amyloid polypeptide (IAPP), α-synuclein, AA amyloid, PrP, β$_2$-microglobulin amyloid, transthyretin, prealbumin, and procalcitonin. In some embodiments compounds and/or pharmaceutical compositions according to the invention may be useful for treating diseases and/or conditions characterized by a formation of oligomers or fibers of Aβ, or its Aβ$_{42}$ alloform.

In one aspect, compounds and/or pharmaceutical compositions according to the invention may be useful for treating diseases selected from Alzheimer's Disease (AD), type 1 diabetes, type 2 diabetes, Parkinson's disease, Mild Cognitive Impairment (MCI), inclusion body myositis, cerebral amyloid angiopathy, systemic AA amyloidosis, Lewy body diseases including Lewy body dementia, multiple system atrophy, Down's syndrome, hereditary cerebral hemorrhage with amyloidosis of the Dutch type, inclusion body myositosis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid.

In another aspect of the invention, methods for modulating oligomerization and/or fibrillation of amyloidogenic peptides with compounds and/or pharmaceutical compositions of the present invention are provided. In some embodiments, methods of modulating oligomerization and/or fibrillation of amyloidogenic peptides are provided, including, without limitation, methods of modulating oligomerization and/or fibrillation of Aβ, islet amyloid polypeptide (IAPP), α-synuclein, AA amyloid, PrP, β$_2$-microglobulin amyloid, transthyretin, prealbumin, and procalcitonin.

In another aspect of the invention, methods for inhibiting oligomerization and/or fibrillation of amyloidogenic peptides with compounds and/or pharmaceutical compositions of the present invention are provided. In some embodiments, methods of inhibiting oligomerization and/or fibrillation of amyloidogenic peptides are provided, including, without limitation, methods of inhibiting oligomerization and/or fibrillation of Aβ, islet amyloid polypeptide (IAPP), α-synuclein, AA amyloid, PrP, β$_2$-microglobulin amyloid, transthyretin, prealbumin, and procalcitonin.

In one aspect, methods of altering the structure of an amyloidogenic peptide with compounds and/or pharmaceutical compositions of the present invention are provided. In some embodiments, methods of altering structures of amyloidogenic peptides including, without limitation, Aβ, islet amyloid polypeptide (IAPP), α-synuclein, AA amyloid, PrP, β$_2$-microglobulin amyloid, transthyretin, prealbumin, and procalcitonin with compounds and/or pharmaceutical compositions of the present invention are provided. In some embodiments methods of altering the structure of Aβ, or its Aβ$_{42}$ alloform with compounds and/or pharmaceutical compositions of the present invention are provided.

In one aspect, methods of inhibiting cytotoxicity of an amyloidogenic peptide with compounds and/or pharmaceutical compositions of the present invention are provided. In some embodiments, methods of inhibiting cytotoxicity of amyloidogenic peptides including, without limitation, Aβ, islet amyloid polypeptide (IAPP), α-synuclein, AA amyloid, PrP, β$_2$-microglobulin amyloid, transthyretin, prealbumin, and procalcitonin with compounds and/or pharmaceutical compositions of the present invention are provided. In some embodiments methods of inhibiting cytotoxicity of Aβ or its Aβ$_{42}$ alloform with compounds and/or pharmaceutical compositions of the present invention are provided.

In one aspect, methods of treating diseases and/or conditions characterized by a formation of oligomers or fibers of amyloidogenic peptides with compounds and/or pharmaceutical compositions of the present invention are provided. In some embodiments, methods of treating diseases and/or conditions characterized by a formation of oligomers or fibers of amyloidogenic peptides including, without limitation, Aβ, islet amyloid polypeptide (IAPP), α-synuclein, AA amyloid, PrP, β$_2$-microglobulin amyloid, transthyretin, prealbumin, and procalcitonin with compounds and/or pharmaceutical compositions of the present invention are provided. In some embodiments methods of treating diseases and/or conditions characterized by a formation of oligomers or fibers of amyloidogenic peptides of Aβ or its Aβ$_{42}$ alloform with compounds and/or pharmaceutical compositions of the present invention are provided.

In one aspect, methods of treating diseases and/or conditions characterized by a formation of oligomers or fibers of amyloidogenic peptides with compounds according to the invention which are capable of inhibiting oligomerization of an amyloidogenic peptide and/or pharmaceutical compositions comprising such compounds are provided. In some embodiments, methods of treating diseases and/or conditions characterized by a formation of oligomers or fibers of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin with compounds according to the invention capable of inhibiting oligomerization of an amyloidogenic peptide and/or pharmaceutical compositions comprising such compounds are provided. In some embodiments methods of treating diseases and/or conditions characterized by a formation of oligomers or fibers of amyloidogenic peptides of Aβ or its $Aβ_{42}$ alloform with compounds according to the invention which are capable of inhibiting oligomerization of an amyloidogenic peptide and/or pharmaceutical compositions comprising such compounds are provided.

In one aspect, methods of treating diseases selected from Alzheimer's Disease (AD), type 1 diabetes, type 2 diabetes, Parkinson's disease, Mild Cognitive Impairment (MCI), inclusion body myositis, cerebral amyloid angiopathy, systemic AA amyloidosis, Lewy body diseases including Lewy body dementia multiple system atrophy, Down's syndrome, hereditary cerebral hemorrhage with amyloidosis of the Dutch type, inclusion body myositosis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid with compounds and/or pharmaceutical compositions of the inventions are provided.

These and other aspects of the present invention will become apparent to those skilled in the art after a reading of the following detailed description of the invention, including the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1a-1e illustrate structures of the protein and small molecules according to embodiments of the disclosure. FIG. 1a shows a generic scheme for the synthesis of tripyridyl-amides according to an embodiment of the disclosure. FIG. 1b shows a generic structure of α-helical mimetics according to an embodiment of the disclosure. FIG. 1c shows a helical wheel presentation of the central α-helical domain of Aβ spanning residues 13-26. The acidic, basic, hydrophobic, and polar residues are represented by red, blue, green, and yellow circles. A presentation of the potential binding sites of the indicated oligopyridylamides on Aβ depicted by blue and red colors. FIG. 1d shows a crystal structure of an exemplary tripyridylamide α-helical mimetic and the positively charged subdomain of Aβ with side chains residues. It is an exemplary presentation for the binding interaction between the negatively charged oligopyridylamide and Aβ. FIG. 1e depicts a presentation of the potential binding sites of two oligopyridylamides ADH-31 and ADH-41 according to the disclosure on Aβ depicted by blue (for ADH-31) and red (for ADH-41) colors.

FIGS. 2a-2e illustrate the effect of the compounds of the invention on the aggregation of $Aβ_{42}$. FIG. 2a shows a graph of the relative fluorescence intensity versus time for $Aβ_{42}$ fibrillation in the absence and presence of the indicated compounds. FIG. 2b shows a bar graph of rel. $t_{50}$ values for the kinetics of $Aβ_{42}$ aggregation in the absence and presence of the indicated compounds. FIG. 2c shows the chemical structures of the indicated compounds according to embodiments of the disclosure. FIG. 2d shows a graph of the rel. fluorescence intensity versus time for $Aβ_{42}$ aggregation in the absence and presence of ADH-41 at indicated concentrations. FIG. 2e shows a bar graph of shows the relative change in the fluorescence intensity of the aggregation of $Aβ_{42}$ fibrils in the presence of various concentrations of ADH-41.

FIGS. 3a-3c illustrate the effect of ADH-41 on Aβ aggregation according to embodiments of the disclosure. FIG. 3a shows the primary sequences of Aβ42 and IAPP. Identical and chemically similar residues are shown blue and green, respectively. Sequences displaying high identity and similarity are underlined in orange. FIG. 3b shows a graph of rel. $t_{50}$ for Aβ42, Aβ40, and IAPP in the absence and presence of ADH-41. FIG. 3c shows a graph of rel. intensity of ThT fluorescence after completion of the fibrillation of Aβ42, Aβ40, and IAPP in the absence and presence of ADH-41.

FIGS. 4a-4l illustrate the effect of ADH-41 on Aβ42 conformation. FIG. 4a shows a frequency distribution plot of diameter Aβ42 in the absence and presence of ADH-41. FIG. 4b shows an AFM image of Aβ42 in the absence of ADH-41, and FIG. 4c shows an AFM image of Aβ42 in the presence of ADH-41. FIGS. 4d-4i show TEM images of Aβ42 in the absence or presence of ADH-41 according to embodiments of the disclosure. FIG. 4j shows an image of samples spotted on a nitrocellulose membrane that were aged with antibody 6E10 or A11 in the absence and presence of ADH-41. FIG. 4k shows samples of Aβ42 in the absence and presence of ADH-41 that were subjected to PICUP and SDS-PAGE-silver staining. FIG. 4l shows a graph of absorbance data in the absence and presence of ADH-41.

FIGS. 5a-5f illustrate a conformational change in the Aβ structure induced by ADH-41. FIG. 5a shows far UV-CD spectra of Aβ12-28 in the absence (black) and in the presence of ADH-41 (red). FIG. 5b shows time-dependent CD spectra of Aβ42 at 0 hours and 12 hours. FIG. 5c shows time-dependent CD spectra of Aβ42 in the presence of ADH-41 at 0 hours and 12 hours. FIG. 5d shows an overlay of the 1H-15N HSQC NMR spectra of Aβ40 in the absence (gray) and in the presence of ADH-41 (red). FIGS. 5e and 5f show the changes in the chemical shift for 1H and 15N resonances, respectively, of Aβ40 induced by ADH-41.

FIG. 6a shows seed-catalyzed aggregation of $Aβ_{40}$. FIG. 6(b) shows seed-catalyzed aggregation of $Aβ_{42}$. FIGS. 6c and 6d show TEM images of the seed-catalyzed fibrillation reaction of Aβ42 in the absence and presence of ADH-41, respectively.

FIG. 7a shows an ITC thermogram for the titration of a solution of Aβ40 with ADH-41. The upper panel provides measurement of μcal/s. The lower panel provides measurement of KJ/mol. FIG. 7b shows a binding curve of ADH-41 against Nα-amino-terminal fluorescein-labeled Aβ40. The inset provides fluorescence spectra of $N^α$-amino-terminal fluorescein-labeled Aβ40 in the absence (black) and presence (red) of ADH-41.

FIG. 8a shows normalized profiles of three readings of $Aβ_{42}$ aggregation in phosphate buffer. FIG. 8b shows a sigmoidal fit of one of the readings depicted in FIG. 8(a).

FIGS. 12a and 12b depict TEM images of 30 µM $A\beta_{40}$ at the time intervals of 24 h (a) and 48 h (b) in the absence of ADH-41. FIGS. 12c and 12d depict TEM images of 30 µM $A\beta_{40}$ in the presence of ADH-41 at the time intervals of 24 h (c) and 5 days (d) at an equimolar ratio.

FIG. 13a shows the aggregation of 20 µM IAPP in the absence (black) and presence of ADH-41 (red) at an equimolar ratio. FIG. 13b shows the kinetic profile of lipid catalyzed self-assembly of 10 µM IAPP in the absence (black) and presence of ADH-41 (red) at an equimolar ratio.

FIG. 17a shows a graph of cell proliferation in the presence of Aβ with or without the indicated compounds after 48 hours and after 72 hours. FIG. 17b shows the chemical structures of the indicated compounds according to an embodiment of the disclosure. ADH-41 is indicated by an asterisk.

FIGS. 24 (b and c) show the effect of the indicated compounds on Aβ-mediated toxicity in Neuro-2a cells.

FIG. 25a shows the sequence similarity between $A\beta_{42}$ and IAPP. FIG. 25b shows the structures of the compounds used (ADH-17 and ADH-41). FIG. 25c shows plots of rel. $t_{50}$ and cell viability in IAPP-treated rat INS cells in the presence and absence of ADH-17. FIG. 25d shows plots of rel. $t_{50}$ and cell viability in $A\beta_{42}$-treated rat neuroblastoma cells in the presence and absence of ADH-41.

FIG. 26a shows a comparison of the antagonist activity of ADH-41 and its various analogs (5 µM) assessed in amyloid aggregation (ThT fluorescence) and cellular assays (MTT) at a stoichiometric ratio of 1:1 (Ligand:$A\beta_{42}$). FIG. 26b shows a comparison of the antagonist activity of ADH-41 and ADH-37 (5 µM) assessed using the amyloid aggregation (ThT fluorescence) and the cellular assays (MTT) at a stoichiometric ratio of 1:1 (Ligand:$A\beta_{42}$). FIG. 26c shows a comparison of the antagonist activity of ADH-41 assessed for $A\beta_{42}$ and IAPP using the amyloid aggregation (ThT fluorescence) and the cellular assays (MTS) at a stoichiometric ratio of 1:1 (Ligand:protein). The concentration for $A\beta_{42}$ and IAPP were 5 µM and 10 µM, respectively. Each cytotoxicity experiment is the average of four on-plate repeats from each of four independently performed replicates (n=16). For solution based assays, the error bars represent standard deviations from the mean of at least three independent experiments.

FIGS. 27a-27m illustrates the binding interaction between an exemplary anionic oligopyridylamide, ADH-31 and Aβ using biophysical and cell based assays. FIG. 27a shows the chemical structure of the dianionic oligopyridylamide ADH-31. FIG. 27b shows the kinetic profile of 5 µM $A\beta_{42}$ amyloid reaction in the absence and presence of ADH-31 at the indicated stoichiometric ratios. FIG. 27c depicts the quantification of $t_{50}$ and fibril mass of 5 µM $A\beta_{42}$ aggregation reaction in the absence and presence of ADH-31 at an equimolar ratio. FIGS. 27d-27e show TEM image analysis of 5 µM $A\beta_{42}$ aggregation in the absence (FIG. 27d) and presence (FIG. 27e) of ADH-31 at an equimolar ratio after incubating $A\beta_{42}$ solutions in buffer for 6 h. FIGS. 27f-27g depicts the analysis of the $A\beta_{42}$ oligomerization (2 µM) in the absence and presence of ADH-31 at an equimolar ratio at indicated time points monitored using ELISA (FIG. 27f) and Dot blot assays (FIG. 27g). FIG. 27h shows time-dependent CD spectra of 25 µM $A\beta_{40}$ transitioning from a random coil (light black) to a β-sheet structure (solid black) in 48 h. Time-dependent CD spectra of 25 µM $A\beta_{42}$ in the presence of ADH-31 at an equimolar ratio at 0 h (light blue) and after 48 h (dark blue). FIG. 27i is an overlay of the $^{1}H$-$^{15}N$ HSQC NMR spectra of 40 µM $^{15}N$-c alone (black) and after the addition of ADH-31 at a stoichiometric ratio of 1:2 ($^{15}N$-$A\beta_{42}$:ADH-31, blue). The region with the highest perturbation in the chemical shifts is presented for clarity. The amino acid residues of $A\beta_{42}$ with the larger changes in the chemical shifts are highlighted with light red color. FIG. 27j shows the residues pointed with arrows representing the potential binding site of ADH-31 on Aβ. FIG. 27k shows the cytotoxicity of 5 µM $A\beta_{42}$ applied to N2a cells in the absence or presence of ADH-31 at the indicated concentrations and measured by an MTS assay after incubation for 72 h. Cells treated with a solution containing serum-free DMEM, 200 µM NaOH, 0.1×PBS and 0.5% (v/v) DMSO was used as control. The % viability was determined form the ratio of the absorbance of the treated cells to the control cells. FIG. 27l shows the dose dependent effect of ADH-31 on 5 µM Aβ$_{42}$ induced toxicity in N2a cells. Each experiment is the average of four on-plate repeats from each of four independently performed replicates (n=16). FIG. 27m shows a comparison of the antagonist activity of ADH-31 assessed for Aβ$_{42}$ and IAPP using the amyloid aggregation (ThT fluorescence) and the cellular assays (MTS) at a stoichiometric ratio of 1:1 (ADH-31:protein). The concentration for Aβ$_{42}$ and IAPP were 5 µM and 10 µM, respectively. For solution based assays, the error bars represent standard deviations from the mean of at least three independent experiments.

FIGS. 28a-28h illustrates the effect of oligopyridylamides on the oligomerization and seed-catalyzed processes mediated by Aft FIG. 28a depicts a representative kinetic profile of the aggregation of 5 µM Aβ$_{42}$ (black) in the absence and presence of indicated oligopyridylamides at an equimolar ratio. The oligopyridylamides were added during the growth phase of Aβ$_{42}$ aggregation indicated by the arrows (at 2 h). FIGS. 28b-28d show TEM images of 5 µM Aβ$_{42}$ aggregation reaction after 2 h in the absence (FIG. 28b) and presence of ADH-41 (FIG. 28c) and ADH-31 (FIG. 28d). FIG. 28e shows ELISA assays to assess the effect of ADH-31 and ADH-41 on the preformed oligomers of 2 µM Aβ$_{42}$ at an equimolar ratio. FIG. 28f shows the effect of ADH-31 and ADH-41 on the cell toxicity induced by the preformed oligomers of Aβ42 at an equimolar ratio. FIG. 28g shows a representative kinetic profile of seed-catalyzed aggregation of Aβ$_{42}$ (5 µM Aβ$_{42}$+10% seeds, v,v) and in the presence of ADH-31 at an equimolar ratio. FIG. 28h depicts the statistical analysis of the effect of the indicated oligopyridylamides on seed-catalyzed processes including aggregation and cytotoxicity mediated by 5 µM Aβ$_{42}$ (+seeds, 10% v,v). The effect of oligopyridylamides was assessed at a stoichiometric ratio of 1:1 (Ligand:protein). Each cytotoxicity experiment is the average of four on-plate repeats from each of four independently performed replicates (n=16). For solution based assays, the error bars represent standard deviations from the mean of at least three independent experiments.

FIGS. 29a-29d illustrates the characterization of the binding interaction between ADH-41 and Aβ in cellular milieu by confocal microscopy. N2a cells were treated with 4 µM Aβ$_{42}$ (FIG. 29a) or 4 µM ADH-41 (FIG. 29b) and their fluorescent variants (25% Aβ$_{TR}$ or ADH-41$_F$) for 24 h before imageanalysis. Under these conditions, the cell viability for Aβ$_{42}$ and ADH-41 were 69% and 98%, respectively. Both the protein and the small molecule were partially colocalized at the mitochondria, which is validated by mitochondrial markers. FIG. 29c shows cell viability measurements for both the protein and small molecule (4 µM each), when were coincubated (with 25% fluorescent analogs) and then introduced to N2a cells for 24 h before confocal image analysis. In parallel, the cell viability was measured for 5 µM Aβ$_{42}$ and Aβ$_{42}$-ADH-41 (5 µM each) complex. FIG. 29d shows a delayed addition experiment, in which 4 µM Aβ$_{42}$ (+1 µM Aβ$_{TR}$) was introduced to N2a cells followed by the addition of 4 µM ADH-41 (+1 µM ADH-41$_F$) after 12 h. The cells were then analyzed using confocal microscopy after incubation for 12 h (total 24 h). A cell toxicity assay was also conducted in parallel where 5 µM Aβ$_{42}$ was added to N2a cells and then ADH-41 was added after 12 h at an equimolar ratio. The cell viability was measured after 12 h (total 24 h) using MTS assay. Each cytotoxicity experiment is the average of four on-plate repeats from each of four independently performed replicates (n=16). The confocal microscopy experiments were performed in triplicate for reproducibility.

FIGS. 36a-36b illustrates the binding characterization of the ADH-41-Aβ$_{42}$ complex in cellular milieu. FIG. 36a shows N2a cells treated with a complex of 4 µM Aβ$_{42}$ (+1 µM Aβ$_{TR}$) and 5 µM ADH-41. The conditions are identical to the experiments performed in FIG. 29c. FIG. 36b shows N2a cells treated with a complex of 4 µM ADH-41 (+1 µM ADH-41$_F$) and 5 µM ADH-41. The conditions are identical to the experiments performed in FIG. 29c. In both the experiments, the cell viability in the presence of Aβ$_{42}$ and Aβ$_{42}$+ADH-41 was 67% and 99%, respectively.

DETAILED DESCRIPTION

Figure 6A:
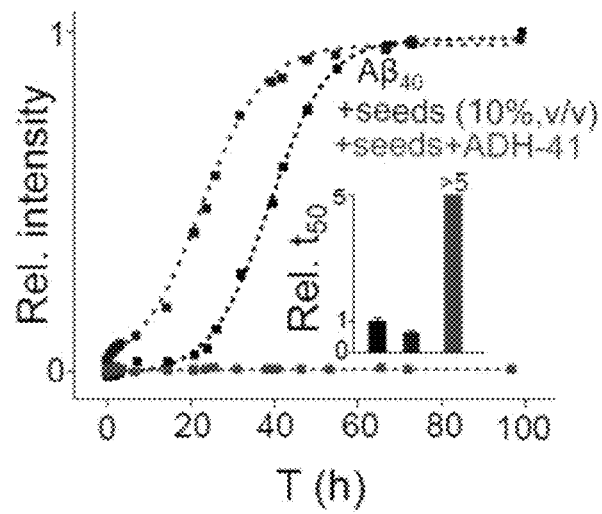
FIGS. 6a-6d illustrate seed-catalyzed aggregation of Aβ in the absence and presence of ADH-41.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Definitions

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "oligomerization", as it relates to amyloidogenic peptides, refers to a chemical process that converts individual peptide molecules into a chain consisting of a finite number of the peptide molecules. These chains are referred to as "oligomers", and they are typically soluble. As stated above, it is believed that these soluble oligomers, and not the later-stage insoluble fibrils, that are the key neurotoxic species.

The term "aggregation", as it relates to amyloidogenic peptides, refers to a process of conversion of soluble peptide oligomers into non-specific insoluble material. Under certain conditions amyloidogenic peptide oligomers aggregate into fibrils, a process referred to as fibrillation.

The term "fibrillation", as it relates to amyloidogenic peptides, refers to a process of forming fibrils. As stated above, the soluble oligomers of amyloidogenic peptides undergo the process of fibrillation, where they combine into insoluble fibrils.

The term "modulating oligomerization" or "modulating fibrillation" may refer to promoting, or agonizing, or, alternatively, inhibiting, or antagonizing, the formation of oligomers and/or fibers of a protein or a peptide.

The term "altering the structure" of a protein or a peptide refers to changing, modifying, adjusting, shifting, transforming, or causing to change, modify, adjust, shift, or transform the structural conformation of a protein or a peptide, including secondary or tertiary structure of a protein or a peptide.

The term "dipyridylamide" refers to a compound having two pyridyl rings connected via an amide (—(C=O)—NH—) bond. The term "tripyridylamide" refers to a compound having three pyridyl rings connected via amide bonds. The term "tetrapyridylamide" refers to a compound having four pyridyl rings connected via amide bonds. The term "oligopyridylamide" refers to any of the above compounds having from two to four pyridyl rings connected via amide bonds.

Compounds of the Invention

In accordance with the foregoing objective and others, the present invention provides compounds, pharmaceutical compositions, and methods for treating amyloid diseases and other diseases and conditions characterized by oligomerization and/or fibrillation of an amyloidogenic peptide (e.g., amyloid-beta peptide (Abeta or Aβ) or its alloforms, e.g., the Aβ$_{42}$ alloform).

The compounds of the invention are useful for altering structures of one or more amyloidogenic peptides including, without limitation, Aβ, islet amyloid polypeptide (IAPP), α-synuclein, AA amyloid, PrP, β$_2$-microglobulin amyloid, transthyretin, prealbumin, and procalcitonin. Some of the compounds of the invention which are useful for altering the structure of Aβ, or its Aβ$_{42}$ alloform, display specificity and/or selectivity for Aβ. Without wishing to be bound by any theory, it is postulated that some of the compounds of the invention may induce α-helical conformation of Aβ, which surprisingly and unexpectedly not only inhibits the formation of Aβ fibrils, but also suppresses Aβ oligomerization in solution. These specific interactions may play a part in the inventive compounds' surprising and unexpected specificity and/or selectivity for Aβ as compared to structurally related amyloidogenic peptides, such as, e.g., IAPP, decreasing the chances of undesirable side-effects upon their use in vivo.

Oligopyridylamides are emerging as powerful tools to gain insight into the kinetic pathways of amyloidogenic proteins. In the present application, an oligopyridylamide-based α-helical mimetic approach has been implemented to target the amyloidogenic peptide Aβ and alter its solution-based behavior.

In one embodiment, a library of oligopyridylamides functionalized with negatively charged (e.g., —$CO_2H$), positively charged (e.g., —$NH_2$), and neutral (e.g., alkyl (linear, branched, and cylic), and benzyl) groups has been designed. (FIG. 1b) In this embodiment, the library was designed to target the α-helical surface of Aβ$_{42}$ which spans residues 13 to 26 (FIG. 1c). In one non-limiting example, to complement His13, Lys16, and Phe20 of Aβ, a tripyridylamide was designed by incorporating —COOH, —COOH, and benzyl as surface functionalities in similar arrangement (FIG. 1d). In another non-limiting embodiment, a tetrapyridylamide ligand was developed to stabilize Aβ in an α-helical conformation.

The preparation of pyridyl- and aryl-carboxamide oligomers as α-helical mimetics has been previously reported (Cummings, C. G.; Hamilton, A. D. Curr. Opin. Chem. Biol. 2010, 14, 341-346; Azzarito, V.; Long, K.; Murphy, N. S.; Wilson, A. J. Nat Chem 2013, 5, 161-173; Orner, B. P.; Ernst. J. T.; Hamilton, A. D. J. Am. Chem. Soc. 2001, 123, 5382-5383; Yin, H.; Hamilton, A. D. Angew. Chem. Int. Ed. 2005, 44, 4130-4163). Pyridyl-based systems have a particular advantage in that they form a network of intramolecular hydrogen bonds stabilizing a single conformation that projects substituents from one face. Over 50 oligopyridylamides have been synthesized by varying the length of the pyridyl scaffold from one to four units using an established protocol (Kumar, S.; Schlamadinger, D.; Brown, M.; Dunn, J.; Mercado, B.; Hebda, J.; Saraogi, I.; Rhoades, E.; Hamilton, A.; Miranker, A. Chem. Biol. 2015, 22, 369-378).

Figure 16:
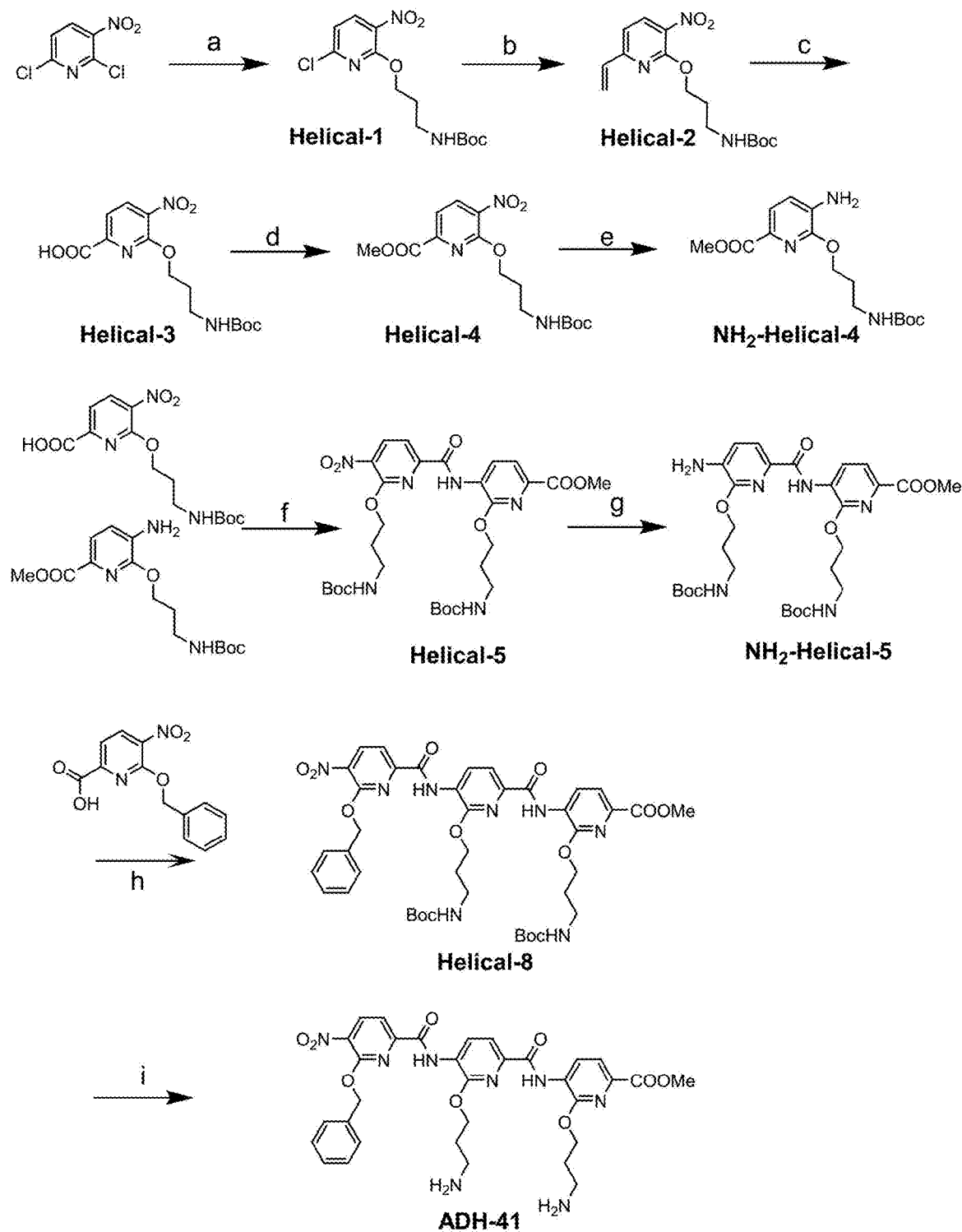
FIG. 16 represents a synthetic route for the synthesis of ADH-41, a tripyridylamide according to an embodiment of the disclosure.

Following the monomer synthesis, the chain elongation of pyridylamides was achieved using iterative amide coupling between oligo-pyridylamines and monomeric-pyridylacids using 2-chloro-1-methylpyridinium iodide (Mukaiyama's reagent) followed by reduction of the nitro groups (FIG. 16). The acid labile tert-butyl esters and NH-Boc groups were cleaved using a trifluoroacetic acid (TFA) cocktail (dichloromethane/TFA/triethylsilane, 80:15:5, v/v/v) in the final step to afford the series of oligopyridylamides.

Oligopyridylamide-based α-helical mimetics have been previously designed to target the membrane-associated α-helical conformation of islet amyloid polypeptide (IAPP) (Kumar, S.; Schlamadinger, D.; Brown, M.; Dunn, J.; Mercado, B.; Hebda, J.; Saraogi, I.; Rhoades, E.; Hamilton, A.; Miranker, A. Chem. Biol. 2015, 22, 369-378; Hebda, J. A.; Saraogi, I.; Magzoub, M.; Hamilton, A. D.; Miranker, A. D. Chem. Biol. 2009, 16, 943-950; Saraogi, I.; Hebda, J.; Becerril, J.; Estroff, L.; Miranker, A.; Hamilton, A. Angew. Chem. Int. Ed. 2010, 49, 736-739; Kulikov, O. V.; Kumar, S.; Magzoub, M.; Knipe, P. C.; Saraogi, I.; Thompson, S.; Miranker, A. D.; Hamilton, A. D. Tet. Lett. 2015, 56, 3670-3673; Kumar, S.; Birol, M.; Miranker, A. D. Chem. Comm. 2016, 52, 6391-6394). Certain α-helical mimetics were strong antagonists of membrane-catalyzed IAPP aggregation. SAR studies were conducted to optimize the inhibitory activity against IAPP self-assembly via charge complementarity and hydrophobic interactions. In addition to the solution biophysical assays, the α-helical mimetics were very effective in rescuing an insulin secreting cell line from IAPP-mediated cytotoxicity.

A variety of oligopyridylamides have been synthesized and screened to target the central α-helix subdomain of Aβ. The binding interaction of oligopyridylamides with Aβ is sensitive to the side chain functionalities present on their surface. Spectroscopic techniques (CD and NMR) suggest the conformational organization of Aβ into a strong α-helical structure. PICUP, DLS, and immunoassays support the inhibition of the oligomeric state of Aβ. Oligopyridylamides of the invention are useful as therapeutic agents for the treatment of diseases characterized by a formation of Aβ oligomers and/or fibers, e.g., Alzheimer's Disease.

It has been surprisingly discovered that the inhibition of Aβ$_{42}$ oligomerization and/or fibrillation appears to be specific to the side chain functionalities present on the α-helical mimetic compounds of the invention.

Screening of a library of α-helical mimetics led to the identification of tripyridylamide ADH-41 (shown below), as an effective antagonist of oligomerization, fibrillation, and/or aggregation of Aβ$_{42}$ (see e.g., FIG. 2a-2d).

ADH-41

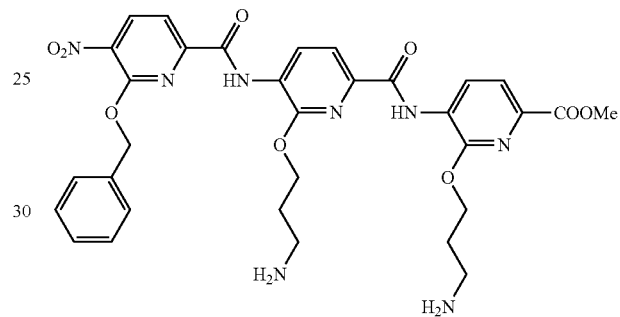

Figure 9:
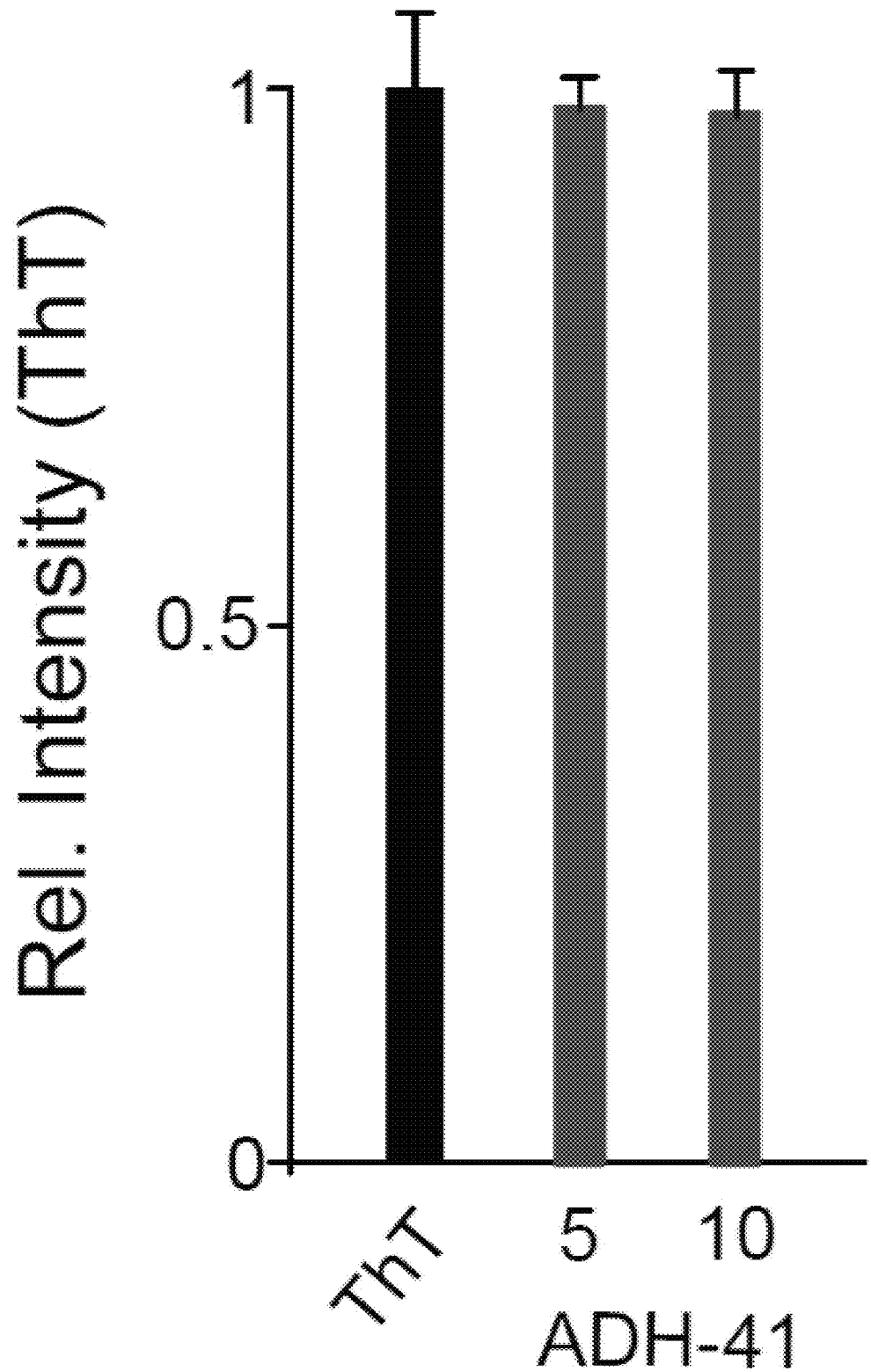
FIG. 9 is a graph of the relative intensity of ThT in the absence and presence of ADH-41.

It has surprisingly been discovered that ADH-41 completely inhibits oligomerization of Aβ$_{42}$ at an equimolar ratio (FIG. 2a-2e) over a 24 h measurement time-period. Even at sub-stoichiometric ratios of 1:0.5 and 1:0.1 (Aβ$_{42}$:ADH-41), the ThT fluorescence intensity characteristic of Aβ$_{42}$ oligomers was observable at only <10% (FIG. 2d, 2e). In a control reaction (without Aβ$_{42}$) and under matched conditions, no change in ThT fluorescence intensity was observed in the presence of ADH-41 (FIG. 9). Plainly, ADH-41 is a very potent inhibitor of Aβ$_{42}$ oligomerizaiton and/or fibrillation.

Even more surprisingly, compound ADH-39 (shown below) has been observed to accelerate oligomerizaiton and/or fibrillation of Aβ$_{42}$. Despite this observation, ADH-39 has ben shown to be effective at inhibiting cytotoxicity of Aβ$_{42}$ in cell-based assays.

ADH-39

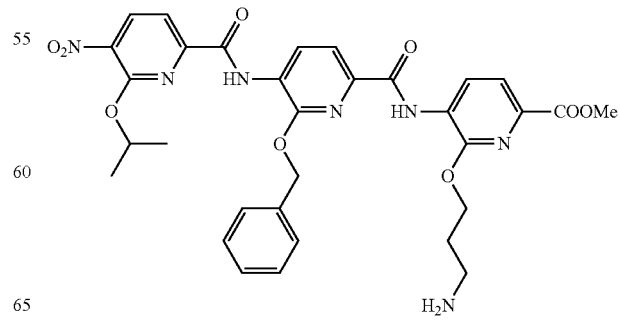

To assess the structure/activity importance of different chemical features of this class of molecules, a range of derivatives of ADH-41 were tested against Aβ$_{42}$ oligomerization (FIG. 2c). No noticeable effect was observed on Aβ$_{42}$ oligomerization by monomeric ADH-3 and ADH-5 at an equimolar ratio (FIG. 2b), whereas the dipyridylamides, ADH-43 and ADH-44 delayed the aggregation by factors of 3.3±0.4 and 2.4±0.3, respectively (FIG. 2b). ADH-19, a tripyridylamide with three amine groups, delayed the aggregation by a factor of 3.2±0.3 (FIG. 2b), but is far less effective than ADH-41, indicating the importance of the balance of hydrophobic and electrostatic interactions in inhibiting Aβ$_{42}$ oligomerization.

Figure 33:
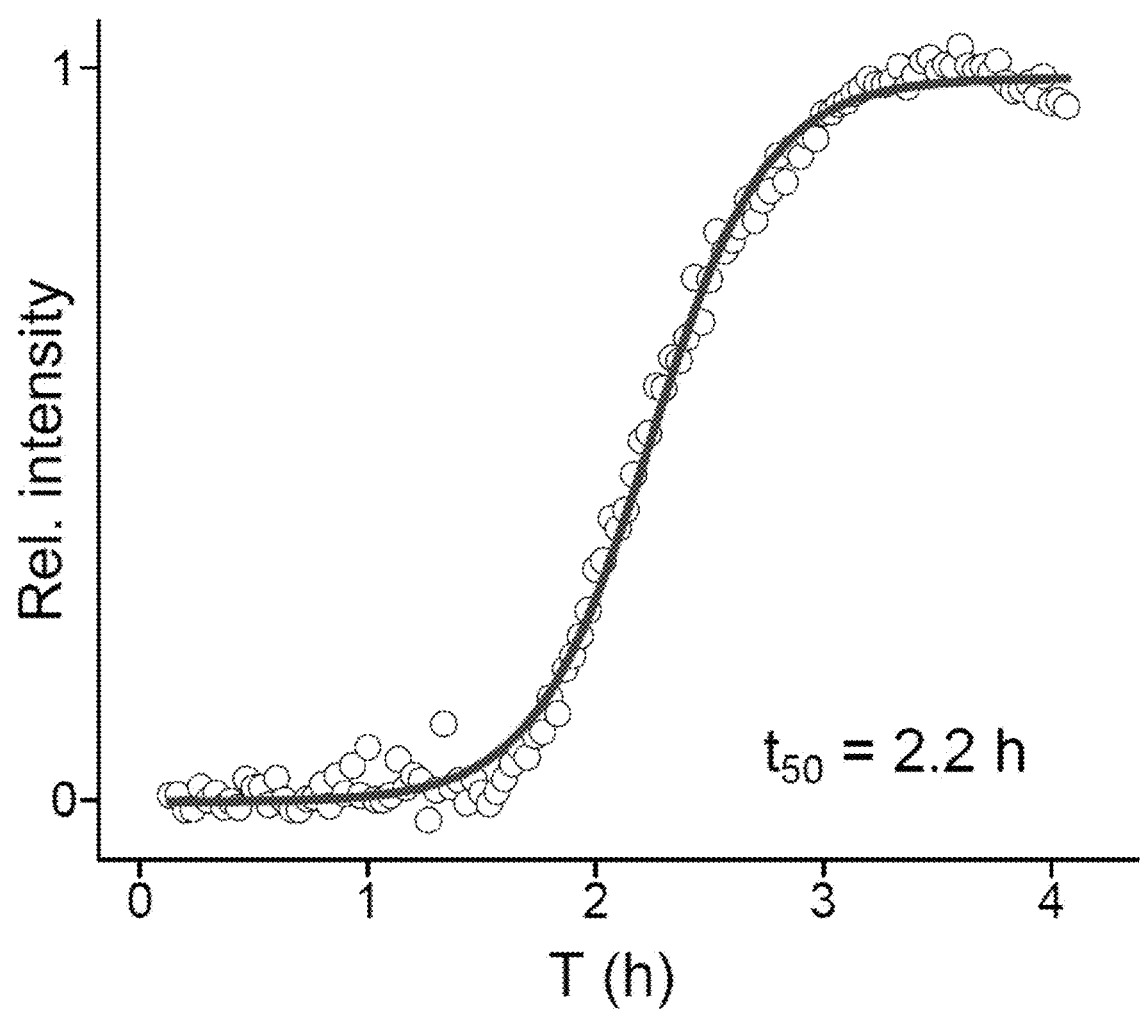
FIG. 33 depicts a representative plot for the kinetic curve of Aβ$_{42}$ (5 µM) aggregation. Kinetic curves were fit using the built-in sigmoidal fit to extract $t_{50}$ value (time required to reach 50% of the maximum ThT fluorescence intensity). Each run was fit independently to extract the $t_{50}$. Kinetic profiles were processed using Origin (version 9.1). Error bars represent standard deviations from the mean of at least three independent experiments.

A second set of compounds was identified as potent inhibitors of Aβ aggregation. In contrast to ADH-41, they are negatively charged. Among anionic oligopyridylamides, ADH-31, a dianionic tetrapyridylamide, was the most effective antagonist of Aβ aggregation as measured by ThT-based amyloid kinetic assays (FIG. 27a). The kinetic profile of 5 μM Aβ$_{42}$ showed a sigmoidal response, which yielded a $t_{50}$ (time required to reach 50% ThT fluorescence) of 2.1±0.2 h (FIG. 27b, FIG. 33). The aggregation of Aβ$_{42}$ was wholly suppressed, with very little formation of ThT positive fibers in the presence of ADH-31 at an equimolar ratio (FIG. 27b, c). Immunoassays and TEM image analysis revealed that ADH-31 inhibited the formation of the neurotoxic Aβ oligomers. TEM images showed that 5 μM Aβ$_{42}$ forms fibers in 12 h (FIG. 27d); however, no fibers were recorded in the presence of ADH-31 after 12 h at an equimolar ratio (FIG. 27e). An ELISA assay was employed to assess the effect of ADH-31 on the oligomerization of Aβ$_{42}$ (FIG. 27f). Samples of 2 μM Aβ$_{42}$ were incubated in the absence and presence of ADH-31 at an equimolar ratio for 0 h, 3 h and 6 h and then detected using an Aβ oligomer-specific monoclonal antibody (OMAB) (FIG. 27f). The absorbance increased gradually from 0 to 6 h indicating an increase in the amount of soluble oligomers of Aβ$_{42}$. In marked contrast, the absorbance of the ADH-31-Aβ$_{42}$ complex was significantly lower at all time points (FIG. 27f). An orthogonal dot blot assay was utilized to examine the effect of ADH-31 on Aβ oligomer formation. 2 μM Aβ$_{42}$ was incubated in the absence and presence of ADH-31 at an equimolar ratio for various durations, and the samples were applied to a nitrocellulose membrane and detected using a polyclonal antibody (A11) specific for Aβ oligomers (FIG. 27g). A time-dependent increase in the amount of the A11-sensitive Aβ$_{42}$ oligomeric structures was reflected in the progressive enhancement in the chemiluminescence intensity of the dots, which reached a maximum intensity around 6 h (FIG. 27g). The intensity decreased after 12 h, due to formation of fibers that are not sensitive to the A11 antibody. In the presence of ADH-31 at an equimolar ratio, under matched conditions, weak intensities of the dots were observed during the whole time course of the amyloid reaction (FIG. 27g). Results from the dot blot assay strongly corroborate the ELISA assay and indicate that ADH-31 inhibits Aβ$_{42}$ oligomerization. The antagonist activity of ADH-31 towards Aβ fibrillation could be attributed to stabilization of a secondary structure in Aβ. The far UV-CD spectrum of a sample of 20 μM Aβ$_{40}$ transitioned from that of a random coil to a β-sheet conformation over 24 h (FIG. 27h). However, no β-sheet formation was observed in the presence of ADH-31. Instead, Aβ$_{40}$ adopts an α-helical conformation in the presence of ADH-31 at an equimolar ratio, characterized by two minima at 208 nm and 222 nm, which remained stable even after 48 h (FIG. 27h).

In one implementation, the compounds of the invention (e.g., the modulators of oligomerization of amyloidogenic peptides, such as Aβ) have the structure of formula (I):

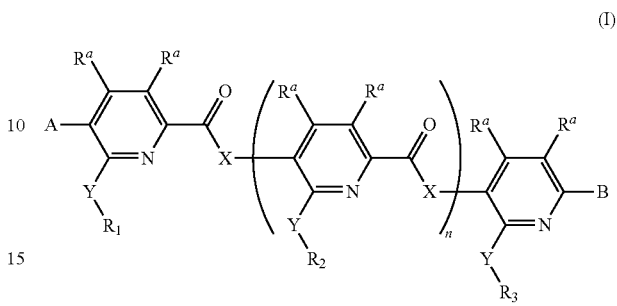

and pharmaceutically acceptable salts thereof.

In formula (I), $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$.

In some embodiments, $R^a$ is present at 0, 1, or 2 different positions on the ring.

In some embodiments, $R^a$ is hydrogen at all occurrences.

X is independently at each occurrence selected from —O—; —S—; —NH—; —NR*—; and —C(R*)$_2$.

In some embodiments X is —NH— or —NR*—, such that (C=O)—X— is an amide bond, at all occurrences. In some embodiments X is NH—.

In some embodiments X is not —O—. In some embodiments X is not —S—. In some embodiments X is not C(R*)$_2$.

Y is independently at each occurrence selected from —O—; —S—; —NH—; and —NR*—.

In some embodiments Y is —O—at all occurrences.

In some embodiments Y is not —S—. In some embodiments Y is not —NH— or —NR*—.

$R_1$, $R_2$, and/or $R_3$ are independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof.

In some embodiments $R_1$, $R_2$, and/or $R_3$ are independently at each occurrence selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof.

In some embodiments R$_1$, R$_2$, and/or R$_3$ are independently at each occurrence a straight chained, branched or cyclic aliphatic C$_1$-C$_{20}$ hydrocarbon, optionally substituted with one or more of —NH$_2$; —NHR*; —N(R*)$_2$; —N(R*)$_3^+$; —(C=O)—R*; —CO$_2$H; or —CO$_2$R*; and combinations thereof.

In some embodiments R$_1$, R$_2$, and/or R$_3$ are independently at each occurrence a straight chained, branched or cyclic C$_1$-C$_{20}$ hydrocarbon, optionally substituted with one or more of —NH$_2$; —NHR*; —N(R*)$_2$.

In some embodiments R$_1$, R$_2$, and/or R$_3$ are independently at each occurrence a straight chained, branched or cyclic aliphatic C$_1$-C$_{20}$ hydrocarbon, optionally substituted with —CO$_2$H. In some embodiments R$_1$, R$_2$, and/or R$_3$ may independently at each occurrence be —CH$_2$CO$_2$H.

In some embodiments R$_1$, R$_2$, and/or R$_3$ at all occurrences do not contain —CO$_2$H. In some embodiments R$_1$, R$_2$, and/or R$_3$ are not —CH$_2$CO$_2$H at all occurrences.

In some embodiments R$_1$, R$_2$, and/or R$_3$ are independently at each occurrence selected from an aromatic C$_6$-C$_{20}$ hydrocarbon; a heteroaromatic C$_1$-C$_{20}$ hydrocarbon; an aryl C$_6$-C$_{20}$ hydrocarbon; or a heteroaryl C$_1$-C$_{20}$ hydrocarbon optionally containing 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*.

In some embodiments, R$_1$, R$_2$, and/or R$_3$ are independently at each occurrence selected from a substituted or unsubstituted phenyl, benzyl, naphthyl, indolyl, pyrrolidinyl, pyrrolyl, imidazolyl, pyrazolyl, oxazolyl, isoxazolyl, thiazolyl, isothiazolyl, histidinyl (i.e., —CH$_2$-imidazole), triazolyl, pyridyl, pyranyl, diazinyl, oxazinyl, thiazinyl, or triazinyl.

A and B are independently selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —ON(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; C$_1$-C$_8$ perfluorocarbon; an aliphatic C$_1$-C$_{12}$ hydrocarbon; an aromatic C$_1$-C$_{12}$ hydrocarbon; and a C$_1$-C$_{12}$ heteroaryl.

In some embodiments A is selected from —NO$_2$; —NH$_2$; —NHR*; —N(R*)—(C=O)—R*, —N(R*)$_2$. In some embodiments A is —NO$_2$. In some embodiments A is NH$_2$; —NHR*; or —N(R*)$_2$.

In some embodiments A is not —N(R*)—(C=O)—R*. In some embodiments A is not NH$_2$; —NHR*; or —N(R*)$_2$.

In some embodiments B is selected from —(C=O)—R*; —CO$_2$H; —CO$_2$R*. In some embodiments B may be —CO$_2$R*, where R* is a C$_1$-C$_{12}$ hydrocarbon. In some embodiments B is —CO$_2$R* and R* is selected from methyl, ethyl, propyl, or butyl groups. In some embodiments A is —CO$_2$R* and R* is methyl.

In some embodiments B is not —CO$_2$H. In some embodiments B is not —(C=O)—R*.

R* is independently selected at each occurrence from hydrogen or C$_1$-C$_{12}$ hydrocarbons each of which optionally contains 1-8 heteroatoms selected from halogen, O, N, and S and combinations thereof.

n is an integer from 0 to 2.

In some embodiments, n is 0, i.e., the compound of formula (I) is a dipyridyl. In other embodiments n is 1, i.e., the compound of formula (I) is a tripyridyl. In yet other embodiments, n is 2, i.e., the compound of formula (I) may be a tetrapyridyl.

In some embodiments, n is 0, and X is —NH—, i.e., the compound of formula (I) is a dipyridylamide. In other embodiments n is 1, and X is —NH—, i.e., the compound of formula (I) is a tripyridylamide. In yet other embodiments, n is 2, and X is —NH—, i.e., the compound of formula (I) is a tetrapyridylamide.

In some embodiments, when n is 0, and Y is O, R$_1$ and R$_3$ are not both —CH$_2$CO$_2$H.

In some embodiments, when n is 1, Y is O, and R$_1$ and R$_3$ are both —CH$_2$CO$_2$H, R$_2$ is not —CH$_2$CO$_2$H or a straight chained, branched or cyclic aliphatic or aryl C$_1$-C$_{12}$ hydrocarbon, or R$_2$ does not have the structure —C(CH$_2$CO$_2$H)$_3$.

In some embodiments, when n is 1, and Y is O, R$_1$ through R$_3$ are not each an unsubstituted C$_1$-C$_8$ hydrocarbon.

In some embodiments, when n is 2, and Y is O, R$_1$ through R$_3$ are not —CH$_2$CO$_2$H at all occurrences.

In one embodiment, the compounds of the invention have the structure of formula (II):

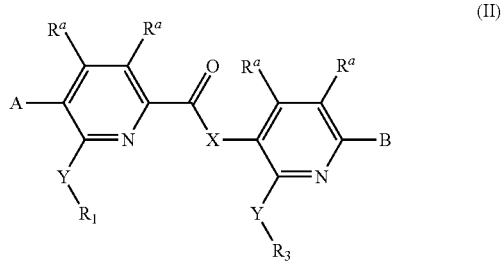

and pharmaceutically acceptable salts thereof, wherein R$^a$, R$_1$, R$_3$, A, B, and X are as described above. In some embodiments X is —NH—, i.e. the compounds of formula (II) are dipyridylamides.

In one embodiment, the compounds of the invention have the structure of formula (III):

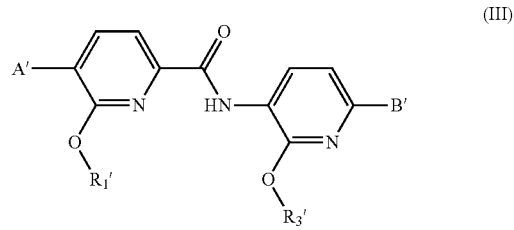

and pharmaceutically acceptable salts thereof.

R$_1'$ and R$_3'$ are independently selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3^+$; —(C=O)—$R^*$; —CHO; —$CO_2H$; —$CO_2R^*$; —(C=O)—S—$R^*$; —O—(C=O)—H; —O—(C=O)—$R^*$; and combinations thereof, where $R^*$ is independently selected at each occurrence from hydrogen or $C_1$-$C_{12}$ hydrocarbons each of which optionally contains 1-8 heteroatoms selected from halogen, O, N, and S and combinations thereof.

In some embodiments $R_1$ and $R_3$ are not both —$CH_2CO_2H$.

A' is selected from —$NO_2$; —$NH_2$; —$NHR^*$; —$N(R^*)$—(C=O)—$R^*$, —$N(R^*)_2$, where $R^*$ is hydrogen or an aliphatic $C_1$-$C_{12}$ hydrocarbon.

B' is selected from —(C=O)—$R^*$; —$CO_2H$; —$CO_2R^*$, where $R^*$ is hydrogen or an aliphatic $C_1$-$C_{12}$ hydrocarbon.

In one embodiment, the compounds of the invention have the structure of formula (IV):

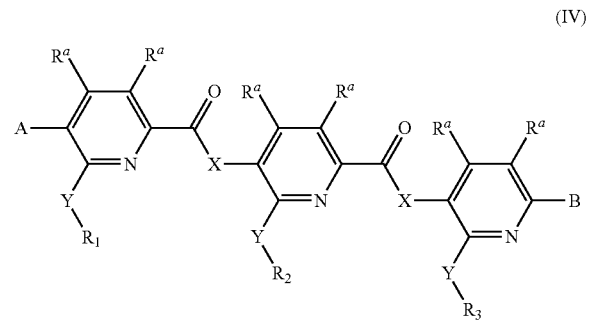

(IV)

and pharmaceutically acceptable salts thereof, wherein $R^a$, $R_1$, $R_2$, $R_3$, A, B, and X are as described above. In some embodiments X is —NH—, i.e. the compounds of formula (IV) are tripyridylamides.

In one embodiment, the compounds of the invention have the structure of formula (IV):

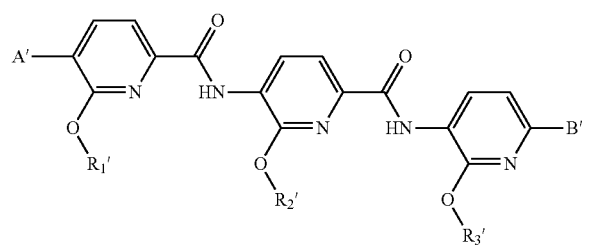

(V)

and pharmaceutically acceptable salts thereof.

$R_1'$, $R_2'$, and $R_3'$ are independently selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3^+$; —(C=O)—$R^*$; —CHO; —$CO_2H$; —$CO_2R^*$; —(C=O)—S—$R^*$; —O—(C=O)—H; —O—(C=O)—$R^*$; and combinations thereof, where $R^*$ is independently selected at each occurrence from hydrogen or $C_1$-$C_{12}$ hydrocarbons each of which optionally contains 1-8 heteroatoms selected from halogen, O, N, and S and combinations thereof.

A' is selected from —$NO_2$; —$NH_2$; —$NHR^*$; —$N(R^*)$—(C=O)—$R^*$, —$N(R^*)_2$, where $R^*$ is hydrogen or an aliphatic $C_1$-$C_{12}$ hydrocarbon.

B' is selected from —(C=O)—$R^*$; —$CO_2H$; —$CO_2R^*$, where $R^*$ is hydrogen or an aliphatic $C_1$-$C_{12}$ hydrocarbon.

In some embodiments, when $R_1$ and $R_3$ are both —$CH_2CO_2H$, $R_2$ is not —$CH_2CO_2H$ or a straight chained, branched or cyclic aliphatic $C_1$-$C_{12}$ hydrocarbon.

In some embodiments, when $R_1$ and $R_3$ are both —$CH_2CO_2H$, $R_2$ does not have the structure —$C[CH_2CO_2H]_3$.

In some embodiments, $R_1$ through $R_3$ are not each an unsubstituted $C_1$-$C_8$ hydrocarbon.

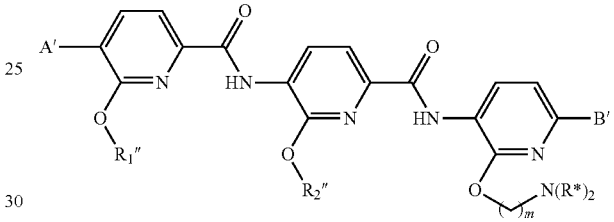

(VI)

and pharmaceutically acceptable salts thereof.

In one embodiment, $R_1''$ and $R_2''$ are each independently a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, optionally substituted with —$NH_2$; —$NHR^*$; or —$N(R^*)_2$.

In another embodiment, $R_1''$ and $R_2''$ are each independently selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3^+$; —(C=O)—$R^*$; —CHO; —$CO_2H$; —$CO_2R^*$; —(C=O)—S—$R^*$; —O—(C=O)—H; —O—(C=O)—$R^*$; and combinations thereof.

In yet another embodiment $R_1''$ is a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, optionally substituted with —$NH_2$; —$NHR^*$; or —$N(R^*)_2$; and $R_2''$ is a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3^+$; —(C=O)—$R^*$; —CHO; —$CO_2H$; —$CO_2R^*$; —(C=O)—S—$R^*$; —O—(C=O)—H; —O—(C=O)—$R^*$; and combinations thereof.

A' is selected from —NO$_2$; —NH$_2$; —NHR*; —N(R*)—(C=O)—R*, —N(R*)$_2$.

B' is selected from —(C=O)—R*; —CO$_2$H; —CO$_2$R*.

R* is hydrogen or an aliphatic C$_1$-C$_{12}$ hydrocarbon.

m is an integer from 1 to 12.

In one embodiment, a compound of the invention has the structure of formula (VII):

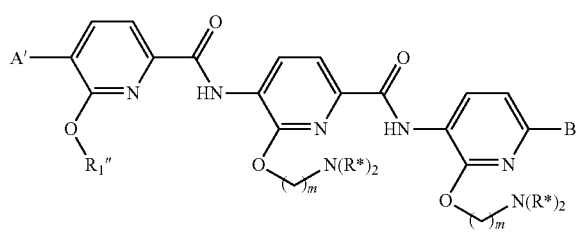

(VII)

and pharmaceutically acceptable salts thereof.

R$_1$″ is selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, optionally substituted with —NH$_2$; —NHR*; or —N(R*)$_2$.

A' is selected from —NO$_2$; —NH$_2$; —NHR*; —N(R*)—(C=O)—R*, —N(R*)$_2$.

B' is selected from —(C=O)—R*; —CO$_2$H; —CO$_2$R*.

R* is independently at each occurrence hydrogen or an aliphatic C$_1$-C$_{12}$ hydrocarbon.

m is independently at each occurrence an integer from 1 to 12.

In one embodiment, the compounds of the invention have the structure of formula (VIII):

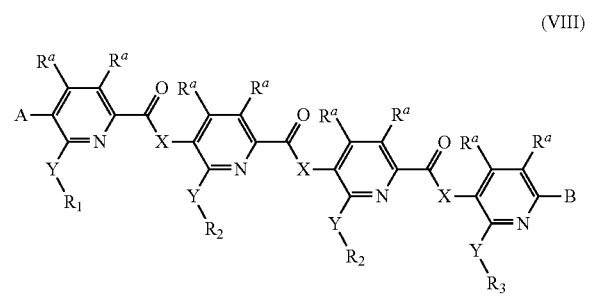

(VIII)

and pharmaceutically acceptable salts thereof, wherein R$^a$, R$_1$, R$_2$, (independently at each occurrence), R$_3$, A, B, and X are as described above. In some embodiments X is —NH—, i.e. the compounds of formula (VIII) are tetrapyridylamides.

In one embodiment, the compounds of the invention have the structure of formula (IX):

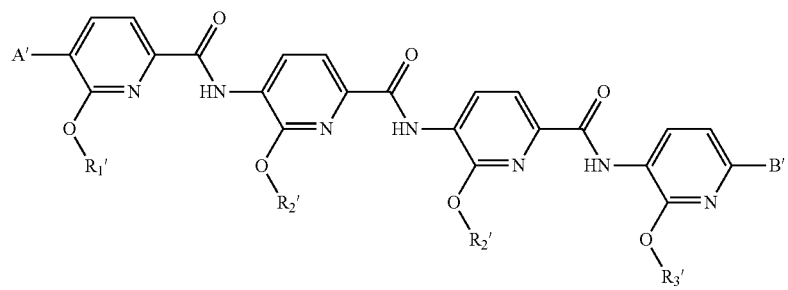

(IX)

and pharmaceutically acceptable salts thereof.

R$_1$', R$_2$', and R$_3$' are independently at each occurrence selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3$$^+$; —(C=O)—R*; —CHO; —CO$_2$H; —CO$_2$R*; —(C=O)—S—R*; —O—(C=O)—H; —O—(C=O)—R*; and combinations thereof, where R* is independently selected at each occurrence from hydrogen or C$_1$-C$_{12}$ hydrocarbons each of which optionally contains 1-8 heteroatoms selected from halogen, O, N, and S and combinations thereof.

A' is selected from —NO$_2$; —NH$_2$; —NHR*; —N(R*)—(C=O)—R*, —N(R*)$_2$, where R* is hydrogen or an aliphatic C$_1$-C$_{12}$ hydrocarbon.

B' is selected from —(C=O)—R*; —CO$_2$H; —CO$_2$R*, where R* is hydrogen or an aliphatic C$_1$-C$_{12}$ hydrocarbon.

In some embodiments, when R$_1$ and R$_3$ are both —CH$_2$CO$_2$H, R$_2$ is not —CH$_2$CO$_2$H or a straight chained, branched or cyclic aliphatic C$_1$-C$_{12}$ hydrocarbon at all occurrences. E.g., when R$_1$ and R$_3$ are both —CH$_2$CO$_2$H, R$_2$ may be —CH$_2$CO$_2$H at one occurrence, and R$_2$ may be—a straight chained, branched or cyclic aliphatic C$_1$-C$_{12}$ hydrocarbon at one occurrence, but R$_2$ may not be —CH$_2$CO$_2$H or a straight chained, branched or cyclic aliphatic C$_1$-C$_{12}$ hydrocarbon at both occurrences.

In some embodiments, when R$_1$ and R$_3$ are both —CH$_2$CO$_2$H, R$_2$ does not have the structure —C[CH$_2$CO$_2$H]$_3$.

In some embodiments, R$_1$ through R$_3$ are not each an unsubstituted C$_1$-C$_8$ hydrocarbon.

In some embodiments, R$_1$ through R$_3$ are not each —CH$_2$CO$_2$H.

In one embodiment, a compound of the invention has the following structure:

(ADH-41)

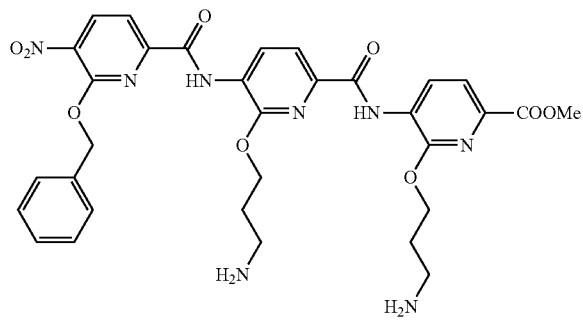

or a pharmaceutically acceptable salt thereof.

In another embodiment, a compound of the invention has the following structure:

(ADH-39)

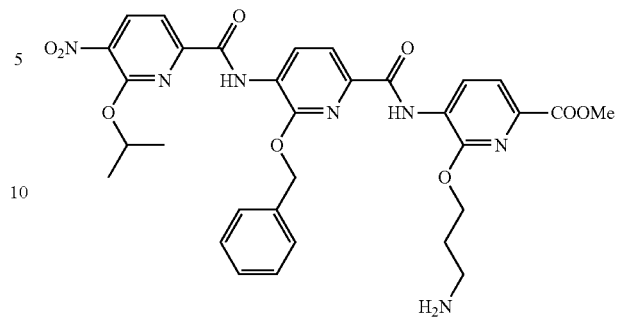

or a pharmaceutically acceptable salt thereof.

In yet another embodiment, a compound of the invention has the following structural formula:

(ADH-31)

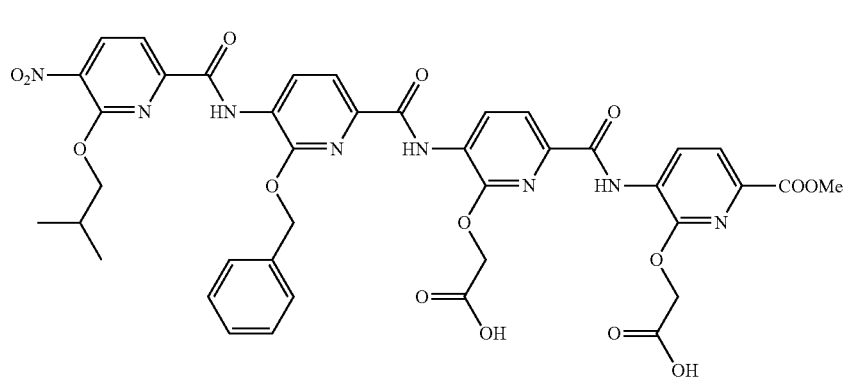

or a pharmaceutically acceptable salt thereof.

Some exemplary non-limiting embodiments of the compounds of the invention (and their monomer precursors) are shown below:

ADH-1

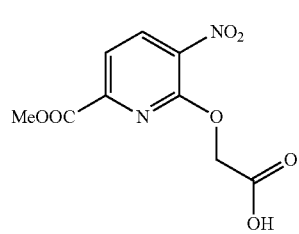

ADH-2

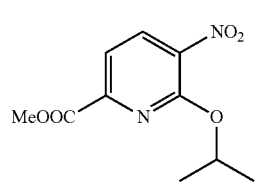

ADH-3

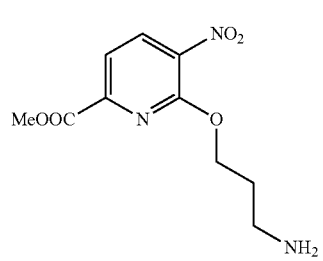

ADH-3a

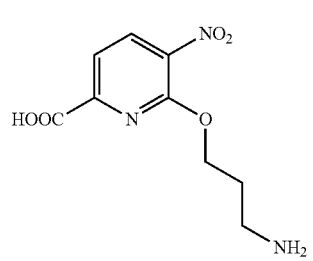

-continued
ADH-4
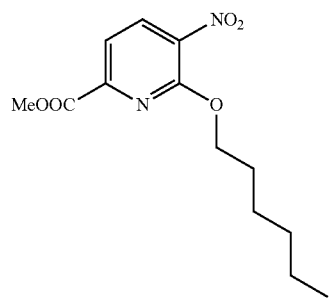
ADH-5
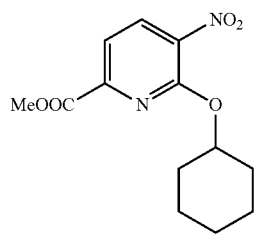
ADH-6
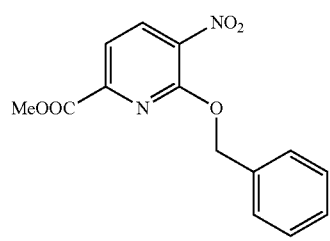
ADH-6a
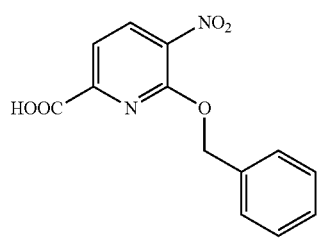
ADH-7
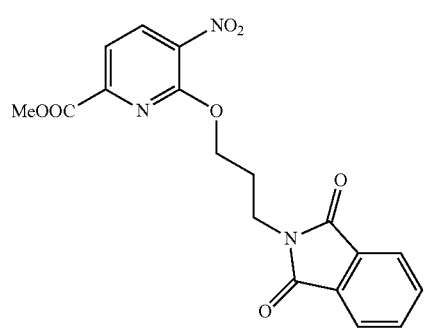
ADH-8
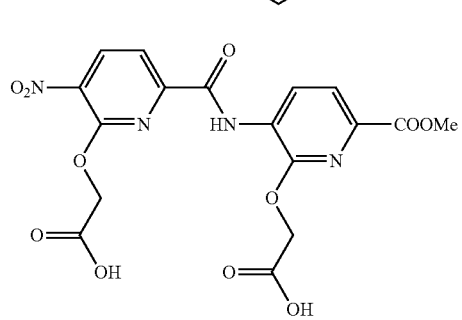
ADH-9
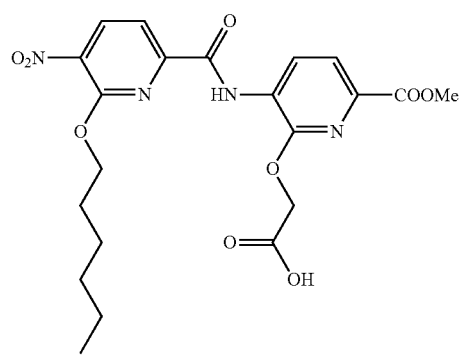
ADH-10
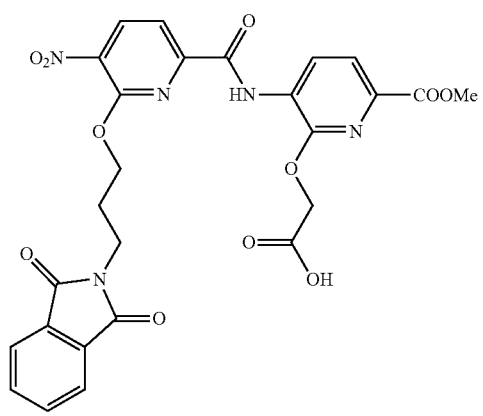
ADH-11
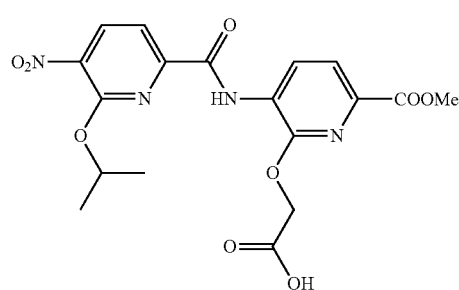
ADH-12
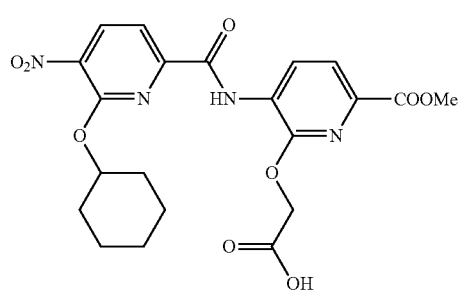

-continued
ADH-13
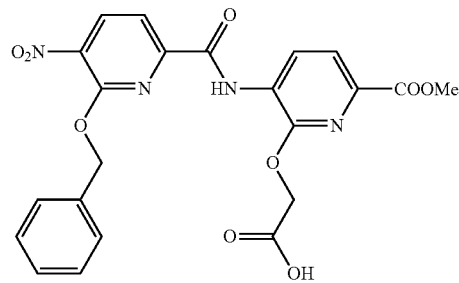
ADH-14
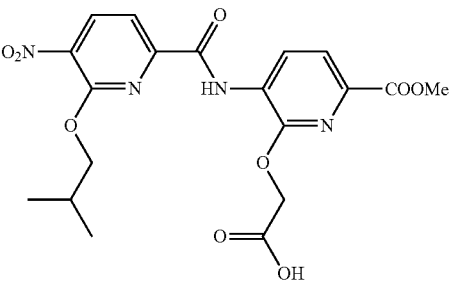
ADH-15
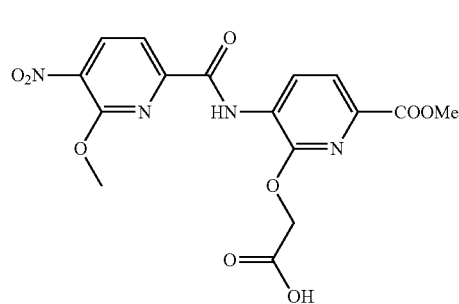
ADH-16
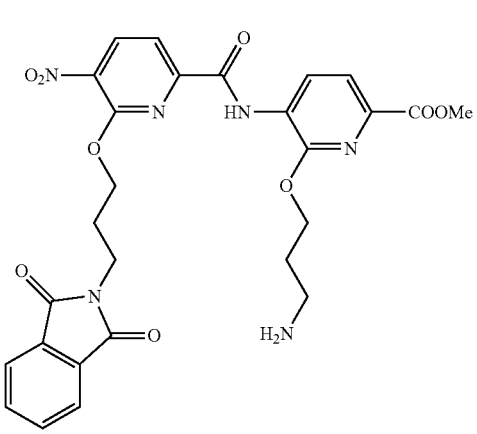
ADH-17
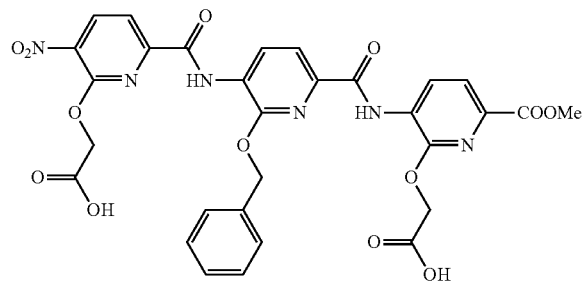
ADH-18
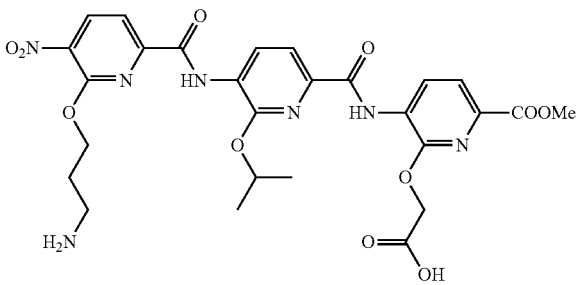
ADH-19
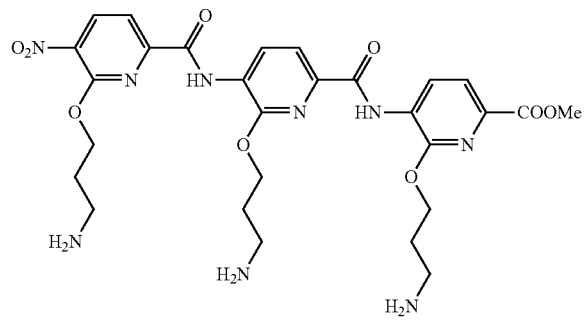
ADH-20
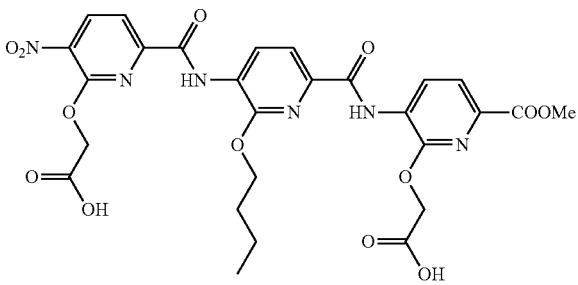

-continued
ADH-21
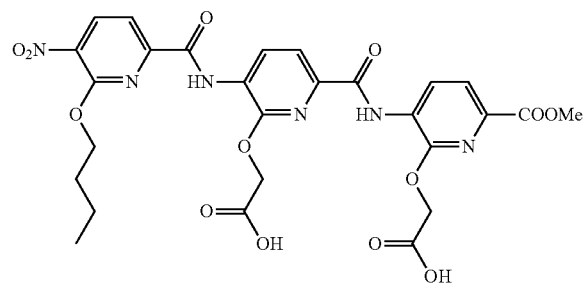
ADH-22
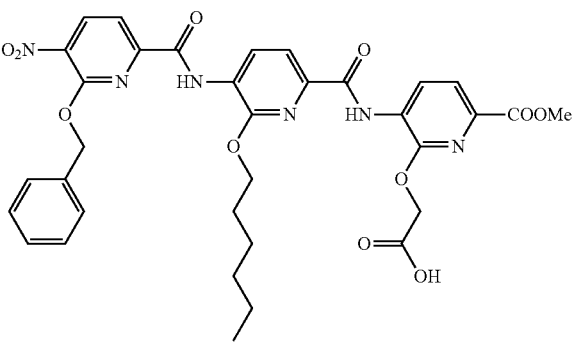
ADH-23 ADH-24
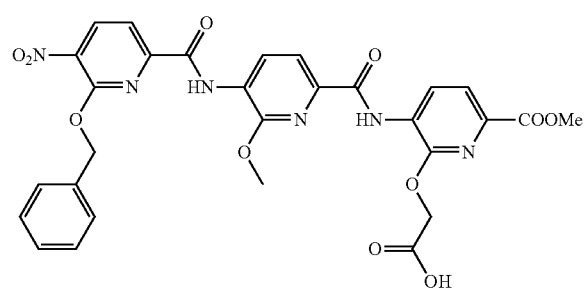
ADH-25 ADH-26
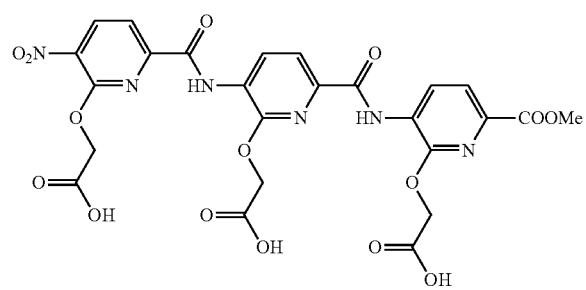
ADH-27 ADH-28
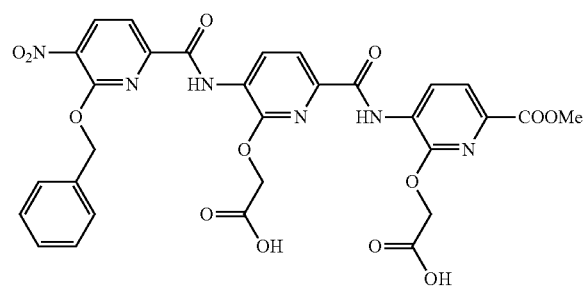
ADH-29
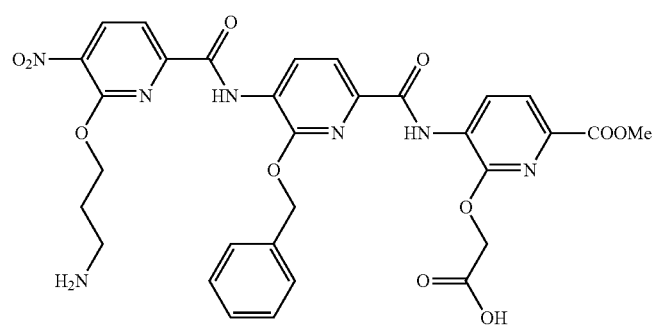

-continued
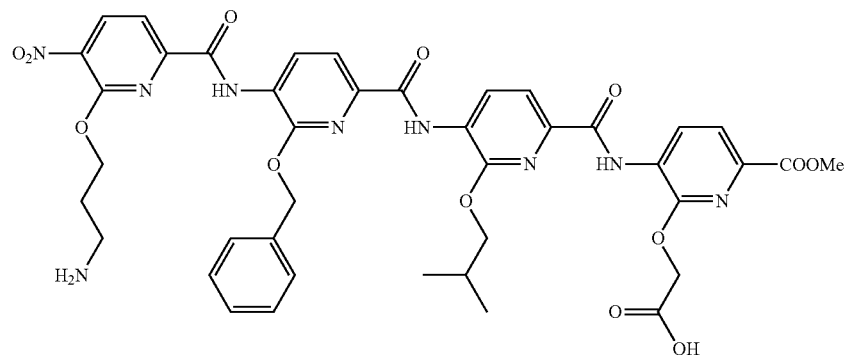
ADH-30
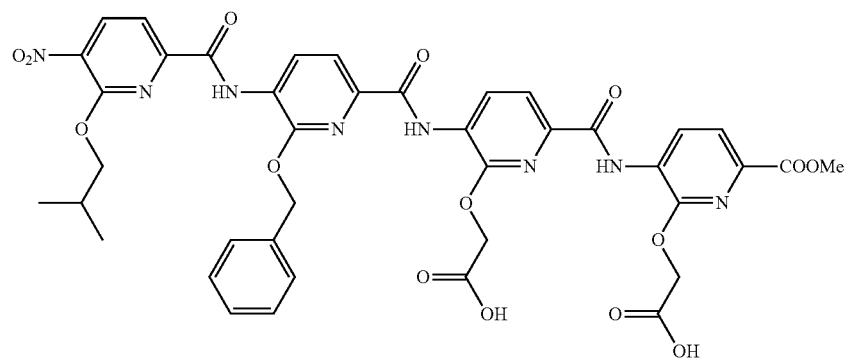
ADH-31
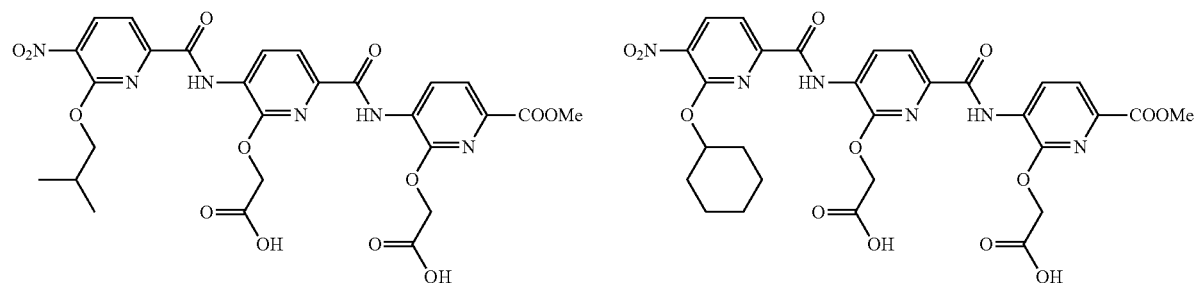
ADH-32           ADH-33
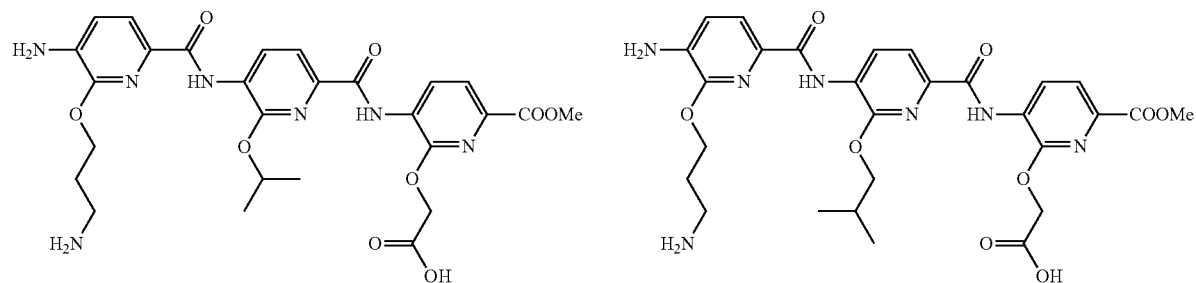
ADH-34           ADH-35

-continued
ADH-36
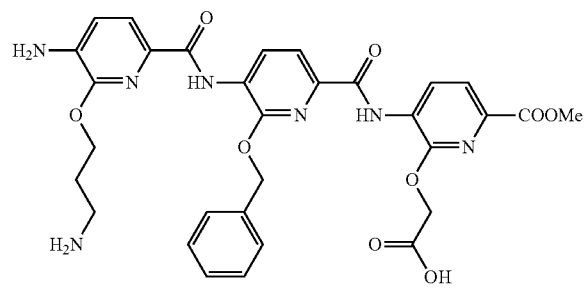
ADH-37
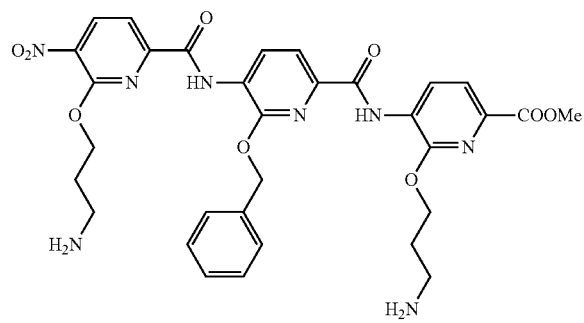
ADH-38
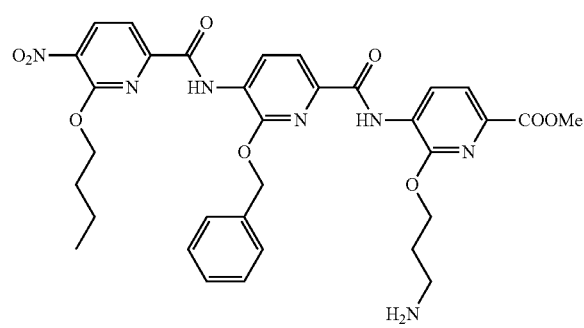
ADH-39
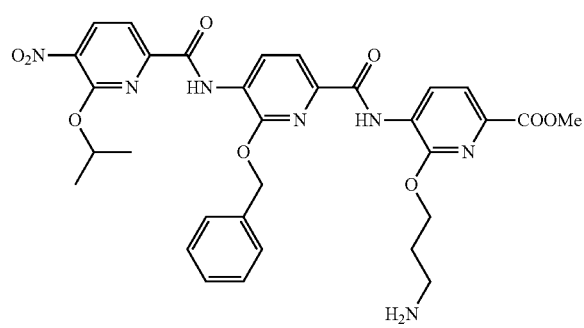
ADH-40
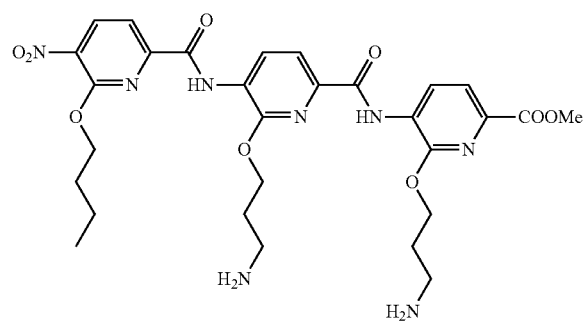
ADH-41
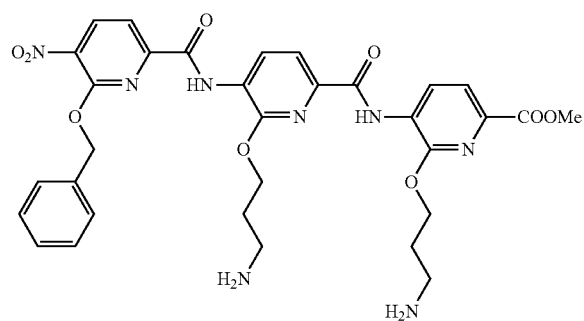
ADH-43
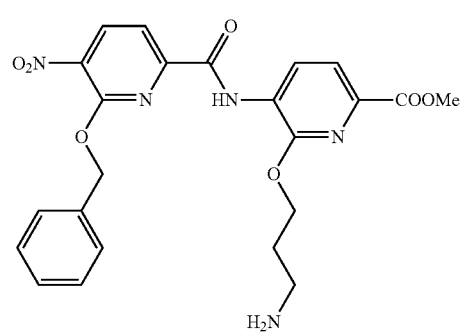
ADH-44
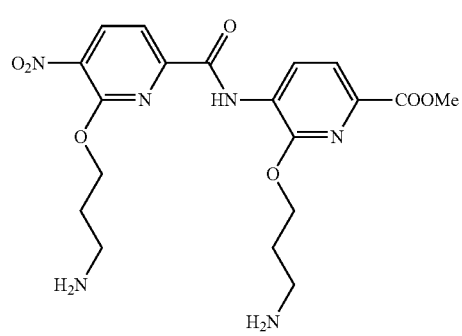

ADH-45
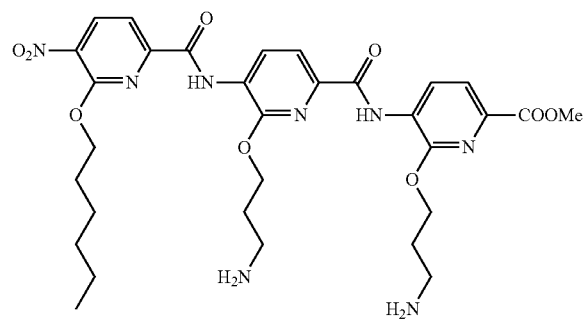
ADH-45A
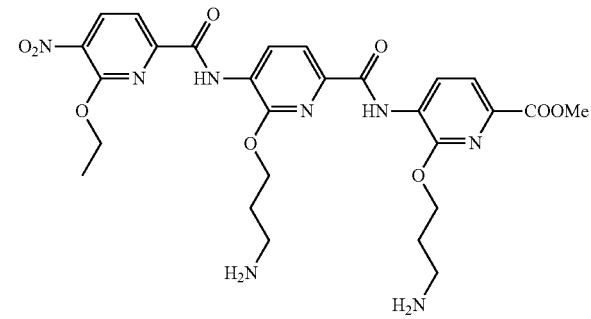
ADH-46
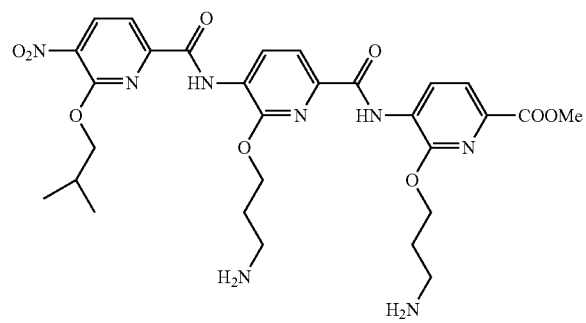
ADH-47
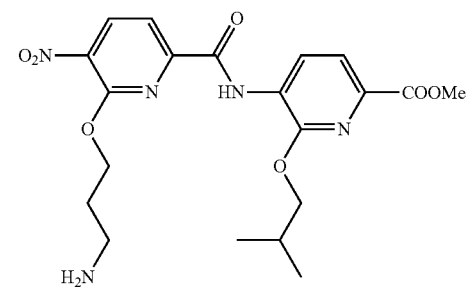
ADH-48
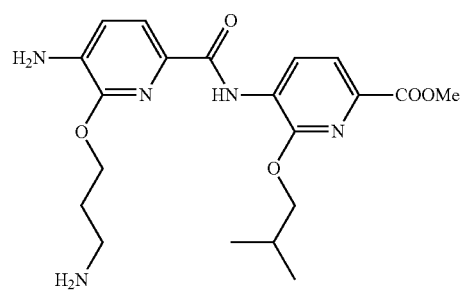
ADH-49
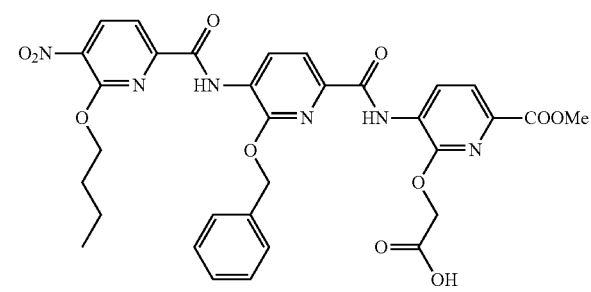
ADH-50
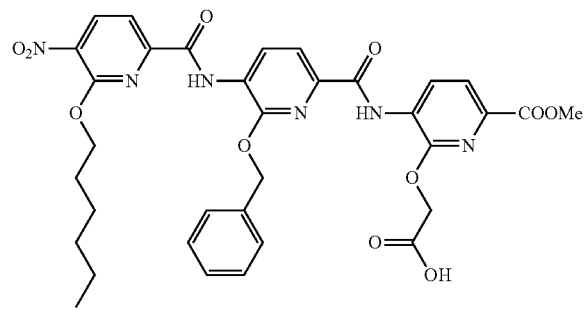
ADH-51
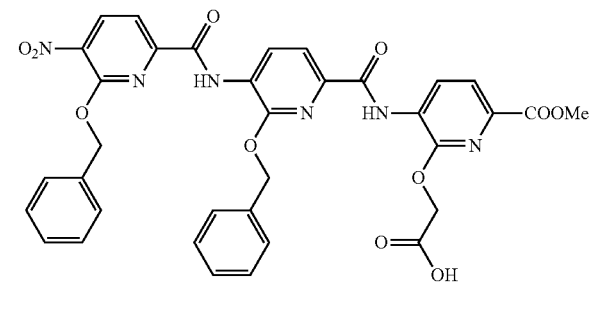

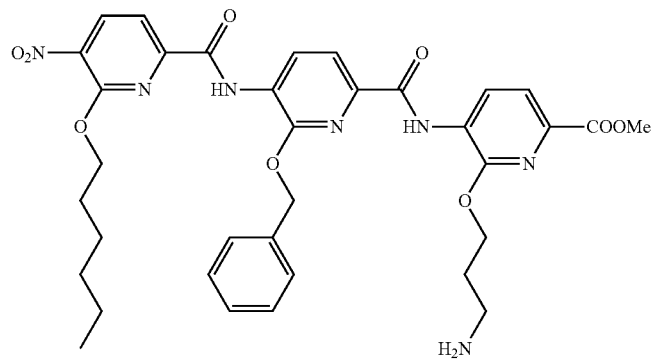

ADH-52

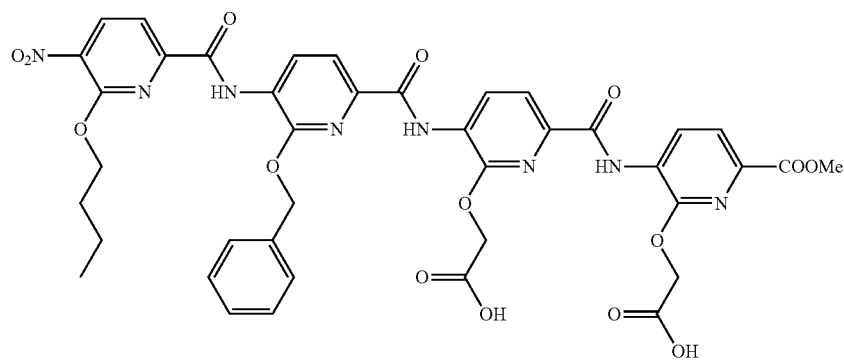

ADH-53

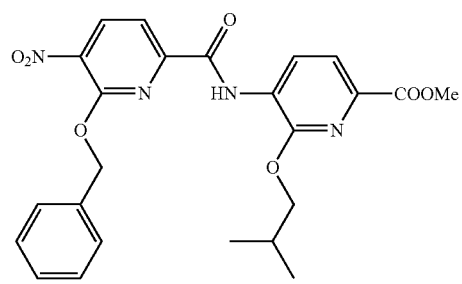

ADH-54

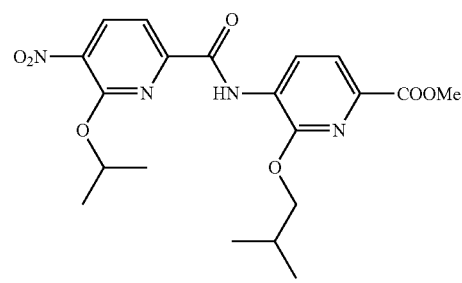

ADH-55

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, $H_2SO_4$) or organic acid (such as acetic acid, benzoic acid, trifluoroacetic acid salts of basic residues such as amines; alkali (such as Li, Na, K, Mg, Ca) or organic (such as trialkylammonium) salts of acidic residues such as carboxylic acids; and the like. The salts of the present application can be synthesized from the parent compound which contains a basic or acidic moiety conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977). The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene Protective Groups in Organic Synthesis,* 4th Ed., John Wiley & Sons: N.Y., 2006.

Pharmaceutical Compositions and Dosage Forms

The present invention also provides pharmaceutical compositions comprising the compounds described herein. When employed as pharmaceuticals, the compounds of the invention can be administered in the form of pharmaceutical compositions which is a combination of the compounds of the invention and a pharmaceutically acceptable carrier. These compositions can be prepared in a manner well known in the pharmaceutical art, and can be administered by a variety of routes. Such pharmaceutical compositions can be administered systemically. The term "systemic" as used herein includes parenteral, topical, transdermal, oral, by inhalation/pulmonary, rectal, nasal, buccal, and sublingual administration. The term "parenteral" as used herein includes subcutaneous, intradermal, intravenous, intramuscular, intracranial, and intraperitoneal administration. Preferably, the compounds are administered intramuscularly, subcutaneously, orally, or intranasally in therapeutically effective amounts to treat diseases characterized by a formation of oligomers and/or fibers of amyloidogenic peptides (e.g., Aβ).

Pharmaceutical compositions containing the compounds of the invention can be prepared in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, the pharmaceutical composition of the invention is in liquid form. Liquid forms include, by way of non-limiting example, emulsions, solutions, suspensions, syrups, slurries, dispersions, colloids and the like. In some embodiments, a pharmaceutical composition described herein is in liquid, semi-solid or solid (e.g., powder) form. In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, the pharmaceutical composition of the invention is a solid dosage form, such a tablet, a granule, a sachet, or a powder. Also provided are pharmaceutical compositions comprising a compound of the invention or a pharmaceutically acceptable salt thereof in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in DPI).

In some embodiments, a composition is in a unit dose formulation for oral, intranasal, or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the compounds or compositions described herein are administered intranasally. As used herein, "nasal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired nasal delivery characteristics (e.g., as measured at the site of delivery, or at a selected target site of activity such as the brain) of the compounds or compositions of the invention. Enhancement of mucosal delivery can thus occur by any of a variety of mechanisms, for example by increasing the diffusion, transport, persistence or stability of the compounds or compositions of the invention, enzyme inhibition, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, increasing nasal blood flow and other mechanisms. Suitable mucosal delivery enhancing agents will be clear to a person skilled in the art of pharmacology and are further described hereafter.

Compositions of the invention can be simple aqueous (e.g., saline) solutions. Alternatively, they can contain various additional ingredients which enhance stability and/or nasal delivery of the compounds of the invention. Such additional ingredients are well known in the art. Non-limiting examples of useful additional ingredients for enhancing nasal delivery include, e.g., (a) aggregation inhibitory agents (e.g., polyethylene glycol, dextran, diethylaminoethyl dextran, and carboxymethyl cellulose), (b) charge modifying agents, (c) pH control agents, (d) degradative enzyme inhibitors (e.g., amastatin and bestatin [see, e.g., O'Hagan et al., *Pharm. Res.* 1990, 7: 772-776 and WO 05/120551]; (e) mucolytic or mucus clearing agents (e.g., n-acetyl-cysteine, propyl gallate and cysteine methionine dimers, chaotropes [see, e.g., WO 04/093917]), (f) ciliostatic agents; (g) membrane penetration enhancing agents, (h) modulatory agents of epithelial junction physiology, such as nitric oxide (NO) stimulators, chitosan, and chitosan derivatives; (i) vasodilator agents, (j) selective transport-enhancing agents, and (k) stabilizing delivery vehicles, carriers, supports or complex-forming agents. See, e.g., EP 037943, EP 094157, EP 173990, EP 214898, EP 215697, EP 327756, EP 490806, U.S. Pat. Nos. 4,476,116, 5,759,565, WO 04/093917 and WO 05/120551.

Non-limiting examples of membrane penetration-enhancing agents useful in the compositions of the invention include, e.g., (i) a surfactant (e.g., Tween 80, Poloxamer 188, polysorbates; see also EP 490806, U.S. Pat. No. 5,759, 565, and WO04/093917), (ii) a bile salt or bile salt derivative (e.g., unsaturated cyclic ureas and Transcutol), (iii) a phospholipid or fatty acid additive, mixed micelle, liposome, or carrier, (iv) an alcohol, (v) an enamine, (vi) a nitric oxide donor compound (e.g., S-nitroso-N-acetyl-DL-penicillamine, NOR1, NOR4, which are preferably co-administered with an NO scavenger such as carboxy-PITO or doclofenac sodium), (vii) a long-chain amphipathic molecule (e.g., deacylmethyl sulfoxide, azone, sodium lauryl sulfate, oleic acid) (viii) a small hydrophobic penetration enhancer, (ix) sodium salicylate or a salicylic acid derivative (e.g., acetyl salicylate, choline salicylate, salicylamide, etc.), (x) a glycerol ester of acetoacetic acid, (xi) a cyclodextrin or betacyclodextrin derivative, (xii) a medium-chain fatty acid including mono- and diglycerides (e.g., sodium caprate—extracts of coconut oil, Capmul), (xiii) a chelating agent (e.g., citric acid, salicylates), (xiv) an amino acid or salt thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc., inclusive of their alkali metal or alkaline earth metal salts), (xv) an N-acetylamino acid or salt thereof, (xvi) an enzyme degradative to a selected membrane component, (xvii) an inhibitor of fatty acid synthesis, (xviii) an inhibitor of cholesterol synthesis, (xix) cationic polymers, or any combination thereof. The membrane penetration-enhancing agent can be also selected from small hydrophilic molecules, including but not limited to, dimethyl sulfoxide (DMSO), dimethylformamide, ethanol, propylene glycol, and the 2-pyrrolidones. Additional membrane penetration enhancers include emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like; mixed micelles; glycerol esters of acetoacetic acid (e.g., glyceryl-1,3-diacetoacetate or 1,2-isopropylideneglycerine-3-acetoacetate), and triglycerides (e.g., amylodextrin, Estaram 299, Miglyol 810); cyclodextrins and β-cyclodextrin derivatives (e.g., 2-hydroxypropyl-β-cyclodextrin and heptakis (2,6-di-O-methyl-β-cyclodextrin) which can be optionally conjugated with Peptide and further optionally formulated in an oleaginous base; and N-acetyl amino acids (N-acetyl al anine, N-acetylphenyl al anine, Nacetylserine, N-acetylglycine, N-acetyllysine, N-acetylglutamic acid, N-acetylproline, Nacetylhydroxyproline, etc.) and their salts (alkali metal salts and alkaline earth metal salts), as well as other penetration-promoting agents that are physiologically compatible for intranasal delivery. See, e.g., WO 04/093917, WO 05/120551 and Davis and Ilium (*Clin. Pharmacokinet* 2003, 42: 1107-1128).

Non-limiting examples of useful absorption enhancers include, e.g., surfactants, glycosides, cyclodextrin and glycols. Non-limiting examples of useful bioadhesive agents include, e.g., carbopol, cellulose agents, starch, dextran, and chitosan.

In various embodiments of the invention, a compound of the invention is combined with one or more of the nasal delivery-enhancing agents recited above. These nasal agents may be admixed, alone or together, with the nasal carrier and with the compound of the invention, or otherwise combined therewith in a pharmaceutically acceptable formulation or delivery vehicle. For nasal delivery-enhancing agents to be of value within the invention, it is generally desired that any significant changes in permeability of the mucosa be reversible within a time frame appropriate to the desired duration of drug delivery.

Furthermore, there should be no substantial, cumulative toxicity, nor any permanent deleterious changes induced in the barrier properties of the nasal mucosa with long term use.

In addition to the compound of the invention, the nasal carrier and, optionally, one or more further additives and/or agents, the composition of the invention may further comprise one or more additional therapeutic ingredients (or active substances). These therapeutic ingredients can be any compound that elicits a desired activity or therapeutic or biological response in the subject. Non-limiting examples of useful additional therapeutic ingredients is provided in the Combination Treatments section, below.

The proportion of each further component in the nasal composition of the invention may vary depending on the components used. For example, but without being limiting, the amount of nasal carrier may be in the range of from 0.1 to 99.9% by weight of the total weight or volume of the composition. When present, the amount surfactant may be in the range from about 0.01 to about 10% or higher and preferably about 0.05 to about 1.0% by weight of the total volume or weight of the composition, the amount depending on the specific surfactant used. The amount is generally kept as low as possible since above a certain level no further enhancement of absorption can be achieved and also too high of a surfactant level may cause irritation of the nasal mucosa. The amount of delivery enhancing agents may be at least 0.1%, suitably in the range from about 0.5 to 10% of the total weight of the composition. Where the composition is liquid, the enhancing agent may suitably be present in an amount of from 0.1 to 5% w/v of the total composition. Preserving agents may be present in an amount of from about 0.002 to 0.02% by weight of the total weight or volume of the composition.

The useful delivery volume of the pharmaceutical compositions of the invention is limited by the size of the nasal cavity. Suitable delivery volumes will be clear to a person skilled in the art of pharmacology. Preferably, the total composition quantity administered at each nasal application comprises from about 0.02 to 0.5 ml, preferably about 0.07 to 0.3 ml, typically about 0.09-0.1 ml.

The liquid compositions of the invention may be prepared by bringing into intimate admixture a compound the invention in the liquid carrier optionally together with the further ingredients, additives and/or agents. The solid nasal composition of the invention may be prepared in conventional manner. A compound of the invention may be admixed with the carrier particles, e.g. a polymer base or cellulose product in conventional manner, optionally with further ingredients, additives and/or agents as indicated above e.g. a mucosal delivery enhancing agent or surfactant such as disclosed. A compound of the invention may be in solution e.g. an aqueous or alcoholic solution when being mixed with the carrier particles and the solvent evaporated, e.g. under freeze-drying or spray drying. Such drying may be effected under the conventional conditions. Alternatively, the mixture may be compacted or granulated and then be pulverized and/or sieved. If desired the particles may be coated. In one embodiment of the invention, the nasal composition is prepared by lyophilisation. A homogeneous solution, preferably aqueous, containing a compound of the invention and optionally containing further ingredients, additives and/or agents as discussed above, is prepared and then submitted to lyophilisation in analogy with known lyophilisation procedures, and to subsequent drying. The resulting powder may then be dissolved in a liquid excipient or nasal carrier before administration, e.g. to reconstitute nasal drops, gel or spray. Alternatively, it may be administered as such in the form of lyophilized powder or it may be mixed with further ingredients, additives and/or agents as discussed above. For example, a lyophilized powder comprising a compound of the invention but free of any nasal carrier may be prepared and then admixed with the desired nasal carrier or mixture of nasal carriers.

The present invention encompasses any delivery device that is suitable for nasal administration of the compositions of the invention. Preferably, such means administers a metered dosage of the composition. The composition of the present invention may be packed in any appropriate form or container as long as a means is provided to deliver the composition to the nasal mucosa. Non-limiting examples of useful intranasal delivery devices include, e.g., instillation catheters, droppers, unit-dose containers, squeeze bottles pump sprays, airless and preservative-fee sprays, compressed air nebulizers, metered-dose inhalers, insufflators and pressurized metered dose inhalers.

For administration of a liquid in drop form, compositions of the invention can be placed in a container provided with a conventional dropper/closure device, e.g. comprising a pipette or the like, preferably delivering a substantially fixed volume of composition/drop.

For administration of an aqueous solution as a nasal spray, the aqueous solution may be dispensed in spray form by a variety of methods known to those skilled in the art. For example, such compositions will be put up in an appropriate atomising device, e.g. in a pump-atomiser, or the like. The atomising device will be provided with appropriate means, such as a spray adaptor for delivery of the aqueous spray to the naris. Preferably it will be provided with means ensuring delivery of a substantially fixed volume of composition/actuation (i.e. per spray-unit). Examples of nasal sprays include nasal actuators produced by Ing. Erich Pfeiffer GmbH, Radolfzell, Germany (see U.S. Pat. Nos. 4,511,069, 4,778,810, 5,203,840, 5,860,567, 5,893,484, 6,227,415, and 6,364,166. Additional aerosol delivery forms may include, e.g., compressed air-, jet-, ultrasonic-, and piezoelectric nebulizers.

Alternatively, the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present.

A dry powder may be readily dispersed in an inhalation device as described in U.S. Pat. No. 6,514,496 and Garcia-Arieta et al., *Biol. Pharm. Bull.* 2001; 24: 1411-1416.

If desired a powder or liquid may be filled into a soft or hard capsule or in a single dose device adapted for nasal administration. The powder may be sieved before filled into the capsules such as gelatine capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

In another embodiment, the composition of the invention can be provided as a nasal insert having the compound of the invention dispersed therein. The insert may be retained in the naris, but flushed by the nasal mucus, and may be designed to release the compound of the invention at the same place in the naris. Suitable nasal insert types include nasal plugs, tampons and the like. Further examples of nasal inserts, their characteristics and preparation are described in EP 490806.

In one aspect, a composition or unit dosage form according to the invention is formulated for sublingual administration, wherein the unit dosage form is a film including one or more disintegrants (e.g., materials that favor disintegration or fast dissolution by virtue of their solubility in water, such as hydrolyzed starches, sugars, and glycerin, which may play a dual role as a plasticizer and disintegrant) and a plasticizing agent, the film having a first portion including apomorphine hydrochloride, and a second portion including pH neutralizing agent, wherein the unit dosage form includes from 0.5 to 5 mg, from 4 to 10 mg, or from 8 to 20 mg of apomorphine hydrochloride and the pH neutralizing agent is present in an amount sufficient to produce a solution having a pH of between 3.0 and 6.0, preferably between 4.5 and 6.5, (e.g., a pH of between 2.5 and 4.5, 3.0 and 6.0, 3.5 and 6.5, 4.5 and 6.5, or 5.0 and 6.0) when the unit dosage form is placed in unbuffered water at pH 7 (e.g., the pH observed within 5 minutes of placing the unit dosage form in 1, 5, or 10 mL of unbuffered water). The film can include from 1 to 50% (w/w) (e.g., 1±0.75%, 2±1.5%, 3±0.5%, 5±2%, 7.5±2.5%, 10±2%, 14±3%, 18±4%, 22±5%, 25±5%, 30±5%, 35±5%, 40±5%, 45±5%, or 50±5% (w/w)) of the one or more disintegrants. In certain embodiments, the unit dosage form further includes a high molecular weight polymer having a weight average molecular weight of greater than 60 KDa selected from hydroxypropyl cellulose, hydroxypropyl methyl cellulose, hydroxyethyl cellulose, carboxymethyl cellulose, and methyl cellulose. In other embodiments, the unit dosage form further includes a low molecular weight polymer having a weight average molecular weight of from 5 KDa to 50 KDa selected from hydroxypropyl cellulose, hydroxypropyl methyl cellulose, hydroxyethyl cellulose, carboxymethyl cellulose, and methyl cellulose. The pH neutralizing agent can be an organic base (e.g., pyridoxine, meglumine, or any organic base described herein) or an inorganic base (e.g., magnesium hydroxide, sodium bicarbonate, or an inorganic base described herein). In particular embodiments, the unit dosage form includes 35±5% (w/w) disintegrant, from 0.5 to 5 mg, from 4 to 10 mg, or from 8 to 20 mg of apomorphine hydrochloride and pyridoxine present in an amount sufficient to produce a solution having a pH of between 4.5 and 6.5 when the unit dosage form is placed in unbuffered water at pH 7. Suitable film for oral administration of the compositions according to the invention is disclosed in, e.g., U.S. Pat. No. 8,846,074.

In some embodiments, a composition or unit dosage form described herein is administered as an emulsion, a solution, a suspension, a syrup, a slurry, a dispersion, a colloid, a dissolving tablet, a dissolving wafer, a capsule, a gel capsule, a semi-solid, a solid forma gel, a gel matrix, a cream, a paste, a tablet, a granule, a sachet, a powder, or the like. In certain aspects, about 0.000001 mg to about 2000 mg, about 0.00001 mg to about 1000 mg, or about 0.0001 mg to about 750 mg, about 0.001 mg to about 500 mg, about 0.01 mg to about 250 mg, about 0.1 mg to about 100 mg, about 0.5 mg to about 75 mg, about 1 mg to about 50 mg, about 2 mg to about 40 mg, about 5 mg to about 20 mg, or about 7.5 mg to about 15 mg of compound of formula (I) per day or per dose is administered to an individual.

In some embodiments, the compound of the invention is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of corticosteroid administered daily or in a unit dose is between about 0.5 mg and about 3 mg, between about 0.5 mg and about 4 mg, or between about 0.35 mg and about 4 mg. In other embodiments, the amount of the compound present in a unit dose or administered daily is between about 1 and about 3 mg, or between about 1 and about 2 mg, or between about 2 and about 3 mg.

In certain aspects, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of the compound per day or per dose is administered to a patient.

In some embodiments, the compound is present in a unit dose in an amount of between about 5 mg and about 500 mg. In some embodiments, the amount of the compound administered daily or in a unit dose is between about 5 mg and about 300 mg. In other embodiments, the amount of the compound present in a unit dose or administered daily is between about 5 and about 250 mg, or between about 5 and about 200 mg, between about 5 mg and about 150 mg, between about 5 mg and about 100 mg, or between about 5 and about 50 mg.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid pre-formulation composition containing a homogeneous mixture of the compound of Formula I. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.000001 to about 2000 mg of the active ingredient of the present application.

The tablets or pills containing the compound of Formula I can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9. It will be understood that use of certain of the foregoing excipients, carriers, or stabilizers will result in the formation of pharmaceutical salts.

The therapeutic dosage of the compounds of the invention can vary according to, for example, the particular use for which the treatment is made, the manner of administration of the compound, the health and condition of the patient, and the judgment of the prescribing physician. The proportion or concentration of the compounds of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present application also includes pharmaceutical kits useful, for example, in the treatment or prevention of diseases characterized by a formation of oligomers and/or fibers of amyloidogenic peptides, such as A$\beta$, which include one or more containers containing a pharmaceutical composition comprising a therapeutically effective amount of the compounds of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

Methods of Use

In one aspect, compounds and/or pharmaceutical compositions of the invention may be used for altering the structure of an amyloidogenic peptide. In some embodiments, compounds and/or pharmaceutical compositions according to the invention may be useful for altering the conformation and/or structures of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In some embodiments compounds and/or pharmaceutical compositions according to the invention may be useful for altering the structure of Aβ, or its $Aβ_{42}$ alloform.

In one aspect, compounds and/or pharmaceutical compositions of the invention may be used to induce an α-helical conformation in all or a part of an amyloidogenic peptide. In some embodiments, compounds and/or pharmaceutical compositions according to the invention may be used to promote or induce an α-helical conformation in all or a part of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In some embodiments compounds and/or pharmaceutical compositions according to the invention may be used to promote or induce an α-helical conformation in all or a part of Aβ, or its $Aβ_{42}$ alloform. In some embodiments compounds and/or pharmaceutical compositions according to the invention may be used to promote or induce an α-helical conformation in all or a part of IAPP. In some embodiments compounds and/or pharmaceutical compositions according to the invention may be used to promote or induce an α-helical conformation in all or a part of α-synuclein.

In one aspect, compounds and/or pharmaceutical compositions of the invention may be used to inhibit, hinder or prevent an α-helical conformation in all or a part of an amyloidogenic peptide. In some embodiments, compounds and/or pharmaceutical compositions according to the invention may be used to inhibit, hinder or prevent an α-helical conformation in all or a part of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In some embodiments compounds and/or pharmaceutical compositions according to the invention may be used to inhibit, hinder or prevent an α-helical conformation in all or a part of Aβ, or its $Aβ_{42}$ alloform. In some embodiments compounds and/or pharmaceutical compositions according to the invention may be used to inhibit, hinder or prevent an α-helical conformation in all or a part of IAPP. In some embodiments compounds and/or pharmaceutical compositions according to the invention may be used to inhibit, hinder or prevent an α-helical conformation in all or a part of α-synuclein.

In one aspect, compounds of the invention may exhibit selectivity and/or specificity for one or more particular amyloidogenic peptides, i.e. the compounds of the invention may selectively and/or specifically bind one or more particular amyloidogenic peptides. In one aspect, compounds of the invention may exhibit selectivity and/or specificity for one or more particular amyloidogenic peptides, i.e. the compounds of the invention may selectively and/or specifically bind one or more particular amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In one embodiment, compounds of the invention may exhibit selectivity and/or specificity for Aβ, or its $Aβ_{42}$ alloform. In another embodiment, compounds of the invention may exhibit selectivity and/or specificity for IAPP. In another embodiment, compounds of the invention may exhibit selectivity and/or specificity for α-synuclein.

In another aspect, compounds and/or pharmaceutical compositions of the invention may be used for inhibiting oligomerization of an amyloidogenic peptide. In some embodiments, compounds and/or pharmaceutical compositions according to the invention may be useful for inhibiting oligomerization of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In some embodiments compounds and/or pharmaceutical compositions according to the invention may be useful for inhibiting oligomerization of Aβ, or its $Aβ_{42}$ alloform.

In another aspect, compounds and/or pharmaceutical compositions of the invention may be used for inhibiting oligomerization of an amyloidogenic peptide. In some embodiments, compounds and/or pharmaceutical compositions according to the invention may be useful for inhibiting oligomerization of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In some embodiments compounds and/or pharmaceutical compositions according to the invention may be useful for inhibiting oligomerization of Aβ, or its $Aβ_{42}$ alloform.

In another aspect, compounds and/or pharmaceutical compositions of the invention may be used for inhibiting (i.e., reducing, diminishing, decreasing, or antagonizing) cytotoxicity of an amyloidogenic peptide. In some embodiments, compounds and/or pharmaceutical compositions according to the invention may be useful for inhibiting cytotoxicity of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In some embodiments compounds and/or pharmaceutical compositions according to the invention may be useful for inhibiting cytotoxicity of Aβ, or its $Aβ_{42}$ alloform.

In another aspect, compounds and/or pharmaceutical compositions of the invention may be used for treating diseases and/or conditions characterized by a formation of oligomers or fibers of amyloidogenic peptides. In some embodiments, compounds and/or pharmaceutical compositions according to the invention may be useful for treating diseases and/or conditions characterized by a formation of oligomers or fibers of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin. In some embodiments compounds and/or pharmaceutical compositions according to the invention may be useful for treating diseases and/or conditions characterized by a formation of oligomers or fibers of Aβ, or its $Aβ_{42}$ alloform.

In another aspect, compounds and/or pharmaceutical compositions according to the invention may be useful for treating diseases selected from Alzheimer's Disease (AD), type 1 diabetes, type 2 diabetes, Parkinson's disease, Mild Cognitive Impairment (MCI), inclusion body myositis, cerebral amyloid angiopathy, systemic AA amyloidosis, Lewy body diseases including Lewy body dementia, multiple system atrophy, Down's syndrome, hereditary cerebral hemorrhage with amyloidosis of the Dutch type, inclusion body myositosis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid.

In another aspect of the invention, methods for modulating oligomerization and/or fibrillation of amyloidogenic peptides with compounds and/or pharmaceutical compositions of the present invention are provided. In some embodiments, methods of inhibiting oligomerization and/or fibrillation of amyloidogenic peptides are provided, including, without limitation, methods of inhibiting oligomerization and/or fibrillation of Aβ, or its $Aβ_{42}$ alloform, islet amyloid polypeptide (IAPP), α-synuclein, AA amyloid, PrP, $β_2$-microglobulin amyloid, transthyretin, prealbumin, and procalcitonin.

In one aspect, methods of altering the structure of an amyloidogenic peptide with compounds and/or pharmaceutical compositions of the present invention are provided. In some embodiments, methods of altering structures of amyloidogenic peptides including, without limitation, Aβ, or its $Aβ_{42}$ alloform, islet amyloid polypeptide (IAPP), α-synuclein, AA amyloid, PrP, $β_2$-microglobulin amyloid, transthyretin, prealbumin, and procalcitonin with compounds and/or pharmaceutical compositions of the present invention are provided. In some embodiments methods of altering the structure of Aβ, or its $Aβ_{42}$ alloform with compounds and/or pharmaceutical compositions of the present invention are provided.

In one aspect, methods of inhibiting cytotoxicity of an amyloidogenic peptide with compounds and/or pharmaceutical compositions of the present invention are provided. In some embodiments, methods of inhibiting cytotoxicity of amyloidogenic peptides including, without limitation, Aβ, or its $Aβ_{42}$ alloform, islet amyloid polypeptide (IAPP), α-synuclein, AA amyloid, PrP, $β_2$-microglobulin amyloid, transthyretin, prealbumin, and procalcitonin with compounds and/or pharmaceutical compositions of the present invention are provided. In some embodiments methods of inhibiting cytotoxicity of Aβ or its $Aβ_{42}$ alloform with compounds and/or pharmaceutical compositions of the present invention are provided.

In one aspect, methods of treating diseases and/or conditions characterized by a formation of oligomers or fibers of amyloidogenic peptides with compounds and/or pharmaceutical compositions of the present invention are provided. In some embodiments, methods of treating diseases and/or conditions characterized by a formation of oligomers or fibers of amyloidogenic peptides including, without limitation, Aβ, islet amyloid polypeptide (IAPP), α-synuclein, AA amyloid, PrP, $β_2$-microglobulin amyloid, transthyretin, prealbumin, and procalcitonin with compounds and/or pharmaceutical compositions of the present invention are provided. In some embodiments methods of treating diseases and/or conditions characterized by a formation of oligomers or fibers of amyloidogenic peptides of Aβ or its $Aβ_{42}$ alloform with compounds and/or pharmaceutical compositions of the present invention are provided.

In one aspect, methods of treating diseases selected from Alzheimer's Disease (AD), type 1 diabetes, type 2 diabetes, Parkinson's disease, Mild Cognitive Impairment (MCI), inclusion body myositis, cerebral amyloid angiopathy, systemic AA amyloidosis, Lewy body diseases including Lewy body dementia multiple system atrophy, Down's syndrome, hereditary cerebral hemorrhage with amyloidosis of the Dutch type, inclusion body myositosis, amyloidosis associated with chronic inflammation, various forms of malignancy and Familial Mediterranean Fever, inflammation-associated amyloidosis, amyloidosis associated with multiple myeloma and other B-cell dyscrasias, amyloidosis associated with the prion diseases (including, e.g., Creutzfeldt-Jakob disease, Gerstmann-Straussler syndrome, kuru and animal scrapie), amyloidosis associated with long-term hemodialysis or carpal tunnel syndrome, amyloidosis associated with senile cardiac amyloid and Familial Amyloidotic Polyneuropathy, amyloidosis associated with endocrine tumors such as medullary carcinoma of the thyroid with compounds and/or pharmaceutical compositions of the inventions are provided.

Although the methods of the invention may be used in a mammal, for example a human, of any age, in certain examples, the individual is an adult, for example an elderly person, for example a person over the age of 50, 55, 60, 65, or 70 years.

Combination Treatment

In one embodiment of any of the above methods, the method further comprises administering a therapeutic or preventive treatment to the subject. Non-limiting examples of useful drug treatments include, for example, administration of dopamine-replenishing or dopamine mimicking drugs such as, e.g., levodopa or levodopa combination treatments, which may include administration with dopa decarboxylase inhibitors (e.g., carbidopa, benserazide); dopamine enhancers, such as catechol o-methyltransferase (COMT) inhibitors (e.g., entacapone, tolcapone); dopamine receptor agonists (e.g., ropinirole, pramipexole, rotigotine, apomorphine, pergolide, bromocriptine); monoamine oxidase (MAOIs) inhibitors, which can be used alone or with levodopa (e.g., selegiline, rasagiline, zydis selegiline HCl salt); amantadine (used to combat tremor and side effects of levodopa administration); anti-cholinergenics (e.g., trihexyphenidyl, benztropine, donepezil, galantamine, rivastigmine); antiglutamatergics (e.g., memantine, safinomide); riluzole; neurturin therapies; anti-apoptotics (e.g., omigapil, CEP-1347); anti-psychotics (e.g., olanzepine, quetiapine, risperidone, ziprasidone, aripiprazole, paliperidone); promitochondrials (e.g., Coenzyme Q10, creatine); calcium channel blockers, including isradipine, and growth factors such as GDNF; anti-Abeta antibodies, as well as drugs or vaccines targeting alpha-synuclein. Non-limiting examples of useful surgical therapies include, for example, deep brain stimulation (DBS), involving implantation of a battery-powered electrode in the brain; operations directly on neural tissue (e.g., thalamotomy, pallidotomy, subthalmatomy); and dopamergic cell transplant. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms. Non-limiting examples of useful food supplements include, for example, antioxidants such as vitamins C and E, calcium, ginger root, green tea and green tea extracts, St. John's Wort, Ginkgo biloba, milk thistle, vitamin B12, and folic acid. Effective treatment can mean patient improvement (decrease of a biomarker miRNA ratio) or prevention/inhibition of further disease development (biomarker miRNA ratio stays the same or increases slower).

In one embodiment of any of the above methods, the method further comprises administering one or more of the following therapeutic or preventive treatments to the subject to treat AD: apomorphine, donepezil, galantamine, raviastigmine, memantine, anti-psychotics (e.g., olanzepine, quetiapine, risperidone, ziprasidone, aripiprazole, paliperidone), anti-Abeta antibodies, vitamin C, vitamin E, ginger root, green tea and green tea extracts, Ginkgo biloba, milk thistle, vitamin B12, and folic acid. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms. In one embodiment of any of the above methods, the method further comprises administering one or more of the following therapeutic or preventive treatments to the subject to treat PD: administration of dopamine-replenishing or dopamine mimicking drugs such as, e.g., levodopa or levodopa combination treatments, which may include administration with dopa decarboxylase inhibitors (e.g., carbidopa, benserazide); dopamine enhancers, such as catechol o-methyltransferase (COMT) inhibitors (e.g., entacapone, tolcapone); dopamine receptor agonists (e.g., ropinirole, pramipexole, rotigotine, apomorphine, pergolide, bromocriptine); monoamine oxidase (MAOIs) inhibitors, which can be used alone or with levodopa (e.g., selegiline, rasagiline, zydis selegiline HCl salt); amantadine (used to combat tremor and side effects of levodopa administration); anti-cholinergenics (e.g., trihexyphenidyl, benztropine, galantamine, rivastigmine); antiglutamatergics (e.g., safinomide); riluzole; neurturin therapies; anti-apoptotics (e.g., omigapil, CEP-1347); anti-psychotics (e.g., olanzepine, quetiapine, risperidone, ziprasidone, aripiprazole, paliperidone); promitochondrials (e.g., Coenzyme Q10, creatine); calcium channel blockers, including isradipine, and growth factors such as GDNF; drugs or vaccines targeting alpha-synuclein, surgical therapies (e.g., deep brain stimulation (DBS), involving implantation of a battery-powered electrode in the brain; operations directly on neural tissue (e.g., thalamotomy, pallidotomy, subthalmatomy); and dopamergic cell transplant), vitamin C, vitamin E, calcium, ginger root, green tea, green tea extracts, St. John's Wort, and milk thistle. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms.

In one embodiment of any of the above methods, the method further comprises administering one or more of the following therapeutic or preventive treatments to the subject to treat mild cognitive impairment (MCI): vitamin C, vitamin E, ginger root, green tea and green tea extracts, Ginkgo biloba, milk thistle, vitamin B12, and folic acid. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms.

ADDITIONAL EMBODIMENTS

1. A compound according to formula (I):

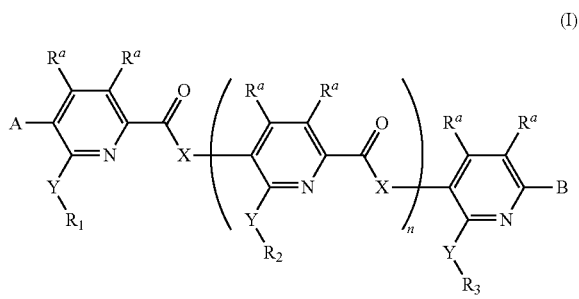

(I)

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and C(R*)$_2$;

Y is independently at each occurrence selected from —O—; —S—; —NH—; and —NR*—;

$R_1$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_2$ is independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO;

—NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂ and combinations thereof;

R₃ is selected from hydrogen or a straight chained, branched or cyclic aliphatic C₁-C₂₀ hydrocarbon; an aromatic C₆-C₂₀ hydrocarbon; a heteroaromatic C₁-C₂₀ hydrocarbon; an aryl C₆-C₂₀ hydrocarbon; a heteroaryl C₁-C₂₀ hydrocarbon, a C₁-C₁₂ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂ and combinations thereof;

A is selected from hydrogen, —F; —Cl; —Br; —I; —OH, —OR*; —NO; —NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂; C₁-C₈ perfluorocarbon; an aliphatic C₁-C₁₂ hydrocarbon; an aromatic C₁-C₁₂ hydrocarbon; and a C₁-C₁₂ heteroaryl;

B is selected from hydrogen, —F; —Cl; —Br; —I; —OH, —OR*; —NO; —NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂; C₁-C₈ perfluorocarbon; an aliphatic C₁-C₁₂ hydrocarbon; an aromatic C₁-C₁₂ hydrocarbon; and a C₁-C₁₂ heteroaryl;

R* is independently selected at each occurrence from hydrogen or C₁-C₁₂ hydrocarbons each of which optionally contains 1-8 heteroatoms selected from halogen, O, N, and S and combinations thereof; and n is an integer from 0 to 2;

with the proviso that (i) when n is 0, and Y is O, R₁ and R₃ are not both —CH₂CO₂H; (ii) when n is 1, Y is O, and R₁ and R₃ are both —CH₂CO₂H, R₂ is not —CH₂CO₂H or a straight chained, branched or cyclic aliphatic or aryl C₁-C₁₂ hydrocarbon, or R₂ does not have the structure —C(CH₂CO₂H)₃; (iii) when n is 1, and Y is O, R₁ through R₃ are not each an unsubstituted C₁-C₈ hydrocarbon; and (iv) when n is 2, and Y is O, R₁ through R₃ are not —CH₂CO₂H at all occurrences, or a pharmaceutically acceptable salt thereof.

2. The compound according to embodiment 1 having the structure of formula (II):

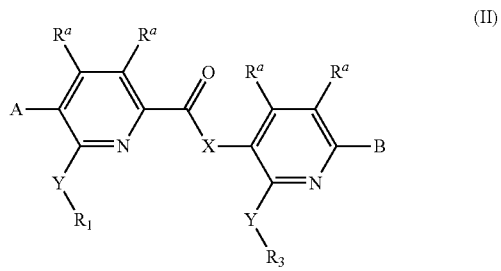

(II)

or a pharmaceutically acceptable salt thereof.

3. The compound according to embodiment 2 having the structure of formula (III):

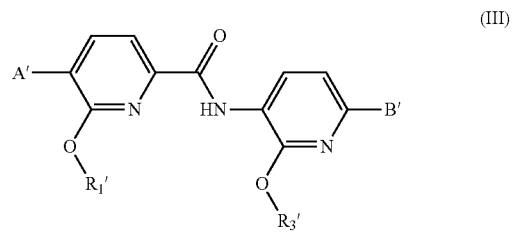

(III)

wherein R₁' is selected from a straight chained, branched or cyclic aliphatic C₁-C₂₀ hydrocarbon; an aromatic C₆-C₂₀ hydrocarbon; a heteroaromatic C₁-C₂₀ hydrocarbon; an aryl C₆-C₂₀ hydrocarbon; a heteroaryl C₁-C₂₀ hydrocarbon, a C₁-C perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

R₃' is selected from a straight chained, branched or cyclic aliphatic C₁-C₂₀ hydrocarbon; an aromatic C₆-C₂₀ hydrocarbon; a heteroaromatic C₁-C₂₀ hydrocarbon; an aryl C₆-C₂₀ hydrocarbon; a heteroaryl C₁-C₂₀ hydrocarbon, a C₁-C₁₂ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

with the proviso that R₁ and R₃ are not both —CH₂CO₂H;

A' is selected from —NO₂; —NH₂; —NHR*; —N(R*)—(C=O)—R*, —N(R*)₂, where R* is hydrogen or an aliphatic C₁-C₁₂ hydrocarbon;

B' is selected from —(C=O)—R*; —CO₂H; —CO₂R*, where R* is hydrogen or an aliphatic $C_1$-$C_{12}$ hydrocarbon, or a pharmaceutically acceptable salt thereof.

4. The compound according to embodiment 1 having the structure of formula (IV):

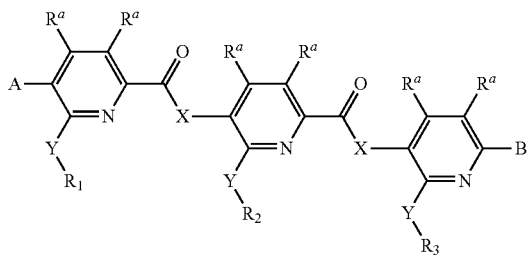

(IV)

or a pharmaceutically acceptable salt thereof.

5. The compound according to embodiment 4 having the structure of formula (V):

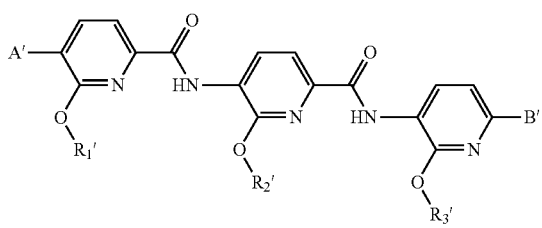

(V)

wherein $R_1'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof, $R_2'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

$R_3'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

A' is selected from —NO₂; —NH₂; —NHR*; —N(R*)—(C=O)—R*, —N(R*)₂, where R* is hydrogen or an aliphatic $C_1$-$C_{12}$ hydrocarbon; and B' is selected from —(C=O)—R*; —CO₂H; —CO₂R*, where R* is hydrogen or an aliphatic $C_1$-$C_{12}$ hydrocarbon; with the proviso that (i) when $R_1$ and $R_3$ are both —CH₂CO₂H, $R_2$ is not —CH₂CO₂H or a straight chained, branched or cyclic aliphatic $C_1$-$C_{12}$ hydrocarbon, or $R_2$ does not have the structure —C[CH₂CO₂H]₃; and (ii)$R_1$ through $R_3$ are not each an unsubstituted $C_1$-$C_8$ hydrocarbon, or a pharmaceutically acceptable salt thereof.

6. The compound according to embodiment 1 having the structure of formula (VI):

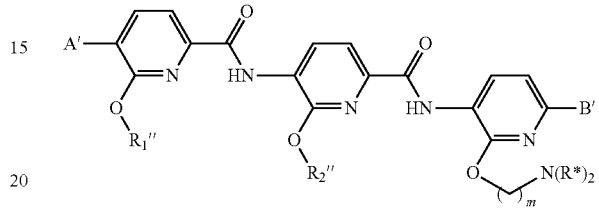

(VI)

wherein $R_1''$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, optionally substituted with —NH₂; —NHR*; or —N(R*)₂;

$R_2''$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

A' is selected from —NO₂; —NH₂; —NHR*; —N(R*)—(C=O)—R*, —N(R*)₂;

B' is selected from —(C=O)—R*; —CO₂H; —CO₂R*;

R* is hydrogen or an aliphatic $C_1$-$C_{12}$ hydrocarbon; and m is an integer from 1 to 12, or a pharmaceutically acceptable salt thereof.

7. The compound according to embodiment 1 having the structure of formula (VI):

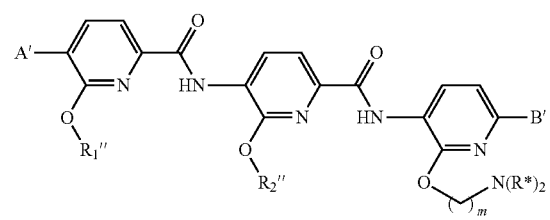

(VI)

wherein $R_1''$ and $R_2''$ are each independently a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, optionally substituted with —NH₂; —NHR*; or —N(R*)₂;

A' is selected from —NO₂; —NH₂; —NHR*; —N(R*)—(C=O)—R*, —N(R*)₂;

B' is selected from —(C=O)—R*; —CO₂H; —CO₂R*;

R* is hydrogen or an aliphatic $C_1$-$C_{12}$ hydrocarbon; and m is an integer from 1 to 12, or a pharmaceutically acceptable salt thereof.

8. The compound according to embodiment 1 having the structure of formula (VII):

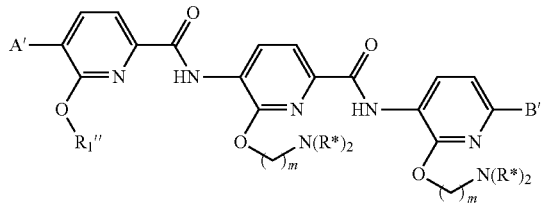

(VII)

wherein $R_1''$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, optionally substituted with —$NH_2$; —NHR*; or —N(R*)$_2$;

A' is selected from —$NO_2$; —$NH_2$; —NHR*; —N(R*)—(C=O)—R*, —N(R*)$_2$;

B' is selected from —(C=O)—R*; —$CO_2H$; —$CO_2R*$;

R* is independently at each occurrence hydrogen or an aliphatic $C_1$-$C_{12}$ hydrocarbon; and m is independently at each occurrence an integer from 1 to 12, or a pharmaceutically acceptable salt thereof.

9. The compound according to embodiment 1 having the structure of formula (VIII):

wherein $R_1'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —NHR*; —N(R*)$_2$; —N(R*)$_3^+$; —(C=O)—R*; —CHO; —$CO_2H$; —$CO_2R*$; —(C=O)—S—R*; —O—(C=O)—H; —O—(C=O)—R*; and combinations thereof;

$R_2'$ is independently at each occurrence selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —NHR*; —N(R*)$_2$; —N(R*)$_3^+$; —(C=O)—R*; —CHO; —$CO_2H$; —$CO_2R*$; —(C=O)—S—R*; —O—(C=O)—H; —O—(C=O)—R*; and combinations thereof;

$R_3'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —NHR*;

(VIII)

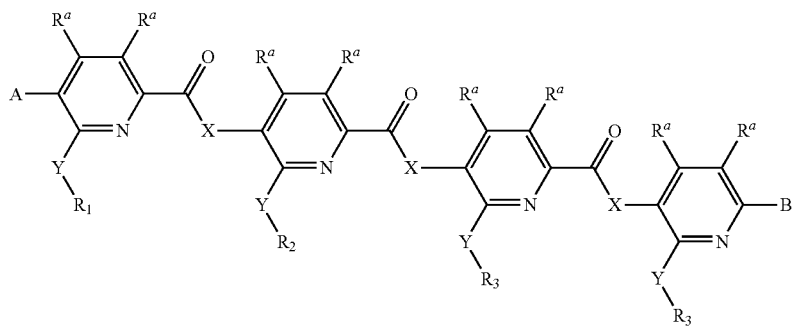

or a pharmaceutically acceptable salt thereof.

10. The compound according to embodiment 1 having the structure of formula (IX):

—N(R*)$_2$; —N(R*)$_3^+$; —(C=O)—R*; —CHO; —$CO_2H$; —$CO_2R*$; —(C=O)—S—R*; —O—(C=O)—H; —O—(C=O)—R*; and combinations thereof;

(IX)

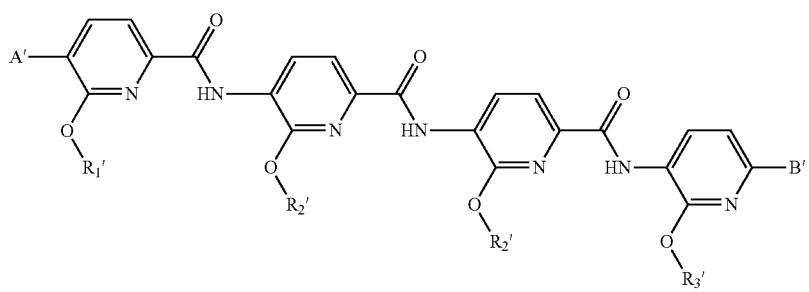

A' is selected from —NO₂; —NH₂; —NHR*; —N(R*)—(C=O)—R*, —N(R*)₂, where R* is hydrogen or an aliphatic $C_1$-$C_{12}$ hydrocarbon; and B' is selected from —(C=O)—R*; —CO₂H; —CO₂R*, where R* is hydrogen or an aliphatic $C_1$-$C_{12}$ hydrocarbon; with the proviso that (i) when $R_1$ and $R_3$ are both —CH₂CO₂H, $R_2$ is not —CH₂CO₂H or a straight chained, branched or cyclic aliphatic $C_1$-$C_{12}$ hydrocarbon at all occurrences, or $R_2$ does not have the structure —C[CH₂CO₂H]₃; and (ii)$R_1$ through $R_3$ are not each an unsubstituted $C_1$-$C_8$ hydrocarbon, or a pharmaceutically acceptable salt thereof.

11. A compound according to the following structural formula:

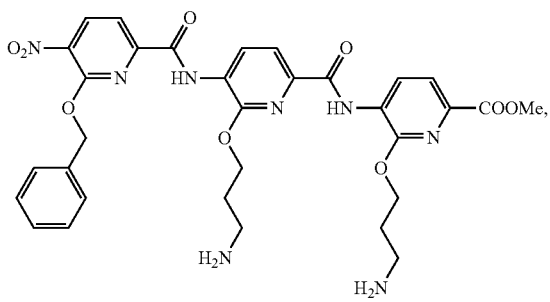 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

12. A compound according to the following structural formula:

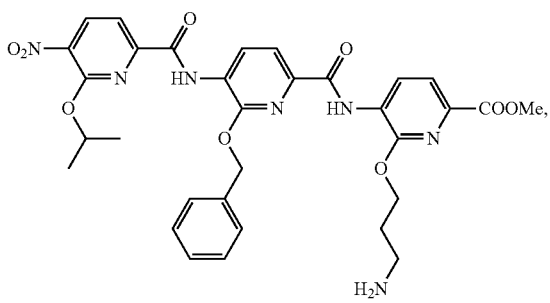

or a pharmaceutically acceptable salt thereof.

13. A compound according to the following structural formula:

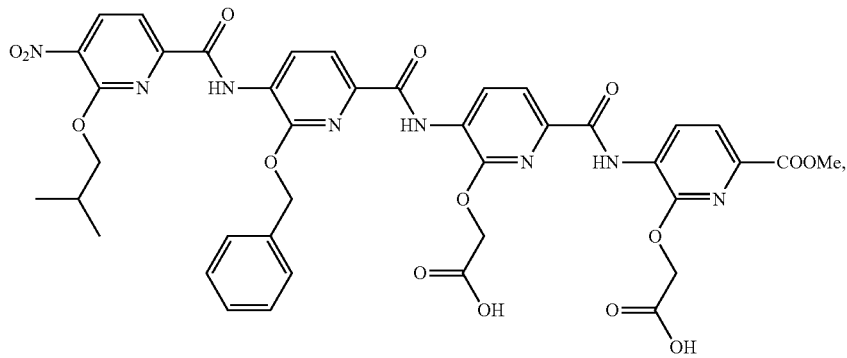 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

14. A pharmaceutical composition comprising the compound of any one of embodiments 1-13 and a pharmaceutically acceptable carrier or excipient.

15. A pharmaceutical composition comprising the compounds of embodiment 11 and embodiment 13 and a pharmaceutically acceptable carrier or excipient.

16. A pharmaceutical dosage form comprising the compound of any one of embodiments 1-13.

17. A method of altering the structure of an amyloidogenic peptide comprising contacting said peptide with an effective amount of the compound of any one of embodiments 1-13.

18. The method of embodiment 17, wherein said amyloidogenic peptide is Aβ, islet amyloid polypeptide (IAPP), or α-synuclein.

19. A method of altering the structure of an Aβ peptide comprising contacting said Aβ peptide with an effective amount of the compound of any one of embodiments 1-13.

20. The method of embodiment 19, wherein said Aβ peptide is Aβ₄₂.

21. A method of modulating oligomerization of an amyloidogenic peptide comprising contacting said peptide with an effective amount of the compound of any one of embodiments 1-13.

22. The method of embodiment 21, wherein said amyloidogenic peptide is selected from Aβ, islet amyloid polypeptide (IAPP), or α-synuclein.

23. The method of embodiment 21 wherein the method of modulating oligomerization of an amyloidogenic peptide comprises inhibiting oligomerization of said amyloidogenic peptide.

24. A method of modulating oligomerization of an Aβ peptide comprising contacting said Aβ with an effective amount of the compound of any one of embodiments 1-13.

25. The method of embodiment 24 wherein the method of modulating oligomerization of an Aβ peptide comprises inhibiting oligomerization of said Aβ peptide.

26. The method of embodiment 24, wherein said Aβ peptide is Aβ₄₂.

27. The method of any one of embodiments 17-26, wherein said contacting is in vivo in a subject.

28. A method of inhibiting cytotoxicity of an amyloidogenic peptide in a subject in need thereof comprising administering to said subject an effective amount of the compound of any one of embodiments 1-13 or the pharmaceutical composition of embodiment 14 or embodiment 15 or the dosage form of embodiment 16.

29. The method of embodiment 28, wherein said amyloidogenic peptide is Aβ, islet amyloid polypeptide (IAPP), α-synuclein, AA amyloid, PrP, $\beta_2$-microglobulin amyloid, transthyretin, prealbumin, or procalcitonin.

30. A method of inhibiting cytotoxicity of Aβ in a subject in need thereof comprising administering to said subject an effective amount of the compound of any one of embodiments 1-13 or the pharmaceutical composition of embodiment 14 or embodiment 15 or the dosage form of embodiment 16.

31. The method of embodiment 30, wherein said Aβ is $A\beta_{42}$.

32. A method of treating a disease in a subject in need of such treatment, wherein the disease is characterized by a formation of Aβ oligomers and/or fibers, comprising administering to said subject an effective amount of the compound of any one of embodiments 1-13 or the pharmaceutical composition of embodiment 12 or embodiment 13 or the dosage form of embodiment 16.

33. The method of embodiment 32, wherein the disease is an amyloid disease.

34. The method of embodiment 32, wherein said disease is Alzheimer's disease, Mild Cognitive Impairment (MCI), Lewy body dementia, inclusion body myositis, or cerebral amyloid angiopathy.

35. The method of any one of embodiments 19, 20, 24-26, and 30-34, wherein said effective amount does not inhibit oligomerization of islet amyloid polypeptide (IAPP).

36. A method of treating a disease in a subject in need of such treatment, wherein the disease is characterized by the formation of amyloidogenic peptide oligomers and/or fibers, comprising administering to said subject an effective amount of the compound of any one of embodiments 1-13, or the pharmaceutical composition of embodiment 14 or embodiment 15, or the dosage form of embodiment 16.

37. The method of embodiment 36, wherein said amyloidogenic peptide is Aβ, islet amyloid polypeptide (IAPP), or α-synuclein.

38. The method of embodiment 36 or 37, wherein said disease is type 1 diabetes, type 2 diabetes, or Parkinson's Disease.

39. A method of treating Alzheimer's disease in a subject in need of such treatment comprising administering to said subject an effective amount of the compound of any one of embodiments 1-13, wherein said compound inhibits oligomerization of an Aβ peptide.

40. A method of treating Alzheimer's disease in a subject in need of such treatment comprising administering to said subject an effective amount of a compound according to the following structural formula:

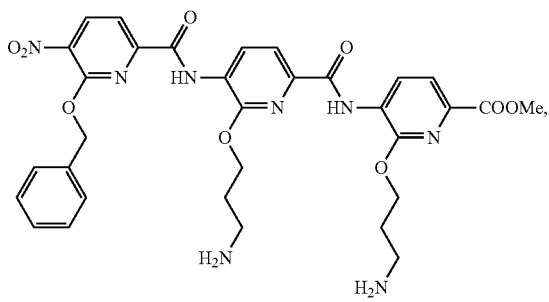 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

41. A method of treating Alzheimer's disease in a subject in need of such treatment comprising administering to said subject an effective amount of a compound according to the following structural formula:

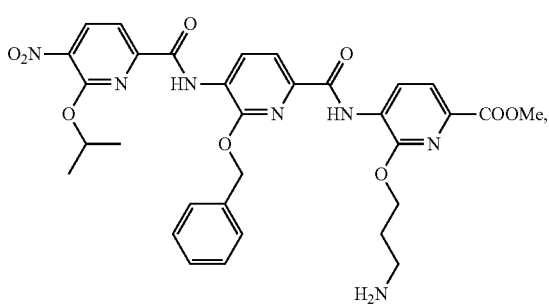 [SMILES: COC(=O)c1ccc(NC(=O)c2ccc(NC(=O)c3ccc([N+](=O)[O-])c(OC(C)C)n3)c(OCc3ccccc3)n2)c(OCCCN)n1]

or a pharmaceutically acceptable salt thereof.

42. A method of treating Alzheimer's disease in a subject in need of such treatment comprising administering to said subject an effective amount of a compound according to the following structural formula:

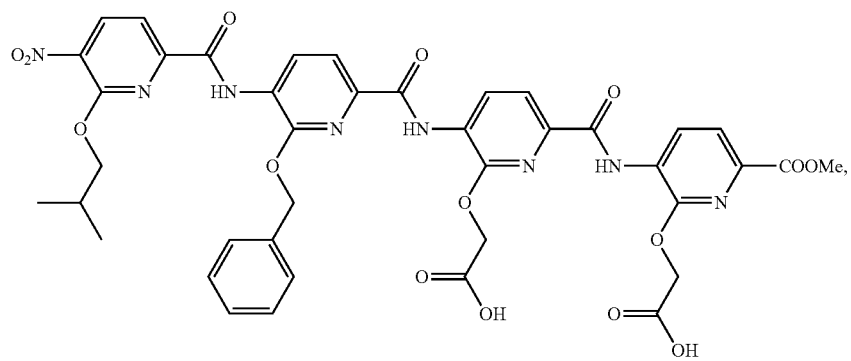 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

43. The method of embodiment 42, further comprising administering to said subject an effective amount of a compound according to the following structural formula:

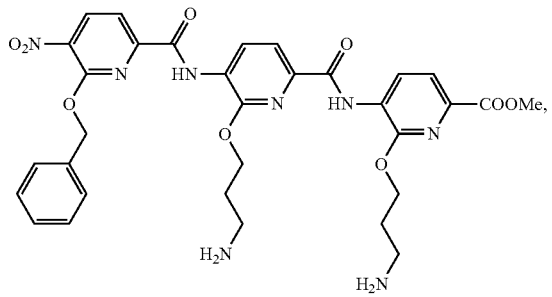 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

44. The method of treating Alzheimer's disease in a subject in need of such treatment comprising administering to said subject an effective amount of the compound of embodiment 5.

45. The method of embodiment 44, further comprising administering to said subject an effective amount of the compound of embodiment 10.

46. The method of any one of embodiments 25-45, wherein the subject is human.

EXAMPLES

The following examples illustrate specific aspects of the instant description. The examples should not be construed as limiting, as the examples merely provide specific understanding and practice of the embodiments and their various aspects.

Materials.

All peptides used in the study (Aβ$_{40}$, Aβ$_{42}$, Aβ$_{12-28}$, and IAPP) were purchased at >98% purity from Anaspec (Fremont, Calif., USA) and used without further purification. $^{15}$N-labeled wild-type human Aβ$_{40}$ was purchased from rPeptide (Bogart, Ga., USA) and used without further purification. ThT was purchased from Acros Organics (N.J., USA). The 96-well plates (black, flat bottom) were purchased from Corning Coster (Corning, N.Y., USA). All chemicals were purchased from commercial suppliers and used without further purification. Silica plates (with UV254, aluminum backed, 200 μm) and silica gel (standard grade, particle size=40-63 μm, 230-400 mesh) for flash column chromatography were purchased from Sorbent Technologies (Norcross, Ga., USA). Dry solvents were purchased from Sigma-Aldrich (St. Louis, Mo., USA). 2,6-Dichloro-3-nitropyridine, alkyl iodides, alkyl alcohols, anhydrous triethylamine, 2-chloro-1-methylpyridinium iodide, tert-butyl bromoacetate, HPLC grade trifluoroacetic acid, and triethylsilane (TES) were purchased from Sigma Aldrich (St. Louis, Mo., USA). Ammonium persulphate, tris (2,2'-bipyridyl) dichlororuthenium (II) hexahydrate, and dithiothreitol were purchased from Sigma Aldrich (St. Louis, Mo., USA). Lipids [dioleoylphosphatidylglycerol (DOPG) and dioleoylphosphatidylcholine (DOPC)] were purchased from Avanti Polar Lipids (Alabster, Ala., USA).

Peptide Preparation. Aβ$_{40}$, Aβ$_{42}$, and IAPP were dissolved in 1,1,1,3,3,3-hexafluoroisopropanol (HFIP) (1 mg/mL) and kept at room temperature for 1 h with occasional vortexing to maintain them in monomeric state. Peptides were then aliquoted into small fractions, lyophilized overnight and stored at −80° C. until use. Peptide concentration was checked by dissolving one of the aliquots in water and measuring absorbance at 280 nm. For solution-based assays, lyophilized samples were allowed to equilibrate at room temperature for 20 min. and then dissolved in pure DMSO (Amresco, Solon, Ohio, USA). The concentration of the stock solution for all the biophysical assays was 0.5-1.0 mM.

Example 1

Compound Synthesis and Characterization

A representative synthetic route for the synthesis of ADH-41 is provided in FIG. 16. ADH-41, a tripyridylamide of the invention, is synthesized from pyridyl precursors via a series of amide coupling reactions alternating with arylamide reduction reactions. The synthetic steps outlined in FIG. 16 are as follows: (a) tert-butyl (3-hydroxypropyl) carbamate, NaH (60% dispersion in mineral oil), toluene (anhydrous), 30 min. at 0° C. and then 4 h at r.t. (b) Tri-n-butyl(vinyl)tin, Pd(PPh3)4, toluene (anhydrous), 110° C., 12 h. (c) KMnO4, NaHCO3, Acetone, r.t., 6 h. (d) MeI, K2CO3, DMF (anhydrous), r.t., 4 h. (e) Pd/C, H2 (g), EtOAc, r.t., 4 h. (f) 2-chloro-1-methylpyridinium iodide, dichloromethane (anhydrous), Et$_3$N (anhydrous), reflux, 5 h. (g) Pd/C, H$_2$ (g), EtOAc, r.t., 10 h. (h) 2-chloro-1-methylpyridinium iodide, dichloromethane (anhydrous), Et3N (anhydrous), reflux, 5 h. (i) dichloromethane/trifluoroacetic acid/triethylsilane (80:15:5, v/v), r.t., 3 h.

A representative synthetic route for the synthesis of ADH-31 is provided in Scheme 1, below. The synthetic steps outlined in Scheme 1 are as follows: (a) 2-chloro-1-methylpyridinium iodide, dichloromethane (anhydrous), Et$_3$N (anhydrous), reflux. (b) Pd/C, H$_2$ (g), EtOAc, r.t., (c) 2-chloro-1-methylpyridinium iodide, dichloromethane (anhydrous), Et$_3$N (anhydrous), reflux. (d) Pd/C, Hz. (e) 2-chloro-1-methylpyridinium iodide, dichloromethane (anhydrous), Et$_3$N (anhydrous), reflux, 5 h. (f) dichloromethane/trifluoroacetic acid/triethylsilane (80:15:5, v/v), r.t.

Scheme 1. Synthetic route for the synthesis of ADH-31.
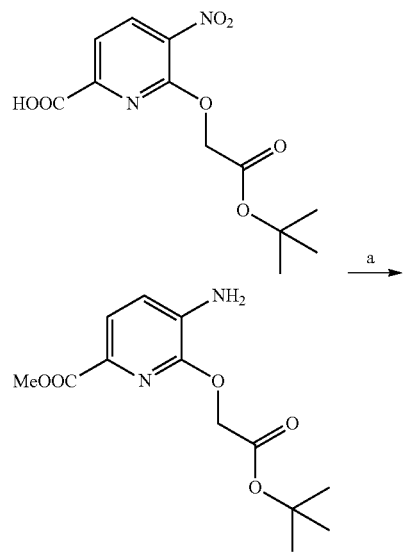
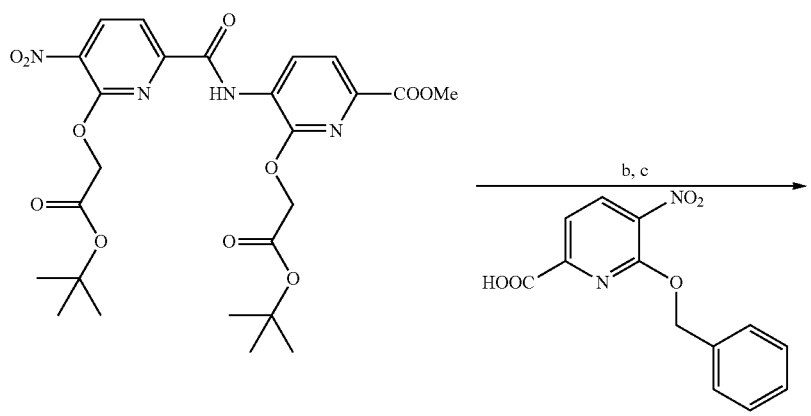
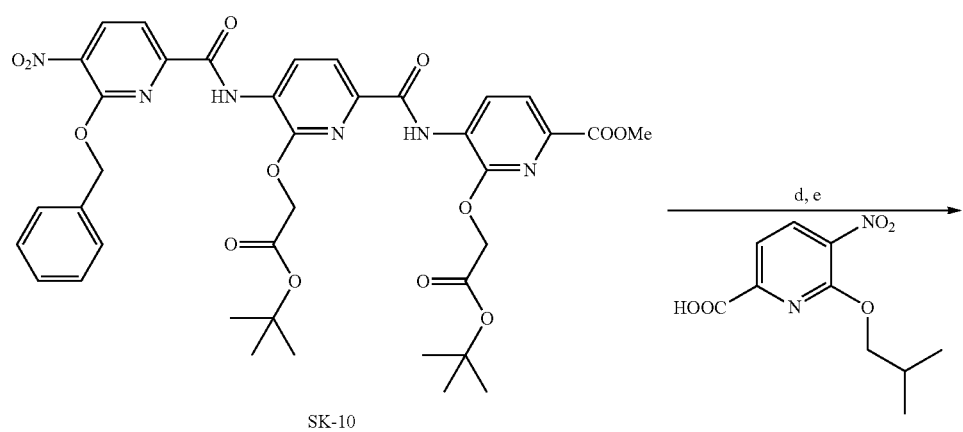
SK-10

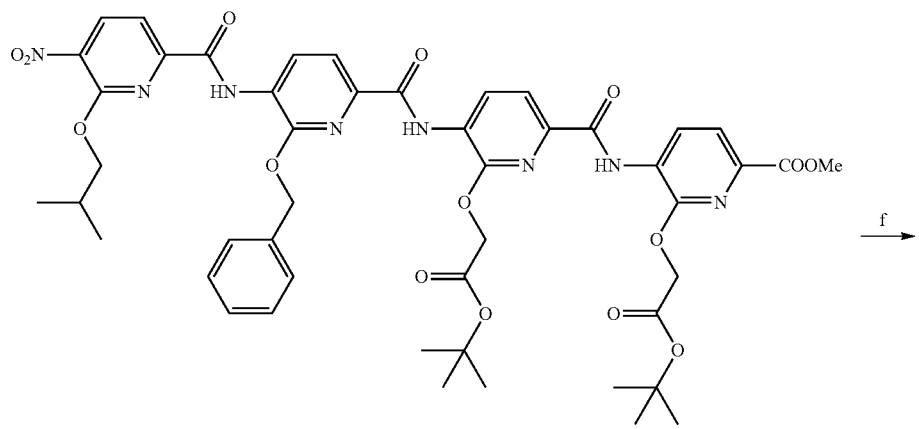

Tert Butyl ADH-31

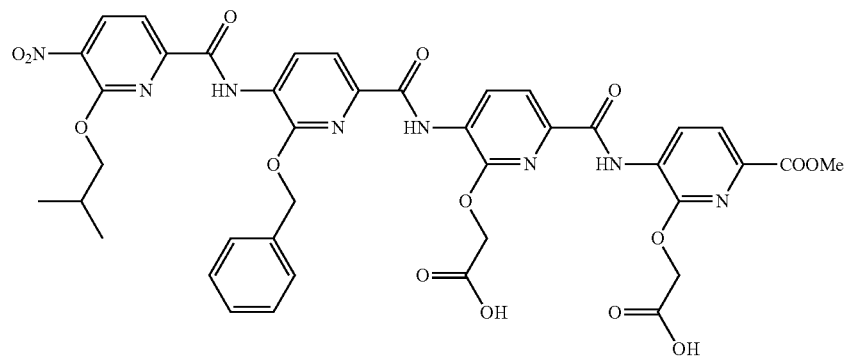

ADH-31

A representative synthetic route for the synthesis of ADH-41$_F$ is provided in Scheme 1, below. The synthetic steps outlined in Scheme 2 are as follows: (a) Pd/C, H$_2$ (g), EtOAc, r.t., 10 h. (b) 1,1'-thiocarbonyldi-2 (1H)-pyridone, dichloromethane, r.t., 6 h. (c) 5-(aminoacetamido) fluorescein, pyridine, DIEA, overnight in dark. (d) dichloromethane/trifluoroacetic acid/triethylsilane, r.t., 4 h.

Scheme 2. Synthetic route for the synthesis of ADH-41$_F$.

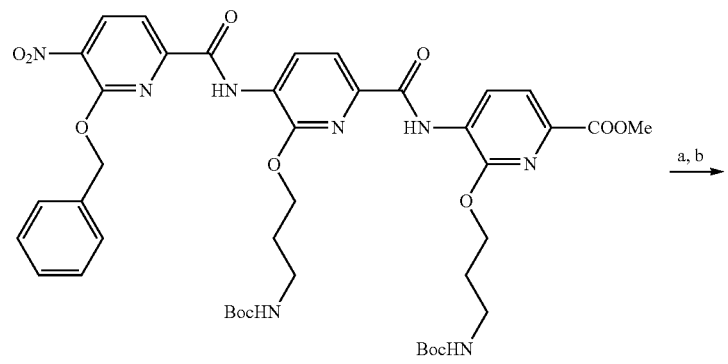

Tert Butyl ADH-41

-continued

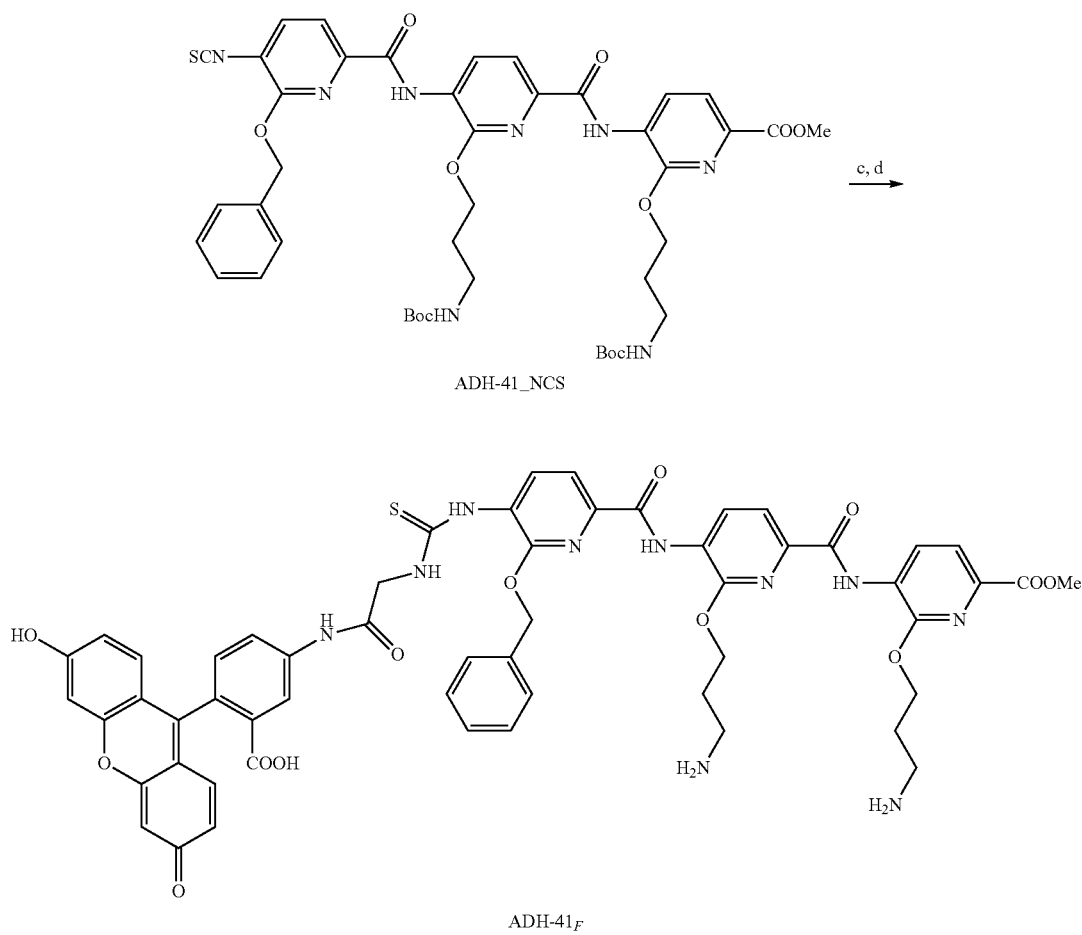

ADH-41_NCS

ADH-41_F

General Method for the Amide Coupling Reaction.

To a solution of 6-(O-substituted)-5-nitropicolinic acid (0.5 mmol) in dichloromethane (10 mL, anhydrous), triethylamine (1 mmol) and 2-chloro-1-methylpyridinium iodide (0.48 mmol) were added and the reaction was stirred for 20 min. at 60° C. 5-amino-6-(O-substituted) picolinic acid (0.4 mmol) in dichloromethane (10 mL, anhydrous) was added and the reaction mixture was stirred at 60° C. for 8 h in the atm. of argon. The volatiles were removed using a rotary evaporator. Column chromatography (0 to 40% ethylacetate in hexane, v/v) afforded the desired product as a yellow solid (see Table 1 for % yield).

TABLE 1

% yield of exemplary compounds according to the invention

| Compound | % yield |
|---|---|
| Helical-5 | 88 |
| Helical-6 | 81 |
| ADH-41 | 80 |
| NHBoc ADH-43 | 89 |
| ADH-43 | 85 |
| ADH-44 | 92 |
| ADH-19 | 84 |
| SK-10 | 89 |
| ADH-31 (for coupling and deprotection) | 78 |
| ADH-37 (for coupling and deprotection) | 81 |

TABLE 1-continued

% yield of exemplary compounds according to the invention

| Compound | % yield |
|---|---|
| ADH-40 (for coupling and deprotection) | 83 |
| ADH-45A (for coupling and deprotection) | 80 |
| ADH-46 (for coupling and deprotection) | 77 |
| ADH-41_NCS | 93 |
| ADH-41_F (for coupling and deprotection) | 68 |

General Method for the Reduction of Arylamides.

To a solution of a nitro arylamide (0.1 mmol) in EtOAc (10 mL) was added Pd/C (10% by wt.). The reaction was stirred constantly in the atmosphere of $H_2$ at room temperature. The progress of the reaction was monitored using thin layer chromatography (TLC). The completion of the reaction was confirmed by the disappearance of the starting material. The reaction mixture was filtered, and the filtrate was dried over a rotary evaporator to afford the desired product as a yellow solid, which is used in subsequent steps without further characterization.

General Method for the Deprotection of Oligopyridylamides

To a solution of the oligopyridylamide (50 μmol) in dichloromethane (5 mL), triethylsilane (250 μL) was added followed by the addition of trifluoroacetic acid (500 μL) and the reaction solution was stirred constantly for 4 h. The reaction solution was dried on a rotary evaporator and washed with cold diethyl ether (3×5 mL), which resulted in a yellow powder.

Example 1A

Synthesis of Helical-1

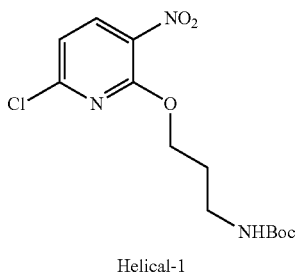 [SMILES: CC(C)(C)OC(=O)NCCCOc1nc(Cl)ccc1[N+](=O)[O-]]

Helical-1

A solution of 2,6-dichloro-3-nitropyridine (10 mmol, 1.91 gm) in toluene (50 mL, anhydrous) was equilibrated at 0° C. for 15 min. followed by the addition of tert-butyl (3-hydroxypropyl)carbamate (12 mmol, 2.1 gm, 1.2 eq.) at 0° C. under the atmosphere of argon. The reaction mixture was stirred at 0° C. for 15 min. after which NaH (60% dispersion in mineral oil, 0.52 gm, 13 mmol, 1.3 eq.) was added portionwise within a time span of 20 min. The reaction mixture was stirred for 30 min. at 0° C. and then at room temperature for 4 h. The completion of the reaction was confirmed by the disappearance of the starting material. The remaining NaH in the reaction mixture was quenched by careful addition of brine solution. The volatiles were removed using a rotary evaporator and the resulting mixture was partitioned between EtOAc and brine solution. The brine solution was extracted with EtOAc two more times. The organic layer was dried over $Na_2SO_4$, filtered, and concentrated. Flash column chromatography (0 to 25% EtOAc in hexane, v/v) afforded the desired product as a pale yellow solid (3.14 gm, 95% yield). $^1$H NMR (600 MHz, Chloroform-d) δ 8.35-8.21 (d, J=8.3 Hz, 1H), 7.09-7.00 (d, J=8.3 Hz, 1H), 5.12-4.99 (s, 1H), 4.62-4.52 (t, J=5.9 Hz, 2H), 3.45-3.24 (q, J=6.2 Hz, 2H), 2.10-1.95 (p, J=6.1 Hz, 2H), 1.47-1.40 (s, 9H). $^{13}$C NMR (151 MHz, CDCl$_3$) δ 156.0, 155.9, 153.0, 137.7, 132.3, 116.7, 79.0, 67.1, 37.9, 28.8, 28.3. MS-ESI (m/z): calculated for $C_{13}H_{18}ClN_3O_5$ (M+H): 332.1, found 332.3.

Example 1B

Synthesis of Helical-2

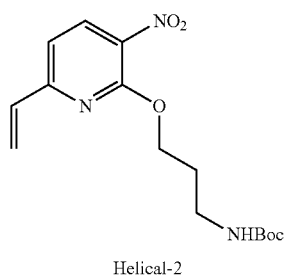 [SMILES: C=Cc1ccc([N+](=O)[O-])c(OCCCNC(=O)OC(C)(C)C)n1]

Helical-2

To a solution of Helical-1 (1.66 gm, 5 mmol) in toluene (anhydrous, 30 mL), tri-n-butyl(vinyl)tin (1.9 mL, 6.5 mmol, 1.3 eq.) was added followed by the addition of Pd(PPh$_3$)$_4$ (117 mg, 2 mol %). The reaction mixture was stirred at 115° C. for 12 h under the atmosphere of argon. After 12 h thin layer chromatography confirmed the completion of the reaction. The reaction mixture was quenched by the addition of 1M KF (40 mL). The mixture was concentrated to ⅓ of the total volume and then partitioned between EtOAc and water (50 mL each). The aqueous layer was then extracted with EtOAc (2×50 mL). The organic portion was dried over $Na_2SO_4$, filtered, and concentrated. Column chromatography afforded the desired product as a pale yellow oil (1.34 gm, 83%). $^1$H NMR (600 MHz, Chloroform-d) δ 8.36-8.22 (d, J=8.1 Hz, 1H), 7.06-6.90 (d, J=8.1 Hz, 1H), 6.83-6.65 (dd, J=17.2, 10.5 Hz, 1H), 6.50-6.33 (d, J=17.2 Hz, 1H), 5.79-5.53 (d, J=10.6 Hz, 1H), 5.32-5.12 (m, 1H), 4.70-4.48 (t, J=5.9 Hz, 2H), 3.49-3.23 (q, J=6.3 Hz, 2H), 2.14-1.96 (p, J=6.0 Hz, 2H), 1.51-1.37 (s, 9H). $^{13}$C NMR (151 MHz, CDCl$_3$) δ 157.8, 156.1, 155.7, 136.2, 134.7, 132.4, 123.0, 114.6, 79.0, 65.9, 38.2, 28.9, 28.4. MS-ESI (m/z): calculated for $C_{15}H_{21}N_3O_5$ (M+H): 324.2, found 324.4.

Example 1C

Synthesis of Helical-3

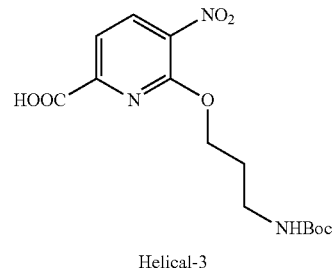 [SMILES: CC(C)(C)OC(=O)NCCCOc1nc(C(=O)O)ccc1[N+](=O)[O-]]

Helical-3

To a solution of Helical-2 (325 mg, 1 mmol) in acetone (10 mL), NaHCO$_3$ (43 mg, 0.5 mmol, 0.5 eq) was added, and the reaction mixture was stirred for 30 min. To this solution, KMnO$_4$ (475 mg, 3 mmol, 3 eq) was added portionwise over a period of 30 min. at r.t. and then stirred for another 6 h. The reaction mixture was quenched with MeOH (1 mL) and H$_2$O (1 mL). The reaction mixture was then partitioned between EtOAc and 1 M HCl. The aqueous layer was further extracted with EtOAc (2×30 mL). The organic layers were combined, dried over Na$_2$SO$_4$, and concentrated using a rotary evaporator. Flash column chromatography (dichloromethane/methanol/acetic acid, 90/9/1, v/v) afforded the desired product as a yellow solid (279 mg, 79%). $^1$H NMR (600 MHz, Chloroform-d) δ 8.52-8.22 (d, J=8.0 Hz, 1H), 8.04-7.82 (d, J=7.9 Hz, 1H), 5.16-4.90 (s, 1H), 4.74-4.62 (t, J=6.0 Hz, 3H), 3.45-3.30 (q, J=6.8 Hz, 3H), 2.15-2.04 (p, J=6.1 Hz, 3H), 1.48-1.41 (s, 9H). MS-ESI (m/z): calculated for $C_{14}H_{19}N_3O_7$ (M+H): 342.1, found 342.3.

Example 1D

Synthesis of Helical-4

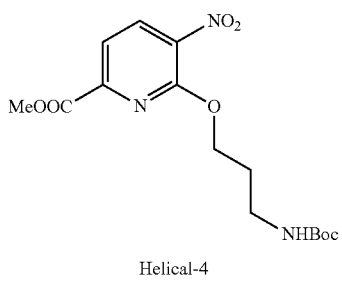 [SMILES: COC(=O)c1ccc([N+](=O)[O-])c(OCCCNC(=O)OC(C)(C)C)n1]

Helical-4

To a solution of Helical-3 (200 mg, 0.6 mmol) in DMF (10 mL), MeI (75 µL, 1.2 mmol, 2 eq) and $K_2CO_3$ (165 mg, 1.2 mmol, 2 eq.) were added, and the reaction was stirred for 5 h at room temperature. The reaction mixture was added to EtOAc/$H_2O$ (30 mL each), and the aqueous layer was extracted with EtOAc (2×30 mL). The organic layers were combined, dried over $Na_2SO_4$, and concentrated to afford the desired product as a yellow solid (160 mg, 76%). $^1$H NMR (400 MHz, Chloroform-d) δ 8.44-8.26 (q, J=6.8 Hz, 1H), 7.96-7.73 (q, J=6.9 Hz, 1H), 5.49-5.27 (s, 1H), 4.81-4.64 (p, J=5.6 Hz, 2H), 4.11-3.98 (t, J=6.0 Hz, 3H), 3.42-3.23 (q, J=6.8, 6.3 Hz, 2H), 2.17-1.97 (p, J=5.9 Hz, 2H), 1.54-1.42 (t, J=6.0 Hz, 9H). $^{13}$C NMR (151 MHz, $CDCl_3$) δ 163.7, 156.1, 155.9, 148.6, 136.1, 135.9, 118.1, 79.1, 66.3, 53.3, 37.7, 28.5. MS-ESI (m/z): calculated for $C_{15}H_{21}N_3O_7$ (M+H): 356.1, found 356.3.

Example 1E

Synthesis of ADH-41—$NH_2$

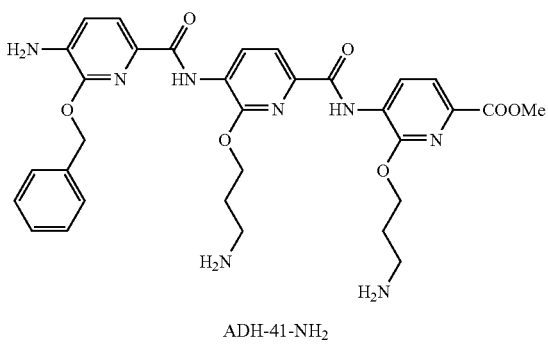 [SMILES: COC(=O)c1ccc(NC(=O)c2ccc(NC(=O)c3ccc(N)c(OCc4ccccc4)n3)c(OCCCN)n2)c(OCCCN)n1]

ADH-41-$NH_2$

To a solution of ADH-41 (0.1 mmol) in EtOAc (10 mL), Pd/C (10% by wt.) was added and the reaction started with constant stirring in the atmosphere of $H_2$ (g) at room temperature. The progress of the reaction was monitored using TLC. The disappearance of the starting material confirms the completion of the reaction (~3 h). The reaction mixture was filtered and the filtrate was dried over rotovap to afford the desired product as a yellow solid (yield=85%), which is used in next step without further characterization.

Example 1F

Synthesis of ADH-41_NCS

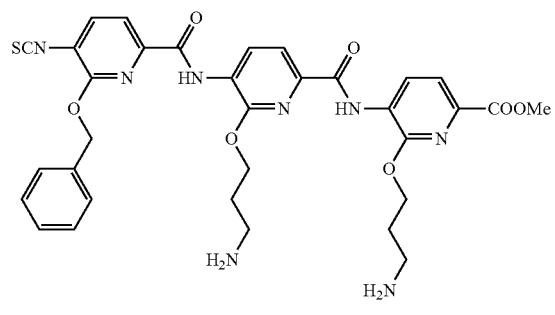

ADH-41_NCS

A solution of ADH-41-$NH_2$ (30 mg, 0.036 mmol) was dissolved in dicholoromethane (anhydrous, 10 mL), followed by the addition of 1,1'-Thiocarbonyldi-2(1H)-pyridone (16.5 mg, 2 equiv). The reaction solution was stirred for 6 h at room temperature under inert atmosphere. The progress of the reaction was monitored by TLC. Flash chromatography (0 to 60% Ethyl acetate in hexane) yielded the desired product as a yellow solid (28.3 mg, 90%). $^1$H NMR (600 MHz, Chloroform-d) δ 10.31-10.29 (s, 1H), 10.29-10.26 (s, 1H), 9.05-8.98 (d, J=8.0 Hz, 1H), 8.94-8.88 (d, J=8.1 Hz, 1H), 8.50-8.45 (d, J=8.0 Hz, 1H), 8.08-8.03 (d, J=7.9 Hz, 1H), 8.02-7.98 (d, J=8.1 Hz, 1H), 7.85-7.81 (d, J=8.0 Hz, 1H), 7.58-7.53 (d, J=7.5 Hz, 2H), 7.48-7.42 (t, J=7.4 Hz, 2H), 7.42-7.37 (t, J=7.4 Hz, 1H), 5.74-5.68 (s, 2H), 4.69-4.64 (t, J=6.4 Hz, 2H), 4.64-4.59 (t, J=6.3 Hz, 2H), 3.98-3.94 (s, 3H), 3.36-3.29 (q, J=9.5, 6.6 Hz, 2H), 3.29-3.23 (m, 2H), 1.76-1.65 (m, 2H), 1.57-1.47 (m, 6H), 1.27-1.26 (m, 9H), 1.26-1.25 (m, 9H). MS-ESI (m/z): calculated for $C_{43}H_{50}N_8O_{11}S$ (M+H): 887.3398, found 887.3389.

Example 1G

Synthesis of Tert Butyl ADH-41$_F$

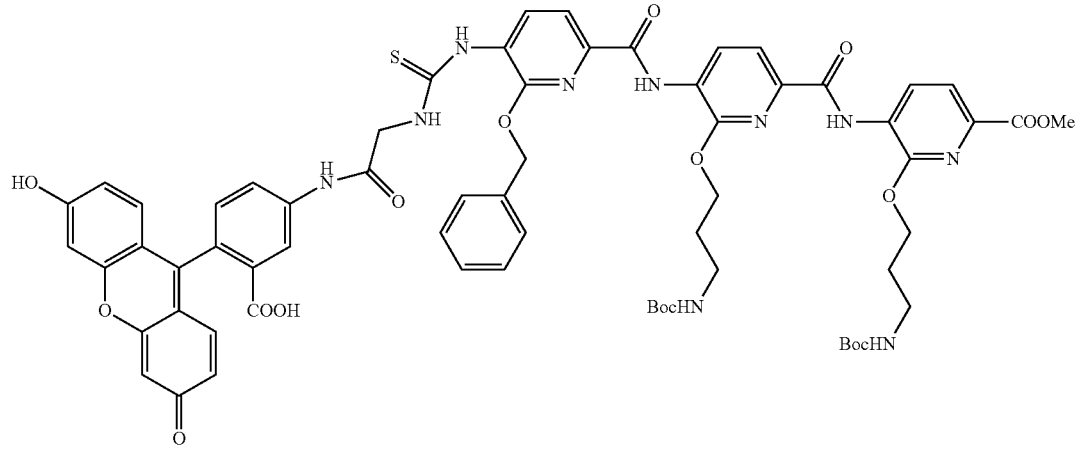

Tert Butyl ADH-41$_F$

To a solution of ADH-41_NCS (25 mg, 0.028 mmol) in pyridine (5 ml, anhydrous), N, N-diisopropylethylamine (0.005 ml, 0.05 mmol) was added and the solution was stirred for 10 min. To this solution, 5-(aminoacetamido) fluorescein (23.1 mg, 0.056 mmol) was added and the reaction was started in dark with continuous stirring under inert atmosphere. The reaction solution was stirred overnight in dark. The product was purified using column chromatography (0-20% methanol in dichloromethane with 1% triethylamine, v/v) as an orange solid (20 mg, 58%). The compound (tert-butyl ADH-41$_F$) was characterized via MALDI-TOF and used in the next step without $^1$H NMR. The $^1$H NMR peaks were very broad potentially because of the stacking of the molecule. We used the compound in the next step without further characterization.

Example 1H

Synthesis of ADH-41$_F$

To a solution of tert-butyl ADH-41$_F$ (16 mg, 0.010 mmol) in dichloromethane (4 ml), triethylsilane (0.1 ml, excess) was added, followed by the addition of trifluoroacetic acid (0.4 ml, excess) and the reaction solution was stirred in dark at room temperature for 4 h. The solution was then dried and the orange solid was washed with cold diethyl ether (3×5 ml), which afforded the desired product (ADH-41$_F$) as an orange solid (13 mg, 72%). $^1$H NMR (600 MHz, DMSO-d$_6$) δ 10.64-10.58 (s, 1H), 10.38-10.35 (s, 1H), 10.29-10.27 (s, 2H), 10.27-10.25 (s, 1H), 9.54-9.52 (s, 1H), 9.05-9.01 (s, 1H), 8.99-8.96 (d, J=8.1 Hz, 1H), 8.94-8.89 (t, J=7.8 Hz, 2H), 8.85-8.80 (dd, J=8.1, 1.9 Hz, 2H), 8.04-8.00 (d, J=7.6 Hz, 1H), 8.00-7.95 (m, 3H), 7.92-7.83 (m, 4H), 6.66-6.63 (d, J=2.2 Hz, 3H), 6.62-6.58 (d, J=8.6 Hz, 3H), 6.57-6.52 (m, 3H), 5.76-5.72 (s, 2H), 4.71-4.65 (t, J=6.1 Hz, 4H), 3.90-3.87 (s, 3H), 3.08-3.01 (q, J=6.3 Hz, 4H), 2.25-2.18 (h, J=6.3 Hz, 4H). MS-ESI (m/z): calculated for $C_{55}H_{50}N_{10}O_{13}S$ (M+H): 1091.3358, found 1091.3347.

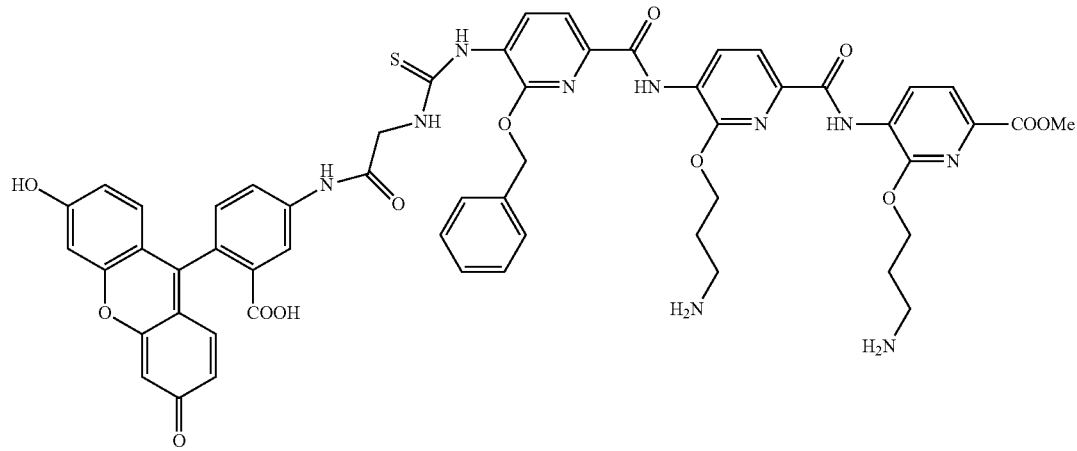

ADH-41$_F$

Example 1I

Characterization Data for Helical-5, Helical-6, ADH-41, and Other Exemplary Compounds and Intermediates According to the Invention

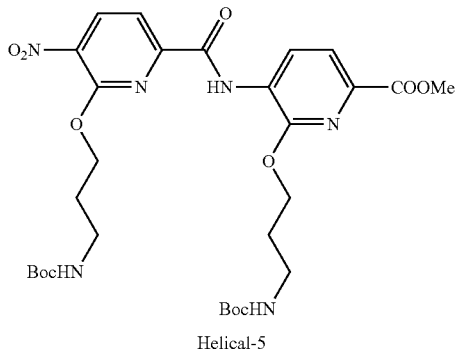 [SMILES: COC(=O)c1ccc(NC(=O)c2ccc([N+](=O)[O-])c(OCCCNC(=O)OC(C)(C)C)n2)c(OCCCNC(=O)OC(C)(C)C)n1]
Helical-5

¹H NMR (600 MHz, Chloroform-d) δ 10.35-10.21 (s, 1H), 8.93-8.82 (d, J=8.1 Hz, 1H), 8.53-8.44 (d, J=8.1 Hz, 1H), 8.09-7.96 (d, J=8.0 Hz, 1H), 7.92-7.83 (d, J=8.1 Hz, 1H), 5.71-5.61 (s, 1H), 5.17-5.08 (m, 1H), 4.74-4.62 (q, J=5.7 Hz, 4H), 4.05-3.97 (s, 3H), 3.44-3.39 (q, J=6.3 Hz, 2H), 3.30-3.22 (q, J=6.4 Hz, 2H), 2.19-2.11 (dq, J=12.4, 6.3, 5.1 Hz, 2H), 2.07-2.01 (q, J=6.7 Hz, 3H), 1.47-1.45 (s, 11H), 1.43-1.39 (s, 9H). MS-ESI (m/z): calculated for C29H40N6O11 (M+H): 649.3, found 649.4.

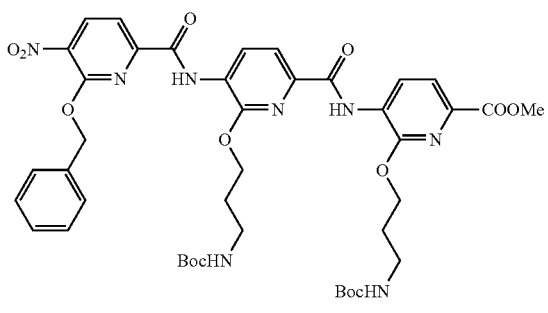
Helical-8

¹H NMR (600 MHz, Chloroform-d) δ 10.33-10.32 (s, 1H), 10.32-10.30 (s, 1H), 9.07-9.02 (d, J=8.1 Hz, 1H), 8.96-8.92 (d, J=8.0 Hz, 1H), 8.53-8.48 (d, J=8.0 Hz, 1H), 8.10-8.07 (d, J=8.0 Hz, 1H), 8.05-8.02 (d, J=8.1 Hz, 1H), 7.89-7.85 (d, J=8.1 Hz, 1H), 7.59-7.56 (m, 2H), 7.49-7.45 (m, 2H), 7.45-7.41 (m, 1H), 5.74-5.72 (s, 2H), 5.67-5.61 (d, J=14.2 Hz, 1H), 4.93-4.83 (s, 1H), 4.73-4.62 (dt, J=19.6, 6.3 Hz, 4H), 4.03-3.96 (s, 3H), 3.38-3.31 (m, 2H), 3.32-3.25 (m, 2H), 2.13-2.03 (m, 5H), 1.49-1.43 (s, 9H). MS-ESI (m/z): calculated for C42H50N8O13 (M+H): 875.4, found 875.4.

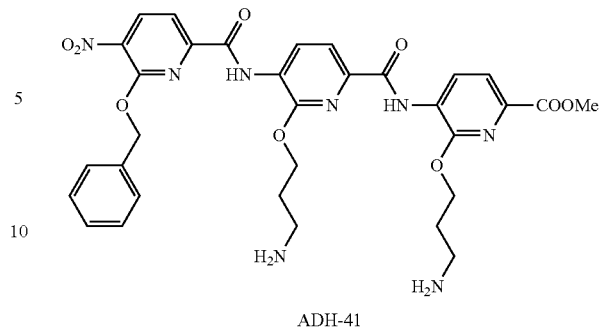
ADH-41

¹H NMR (600 MHz, DMSO-d₆) δ 10.35-10.30 (s, 1H), 10.27-10.24 (s, 1H), 8.84-8.82 (d, J=8.0 Hz, 1H), 8.82-8.79 (d, J=8.1 Hz, 1H), 8.75-8.71 (d, J=8.0 Hz, 1H), 8.01-8.00 (d, J=3.3 Hz, 1H), 8.00-7.97 (d, J=3.2 Hz, 1H), 7.87-7.85 (d, J=8.1 Hz, 1H), 7.61-7.60 (d, J=1.6 Hz, 1H), 7.59-7.58 (d, J=1.0 Hz, 1H), 7.51-7.47 (m, 2H), 7.44-7.41 (m, 1H), 5.78-5.70 (s, 2H), 4.69-4.62 (t, J=5.8 Hz, 2H), 4.62-4.56 (t, J=6.5 Hz, 2H), 3.90-3.85 (s, 3H), 3.08-2.97 (dq, J=19.5, 6.3 Hz, 4H), 2.22-2.09 (dp, J=20.5, 6.7 Hz, 4H). MS-ESI (m/z): calculated for C32H34N8O9 (M+H): 675.2527, found 675.2518. Anal. Calcd for C32H34N8O9: C, 56.97; H, 5.08; N, 16.61; O, 21.34. Found: C, 56.11; H, 5.19; N, 16.41.

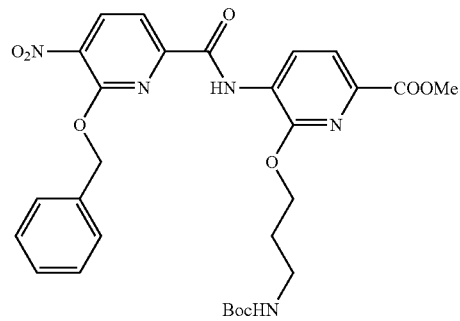
NHBoc ADH-43

¹H NMR (600 MHz, Chloroform-d) δ 10.35-10.31 (s, 1H), 8.96-8.88 (d, J=8.1 Hz, 1H), 8.51-8.44 (d, J=8.0 Hz, 1H), 8.11-8.03 (d, J=8.0 Hz, 1H), 7.94-7.87 (d, J=8.1 Hz, 1H), 7.59-7.53 (m, 2H), 7.46-7.42 (t, J=7.4 Hz, 2H), 7.41-7.38 (dd, J=8.9, 5.8 Hz, 1H), 5.75-5.72 (s, 2H), 4.76-4.68 (t, J=5.8 Hz, 2H), 4.04-4.01 (s, 3H), 3.28-3.19 (q, J=6.3 Hz, 2H), 2.05-1.96 (t, J=6.2 Hz, 2H), 1.50-1.41 (s, 9H). MS-ESI (m/z): calculated for C28H31N5O9 (M+H): 588.2, found 588.2.

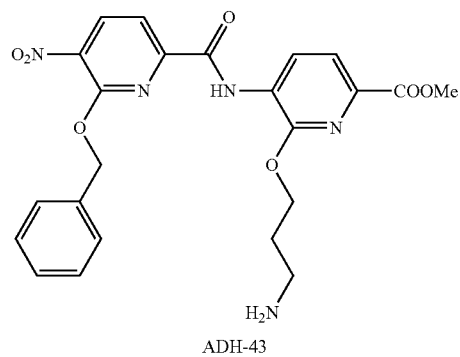 [SMILES: COC(=O)c1ccc(NC(=O)c2ccc([N+](=O)[O-])c(OCc3ccccc3)n2)c(OCCCN)n1 ; "ADH-43"]
ADH-43

¹H NMR (600 MHz, DMSO-d₆) δ 10.33-10.31 (s, 1H), 8.77-8.75 (d, J=8.1 Hz, 1H), 8.75-8.72 (d, J=8.0 Hz, 1H), 8.01-7.99 (d, J=8.0 Hz, 1H), 7.91-7.88 (d, J=8.0 Hz, 2H), 7.59-7.55 (m, 2H), 7.49-7.44 (m, 2H), 7.43-7.39 (m, 1H), 5.75-5.70 (s, 2H), 4.59-4.55 (t, J=6.4 Hz, 3H), 3.90-3.88 (s, 3H), 2.98-2.91 (h, J=6.2 Hz, 2H), 2.12-2.06 (p, J=6.6 Hz, 2H). MS-ESI (m/z): calculated for C23H23N5O7 (M+H): 482.1667, found 482.1678.

¹H NMR (600 MHz, DMSO-d₆) δ 10.30-10.28 (s, 1H), 10.28-10.27 (s, 1H), 8.83-8.81 (d, J=8.1 Hz, 1H), 8.80-8.77 (d, J=8.0 Hz, 1H), 8.77-8.74 (d, J=8.0 Hz, 1H), 8.01-8.00 (d, J=5.0 Hz, 1H), 8.00-7.98 (d, J=4.9 Hz, 1H), 7.91-7.88 (d, J=8.1 Hz, 1H), 4.73-4.69 (t, J=5.6 Hz, 2H), 4.68-4.63 (t, J=6.0 Hz, 2H), 4.63-4.59 (t, J=6.4 Hz, 2H), 3.92-3.86 (s, 3H), 3.09-3.05 (td, J=7.2, 3.5 Hz, 2H), 3.02-2.97 (h, J=5.9 Hz, 4H), 2.23-2.16 (p, J=7.3, 6.9 Hz, 4H), 2.16-2.10 (q, J=6.6 Hz, 2H). MS-ESI (m/z): calculated for C28H35N9O9 (M+H): 642.2636, found 642.2631.

ADH-44

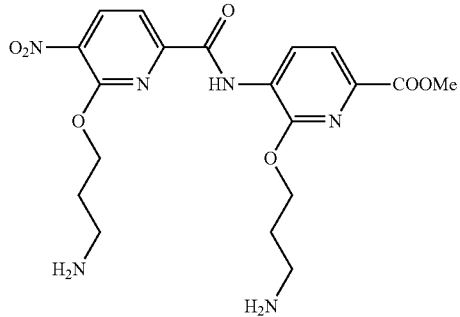

SK-10

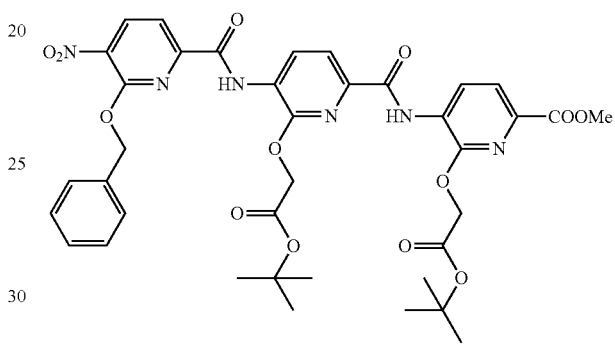

¹H NMR (600 MHz, DMSO-d₆) δ 10.30-10.23 (s, 1H), 8.77-8.75 (d, J=2.1 Hz, 1H), 8.75-8.73 (d, J=2.0 Hz, 1H), 8.03-7.97 (d, J=8.0 Hz, 1H), 7.93-7.86 (d, J=8.1 Hz, 1H), 4.71-4.65 (t, J=5.7 Hz, 2H), 4.61-4.55 (t, J=6.4 Hz, 2H), 3.90-3.87 (s, 3H), 3.09-2.96 (m, 5H), 2.19-2.13 (qd, J=6.9, 5.3 Hz, 2H), 2.13-2.08 (p, J=6.8 Hz, 2H). MS-ESI (m/z): calculated for C19H24N6O7 (M+H): 449.1785, found 449.1780.

ADH-19

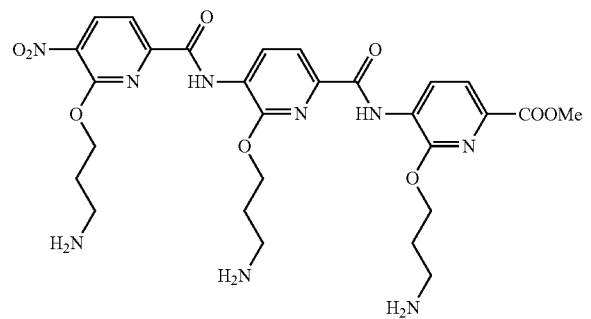

¹H NMR (400 MHz, Chloroform-d) δ 10.40-10.26 (d, J=3.8 Hz, 1H), 10.24-10.10 (d, J=3.7 Hz, 1H), 9.00-8.92 (m, 1H), 8.92-8.85 (d, J=8.2 Hz, 1H), 8.44-8.34 (d, J=8.1 Hz, 1H), 8.03-7.97 (d, J=8.1 Hz, 1H), 7.95-7.89 (d, J=8.1 Hz, 1H), 7.83-7.76 (d, J=8.1 Hz, 1H), 7.50-7.41 (d, J=7.1 Hz, 2H), 7.40-7.25 (m, 3H), 5.64-5.56 (s, 2H), 4.95-4.87 (m, 2H), 4.43-4.32 (m, 2H), 3.89-3.81 (s, 3H), 1.46-1.36 (s, 9H), 1.23-1.11 (s, 9H). MS-ESI (m/z): calculated for C38H41N6O13 (M+H): 789.2732, found 789.2724.

ADH-31

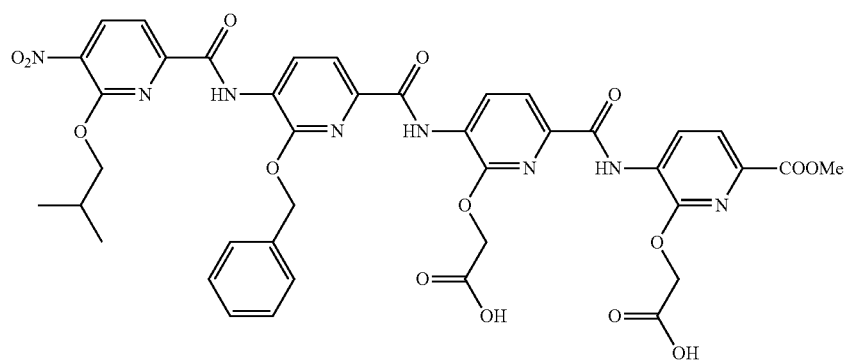

¹H NMR (600 MHz, DMSO-d₆) δ 10.47-10.42 (s, 2H), 10.37-10.35 (s, 1H), 8.97-8.93 (dd, =8.1, 2.3 Hz, 1H), 8.93-8.89 (d, J=8.1 Hz, 1H), 8.85-8.80 (dd, J=8.0, 4.1 Hz, 2H), 8.72-8.68 (dd, J=8.0, 1.5 Hz, 1H), 8.01-7.98 (d, J=8.1 Hz, 1H), 7.98-7.95 (t, J=4.0 Hz, 1H), 7.86-7.83 (d, J=8.2 Hz, 1H), 7.67-7.63 (m, 2H), 7.44-7.40 (t, J=7.6 Hz, 2H), 7.39-7.35 (m, 1H), 5.81-5.78 (s, 2H), 5.25-5.17 (s, 2H), 4.92-4.81 (s, 2H), 4.20-4.15 (d, J=6.0 Hz, 2H), 3.88-3.84 (d, J=2.2 Hz, 3H), 2.03-1.93 (tq, J=12.8, 6.6 Hz, 1H), 0.94-0.91 (dd, J=6.7, 4.2 Hz, 6H). MS-ESI (m/z): calculated for $C_{40}H_{36}N_8O_{15}$ (M+H): 868.2300, found 868.2307. Anal. Calcd for $C_{40}H_{36}N_8O_{15}$: C, 55.30; H, 4.18; N, 12.90; 0, 27.62. Found: C, 55.03; H, 4.30; N, 12.69.

ADH-37

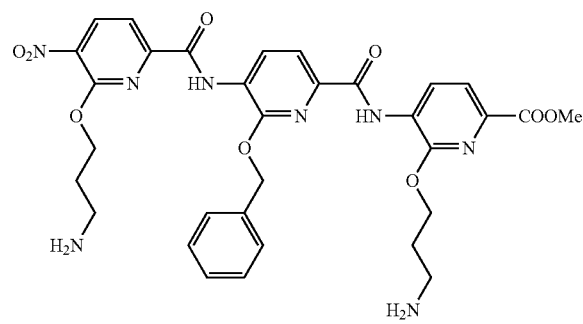

¹H NMR (600 MHz, DMSO-d₆) δ 10.38-10.32 (s, 1H), 10.28-10.23 (s, 1H), 9.00-8.94 (d, J=8.0 Hz, 1H), 8.84-8.78 (d, J=8.1 Hz, 1H), 8.68-8.64 (d, J=8.0 Hz, 1H), 8.04-7.99 (d, J=8.1 Hz, 1H), 7.96-7.91 (d, J=7.9 Hz, 1H), 7.89-7.85 (d, J=8.1 Hz, 1H), 7.75-7.68 (s, 4H), 7.67-7.61 (m, 2H), 7.54-7.40 (m, 3H), 5.70-5.58 (s, 2H), 4.60-4.49 (t, J=6.3 Hz, 2H), 4.21-4.09 (t, J=5.9 Hz, 2H), 3.95-3.79 (s, 3H), 2.98-2.87 (q, J=6.0 Hz, 2H), 2.13-2.02 (p, J=6.6 Hz, 2H), 1.52-1.40 (m, 2H), 1.34-1.26 (m, 2H). MS-ESI (m/z): calculated for $C_{32}H_{34}N_8O_9$ (M+H): 675.2527, found 675.2520. Anal. Calcd for $C_{32}H_{34}N_8O_9$: C, 56.97; H, 5.08; N, 16.61; 0, 21.34. Found: C, 56.22; H, 5.16; N, 16.48.

ADH-40

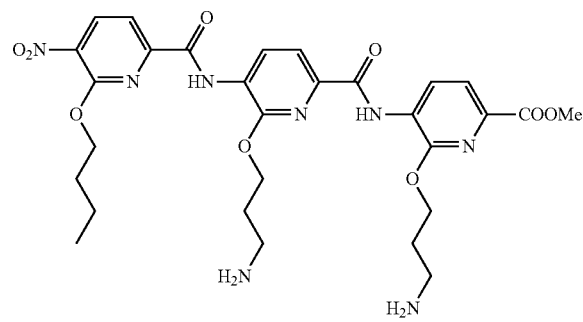

¹H NMR (600 MHz, DMSO-d₆) δ 10.37-10.19 (m, 2H), 8.88-8.84 (d, J=8.0 Hz, 1H), 8.83-8.79 (d, J=8.1 Hz, 1H), 8.72-8.68 (d, J=8.0 Hz, 1H), 8.01-7.98 (d, J=8.0 Hz, 1H), 7.98-7.96 (d, J=8.0 Hz, 1H), 7.90-7.88 (d, J=8.1 Hz, 1H), 7.85-7.75 (br, s, 4H), 4.68-4.63 (q, J=6.4 Hz, 4H), 4.62-4.58 (t, J=6.4 Hz, 2H), 3.91-3.86 (s, 3H), 3.09-2.99 (q, J=6.6 Hz, 4H), 2.21-2.16 (m, 2H), 2.16-2.11 (p, J=6.8 Hz, 2H), 1.92-1.80 (m, 2H), 1.60-1.46 (h, J=7.4 Hz, 2H), 1.05-0.95 (t, J=7.4 Hz, 3H). MS-ESI (m/z): calculated for $C_{29}H_{36}N_8O_9$ (M+H): 641.2683, found 641.2677. Anal. Calcd for $C_{29}H_{36}N_8O_9$: C, 54.37; H, 5.66; N, 17.49; 0, 22.48. Found: C, 54.07; H, 5.73; N, 17.31.

ADH-45A

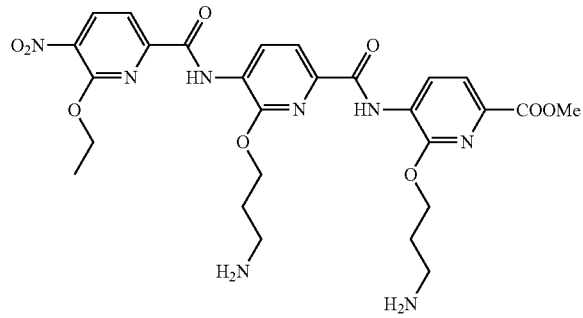

¹H NMR (600 MHz, DMSO-d₆) δ 10.21-10.19 (d, J=5.8 Hz, 2H), 8.87-8.84 (d, J=8.0 Hz, 1H), 8.80-8.77 (d, J=8.0 Hz, 1H), 8.68-8.66 (d, J=8.0 Hz, 1H), 7.99-7.97 (d, J=8.0 Hz, 1H), 7.95-7.91 (m, 5H), 7.84-7.82 (d, J=8.1 Hz, 1H), 4.64-4.60 (q, J=5.7 Hz, 4H), 4.60-4.57 (t, J=6.5 Hz, 2H), 3.91-3.83 (s, 3H), 3.09-3.02 (t, J=6.4 Hz, 4H), 2.24-2.11 (dp, J=23.5, 6.7 Hz, 4H), 0.93-0.88 (t, J=7.0 Hz, 3H). MS-ESI (m/z): calculated for $C_{27}H_{32}N_8O_9$ (M+H): 613.2370, found 613.2366. Anal. Calcd for $C_{27}H_{32}N_8O_9$: C, 52.94; H, 5.27; N, 18.29; O, 23.50; O, 21.34. Found: C, 52.73; H, 5.33; N, 18.07.

ADH-46

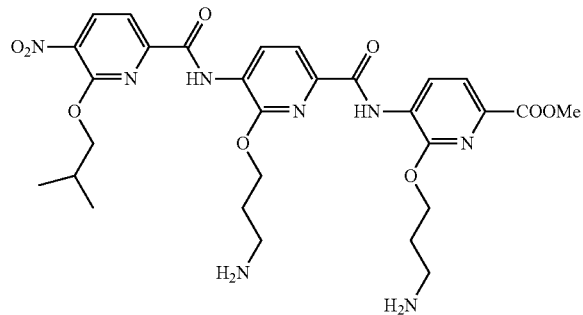

¹H NMR (600 MHz, DMSO-d₆) δ 10.21-10.18 (s, 1H), 10.16-10.14 (s, 1H), 8.85-8.80 (d, J=8.1 Hz, 1H), 8.81-8.77 (d, J=8.0 Hz, 1H), 8.72-8.69 (d, J=8.0 Hz, 1H), 7.99-7.94 (dd, J=9.7, 8.0 Hz, 2H), 7.93-7.87 (br, 4H), 7.82-7.79 (d, J=8.0 Hz, 1H), 4.69-4.64 (t, J=5.6 Hz, 2H), 4.64-4.60 (t, J=6.1 Hz, 2H), 4.26-4.22 (d, J=6.7 Hz, 2H), 3.85-3.82 (s, 3H), 3.08-2.99 (dq, J=12.2, 6.0, 5.4 Hz, 4H), 2.19-2.10 (m, 4H), 2.09-1.99 (m, 1H), 1.07-1.06 (d, J=1.8 Hz, 3H), 1.06-1.05 (d, J=1.6 Hz, 3H). MS-ESI (m/z): calculated for $C_{29}H_{36}N_8O_9$ (M+H): 641.2683, found 641.2680. Anal. Calcd for $C_{29}H_{36}N_8O_9$: C, 54.37; H, 5.66; N, 17.49; 0, 22.48. Found: C, 54.14; H, 5.72; N, 17.33.

Example 2

ThT-Based Kinetic Assays

The aggregation of Aβ₄₂ was monitored using an established exogenous dye, Thioflavin T (ThT) that intercalates between the amyloid fibers along the perpendicular axis without affecting the kinetics of amyloid formation. (see Wolfe, L. S.; Calabrese, M. F.; Nath, A.; Blaho, D. V.; Miranker, A. D.; Xiong, Y. Proc. Natl. Acad. Sci. U.S.A. 2010, 107, 16863-16868; Levine, H. Protein Sci. 1993, 2, 404-410). A representative ThT-based kinetic assay results are depicted in FIG. 2. The oligomerization reaction of $A\beta_{42}$ was initiated by diluting a 1 mM stock solution of $A\beta_{42}$ (in DMSO) to a concentration of 20 µM in phosphate buffer (150 mM KCl, 50 mM NaPi, pH 7.4). $A\beta_{42}$ fibrillation is a nucleation-dependent polymerization process and is characterized by a sigmoidal curve consisting of a lag phase, an elongation phase, and a plateau phase (FIG. 2a). The kinetic reaction was quantified by extracting $t_{50}$, which is the time required to reach 50% of the maximum fluorescence that results from fibrillation. Under standard conditions the tso for $A\beta_{42}$ fibrillation was 2.1±0.2 h (FIG. 2a and FIG. 8).

Kinetic assays were conducted on a FlexStation 3 Multi-Mode Microplate reader from Molecular Devices (Sunnyvale, Calif., USA). Experiments were conducted in triplicate in a 96-well plate with a final volume of 200 µL per well. Every measurement was an average of 50 readings. The aggregation of an amyloidogenic peptide ($A\beta_{40}$, $A\beta_{42}$, or IAPP) was initiated by the addition of the peptide from a stock solution (in DMSO, 0.5-1 mM) to phosphate buffer. The final concentration of each peptide was different based on their aggregation. The stoichiometry of ThT dye for each peptide was 0.5:1 (ThT:peptide). Peptide aggregation was monitored by ThT fluorescence ($\lambda_{ex}$=445 nm and $\lambda_{em}$=485 nm). The blank sample contained all the components of the peptide samples except the peptide. The sample data were processed by subtracting the fluorescence of the blank sample. The fluorescence intensity data was then normalized by setting the maximum value to 1.

Kinetic assays in the presence of the compounds of the invention were conducted under the same conditions. The small molecules were added from a stock solution (1 mM or 10 mM in DMSO) to keep the final concentration of DMSO less than 1.0% (v/v). Small molecules were added to the wells with ThT and buffer and mixed gently with a pipette before adding the peptide. To keep the conditions identical, an equal amount of DMSO was added to the wells with the peptide-only control reactions.

Kinetic profiles were processed using Origin (version 9.1). Kinetic curves were fit using the built-in sigmoidal fit. Each run was fit independently to extract the $t_{50}$ (time required to reach 50% of the maximum fluorescence intensity). Error bars represent standard deviations from the mean of at least three independent experiments.

FIG. 2 shows the effect of the compounds of the invention on the aggregation of $A\beta_{42}$. FIG. 2a shows a graph of the relative fluorescence intensity versus time for the kinetics of $A\beta_{42}$ fibrillation in the absence and presence of the indicated compounds at an equimolar ratio. FIG. 2b shows the rel. $t_{50}$ values (time required to reach 50% ThT fluorescence) for the kinetics of 20 µM $A\beta_{42}$ fibrillation in the absence and presence of the indicated compounds at an equimolar ratio. FIG. 2c shows the chemical structures of the indicated compounds used in this ThT kinetic assay. FIG. 2d depicts representative kinetic profiles of 20 µM $A\beta_{42}$ fibrillation in the absence and presence of ADH-41 at indicated concentrations. FIG. 2e shows the relative change in the fluorescence intensity of the aggregation of $A\beta_{42}$ fibrils in the presence of various concentrations of ADH-41. The error bars for the kinetic assays represent the standard deviation from the mean for three independent experiments. [ThT]=10 µM. Buffer: 150 mM KCl, 50 mM NaPi, pH 7.4.

Figure 8B:
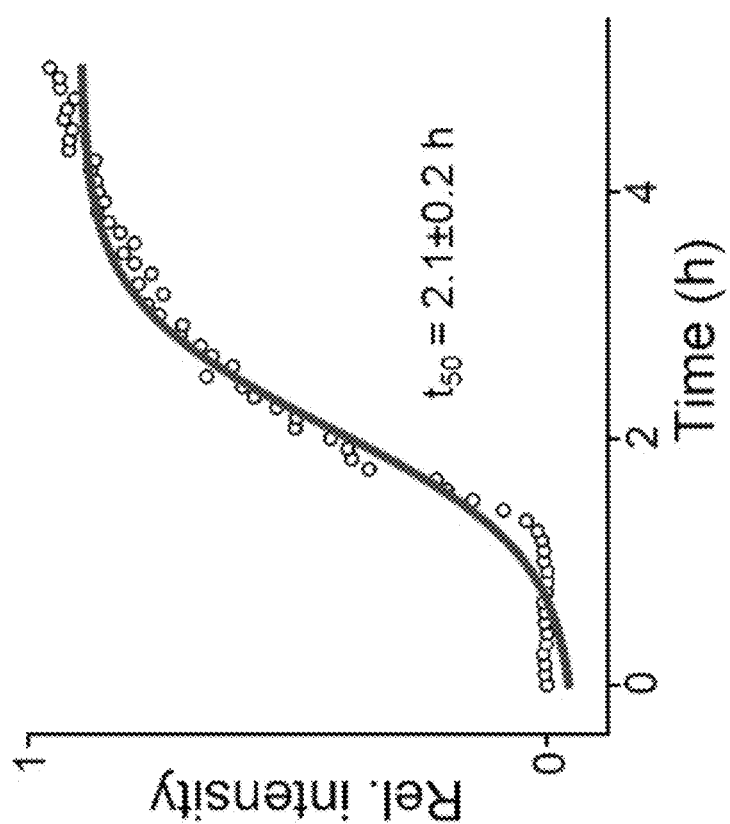
FIGS. 8a and 8b illustrate aggregation data of $Aβ_{42}$.
Figure 8A:
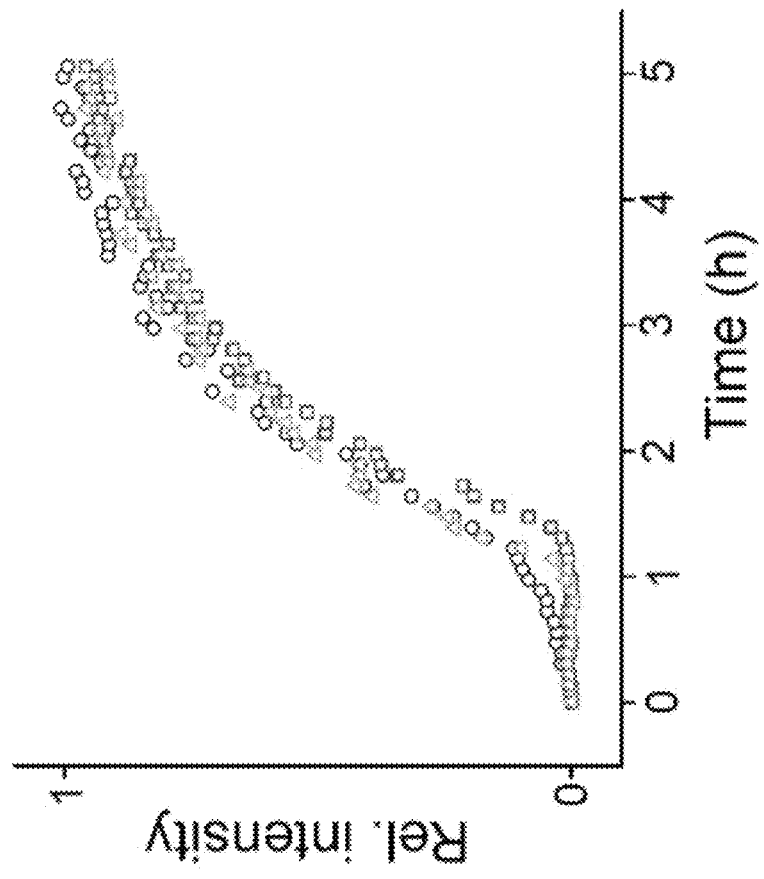

FIG. 8a shows the normalized profiles of three independent readings of the aggregation of 20 µM $A\beta_{42}$ in phosphate buffer depicted in FIG. 2. FIG. 8b shows a sigmoidal fit to extract the $t_{50}$ of one of the traces presented in FIG. 8a.

As can be seen from the ThT-based kinetic assays depicted by FIGS. 2 and 8, ADH-41 effectively blocks aggregation and/or fibrillation of $A\beta_{42}$ even at substoichiometric concentrations. Other compounds according to the invention (e.g., ADH-19 and ADH-43) were also found effective in blocking oligomerization and/or fibrillation of $A\beta_{42}$ at equimolar concentrations.

Example 3

Seed-Catalyzed Kinetic Assay

Seeds of $A\beta_{40}/A\beta_{42}$ were prepared by incubating 200 µM of $A\beta_{40}/A\beta_{42}$ in phosphate buffer at room temperature. The samples were aged for 48 h and the formation of fibers was confirmed by TEM and ThT before storage at −20° C. until use. For the aggregation of $A\beta_{40}$, 10% (based on the monomeric $A\beta_{40}$, v/v) seeds were added along with ThT in phosphate buffer to the 96-well plate. The aggregation was initiated by the addition of monomeric $A\beta_{40}$ followed by gentle mixing. The process was similar in the case of $A\beta_{42}$ except that the seed concentration was 5% (based on the monomeric $A\beta_{42}$, v/v).

The results of the seed-catalyzed aggregation of Aβ in the absence and presence of ADH-41 study are shown in FIG. 6. Seed-catalyzed aggregation of 20 µM $A\beta_{40}$ (FIG. 6a) and 20 µM $A\beta_{42}$ (FIG. 6b) in the absence and presence of ADH-41 at an equimolar ratio. FIGS. 6c and 6d show TEM images of the seed-catalyzed fibrillation reaction of 20 µM $A\beta_{42}$ in the absence (FIG. c) and presence (FIG. d) of ADH-41 at an equimolar ratio after 24 h. The seeds were generated by aging 200 µM Aβ peptides for 48 h in phosphate buffer with occasional vortexing. The concentration of seeds was calculated based on the monomeric concentration of Aβ.

Figure 6B:
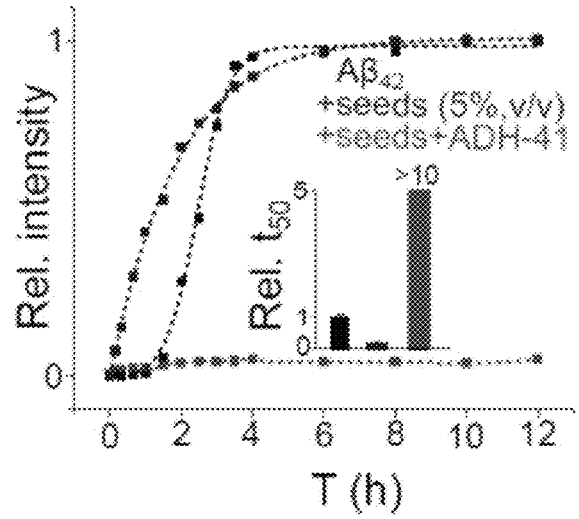
Figure 6C:
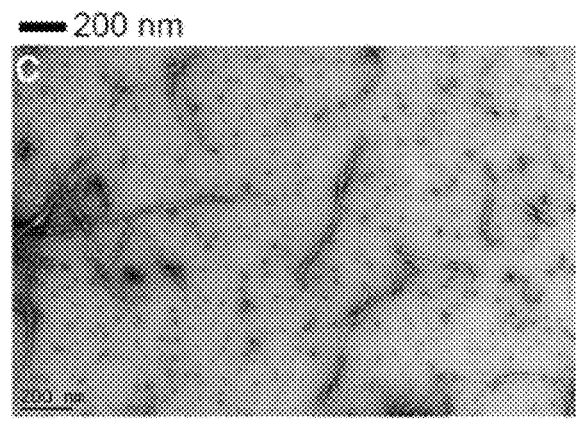
Figure 6D:
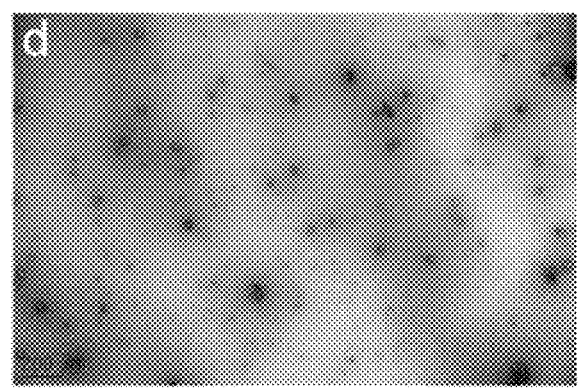
Figure 15:
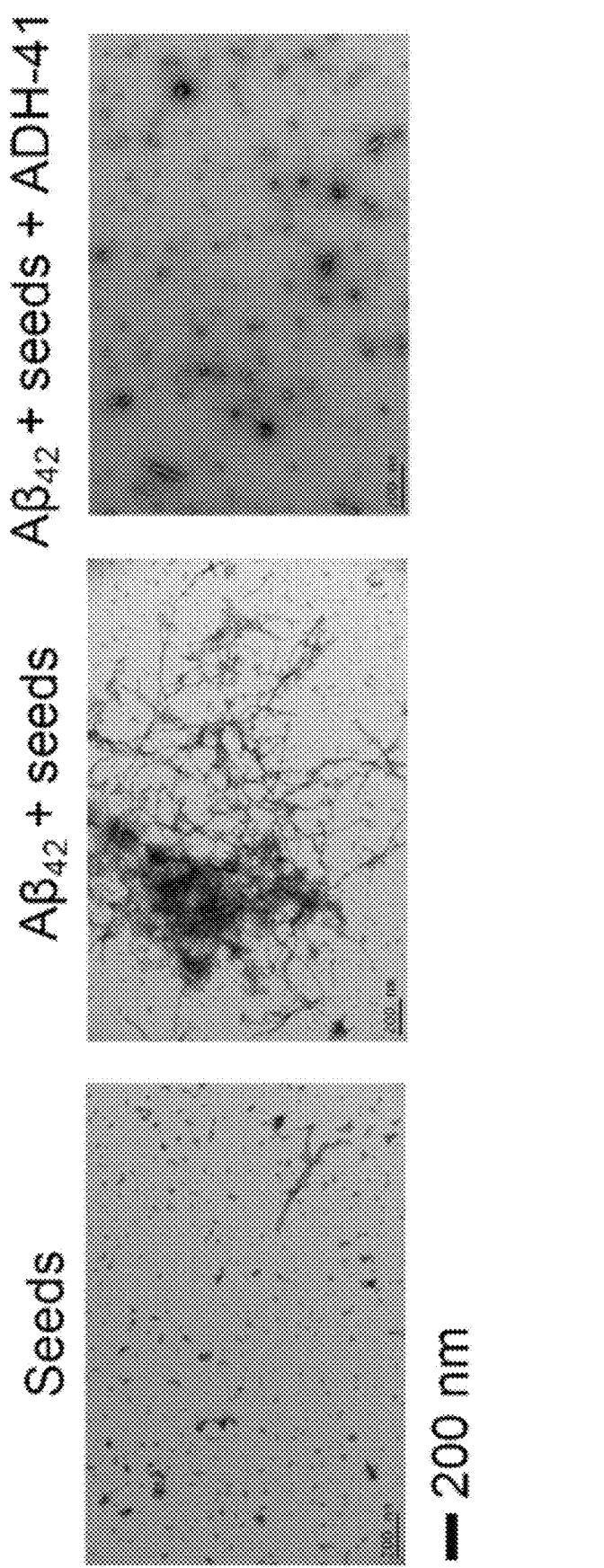
FIG. 15 shows TEM images of the seed-catalyzed fibrillation of 20 µM $A\beta_{42}$ in the absence and presence of ADH-41 at an equimolar ratio after 48 h. The arrows highlight the formation of circular aggregates in the presence of ADH-41.

Fibers of Aβ can promote fibrillation by serving as seeds of elongation and secondary nucleation (Harper, J. D.; Lansbury, P. T. Annu. Rev. Biochem. 1997, 66, 385-407; Harper, J. D.; Lieber, C. M.; Lansbury, P. T. Chem. Biol. 1997, 4, 951-959). In the presence of preformed fibers of $A\beta_{40}$ (10%, v/v), the aggregation of 20 µM $A\beta_{40}$ was dominated by the elongation process which eliminated the lag phase. (FIG. 6a). The aggregation of 20 µM $A\beta_{40}$ yielded a sigmoidal curve with a $t_{50}$ of 38.2±3.2 h which is reduced to 23.8±4.8 h in the presence of seeds (10%, v,v) (FIG. 6a). Under matched conditions, the aggregation for de novo and seed-catalyzed reactions was faster for $A\beta_{42}$ than $A\beta_{40}$ showing a reduction from 2.2±0.2 h to 0.4±0.1 h (FIG. 6b). The kinetics of seed-catalyzed $A\beta_{40}$ and $A\beta_{42}$ fibrillation was completely arrested in the presence of ADH-41 at an equimolar ratio (FIG. 6a). The TEM image of seed-catalyzed $A\beta_{42}$ aggregation displayed an abundance of fibers after 24 h that are a mixture of preexisting fibers (seeds) which are comparatively smaller in size (FIG. 15), and elongated fibers generated from freshly added $A\beta_{42}$ (FIG. 6c). In contrast, no elongated fibers were observed in the presence of ADH-41 at an equimolar ratio even after 24 h (FIG. 6d).

It can be concluded that ADH-41 completely inhibits the seed-catalyzed aggregation of Aβ. It is postulated that ADH-41 binds to the monomeric Aβ and generates alternative, off-pathway structures.

Example 4

Preparation of Large Unilamellar Vesicles (LUVs)

LUVs were prepared using an equimolar ratio of dioleoyl-phosphatidylglycerol (DOPG) and dioleoylphosphatidyl-choline (DOPC). A solution of DOPG and DOPC (10 mg/mL each) in chloroform was mixed, dried over a stream of argon (g) for 1 h, and then lyophilized for 6 h ($0.1 \times 10^{-3}$ bar). The solid was then rehydrated in 1 mL phosphate buffer for 30 min. The turbid solution (10 mg/mL, 1:1, DOPG:DOPC) was then extruded (21 times) through 100 nm diameter filters (Whatman, GE Healthcare, Marlborough, Mass., USA). The concentration of the phospholipid content in the extruded material was confirmed by calculating total phosphorus using total phosphate assay as described in Chen, P. S.; Toribara, T. Y.; Warner, H. *Anal. Chem.* 1956, 28, 1756-1758.

Figure 13B:
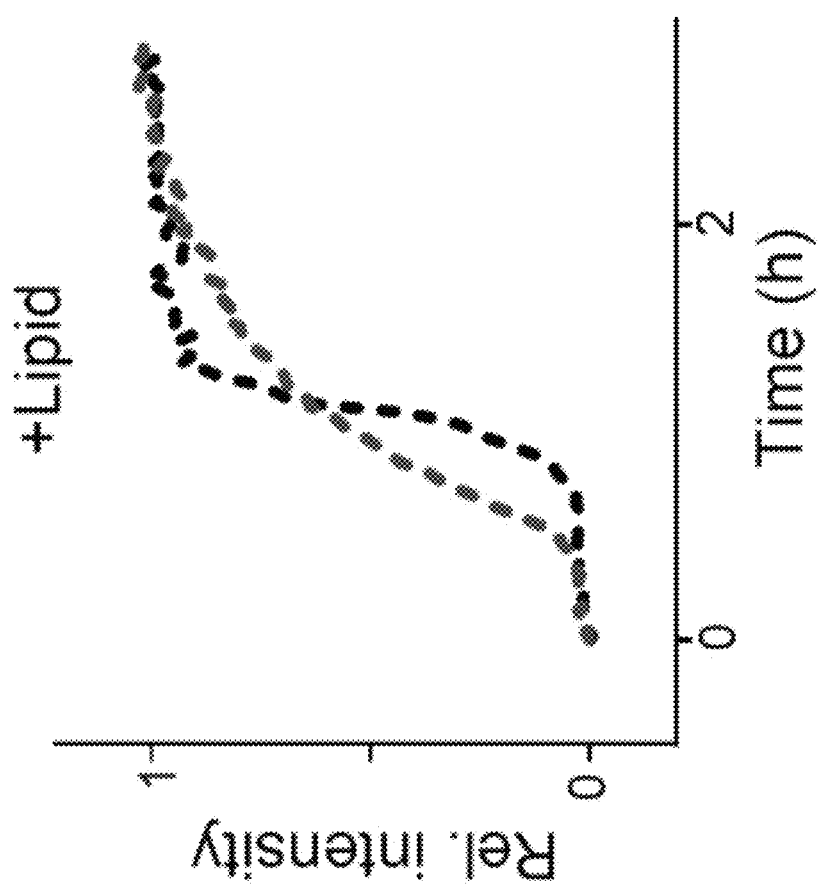
FIGS. 13a-13b demonstrate the effect of ADH-41 on the kinetics of IAPP fibrillation.

The effect of the α-helical mimetics was also assessed on the membrane associated α-helical conformation of IAPP. In the presence of large unilameller vesicles (LUVs, DOPG:DOPC, 1:1, 600 μM, d=100 nm), the aggregation of 10 μM IAPP resulted in a sigmoidal curve with a $t_{50}$ of 1.2±0.2 h (FIG. 3b and FIG. 13b). The rel. $t_{50}$ of IAPP fibrillation was 0.8±0.2 in the presence of ADH-41 at an equimolar ratio (FIG. 3b and FIG. 13b). These results suggest that ADH-41 shows structure specificity in its antagonism and/or inhibition of Aβ oligomerization and/or fibrillation.

Example 5

Transmission Electron Microscopy (TEM) Analysis $Aβ_{42}$ (5 μM) was incubated in phosphate buffer in the absence and presence of the compounds of the invention at various time intervals and stoichiometric ratios. Aliquots of these samples were then applied to glow-discharged carbon-coated 300-mesh copper grids for 2 min and dried. Grids were negatively stained with uranyl acetate (2%, w/v) and dried. Micrographs of grids were examined on a Phillips CM12 Cryoelectron Microscope equipped with Gatan 4k×2.7k CCD camera at 120-kV accelerating voltage.

The anti-amyloidogenic activity of ADH-41 was validated using transmission electron microscopy (TEM). Samples of 5 μM $Aβ_{42}$ were aged at different time intervals (4 h and 24 h) in the absence and presence of ADH-41 at various molar ratios (0.1-1.0, ADH-41:$Aβ_{42}$) (FIG. 4d-4i). Formation of spherical aggregates of $Aβ_{42}$ was visible after 4 h of incubation (FIG. 4d). The spherical aggregates eventually converted into extensive fibers after 24 h (FIG. 4e). In marked contrast, no formation of oligomers/fibers was observed for $Aβ_{42}$ in the presence of ADH-41 even after 2 days (FIG. 4f-4i) at stoichiometric ratios of 1:1 or 1:0.5 ($Aβ_{42}$:ADH-41). However, incubating $Aβ_{42}$ with ADH-41 for 24 h at a stoichiometric ratio of 1:0.1 ($Aβ_{42}$:ADH-41) resulted in a sparse population of fibers (FIG. 4h).

TEM images of $Aβ_{40}$ incubated with ADH-41 show scant evidence of fiber formation even after 5 days (FIG. 12). No aggregates were visible in the presence of ADH-41 at an equimolar ratio, though short protofibrils of $Aβ_{40}$ were present at substoichiometric ratios (1:0.1, $Aβ_{40}$: ADH-41). The fluorescence intensity of the kinetic reaction of Aβ ($Aβ_{40}$ and $Aβ_{42}$) was decreased significantly in the presence of ADH-41 (FIG. 3b). Taken together these results suggest that ADH-41 not only manipulates the kinetic pathways of Aβ but also alters the morphology of amyloid fibers which are not ThT sensitive.

Example 6

Circular Dichroism (CD) Spectroscopy

A freshly prepared stock solution of $Aβ_{42}$ (500 μM) was diluted to 15 μM in phosphate buffer for CD measurements. The spectra of $Aβ_{42}$ in the absence and presence of the compounds of the invention were recorded at 0.5 nm intervals from 190 to 260 nm with an averaging time of 10 sec. and an average of three repeats on a Aviv Stopped Flow CD Spectropolarimeter (Model 202SF). In the presence of ADH-41, $Aβ_{42}$ was diluted in the solution of ADH-41 in phosphate buffer at an equimolar ratio. The CD spectra of 15 μM $Aβ_{12-28}$ were recorded in the absence and presence of ADH-41 at an equimolar ratio in 20% TFE, v/v in 150 mM KCl, 50 mM NaPi, pH 7.4.

$Aβ_{12-28}$, a well-characterized subdomain of $Aβ_{42}$ that contains the α-helical region, was used for CD spectroscopy (Nerelius, C.; Sandegren, A.; Sargsyan, H.; Raunak, R.; Leijonmarck, H.; Chatterjee, U.; Fisahn, A.; Imarisio, S.; Lomas, D. A.; Crowther, D. C.; Stromberg, R.; Johansson, J. *Proc.. Natl. Acad. Sci. U.S.A.* 2009, 106, 9191-9196). The far UV-CD spectrum of 25 μM $Aβ_{12-28}$ suggests a weak α-helical character for the peptide in the presence of 20% TFE (v/v) characterized by two minima at ~208 and ~222 nm (FIG. 5a, black dot). A strong α-helical conformation emerged in the presence of ADH-41 at an equimolar ratio (FIG. 5a, red dot). The far UV-CD spectrum of a freshly incubated sample of 15 μM $Aβ_{42}$ showed a random coil state, which transitioned to a β-sheet-rich structure in 12 h (FIG. 5b). No formation of β-sheet structure was observed in the presence of ADH-41 even after 24 h at an equimolar ratio (FIG. 5c). Instead a stable α-helical structure appears to be present.

CD data suggest a conformation transition in $Aβ_{40}$ from a random coil to an α-helical in the presence of ADH-31. $Aβ_{40}$ has the tendency to undergo a transition from a weakly folded state to an α-helix conformation from residues 13-24 and 28-36 in the presence of a cationic oligopyridylamide ADH-41. However, surprisingly, the binding site of the cationic oligopyridylamide ADH-41 is different than that is for the anionic oligopyridylamide ADH-31. This is unprecedented that two molecules with similar scaffold interact with different domains of Aβ and inhibit aggregation and oligomerization.

Example 7

Ultraviolet-Visible (UV-Vis) Spectroscopy

UV-Vis was employed to probe the chemical aggregation of ADH-41 under kinetic assay conditions. The measurements were carried out on a double beam Carry 100 Bio spectrophotometer (Agilent Technologies, Santa Clara, Calif.) controlled by Cary WinUV software (version=3.0). A stock solution of ADH-41 (10 mM in DMSO) was subjected to a series of dilutions with a concentration range from 10 to 150 μM (Total DMSO=1.5% (v,v) in 150 mM KCl, 50 mM NaPi, pH 7.4). The spectra of ADH-41 were recorded at 1.0 nm intervals from 500 to 200 nm with a scan rate of 300 nm/min. Subsequently, the solutions of ADH-41 were filtered (size=0.2 μm, VWR sterile syringe filter) and the spectra were recorded from 500 to 200 nm.

Example 8

Dynamic Light Scattering

Figure 14:
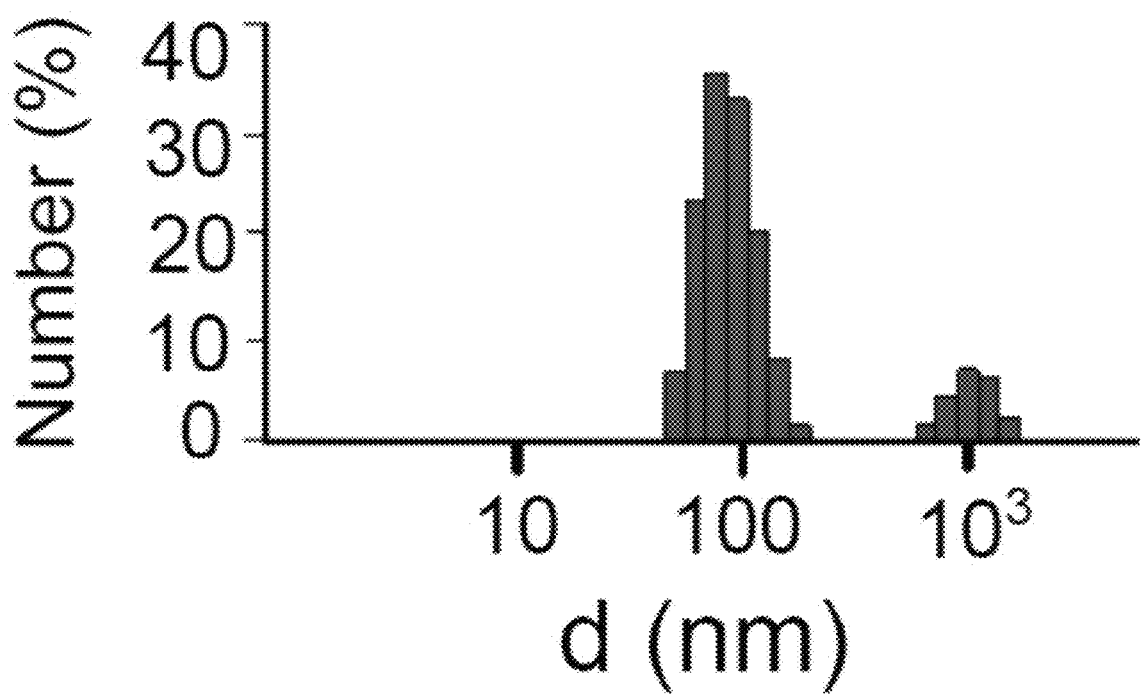
FIG. 14 depicts dynamic light scattering data for 5 µM $A\beta_{42}$ in the presence of ADH-41 at an equimolar ratio after 3 days. The frequency distribution is plotted against the diameter of $A\beta_{42}$ fibril.

Dynamic light scattering was employed to assess the effect of ADH-41 on the size distribution of various $A\beta_{42}$ species (FIG. 4a). The particle size distribution of 5 μM $A\beta_{42}$ increased from a range of hydrodynamic radii of 40-80 nm to 100-500 nm after incubation for 24 h (FIG. 4a). Under matched conditions, the hydrodynamic radii of $A\beta_{42}$ particles were 50-100 nm in the presence of ADH-41 at an equimolar ratio (FIG. 4a). No change was seen in the particle size of the $A\beta_{42}$-ADH-41 complex even after 3 days (FIG. 14).

We have shown in different aggregation assays that the fluorescence intensity of the $A\beta_{42}$: ADH-41 mixture decreased significantly in comparison to the control reaction ($A\beta_{42}$ only) suggesting the formation of alternate structures that are insensitive to ThT dye. Without wishing to be bound by theory, it is postulated that ADH-41 alters the structure of $A\beta_{42}$ which results in the bypass of the intermediate oligomeric structures.

Figure 10:
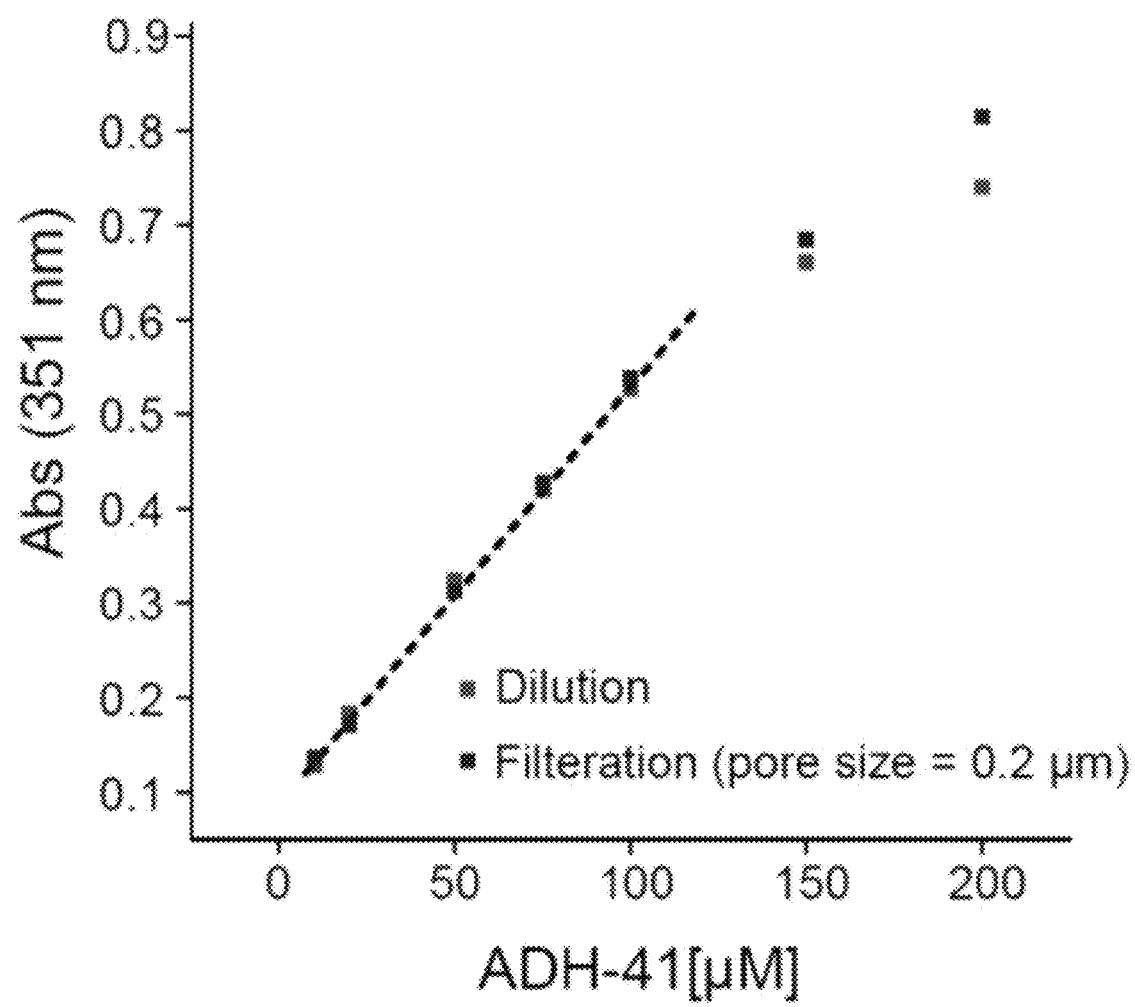
FIG. 10 is a graph of absorption values (351 nm) at different concentrations of ADH-41.

One may hypothesize that the inhibition of $A\beta_{42}$ fibrillation is stemmed from colloidal aggregates of ADH-41 due to the positively charged conjugated aromatic scaffold of ADH-41. Dynamic light scattering (DLS) and ultraviolet-visible (UV-Vis) spectroscopy was employed to probe the micelle forming capacity of ADH-41. The diameter (from volume) of ADH-41 particles was below 10 nm under phosphate buffer (150 mM KCl, 50 mM NaPi, pH 7.4, temp 20° C.) measured by DLS. Furthermore, the absorbance of ADH-41 was linear over a concentration range from 10-100 μM. The absorbance of ADH-41 starts deviating from linearity above 100 μM (FIG. 10, which shows the plot of absorption values at 351 nm with increasing concentrations of ADH-41 under indicated conditions.). These data indicate that the inhibition of oligomerization/fibrillation of $A\beta_{42}$ by ADH-41 is via direct and specific binding and not due to colloidal aggregation.

Example 9

Photo-Induced Cross-Linking of Unmodified Proteins (PICUP) SDS-PAGE Gel

A stock solution of $A\beta_{42}$ (0.5 mM) in water was diluted to a final concentration of 5 μM in phosphate buffer and incubated with the cross-linking agent, ammonium persulphate (20 mM, 1 μL) and tris (2,2'-bipyridyl) dichlororuthenium (II) hexahydrate (1 mM, 1 μL) for time intervals of 2 h, 6 h, 12 h, and 36 h. The reaction mixture was irradiated for 30 s using filament lamp (power=150 W) by keeping it 20 cm away from the bottom of the reaction tubes. The cross-linking reaction was then quenched immediately with dithiothreitol (1 M, 1 μL, Sigma Aldrich, St. Louis, Mo., USA). The samples were incubated on ice for 15 min. followed by the addition of SDS buffer. The samples were heated at 90° C. for 5 min. and then centrifuged. A similar process was repeated in the presence of ADH-41 at an equimolar ratio. The samples were applied to Nu-PAGE electrophoresis in 12% Bis-Tris gels with SDS-PAGE buffer. The protein samples were stained with a silver stain kit from Sigma Aldrich (St. Louis, Mo., USA).

The technique of photo-induced cross-coupling of unmodified proteins (PICUP) was used to assess the effect of ADH-41 on the oligomerization of $A\beta_{42}$ (Bitan, G. *Methods Enzymol* 2006, 413, 217-236). Samples of 5 μM $A\beta_{42}$ were incubated in phosphate buffer at various time intervals in the absence and presence of ADH-41 at an equimolar ratio. The samples were subjected to PICUP and analyzed using SDS-PAGE and silver staining (FIG. 4k). $A\beta_{42}$ oligomers of various sizes ranging from 10 to 80 kD were observed within 2 h (FIG. 4k, lane 1). A similar intensity of $A\beta_{42}$ oligomeric bands was observed for samples incubated for 12 h (FIG. 4k, lane 2, 3). In contrast, no higher order oligomers of $A\beta_{42}$ were observed in the presence of ADH-41 up to 12 h (FIG. 4k, lane 6, 7) and only sparse populations were observed at 24 h and 36 h (FIG. 4k, lane 4, 5). PICUP and dot blot assays suggest that ADH-41 inhibits the formation of $A\beta_{42}$ oligomers.

Example 10

Dot Blot Assay

Samples of $A\beta_{42}$ at concentrations from 2 μM to 5 μM were incubated at various time intervals in the absence and presence of the compounds of the invention at an equimolar ratio (see FIG. 4j). The samples were then applied to a nitrocellulose membrane and dried at room temperature for 1 h or overnight at 4° C. The membranes were then blocked with 5% nonfat milk in Tris buffer (20 mM Tris, pH 7.4) for 1 h at room temperature. The nitrocellulose membranes were then washed (×3) with 20 mM Tris, pH 7.4 supplemented with 0.01% Tween-20 (TBST) and incubated with polyclonal A11 antibody (1/1000 dilution in 5% nonfat milk in TBST, Life Technologies Corp., Grand Island, N.Y., USA) overnight at 4° C. Samples were then washed (×3) with TBST buffer and incubated with horseradish peroxidase (HRP) conjugated anti-rabbit IgG (1/500 dilution in 5% nonfat free milk in TBST) at r.t. for 1 h. The dot blots were then washed with TBST buffer (×3), developed using the ECL reagent kit (Amersham, Piscataway, N.J., USA), and imaged using a Typhoon FLA 9000 instrument (GE Healthcare Life Sciences, Pittsburgh, Pa., USA) using chemiluminescence settings. A similar experiment was repeated using 6E10 antibody (1/1000 dilution in 5% nonfat free milk in TBST, Biolegend, San Diego, Calif., USA) for comparison.

A dot blot assay was utilized to examine the effect of ADH-41 on Aβ oligomer formation (see Kayed, R.; Head, E.; Thompson, J. L.; McIntire, T. M.; Milton, S. C.; Cotman, C. W.; Glabe, C. G. *Science* 2003, 300, 486-489). Briefly, 5 μM $A\beta_{42}$ was incubated in the absence and presence of ADH-41 at an equimolar ratio at various time intervals (FIG. 4j). The samples were applied to a nitrocellulose membrane and detected using polyclonal antibody A11, an antibody specific for oligomeric structures of Aβ (FIG. 4j). Equal amounts of samples were loaded and tested with a sequence-specific antibody (6E10) to verify loading quality and reproducibility. In the absence of ADH-41, a time-dependent increase in the amount of A11-sensitive conformations was observed, which reached a maximum intensity around 24 h. The intensity decreased gradually after 24 h, presumably because of the formation of fibers that are not detected by the A11 antibody. In the presence of ADH-41 at an equimolar ratio, the A11 signal intensity was significantly weaker during the whole time course (FIG. 4j). No change in the signal intensity was observed for Aβ42 in the absence and presence of ADH-41 when stained with 6E10.

Example 11

ELISA

The ELISA was performed according to a previously published method (see Lindhagen-Persson, M.; Brännström, K.; Vestling, M.; Steinitz, M.; Olofsson, A. *PLoS ONE* 2010, 5, e13928). A Nunc-Immuno MaxiSorp plate (Sigma Aldrich, St. Louis, Mo., USA) was incubated with 2 μg mL$^{-1}$ Aβ oligomer-specific antibody (OMAB, Agrisera, Sweden) in PBS buffer overnight at 4° C. (200 μl/well). Wells were blocked with 5% fat-free milk in PBS buffer with 0.1% Tween 20 (PBST) for 1 h at 4° C. and washed with PBST buffer (×3). Wells were then treated with Aβ$_{42}$ samples overnight at 4° C. Aβ$_{42}$ samples were prepared by incubating 30 μM Aβ$_{42}$ in the absence and presence of ADH-41 at an equimolar ratio at various time intervals at room temperature. Samples were diluted by 1:30 in PBS buffer before adding to a 96-well plate. After adding Aβ$_{42}$ samples, the wells were washed (×3) with PBST buffer followed by the addition of 6E10 antibody (1/1000 dilution in 5% nonfat free milk in PBST buffer) for 1 h at r.t. Wells were washed (×5) with PBST buffer and treated with an anti-mouse HRP-conjugated IgG (1/10,000 dilution in 5% nonfat free milk in PBST buffer). Wells were washed (×5) with PBST buffer and treated with TMB Peroxidase EIA Substrate Kit (Biorad, Hercules, Calif., USA). The plates were developed until the color of the solution turned blue. The reaction was stopped by adding 100 μL of 1N H$_2$SO$_4$ to each well. The color of the solution changed to yellow from blue. The absorbance was recorded at 450 nm on a FlexStation 3 Multi-Mode Microplate reader from Molecular Devices (Sunnyvale, Calif., USA). Each sample was repeated in triplicate.

An orthogonal ELISA assay (Lindhagen-Persson, M.; Brännström, K.; Vestling, M.; Steinitz, M.; Olofsson, A. *PLoS ONE* 2010, 5, e13928) was employed to follow the kinetics of Aβ$_{42}$ aggregation in the absence and presence of ADH-41 at an equimolar ratio (FIG. 4*l*). The samples of Aβ$_{42}$ were aged in the absence and presence of ADH-41 for 18 h and 36 h and detected using an Aβ oligomer-specific monoclonal antibody (OMAB) (FIG. 4*l*). The absorbance increased from 0 to 36 h reflecting a gradual increase in the amount of soluble oligomers of Aβ$_{42}$. The absorbance of Aβ$_{42}$ samples incubated for more than 40 h decreased significantly probably because of the fiber formation and could not be detected by OMAB. In marked contrast, the absorbance of Aβ$_{42}$ samples incubated with ADH-41 was significantly lower at all time points (FIG. 4*l*).

Results from the ELISA assay corroborate well with both PICUP and dot blot assays suggesting that ADH-41 inhibits the oligomerization of Aβ$_{42}$.

Example 12

Two-Dimensional HSQC NMR Spectroscopy

Two-dimensional $^1$H-$^{15}$N HSQC NMR experiments were performed on a 600 MHz Bruker instrument. Uniformly labeled $^{15}$N-Aβ$_{40}$ was purchased from rpeptide (Bogart, Ga., USA). The stock solution of 1 mg mL$^{-1}$ was dissolved in 10 mM NaOH, aliquoted into small fractions, lyophilized, and stored at −80° C. until use. The concentration of each aliquot was determined spectroscopically at 280 nm using an extinction coefficient of 5690 M$^{-1}$ cm$^{-1}$. Experiments were carried out in 20 mM NaPi, pH 7.4 by maintaining a solution ratio of 90:10 (H$_2$O: D$_2$O) according to a previously published method (see Wahlstrom, A.; Hugonin, L.; Peralvarez-Marin, A.; Jarvet, J.; Graslund, A. *FEBS J.* 2008, 275, 5117-5128) to ensure that Aβ$_{40}$ is in the monomeric state. A stock solution of 20 mM of the compound of the invention was prepared in DMSO-d$_6$ (pure, HPLC grade). For each NMR experiment, a freshly prepared aliquot of $^{15}$N-Aβ$_{40}$ was used to avoid potential complication from amyloid formation. NMR spectra were recorded using fresh sample of 60 μM $^{15}$N-Aβ$_{40}$ in 20 mM NaPi, pD 7.4 in the absence and presence of the oligopyridylamide compound of the invention at a stoichiometric ratio of 1:2 (Aβ$_{40}$: oligopyridylamide compound) at 7° C. on 600 MHz Bruker equipped with a triple resonance HCN cryoprobe. The maximum dilution of $^{15}$N-Aβ$_{40}$ sample with the titration of the oligopyridylamide compound was <1.5%. The dilution was corrected when calculating the change in the chemical shifts of $^1$H and $^{15}$N resonances. For $^1$H-$^{15}$N HSQC NMR experiments, data for the $^1$H and $^{15}$N frequencies were acquired using 1024 and 512 points, respectively. Apodization was achieved in the $^1$H and $^{15}$N dimensions using a sine square function shifted by 90°. The NMR spectra were processed and analyzed using MNova software. The chemical shift changes for $^1$H and $^{15}$N resonances were analyzed using MNova and transferred to an Excel file. Resonance assignments (both $^1$H and $^{15}$N) of all the residues were determined according to a previously published method. The combined perturbation in the chemical shifts for both the resonances ($^1$H-$^{15}$N) was determined using the following equation:

$$\Delta ppm=[(5*\Delta^1H)^2+(\Delta^{15}N)^2]^{1/2}$$

Two dimensional NMR further suggests that ADH-41 induces secondary structure in Aβ$_{40}$ (which was used for the NMR study instead of Aβ$_{42}$ because of its slower aggregation rate and higher solubility). To probe the binding interaction between Aβ$_{40}$ and ADH-41, $^1$H-$^{15}$N heteronuclear single quantum coherence (HSQC) 2D-NMR experiments were conducted using 60 μM Aβ$_{40}$ (10 mM NaPi, pH 7.4) in the absence and presence of various concentrations of ADH-41 (FIG. 5*d*). An instant change in many of the $^1$H and $^{15}$N resonances was noticed in the presence of ADH-41 at an equimolar ratio, indicating the formation of a fast complex between Aβ$_{40}$ and ADH-41. We restricted our study to a stoichiometric ratio of 1:3 (Aβ$_{40}$: ADH-41) because of the formation of a precipitate at higher doses of ADH-41 reflected by the decrease in the NMR signal intensities. The largest chemical shift changes are observed for residues 15-24, 28-35, and the C-terminus (FIG. 5*d*-5*f*). Aβ$_{40}$ adopts a secondary structure based on the solution environment (Jarvet, J.; Danielsson, J.; Damberg, P.; Oleszczuk, M.; GrÅslund, A. *J. Biomol. NMR* 2007, 39, 63-72) and undergoes a conformational switch from a weak left-handed 3$_1$-helix structure (Danielsson, J.; Jarvet, J.; Damberg, P.; Gräslund, A. *FEBS J.* 2005, 272, 3938-3949) to a strong α-helical or β-hairpin structure in the presence of sodium dodecyl sulfate micelles or affibody protein (Hoyer, W.; Grönwall, C.; Jonsson, A.; Ståhl, S.; Härd, T. *Proc. Natl. Acad. Sci. U.S.A.* 2008, 105, 5099-5104), respectively. The pattern for the changes in the chemical shifts of the Aβ$_{40}$: ADH-41 complex resembles those of the Aβ$_{40}$: SDS micelle complex albeit with a lesser change in the chemical shifts (FIG. 5*e*, 5*f*). Without wishing to be bound by theory, it may be inferred that ADH-41 induces an α-helical conformation in Aβ$_{40}$ specifically in regions Aβ$_{15-24}$ and Aβ$_{28-35}$ (FIG. 5*e*, 5*f*) with the benzyl side chain of ADH-41 likely interacting with Phe19 and/or Phe20 residues as reflected by their large chemical shift changes. Part of the anti-amyloidogenic activity of ADH-41 may be due to the disruption of π-π aromatic interactions from Phe19/Phe20 residues which are known to play a role in Aβ fibrillation (Gazit, E. *FASEB J.* 2002, 16, 77-83). Taken together with the CD data, it is postulated that ADH-41 interacts with the monomeric state of Aβ and alters its structure by inducing an α-helical conformation, which subsequently alters the kinetic pathways of Aβ fibrillation.

2D HSQC NMR was also employed to investigate the structural changes in Aβ induced by another oligopyridylamide of the invention, namely ADH-31. To minimize the aggregation and precipitation of the complex, the concentrations of Aβ$_{42}$ and ADH-31 were restricted to 40 and 80 µM, respectively. The assignments for chemical shifts of Aβ$_{42}$ residues were carried out according to Jarvet, J.; Danielsson, J.; Damberg, P.; Oleszczuk, M.; GrÃslund, A. *J. Biomol. NMR* 2007, 39, 63-72; Danielsson, J.; Jarvet, J.; Damberg, P.; Gräslund, A. *FEBS J.* 2005, 272, 3938-3949. There was a perturbation observed in the structure of Aβ$_{42}$ in the presence of ADH-31 reflected by the change in the chemical shifts related to various residues (FIG. 27*i*). The highest change in the chemical shifts was localized to residues spanning from Glu11 to Phe20 (FIG. 27*i, j*). The data suggest that this region is a potential binding site of ADH-31. Without wishing to be bound by theory, it is postulated that the two negatively charged carboxylate functional groups of ADH-31 potentially interact and form salt bridges with the positively charged domain of Aβ$_{42}$ (His$^{13}$-Lys$^{16}$), and the hydrophobic side chains of ADH-31 stabilize the hydrophobic domain of Aβ$_{42}$ (Ile17 to Phe20).

Example 13

Isothermal Titration Calorimetry (ITC)

ITC experiments were performed in a NANO-ITC (TA instruments, New Castle, Del., USA). A stock solution of 100 µM ADH-41 (in 20 mM NaPi, pH 7.4) was serially added (2 µL injections in 10 seconds via rotary syringe, stirring speed=300 rpm) into a sample cell containing 250 µL of 10 µM Aβ$_{40}$ in the same buffer at 240 sec intervals. The heat associated with each injection was calculated by integrating each heat burst curve using NanoAnalyze software (New Castle, Del., USA). The associated heat for each injection was corrected by subtracting heat resulted from the titration of ADH-41 into buffer under identical conditions. Corrected heats were plotted as a function of the molar ratio of ADH-41 to Aβ$_{40}$ and fitted using a one binding site model. No parameter was constrained during the fitting. The data were extracted from the best fit after 10,000 iterations.

Figure 7B:
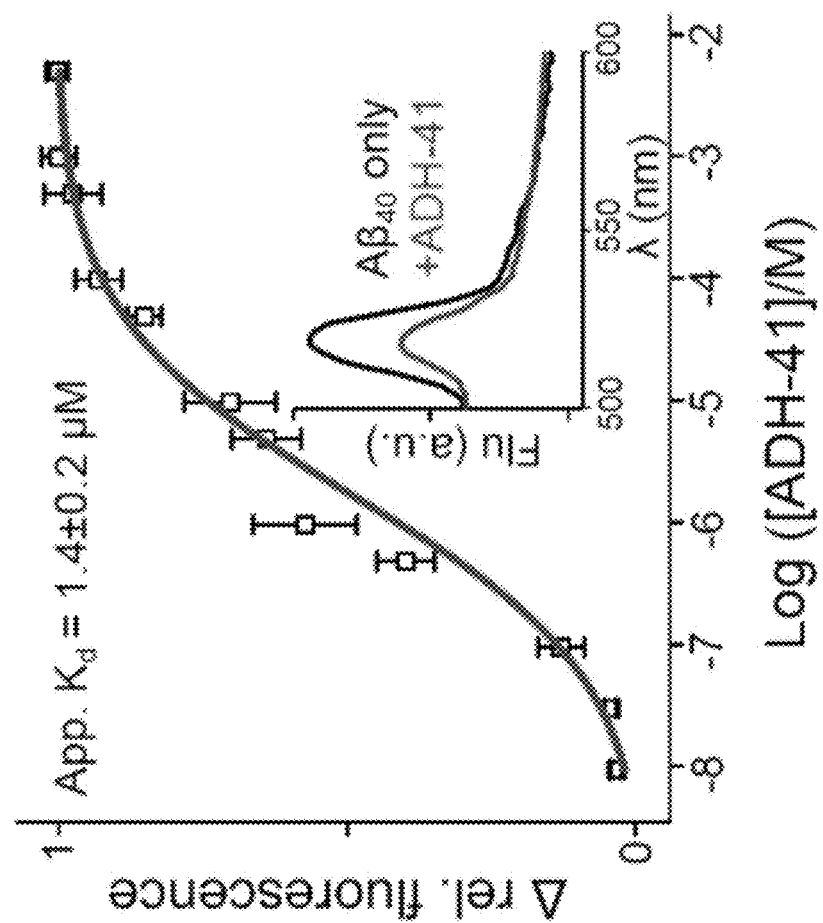
FIGS. 7a and 7b illustrate the binding affinity of ADH-41 with Aβ40.
Figure 7A:
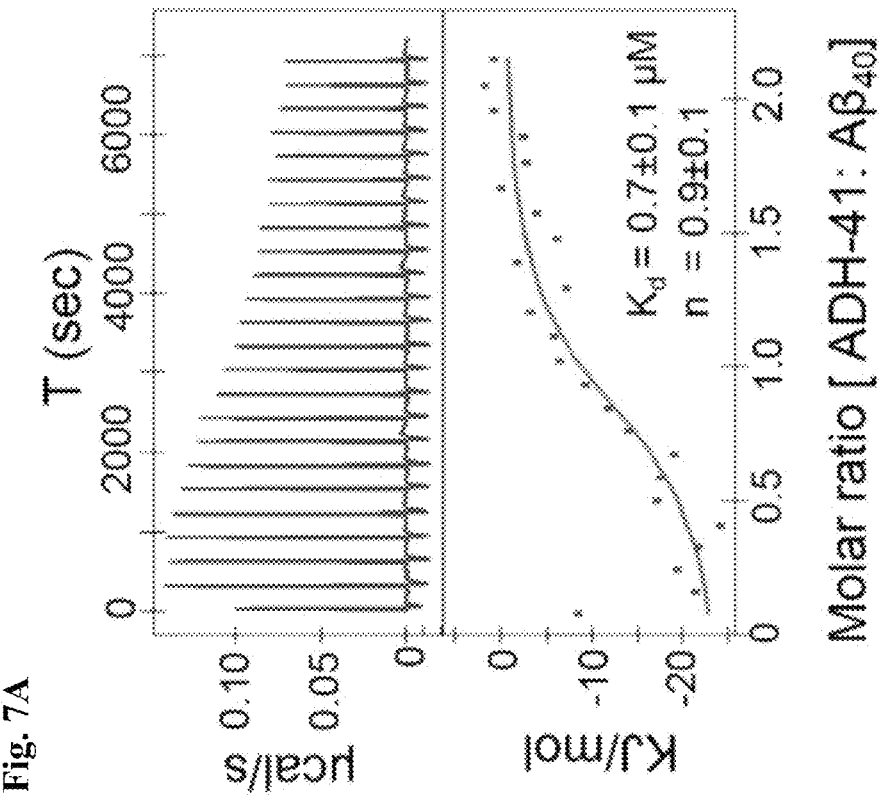

ITC was employed to characterize the binding interaction between Aβ and ADH-41. Briefly, a 10 µM solution of Aβ$_{40}$ was titrated with a constant amount of 100 µM ADH-41, resulting in an endothermic binding profile (FIG. 7*a*) that was fitted using an independent binding model and yielded a binding stoichiometry of approximately 1:1 (ADH-41: Aβ$_{40}$) and a K$_d$ of 0.7±0.1 µM (FIG. 7*a*).

Example 14

Fluorescence Titration

N$^α$-amino-terminal fluorescein-labeled Aβ$_{40}$ was purchased from Anaspec (Fremont, Calif., USA) and used without further purification. To ensure the monomeric state of N$^α$-amino-terminal fluorescein-labeled Aβ$_{40}$, the peptide was treated similar to other peptides and stored at −80° C. in the dark until use. Fluorescence measurements were performed on a FlexStation 3 Multi-Mode Microplate reader from Molecular Devices (Sunnyvale, Calif., USA). Fluorescence titrations were conducted in triplicate in a 96-well plate with a final well volume of 200 µL. For fluorescence measurements, the fluorescein dye was excited at 492 nm and the spectra were recorded from 500 nm to 600 nm. A 10 nM N$^α$-amino-terminal fluorescein-labeled Aβ$_{40}$ solution in fluorescence assay buffer (20 mM NaPi, 1% TFE, pH 7.4) was titrated with incremental amounts of ADH-41 (in DMSO) and the spectra were recorded from 500 nm to 600 nm. A number of high concentration stock solutions of ADH-41 were prepared to minimize the amount of DMSO in the fluorescence titrations (<3%). The addition of ADH-41 was continued until no further change in the fluorescence was observed. To determine the binding affinity of ADH-41 against Aβ$_{40}$, the change in the fluorescence intensity ($\lambda_{max}$=522 nm) was plotted as a function of the concentration of ADH-41. The plot was fitted using a sigmoidal fit to extract the apparent binding affinity.

Fluorescence titration was employed to quantify the binding interaction using an established protocol (Andreetto, E.; Yan, L.; Tatarek—Nossol, M.; Velkova, A.; Frank, R.; Kapurniotu, A. *Angew. Chem. Int. Ed.* 2010, 49, 3081-3085). N$^α$-amino-terminal fluorescein-labeled Aβ$_{40}$ (10 nm) was titrated with ADH-41 (FIG. 7*b*, inset) in 20 mM NaPi, 1% TFE, pH 7.4. The fluorescence intensity increased significantly with increasing amount of ADH-41 and a plot of the change in fluorescence intensity as a function of the log [ADH-41] yielded a sigmoidal curve (FIG. 7*b*) which was used to extract the apparent binding affinity (app. K$_d$). The app. K$_d$ of ADH-41 against Aβ$_{40}$ was 1.4±0.2 µM which was in good agreement with that determined from ITC.

Example 15

Aβ-Specificity of ADH-41 and ADH-31 Oligomerization Inhibition

To assess the binding specificity of the oligopyridylamides of the invention toward their target protein, the antagonist activity of ADH-41 was tested against the aggregation of Aβ$_{40}$ and IAPP mediated cytotoxicity and aggregation processes.

Figure 11:
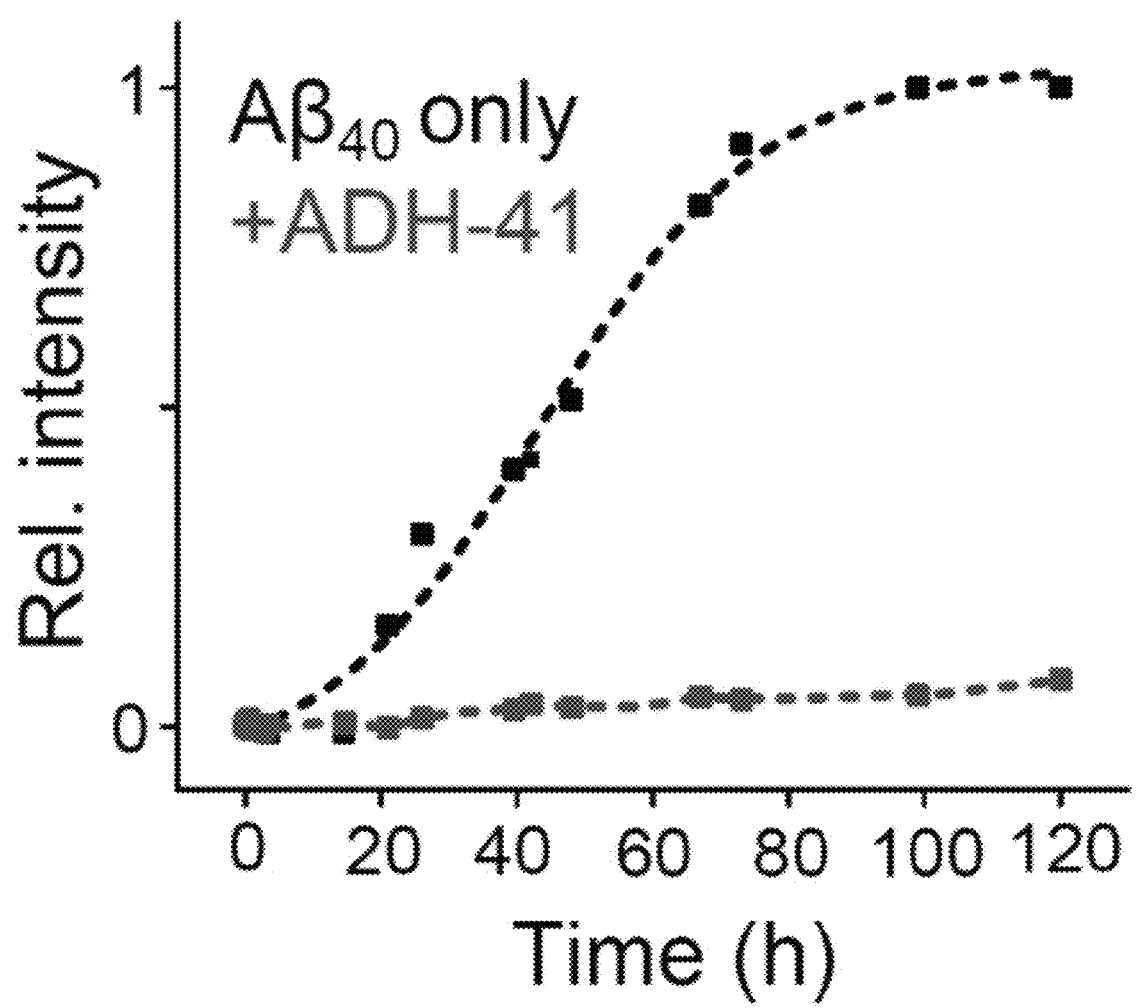
FIG. 11 is a normalized kinetic profile of $A\beta_{40}$ self-assembly in the absence (black) and presence of ADH-41 (red) at an equimolar ratio.
Figure 12C:
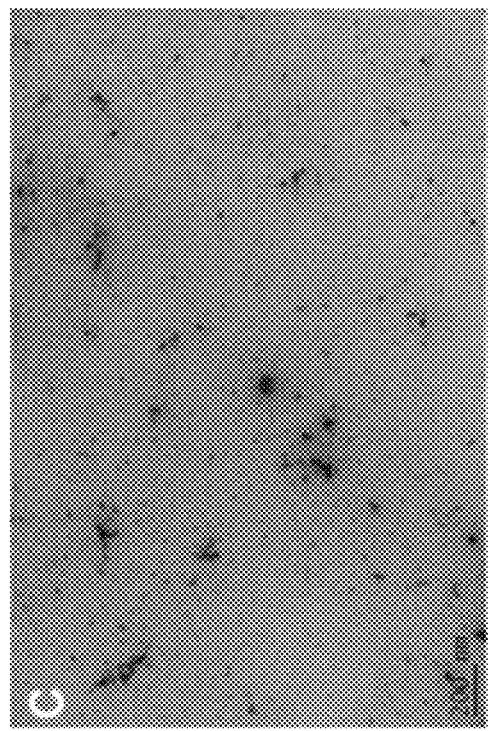
FIGS. 12a-12d shows the effect of ADH-41 on the kinetics of $A\beta_{40}$ fibrillation using TEM.
Figure 12D:
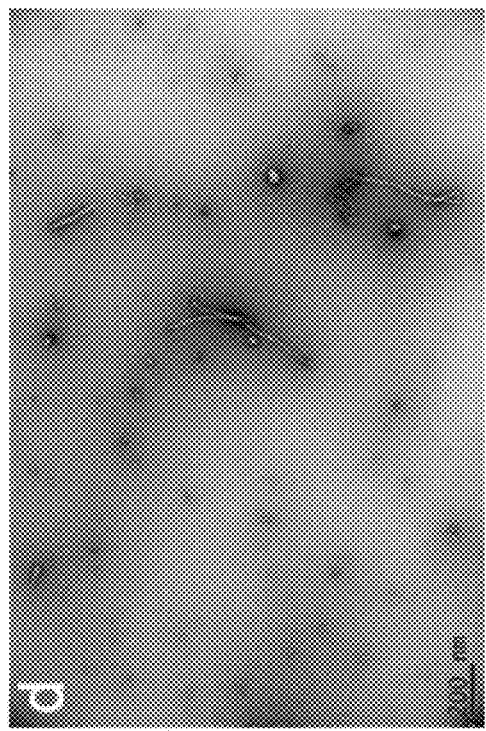
Figure 12A:
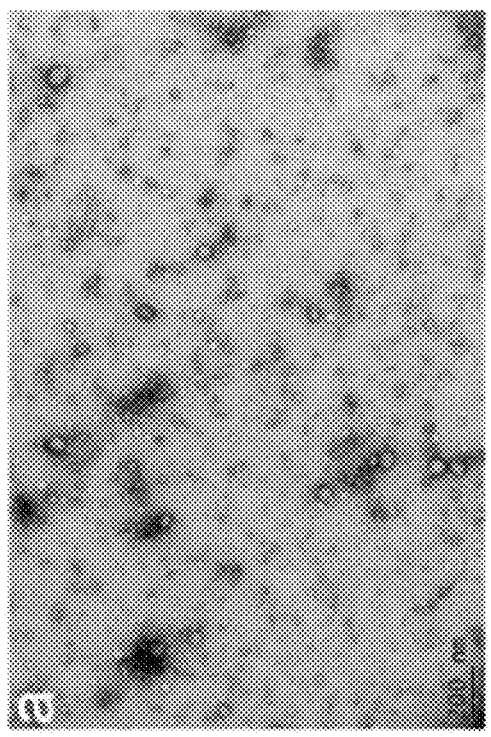
Figure 12B:
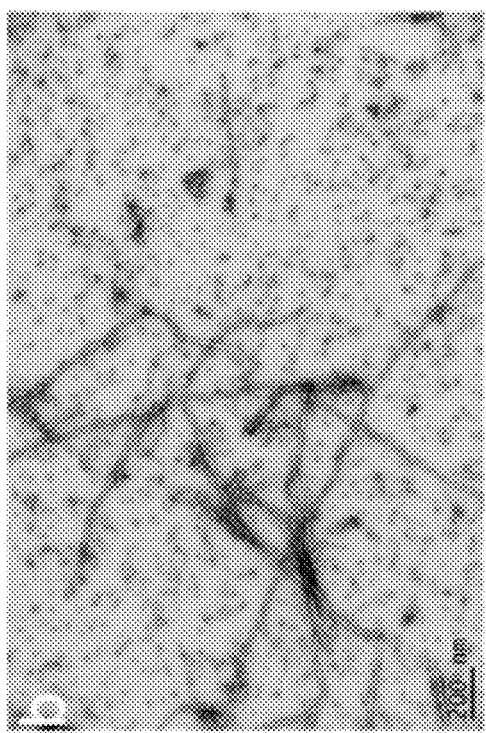

Under matched conditions, the aggregation of 40 µM Aβ$_{40}$ resulted in a sigmoidal curve with a reaction midpoint (t$_{50}$) of 42±5 h (see FIG. 11, which depicts the normalized kinetic profile of the self-assembly of 20 µM Aβ$_{40}$ in the absence (black) and presence of ADH-41 (red) at an equimolar ratio. Buffer conditions: 150 mM KCl, 50 mM NaPi, pH 7.4, [ThT]=2 µM.). ADH-41 completely arrested Aβ$_{40}$ aggregation at an equimolar ratio (see FIGS. 3*b* and 3*c*).

IAPP and Aβ share ~50% sequence similarity with the Aβ(15-21) and Aβ(26-32) sequences sharing particular commonality with those of IAPP(10-16) and IAPP(21-27), respectively (FIG. 3*a*, see also Yan, L.; Velkova, A.; Tatarek-Nossol, M.; Andreetto, E.; Kapurniotu, A. *Angew. Chem. Int. Ed.* 2007, 46, 1246-1252; and Andreetto, E.; Yan, L.; Tatarek-Nossol, M.; Velkova, A.; Frank, R.; Kapurniotu, A. *Angew. Chem. Int. Ed.* 2010, 49, 3081-3085). These regions are further thought to participate in amyloidogenesis (see Andreetto, E.; Yan, L.; Tatarek-Nossol, M.; Velkova, A.; Frank, R.; Kapurniotu, A. *Angew. Chem. Int. Ed.* 2010, 49, 3081-3085; Andreetto, E.; Yan, L.; Caporale, A.; Kapurniotu, A. *ChemBioChem* 2011, 12, 1313-1322; Seeliger, J.; Evers, F.; Jeworrek, C.; Kapoor, S.; Weise, K.;

Andreetto, E.; Tolan, M.; Kapurniotu, A.; Winter, R. *Angew. Chem. Int. Ed.* 2012, 51, 679-683; Andreetto, E.; Malideli, E.; Yan, L.; Kracklauer, M.; Farbiarz, K.; Tatarek-Nossol, M.; Rammes, G.; Prade, E.; Neumüller, T.; Caporale, A.; Spanopoulou, A.; Bakou, M.; Reif, B.; Kapurniotu, A. *Angew. Chem. Int. Ed.* 2015, 54, 13095-13100).

Figure 13A:
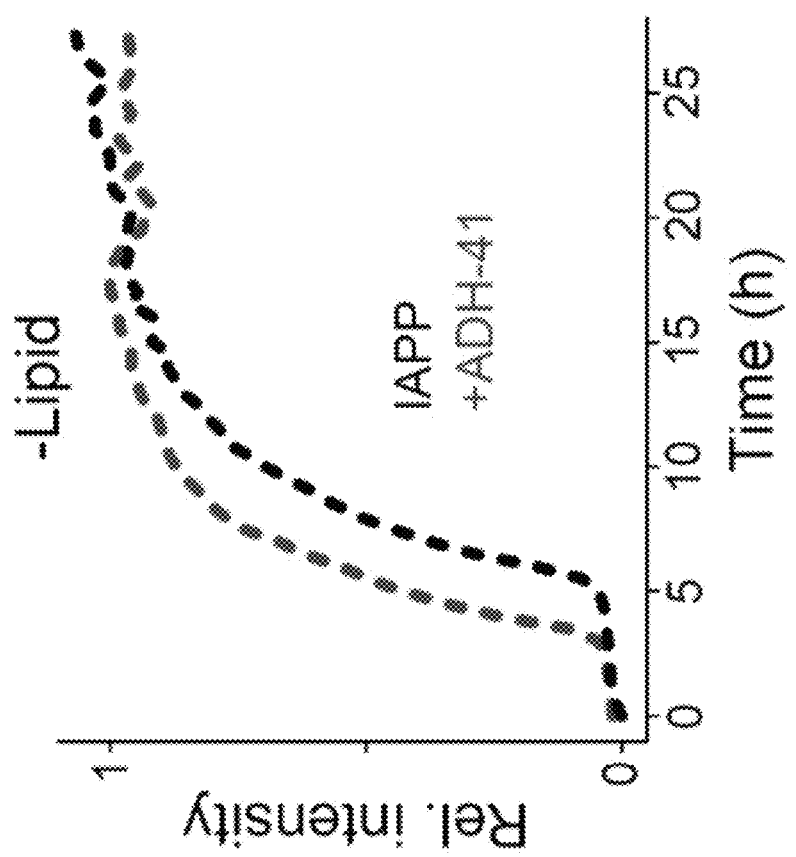
Figure 26B:
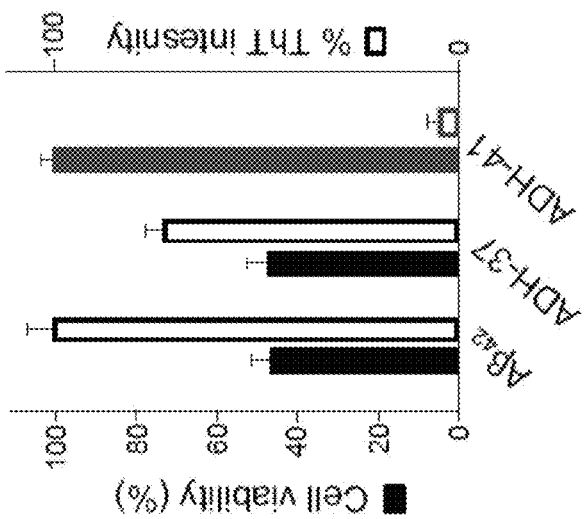
FIGS. 26a-26c illustrates the effect of the compounds of the disclosure on $A\beta_{42}$ mediated cytotoxicity in mouse neuroblastoma (N2a) cells.
Figure 26A:
Figure 26C:
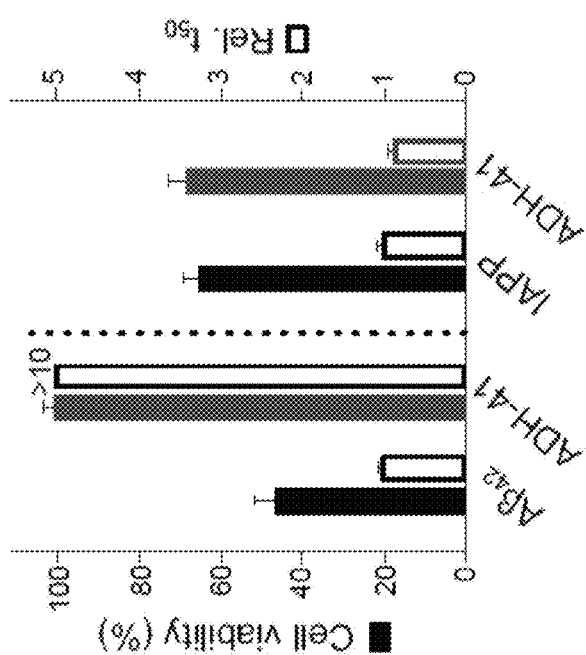

These similarities likely account for the observation that many Aβ antagonists also inhibit IAPP amyloid formation and vice versa. Surprisingly, under matched conditions, the kinetics of IAPP fibrillation results in a sigmoidal curve with a reaction time midpoint ($t_{50}$) of 6.5±0.5 h (FIG. 3b, 3c and FIG. 13a) indicating that ADH-41 acts as an agonist of the aggregation of IAPP at an equimolar ratio (FIG. 3b, 3c and FIG. 13). Although ADH-41 completely inhibited $A\beta_{42}$ mediated toxicity and fibrillation, it did not have any effect on IAPP fibrillation or toxicity in rat INS-1 cells (FIG. 26c). Taken together, these studies suggest that the binding interaction between ADH-41 and Aβ is protein specific and sensitive to the functionalities presented on the surface of the inhibitor.

Example 16

Cell Based Assays

A study of the effects of α-helix mimetics on Aβ mediated toxicity in mouse neuroblastoma (N2a) cells is presented herein. The study illuminates the role of Aβ oligomerization in inducing toxicity and demonstrates the targeting of Aβ by two oligopyridyalmides (ADH-31 and ADH-41) equipped with contrasting functional groups.

The oligopyridylamides are very effective in inhibiting fibrillation and ameliorating Aβ mediated cytotoxicity in N2a cells. NMR and the chemical nature of the oligopyridylamides suggests that they are potentially binding to two different subdomains of Aβ. This is useful from mechanistic and therapeutic points of view as it provides important insights into the role of different domains in Aβ self-assembly processes and desired chemical nature for efficient antagonists of Aβ toxic functions. More importantly, the study underscores a strategy for a dual recognition as an approach towards more potent inhibitors of Aβ aggregation and cytotoxicity.

Figure 17B:
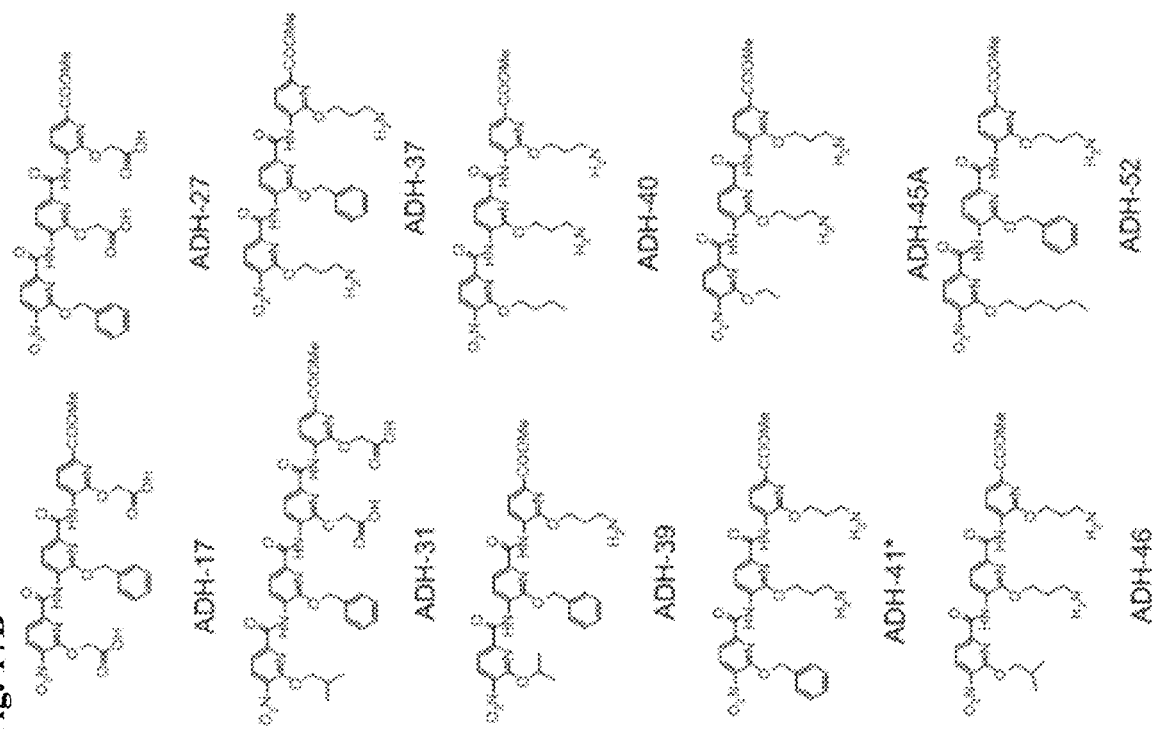
FIGS. 17a and 17b illustrate the effect of indicated compounds on $A\beta_{42}$-mediated toxicity in Neuro-2a cells.
Figure 17A:
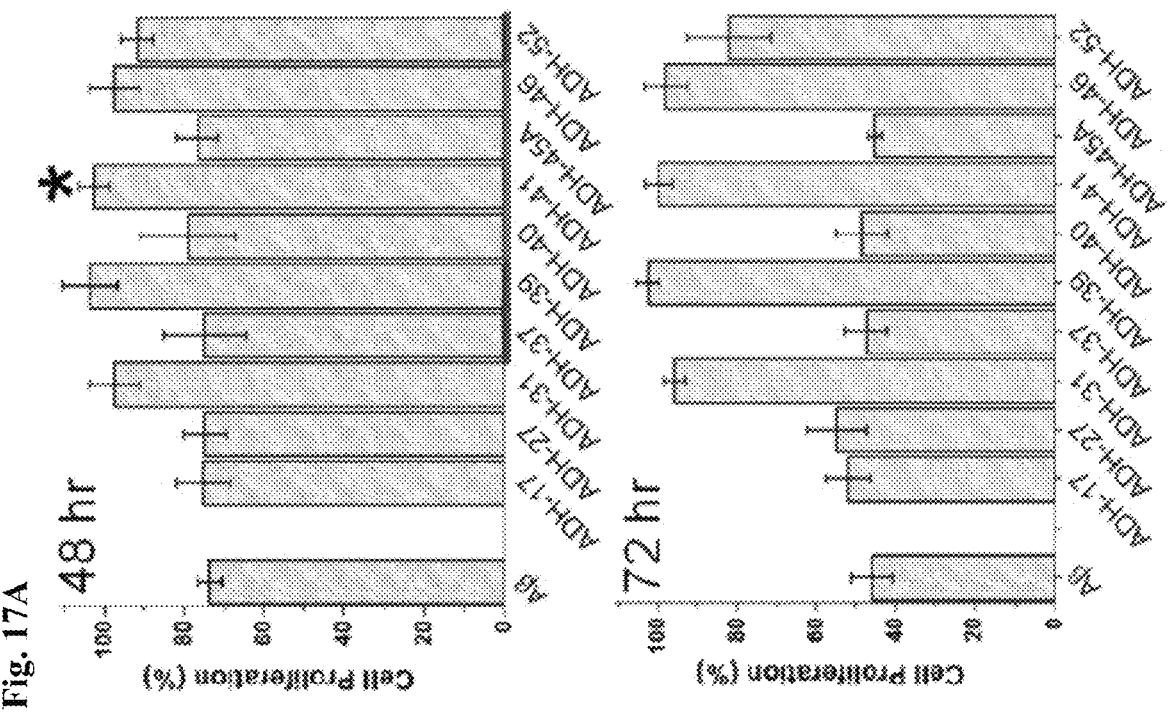
Figure 18:
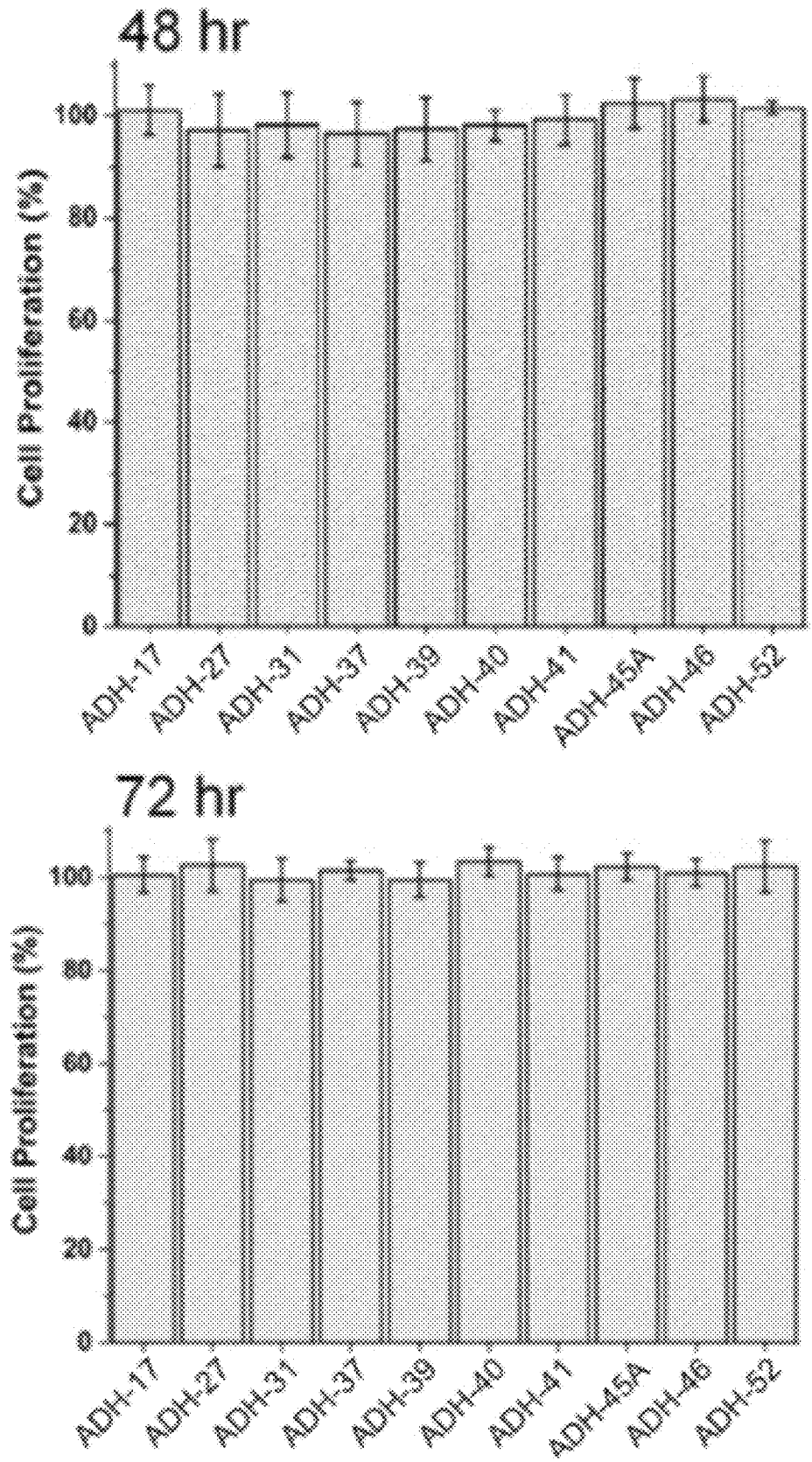
FIG. 18 shows the effect of select compounds according to the disclosure on Neuro-2a cells at 48 hours and 72 hours.
Figure 19A:
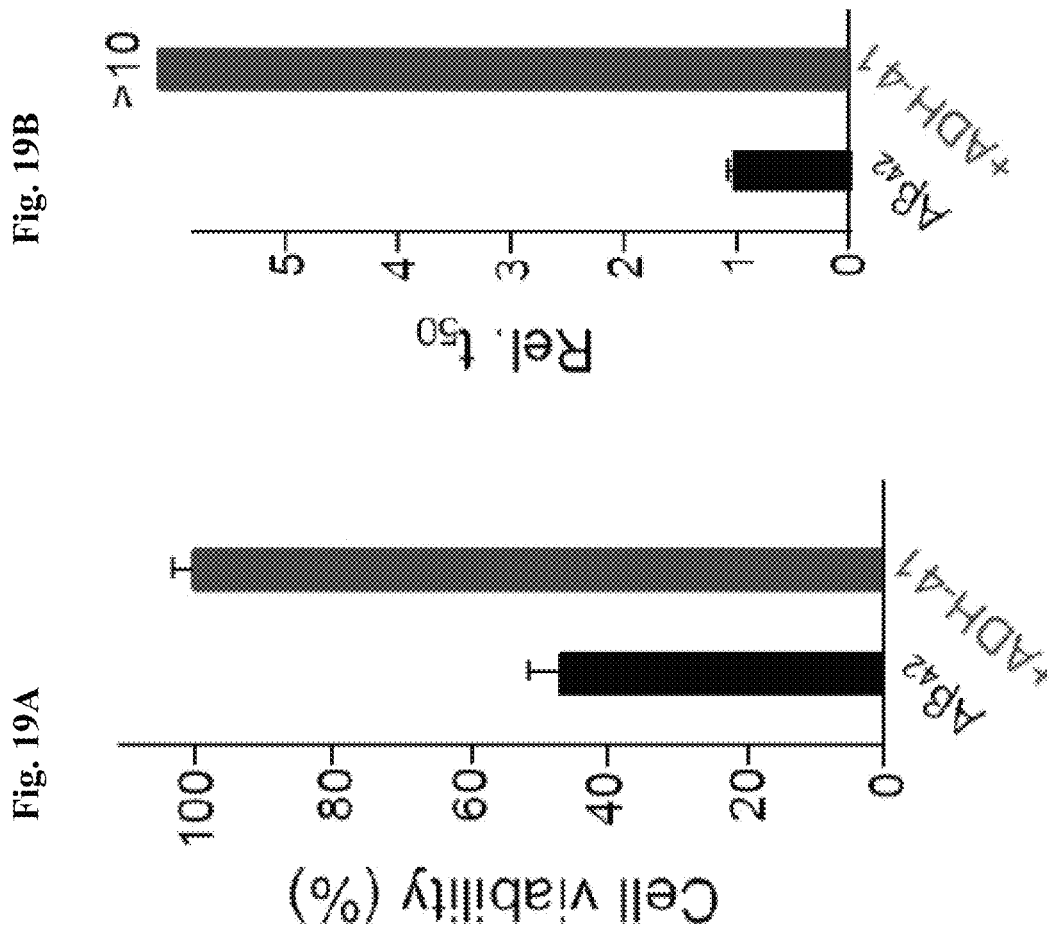
FIG. 19a shows a plot of cell viability in the presence and absence of ADH-41.
Figure 19B:
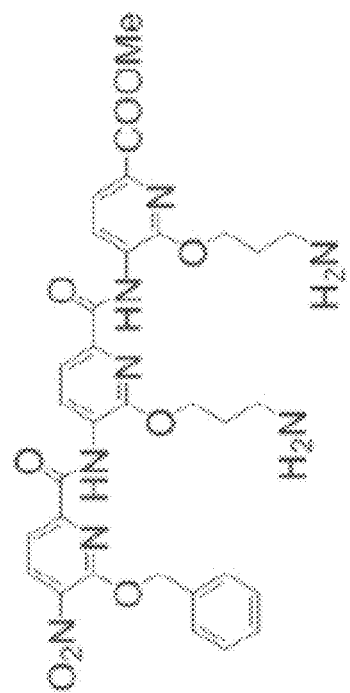
FIG. 19b shows a plot of rel. $t_{50}$ of $A\beta_{42}$ amyloid formation in the presence and absence of ADH-41 at an equimolar ratio.

The effect of several compounds of the invention on Aβ-mediated toxicity in Neuro-2a cells was measured in a cell-based assay. FIG. 17a shows a graph of cell proliferation in the presence of Aβ with or without the indicated compounds after 48 hours and after 72 hours. FIG. 17b shows the chemical structures of the indicated compounds of the invention. ADH-41 is indicated by an asterisk. FIG. 18 shows the effect of the inventive compounds on Neuro-2a cells.

Cell viability was determined using a CellTiter 96® AQueous One Solution Cell Proliferation Assay (MTS) kit (Promega), which measures the reduction of the tetrazolium compound MTS (3-(4,5-dimethylthiazol-2-yl)-5-(3-carboxymethoxyphenyl)-2-(4-sulfophenyl)-2H-tetrazolium, inner salt) to soluble formazan by mitochondrial dehydrogenase enzyme in living cells. Formazan can be measured at 490 nm according to the manufacturer's instructions.

Neuro-2a cells (ATCC® CCL-11) were maintained in serum-containing media [Dulbecco's Modified Eagle's Medium—high glucose (DMEM, Sigma) supplemented with 10% foetal bovine serum (FBS), 4 mM L-Glutamine (Sigma), and 1% penicillin/streptomycin (Sigma)] in 5% $CO_2$ at 37° C. Once the cells reached ~95% confluence, they were split (using 0.25% trypsin-EDTA, Sigma, St. Louis, USA), seeded at a density of 5×10³ cells/well in 100 μL complete medium in 96-well plates and cultured for 48 h. Thereafter, the media was removed, the cells washed with phosphate buffered saline (PBS), and 90 μL of serum-free DMEM was added to the wells. A solution (A) containing 50 μM $A\beta_{42}$ in NaOH (pH 10.5) was prepared and kept on ice, and a solution (B) containing 50 μM of the oligopyridylamide compound, $H_2O$ (2.33 μL/well) and 1× and 10×PBS was prepared and kept at room temperature. The solutions were combined, vortexed and 10 μL of this solution immeadiatly added to each well. The final concentrations in the wells were: 5 μM $A\beta_{42}$, 5 μM oligopyridylamide, 200 μM NaOH, 0.1×PBS and 0.5% (v/v) DMSO.

To investigate the toxic effect of the peptide alone on cell viability, solution (B) without the oligopyridylamide compound was mixed with solution (A), while the effect of the oligopyridylamide compound alone was determined by adding solution (A) without peptide to solution (B). The effect of oligopyridylamides on seed-catalyzed $A\beta_{42}$ aggregation was probed by preparing an additional solution (C) containing 0.5 μM seeds. The volume contributed by solution (C) was taken into account in preparing solution (B). Solution (C) was mixed with solution (B), and the resulting mixture was then added to solution (A) shortly before addition to the wells. To study the effect of oligopyridylamides on the oligomeric states of $A\beta_{42}$, solution (A) was mixed with solution (B) without inhibitor and incubated at room temperature for 1, 2 or 3 h. Subsequently, 50 μM oligopyridylamides was added to the mixture, which was then immediately added to the cells. After culturing for 72 h in 5% $CO_2$ at 37° C., 20 μL of MTS reagent was added to each well. The MTS reagent was incubated for 2.5 h at 37° C., and absorbance of the soluble formazan product ($\lambda$=490 nm) of MTS reduction was measured on a Synergy H1MF Multi-Mode microplate-reader (BioTek, Winooski, Vt., USA), with a reference wavelength of 650 nm to subtract the background. Wells treated with a solution containing serum-free DMEM, 200 μM NaOH, 0.1×PBS and 0.5% (v/v) DMSO served as control. MTS reduction was determined from the ratio of the absorbance of the treated wells to the control wells. Each data point represents an average of four independent quadruplet-well trials.

As FIGS. 17 and 18 demonstrate, inventive compounds (e.g., ADH-31, ADH-39, ADH-41, ADH-46, and ADH-52) are effective at rescuing cells from cytotoxicity mediated by $A\beta_{42}$.

Under matched cytotoxic experimental conditions, the oligopyridylamides (ADH-17, 27, 31, 39, 40, 41, 45A, and ADH-52) were not toxic to rat neuroblastoma cells (Neuro-2a cells, ATCC® CCL-11) (FIG. 18).

Figure 20A:
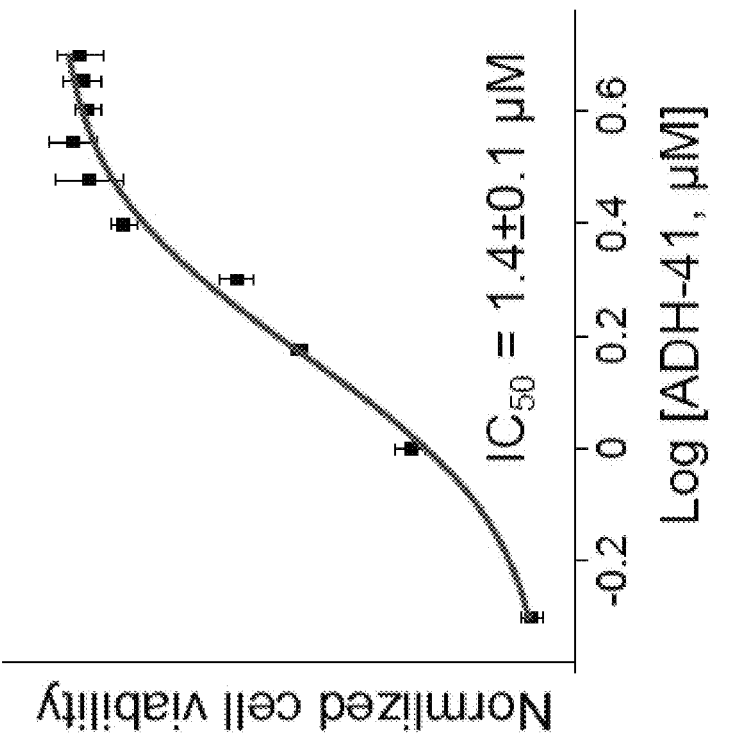
FIGS. 20a and 20b show the dose dependent effect of ADH-41 on Aβ-mediated toxicity in Neuro-2a cells.
Figure 20B:
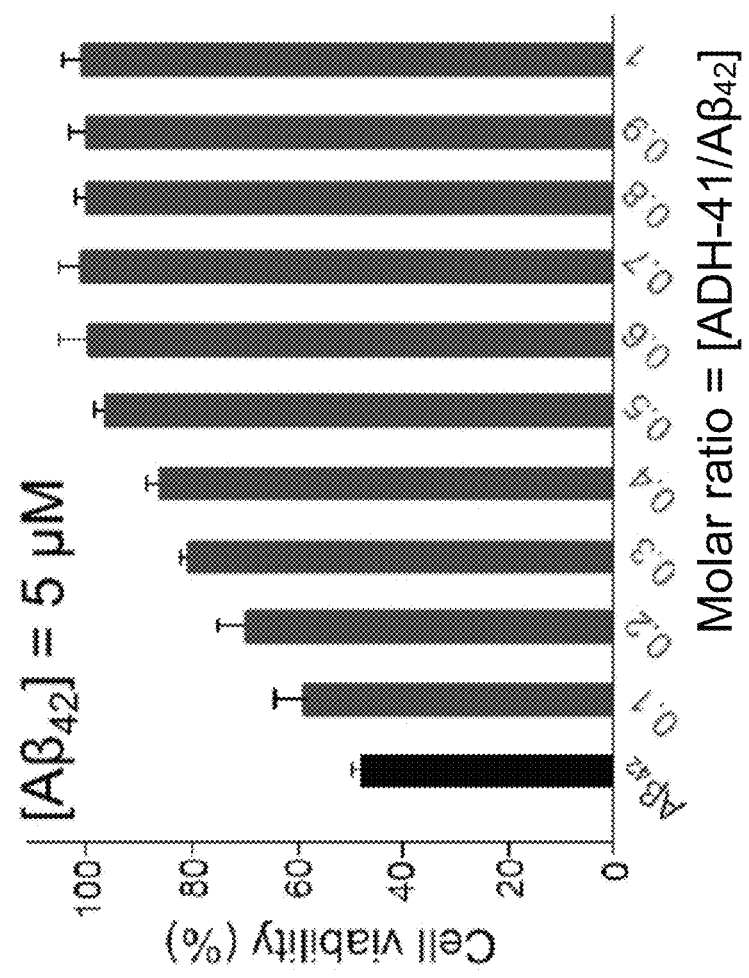
Figure 22:
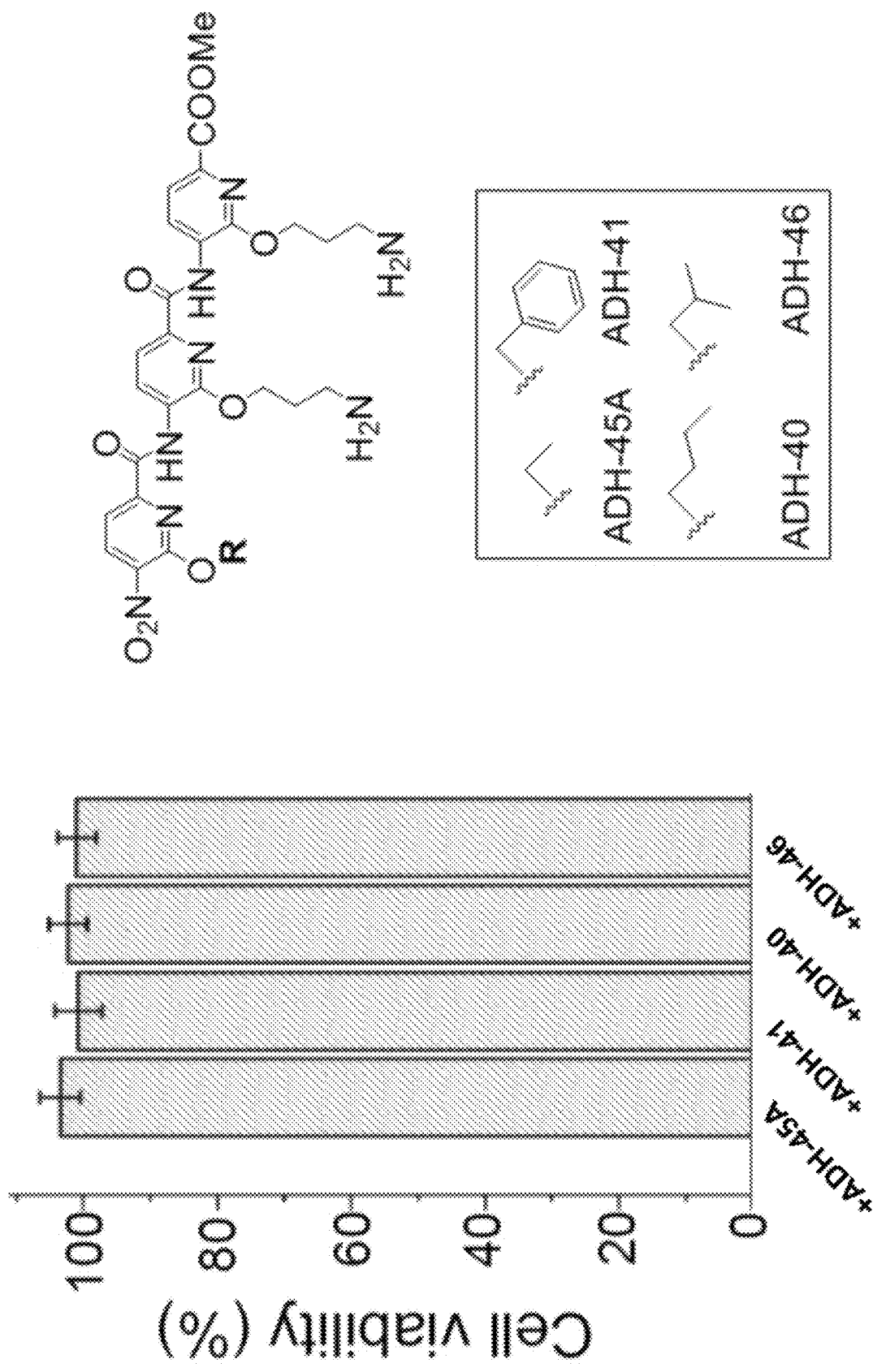
FIG. 22 shows the effect of the indicated compounds on Neuro-2a cells.

Compound ADH-41 rescued the cell toxicity in a dose dependent manner (FIG. 22). The $IC_{50}$ (concentration required to inhibit 50% cell toxicity induced by 5 μM $A\beta_{42}$) for ADH-41 against 5 μM $A\beta_{42}$ mediated toxicity was 1.45±15 μM (FIG. 20).

Figure 21:
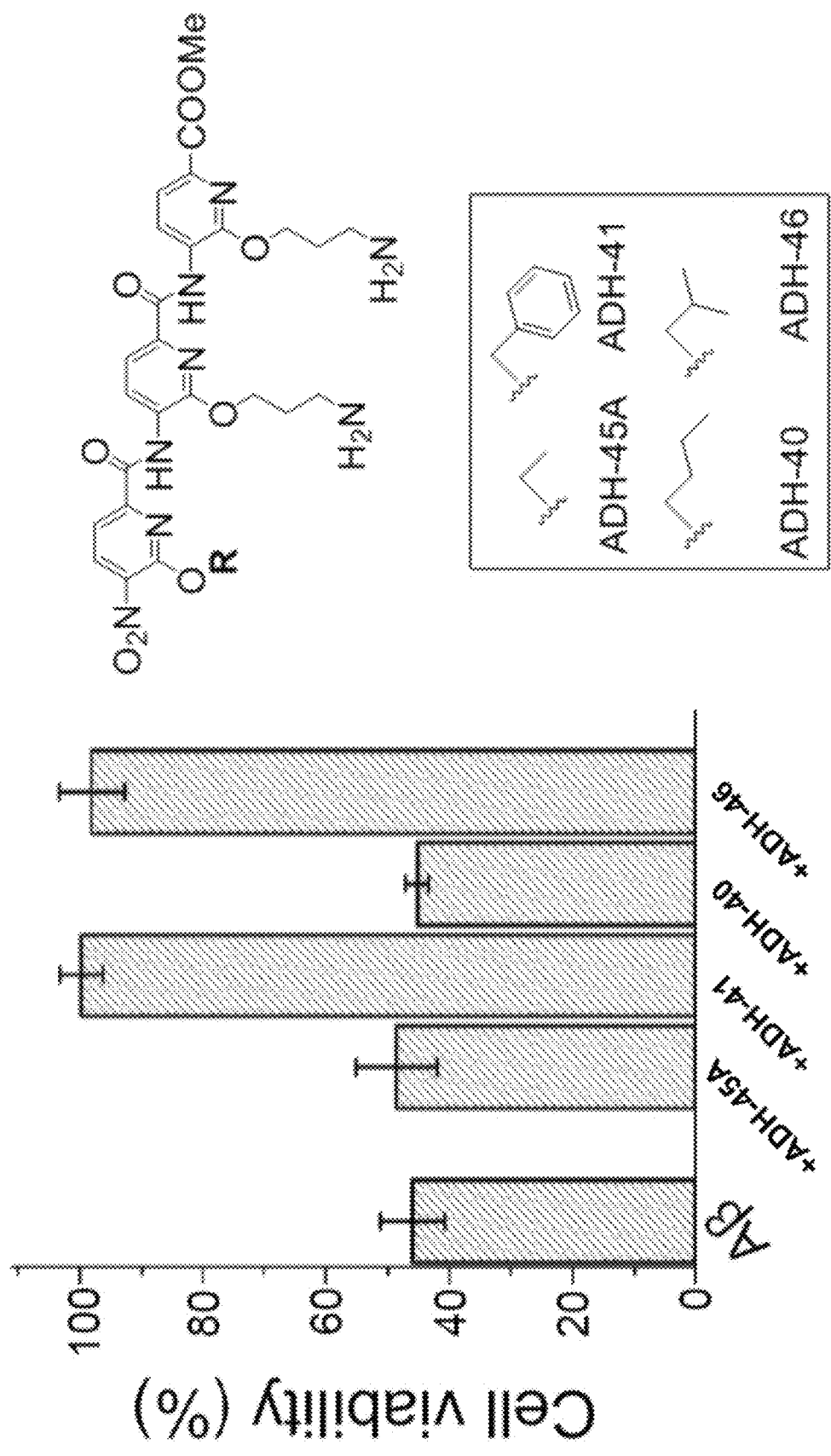
FIG. 21 shows the effect of the derivatives of compound ADH-41 on Aβ-mediated toxicity in Neuro-2a cells.

The antagonist activity of ADH-41 towards $A\beta_{42}$ mediated cytotoxicity and aggregation is dependent on the side chain functionalities projected from the surface of the oligopyridylamide. A structure activity relationship study was employed where analogs of ADH-41 were designed by varying the hydrophobicity of the side chains (FIG. 21, FIG. 26). The rank order for the antagonist activity of the oligopyridylamides is ADH41>ADH46>ADM-40≥ADM-45A for $A\beta_{42}$ mediated cytotoxicity and aggregation (FIG. 26a) following the order of their hydrophobicity. Thus, a decrease in hydrophobicity is detrimental to the antagonist activity of the oligopyridylamides against $A\beta_{42}$ mediated cytotoxicity.

Figure 23:
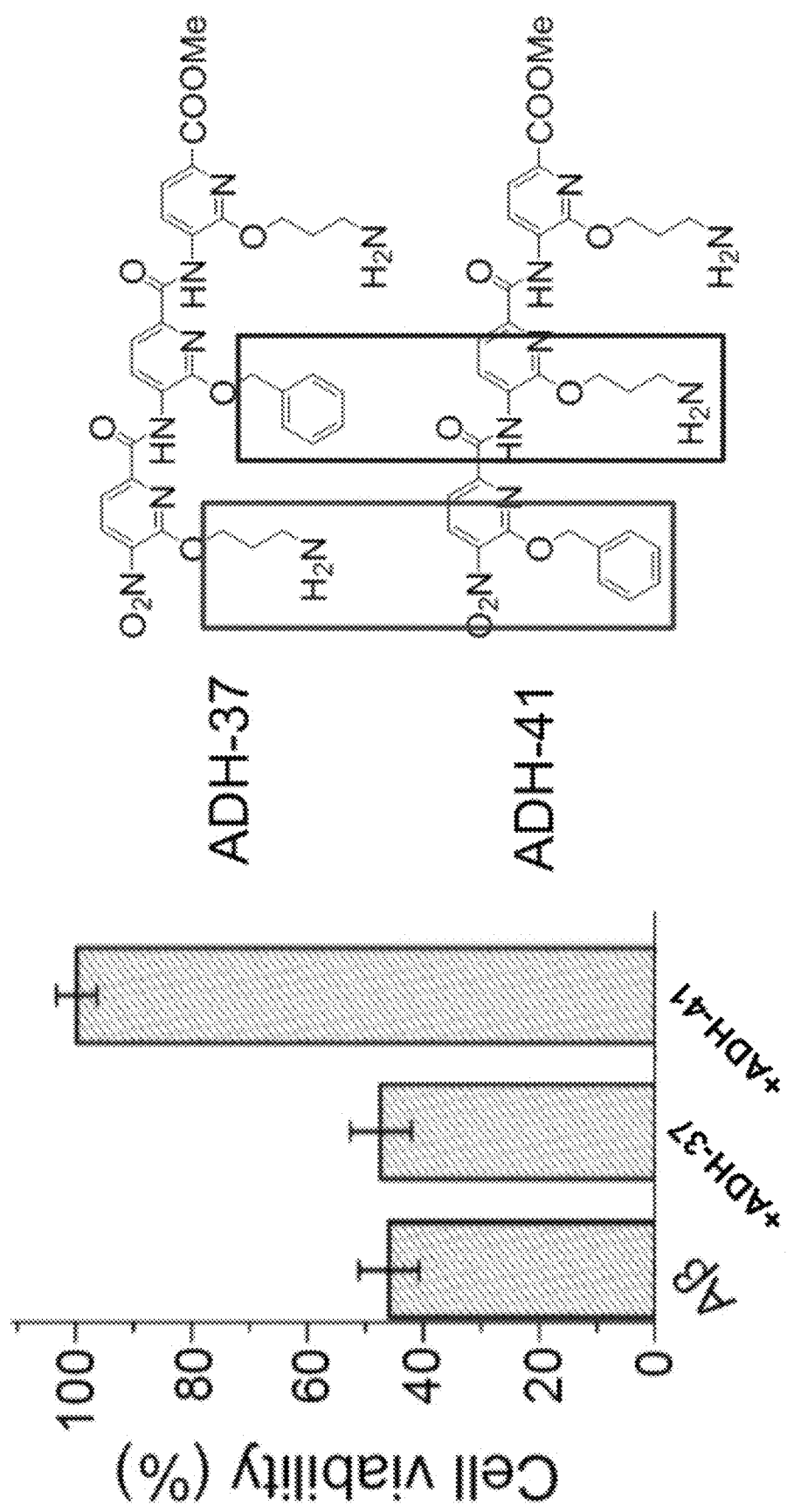
FIG. 23 shows the position of functional groups present in various embodiments of the disclosure in relation to the effect of indicated compounds on Aβ-mediated toxicity in Neuro-2a cells.
Figure 24C:
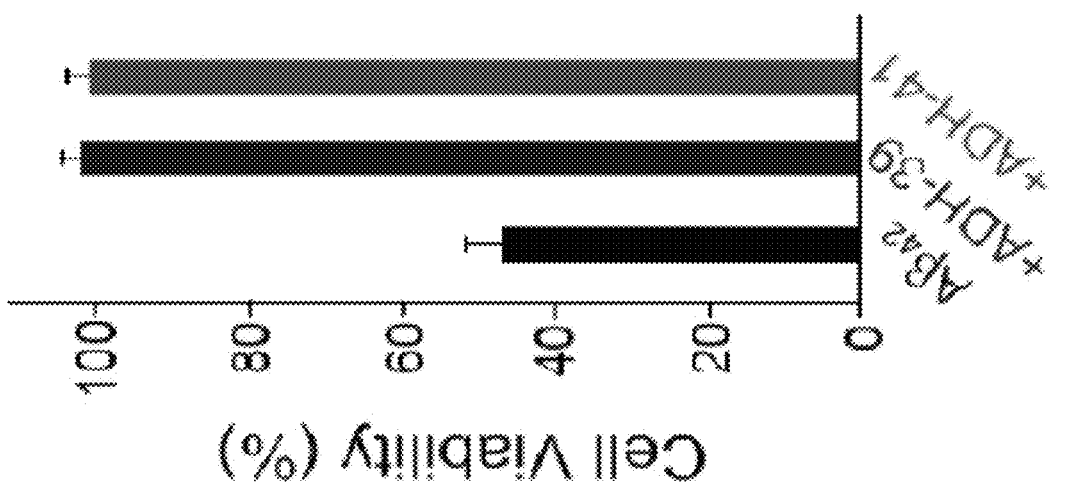
FIG. 24c provides a plot of cell viability in the presence or absence of ADH-39 or ADH-41 at an equimolar ratio ($A\beta_{42}$:ligand, 1:1, 5 µM).
Figure 24B:
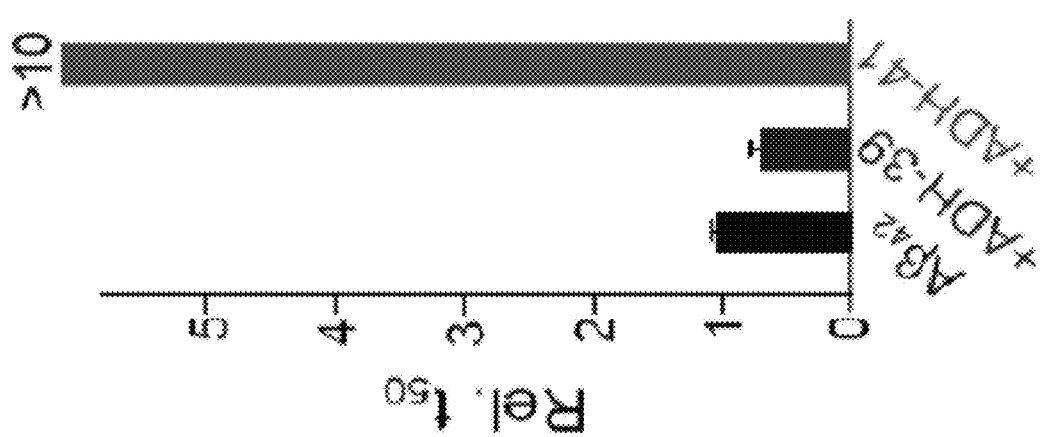
FIG. 24b provides a plot of rel. $t_{50}$ of $A\beta_{42}$ amyloid formation in the presence and absence of ADH-39 or ADH-41.
Figure 24A:
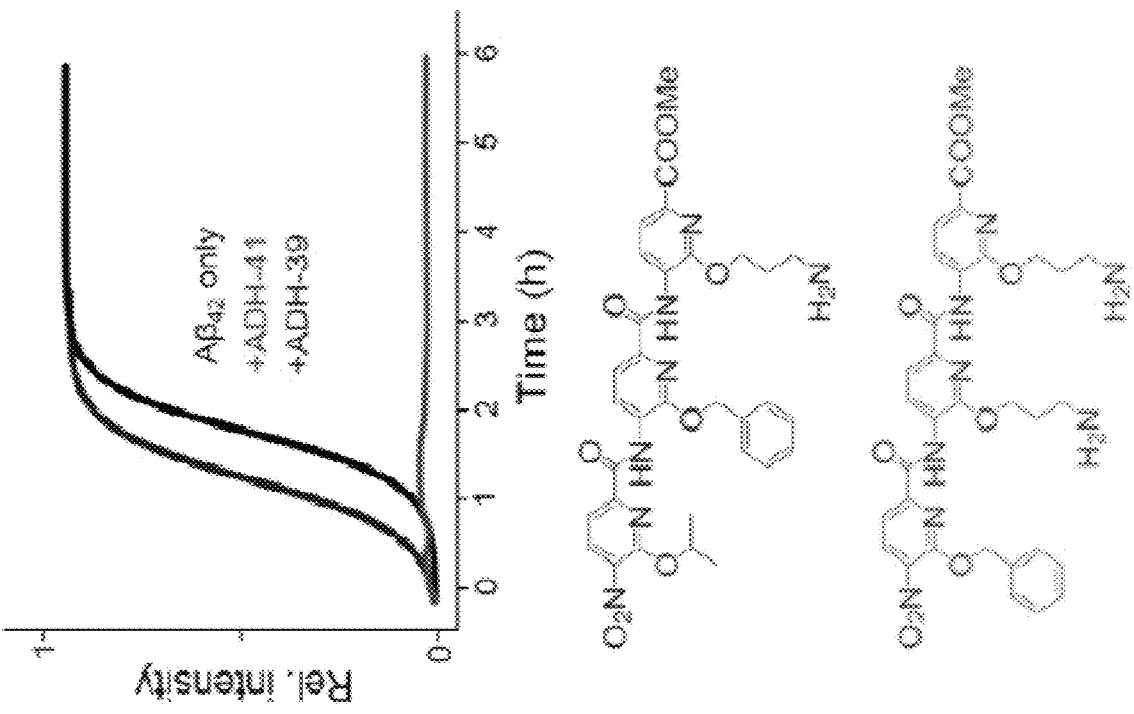
FIG. 24a shows the kinetic curve for the aggregation of 20 µM a$\beta_{42}$ in the absence and presence of the indicated molecules at an equimolar ratio.

The spatial arrangement of the surface functionalities of oligopyridylamides is also essential for their antagonist activity. Compounds ADH-41 and ADH-37 are similar in chemical composition, but differ in the spatial arrangement of their surface functionalities (FIG. 23). In marked contrast to ADH-41, ADH-37 did not have a noticeable effect on the cytotoxicity incurred in N2a cells by $A\beta_{42}$ (FIG. 26b). ADH-37 was also a weak inhibitor of $A\beta_{42}$ aggregation as it only decreases the ThT fluorescence intensity of the amyloid reaction from 100% to 74% (FIG. 26b). Clearly, the functionalities and their spatial location projected on the surface of the oligopyridylamides are essential in exerting antagonist activities.

Two oligopyridylamides, ADH-39 and ADH-41 with different surface functionalities, were equally effective in inhibiting cytotoxicity in Neuro-2a cells. In marked contrast, ADH-41 completely inhibited $A\beta_{42}$ amyloid formation; however, ADH-39 accelerated the amyloid formation. The observation suggests (1) that the binding sites of both the molecules are different on $A\beta_{42}$ and (2) the possibility of two distinct pathways to rescue cytotoxicity.

Figure 31:
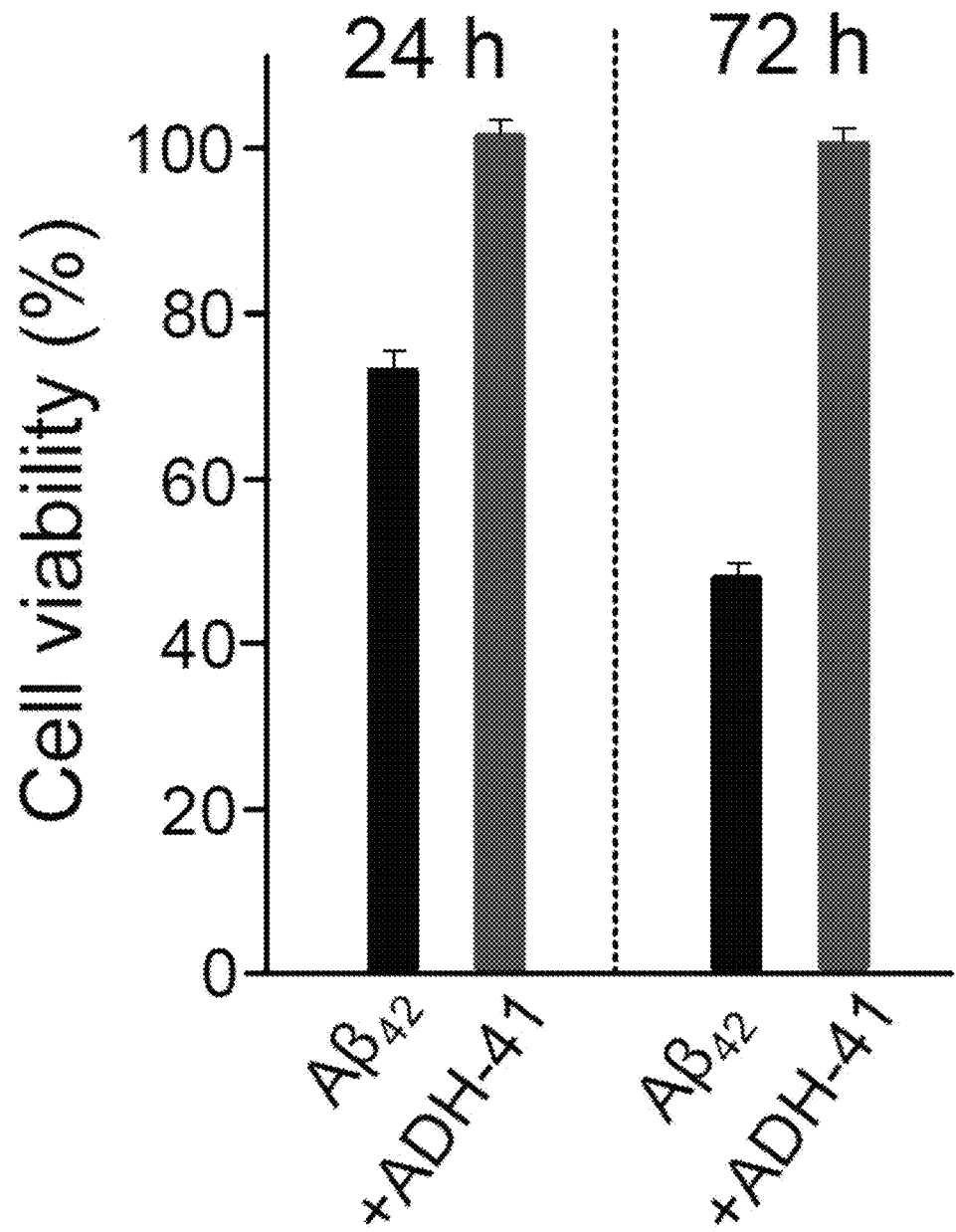
FIG. 31 demonstrates the effect of ADH-41 on Aβ-mediated cytotoxicity in N2a cells. Cells were incubated with Aβ$_{42}$ (5 µM) at the indicated time points in the absence and presence of ADH-41 at an equimolar ratio. The cell viability was measured using cell titer blue assay. Each cytotoxicity experiment is the average of four on-plate repeats from each of four independently performed replicates (n=16).
Figure 32:
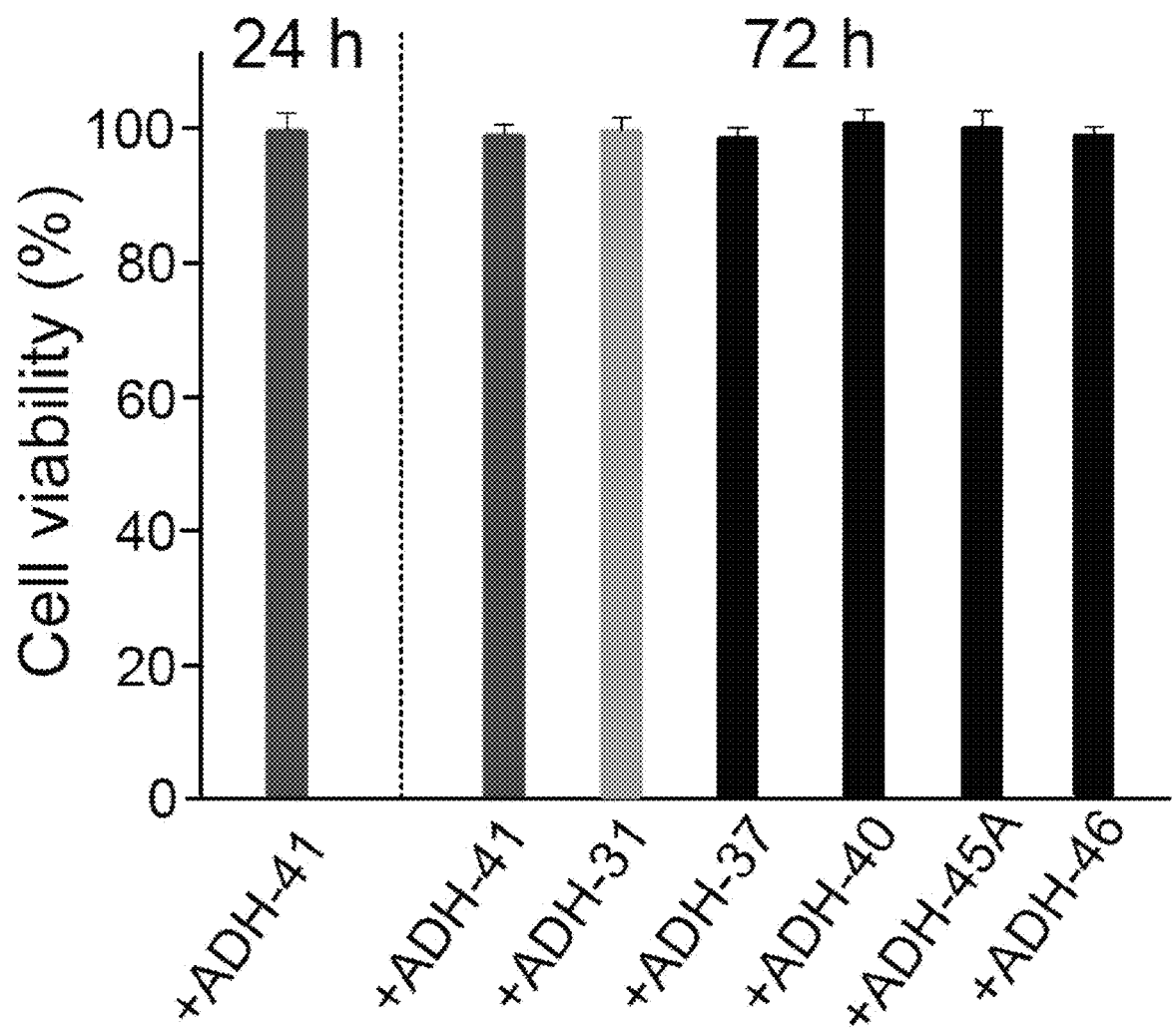
FIG. 32 demonstrates the effect of the oligopyridylamides according to the disclosure on the cell viability of N2a cells. Cells were incubated with the indicated oligopyridylamides (5 µM) at the indicated time points. The cellular conditions were identical to the cytotoxicity assays except no Aβ$_{42}$ was added to the media. The cell viability was measured using cell titer blue assay. Each cytotoxicity experiment is the average of four on-plate repeats from each of four independently performed replicates (n=16).

The effects of ADH-41 on $A\beta$ mediated toxicity were further investigated. The cell-based experiments were conducted using mouse neuroblastoma cells (N2a), and cell viability was quantified using the CellTiter 96 Aqueous One Solution (MTS) assay. Treatment with 5 μM $A\beta_{42}$ reduced the viability of N2a cells to 73±3% and 48±2% after 24 and 72 h, respectively (FIG. 20a and FIG. 31). At an equimolar ratio of ADH-41, the cell viability increased to 99±2% and 98±2% at 24 h and 72 h, respectively (FIG. 20a, FIG. 31). Importantly, ADH-41 was equally effective in rescuing cells from $A\beta_{42}$ toxicity at substoichiometric ratios and rescuing cytotoxicity in a dose dependent manner with an $IC_{50}$ of 1.4±0.1 μM (FIG. 2a, b). ADH-41 alone was not toxic to N2a cells under the conditions used for the cell viability assays (FIG. 32).

Figure 34:
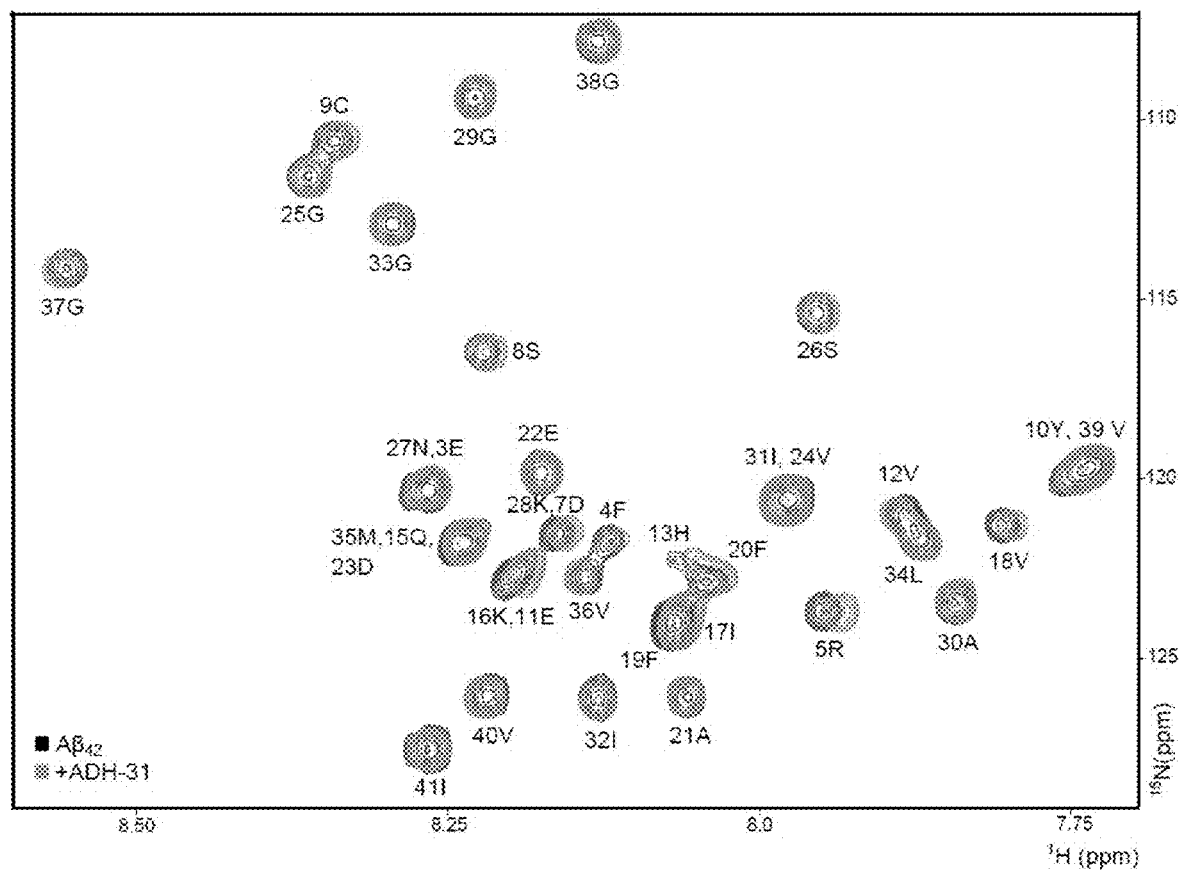
FIG. 34 depicts an overlay of 2D HSQC NMR spectra of $^{15}$N-isotopically labeled Aβ$_{42}$ (40 µM) in the absence (grey) and presence (light blue) of ADH-31 (80 µM). Each peak represents the correlation between the nitrogen and the amide proton of individual amino acid residues of Aβ$_{42}$. The spectra were processed using Mnova NMR software.

ADH-31 rescues $A\beta_{42}$ induced cytotoxicity in N2a cells. The viability of N2a cells decreases to 44±1% upon exposure to 5 μM $A\beta_{42}$, but was rescued to 97%±1% when ADH-31 was added at an equimolar ratio (FIG. 27i), with a dose dependent profile and an $IC_{50}$ of 2.5±0.1 μM (FIG. 3i, j). In contrast to ADH-41, ADH-31 is very effective in inhibiting IAPP mediated fibrillation and cytotoxicity. ThT-based amyloid assay for the aggregation of IAPP yielded a $t_{50}$ of 3.5±0.3 h (FIG. 34). In the presence of ADH-31 at an equimolar ratio, IAPP aggregation was completely suppressed (FIG. 27k), and IAPP induced toxicity in rat insulinoma cells (INS-1) was rescued from 65±6% to 98±4% (FIG. 27k). Certain negatively charged oligopyridylamides inhibiting IAPP mediated toxicity and fibrillation have previously reported. The binding site for the negatively charged oligopyridylamides on IAPP is suggested to involve residues R11 to H18, which is the common domain of IAPP and $A\beta$ and linked to the amyloidogenesis (FIG. 3a, orange line).

From NMR, ThT amyloid and cytotoxicity assays it has been postulated that the binding site of ADH-31 is in the vicinity of this common domain of $A\beta$ and IAPP as it contains dominant positively charged (His13, His14, and Lys16) and hydrophobic (Leu17, Val18, Phe19, and Phe20) regions that complement the surface functionalities of ADH-31.

Example 17

Target Specificity

Two compounds of the invention, ADH-41 and ADH-17, were tested against two peptides $A\beta_{42}$ and IAPP. IAPP and $A\beta$ share ~50% sequence similarity (FIG. 25a), with $A\beta$(15-21) and $A\beta$(26-32) sequences sharing particular commonality with those of IAPP(10-16) and IAPP(21-27), respectively. These regions are further thought to participate in amyloidogenesis. These similarities likely account for the observation that many $A\beta$ antagonists also inhibit IAPP amyloid formation and vice versa.

Figures 25A, 25B, 25C, 25D:
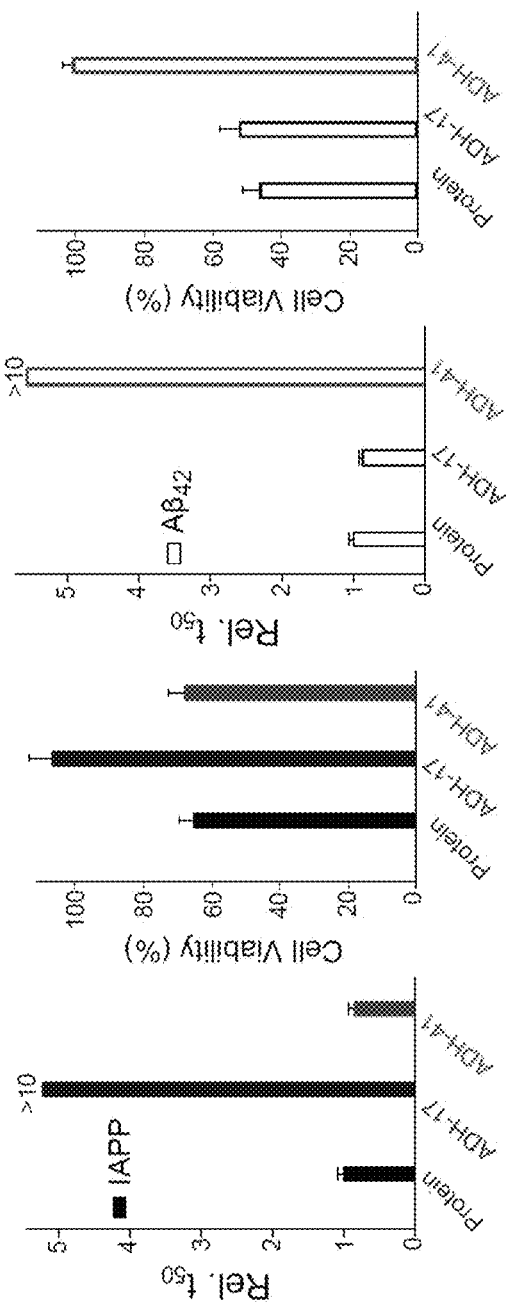
FIG. 25a-d illustrates the target specificity of select compounds according to the disclosure.

ADH-41 completely inhibited $A\beta_{42}$ fibrillation at an equimolar ratio (FIG. 25d). In addition, ADH-41 completely rescues cell toxicity mediated by $A\beta_{42}$ in neuro-2a cells at an equimolar ratio (FIG. 25d). However, ADH-41 showed no effect on the IAPP amyloid formation or IAPP mediated toxicity in rat INS-1 cells. On the contrary, ADH-17, a dianionic tripyridylamide, completely inhibits IAPP amyloidogenesis and IAPP mediated toxicity in rat INS-1 cells at an equimolar ratio (FIG. 25c). Likewise, compound ADH-17 showed no effect on $A\beta_{42}$ fibrillation or cell toxicity mediated by $A\beta_{42}$ in neuro-2a cells at an equimolar ratio (FIG. 25c). Both comparisons indicate the specificity with which ADH-41 and ADH-17 target $A\beta_{42}$ and IAPP, respectively.

Example 18

Confocal Fluorescence Microscopy

For confocal imaging, ADH-41 was N-terminally labeled with fluorescein (ADH-41$_F$) and $A\beta_{42}$ was N-terminally labeled with Texas Red ($A\beta_{TR}$, Anaspec, Fremont, Calif., USA). N2a cells were seeded at a density of $5 \times 10^4$ cells/well in 500 μL complete medium in 4-chambered 35 mm glass bottom Cellview cell culture dishes (Greiner Bio-One, Monroe, N.C., USA). After culturing for 48 h in 5% $CO_2$ at 37° C., the medium was replaced with phenol red- and serum-free medium containing 5 μM peptide (4 μM $A\beta_{42}$+1 μM $A\beta_{TR}$), 5 μM inhibitor (4 μM ADH-41+1 μM ADH-41$_F$), or an equimolar mixture of peptide and inhibitor, and incubated for 24 h. For mitochondrial colocalization experiments, 50 nM MitoTracker Red FM or MitoTracker Green FM (Thermo Fisher Scientific, Waltham, Mass., USA) was added to the chambers and incubated for 15 min. Thereafter, the medium was removed, the cells were washed with PBS to remove any extracellular peptide, inhibitor or organelle marker, and 300 μL phenol red- and serum-free medium was added to each chambers of the cell culture dish. Imaging was done on an Olympus Fluoview FV1000MPE Confocal/2—Photon microscope, using a 63× Plan-Apo/1.3 NA oil immersion objective with DIC capability. Image processing was done using the Fiji image processing software according to known methodology (Schindelin, J.; Arganda-Carreras, I.; Frise, E.; Kaynig, V.; Longair, M.; Pietzsch, T.; Preibisch, S.; Rueden, C.; Saalfeld, S.; Schmid, B.; Tinevez, J. Y.; White, D. J.; Hartenstein, V.; Eliceiri, K.; Tomancak, P.; Cardona, A. Nat. Methods 2012, 9, 676-682).

Confocal imaging has been employed to monitor the interactions between $A\beta_{42}$ and ADH-41 in cellular milieu. ADH-41 and $A\beta_{42}$ were labeled with fluorescein (ADH-41$_F$) and Texas-Red ($A\beta_{TR}$), respectively. Confocal fluorescence imaging confirmed the cellular uptake of both $A\beta_{42}$ peptide (4 μM $A\beta_{42}$+1 μM $A\beta_{TR}$) and ADH-41 (4 μM ADH-41+1 μM ADH-41$_F$) by N2a cells within 24 h of incubation (FIG. 29a). The observation that $A\beta_{42}$ is readily taken by the cells is consistent with reports that suggest $A\beta$ partially exerts its neurotoxic effects via disruption of mitochondrial function. ADH-41 exhibited good cell permeability; it is a di-cation with a calculated partition coefficient (log P) of 1.8 (theoretical=1.4). The cell viability decreased from 100% to 65% when N2a cells were incubated with 4 μM Aβ$_{42}$ (+1 μM Aβ$_{TR}$) for 24 h (FIG. 29a). There was no inherent toxicity associated with ADH-41 as the cell viability was 98% in the presence of ADH-41 alone (4 μM ADH-41+1 μM ADH-41$_F$) (FIG. 29b).

To monitor the effect of ADH-41 on Aβ$_{42}$-mediated cytotoxicity, a solution of Aβ$_{42}$ (4 μM Aβ$_{42}$+1 μM Aβ$_{TR}$) was premixed with ADH-41 (4 μM ADH-41+1 μM ADH-41$_F$) and introduced to the cells. Under matched conditions, the cell viability was completely restored in the presence of ADH-41 at an equimolar ratio (Aβ$_{42}$: ADH-41 1:1, 5 μM each). The Aβ$_{42}$-ADH-41 complex was readily taken up by N2a cells, suggesting that ADH-41 did not affect the cell permeability of Aβ$_{42}$ (FIG. 29c). Moreover, the observation that the Aβ$_{42}$-ADH-41 complex permeates through the cell membrane and localizes intracellularly indicates a tight binding event which is not weakened by the extra- and intra-cellular milieu (FIG. 29c).

Figure 35:
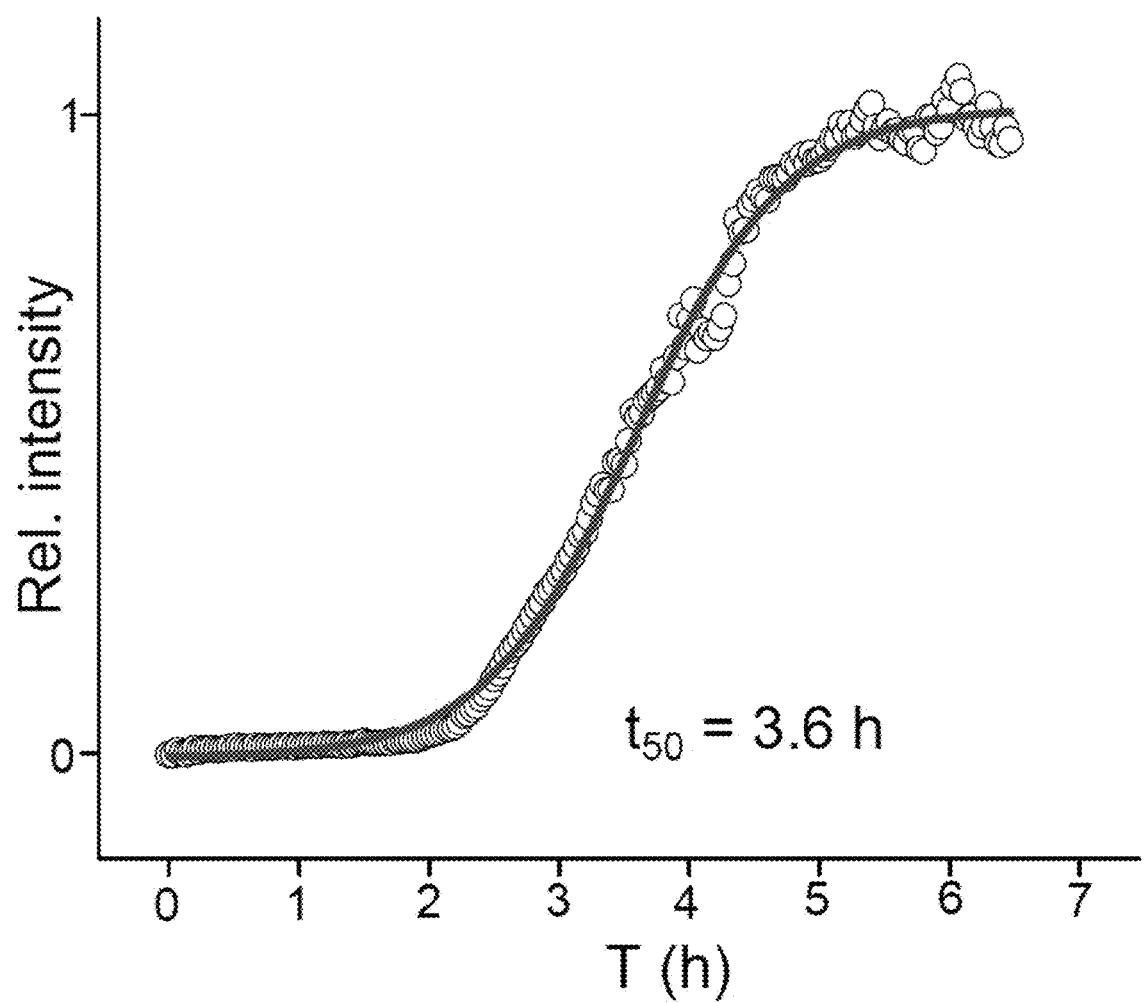
FIG. 35 depicts a representative plot for the kinetic curve of IAPP (5 µM) aggregation. Kinetic curves were fit using the built-in sigmoidal fit to extract tso value (time required to reach 50% of the maximum ThT fluorescence intensity). Each run was fit independently to extract the $t_{50}$. Kinetic profiles were processed using Origin (version 9.1).
Figure 37:
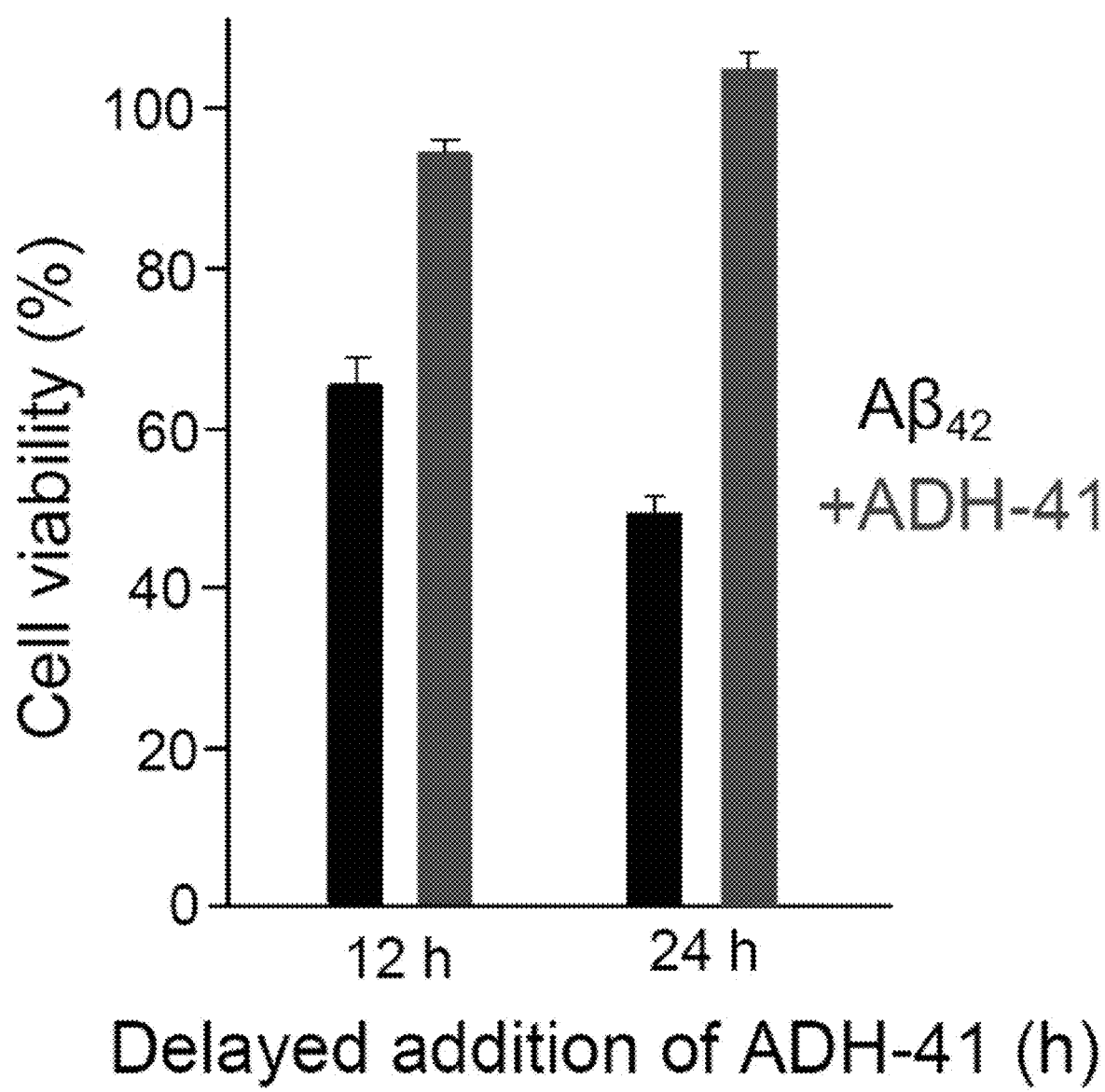
FIG. 37 shows the effect of ADH-41 on the cell viability of N2a cells in delayed experiments. The N2a cells were treated with 5 µM Aβ$_{42}$ for either 12 h or 24 h. The cells were washed and a solution of 5 µM ADH-41 in media was added to the cells. The cells were then tested for viability either after 12 h (for 12 h Aβ$_{42}$) or 48 h (for 24 h Aβ$_{42}$) using CellTiterBlue assay. Each cytotoxicity experiment is the average of four on-plate repeats from each of four independently performed replicates (n=16).

Cell permeability and intracellular localization of the Aβ$_{42}$-ADH-41 complex was compared with that of Aβ$_{42}$ or ADH-41 alone (FIG. 35). A solution of Aβ$_{42}$ (4 μM Aβ$_{42}$+1 μM Aβ$_{TR}$) was premixed with 5 μM unlabeled ADH-41 and introduced to the cells (FIG. 35a). As observed with the peptide and compound alone, the labeled Aβ$_{42}$-unlabled ADH-41 complex was partially localized at the mitochondria. Similarly, the complex of 5 μM unlabeled Aβ$_{42}$ with ADH-41 (4 μM ADH-41+1 μM ADH-41$_F$) partially colocalized with mitochondria (FIG. 35b). The rescue of cytotoxicity in N2a cells is postulated to be a consequence of the colocalization of protein and small molecule. It is hypothesized that ADH-41 rescues toxicity by modulating the toxic structures of Aβ$_{42}$ into non-toxic off-pathway structures without compromising the peptide's cell-permeability.

One of the likely contributors to cytotoxicity has been shown to be the intracellular accumulation of Aβ$_{42}$. The rescue of intracellular cytotoxicity induced by Aβ$_{42}$ has been investigated. N2a cells were treated with a toxic dose of 5 μM Aβ$_{42}$ for 24 h which decreased the cell viability from 100±2% to 64±1% (FIG. 29d). A solution of 5 μM ADH-41 was added to N2a cells pretreated with with 5 μM Aβ$_{42}$ for 12 h, and the cytotoxicity was measured after 12 h (total 24 h). The cell viability was increased from 64±1% to 93±2% when ADH-41 was added 12 h after the addition of Aβ$_{42}$ to N2a cells (FIG. 29d). ADH-41 was very effective even at higher toxic insult induced by Aβ$_{42}$. The cell viability is attenuated to 48±2% for N2a cells when incubated with 5 μM Aβ$_{42}$ for 72 h. The delayed addition of ADH-41 after 24 and 48 h of exposure to Aβ$_{42}$ led to the restoration of the cell viability to 79±2 and 102±2, respectively (FIG. 36). The rescue of toxicity is associated with the colocalization of ADH-41 with Aβ$_{42}$ (FIG. 29d). ADH-41 rescues N2a cells from Aβ$_{42}$ mediated cytotoxicity in both scenarios, either coincubated with Aβ$_{42}$ or added after a delay of 12-48 h. It is hypothesized that the cytotoxicity induced by Aβ occurs partially due to intracellular mechanisms. ADH-41 may disaggregate the intracellular neurotoxic oligomers of Aβ and rescue cytotoxicity, a result that corroborated by the immunoassays and ThT amyloid assays. Overall, ADH-41 binds and modulates the toxic structures of Aβ$_{42}$ into non-toxic conformations with a remarkable selectivity.

Example 19

Assays for Assessing the Effect of Oligopyridylamide Compounds of the Invention on Preformed Oligomers of Aβ

In the delayed addition experiments, where the oligopyridylamides were added at various time points during Aβ amyloid reaction, the conditions were same (as used for the assays where Aβ was preincubated with the oligopyridylamides). The Aβ oligomerization process was initiated by dissolving Aβ into buffer solution and then oligopyridylamides were added to this solution at indicated time points (depend on the assay) at an equimolar ratio.

The effect of the oligopyridylamides ADH-31 and ADH-41 on the preformed oligomers and seed-catalyzed processes has further been assessed. ADH-31 and ADH-41 were added during the growth phase of an Aβ$_{42}$ (5 μM) amyloid reaction (FIG. 28a). Both oligopyridylamides were effective in inhibiting Aβ$_{42}$ when added during the lag period (black arrow, 2 h, FIG. 28a). Interestingly, ADH-31 was more effective in inhibiting the growth phase of Aβ$_{42}$ amyloidogenesis than ADH-41. Image analysis of Aβ$_{42}$ fibrillation supports the ThT amyloid assay results. TEM images of Aβ$_{42}$ after 2 h revealed a nearly homogenous distribution of round particles confirming the formation of Aβ$_{42}$ oligomers (FIG. 28b, and zoom in region), as has been previously reported. No formation of Aβ$_{42}$ oligomers was observed when ADH-31 or ADH-41 were added to the preformed Aβ$_{42}$ oligomers at an equimolar ratio (FIG. 28c, d). ELISA assay confirms the formation of Aβ$_{42}$ (2 μM) oligomers after 3 h and 6 h reflected by a gradual increase in the absorbance of the solution (FIG. 28e). In marked contrast, no evidence of oligomers was observed when the oligopyridylamides were added at an equimolar ratio at 3 h and 6 h after the start of Aβ$_{42}$ amyloid reaction (FIG. 28e). It is interesting to note that ADH-31 was more effective than ADH-41 in inhibiting Aβ$_{42}$ oligomerization under matched conditions (FIG. 28e).

The oligopyridylamides were also tested for their effect on the cytotoxicity induced by the preformed oligomers in N2a cells. Aβ$_{42}$ (5 μM) was incubated in buffer for 0, 1, 2, and 3 h and then introduced to the cells, which reduced the cell viability to 48%, 46%, 57%, and 62%, respectively (FIG. 29f). Both oligopyridylamides were effective at rescuing Aβ$_{42}$ mediated toxicity when incubated with the preformed Aβ$_{42}$ oligomers. ADH-41 was able to increase cell viability from 46% to 72%, 57% to 68%, and 62% to 67% when added to Aβ$_{42}$ after 1, 2, and 3 h from the start of the amyloid reaction, respectively. Under matched conditions, ADH-31 rescued cell viability from 46% to 90%, 57% to 89%, and 62% to 95% when added to Aβ42 after 1, 2, and 3 h from the start of the amyloid reaction, respectively (FIG. 28f).

The effect of oligopyridylamides ADH-31 and ADH-41 on the secondary nucleation processes of Aβ$_{42}$ aggregation were compared. Preformed fibers (seeds) catalyze Aβ aggregation via secondary nucleation processes and generate the key neurotoxic oligomers of Aβ$_{42}$. From a therapeutic point of view, it is important to assess the effect of oligopyridylamides on Aβ$_{42}$ aggregation processes predominantly driven by secondary nucleation. The aggregation of 5 μM Aβ$_{42}$ bypasses the lag phase in the presence of preformed fibers (10% v/v) and decreases the tso from 2.7±0.2 h to 0.3±0.1 h (FIG. 28g). In the presence of ADH-31 and ADH-41, the seed catalyzed fibrillation of 5 μM Aβ$_{42}$ was completely suppressed at an equimolar ratio (FIG. 28g, h) as reflected in a small change in the fluorescence intensity in comparison to the control reaction (Aβ$_{42}$+seeds, FIG. 28g, h). The effect of the oligopyridylamides on seed-induced Aβ$_{42}$ cytotoxicity in N2a cells was also assessed. The cell viability decreased from 47% to 31% in the presence of 5 μM Aβ$_{42}$ and 5 μM Aβ$_{42}$+seeds (10% v/v), respectively (FIG. 29h), an observation consistent with earlier reported work (Cohen, S. I. A. et al. *Proc Nat Acad Sci* 2013, 110, 9758-9763). Under identical conditions, the cell viability was rescued from 31% to 69% and 63% in the presence of ADH-31 and ADH-41 (5 µM each), respectively.

ADH-41 is a better antagonist than ADH-31 of $A\beta_{42}$ primary nucleation processes, including aggregation and cytotoxicity. In contrast, ADH-31 is a better antagonist than ADH-41 of Aβ oligomerization and secondary nucleation processes. These results suggest that ADH-31 interacts with an Aβ subdomain that may be required to initiate the secondary nucleation processes. ADH-41 is a moderate inhibitor of secondary nucleation and oligomerization, indicating that the binding domain of ADH-41 (Ile17 to Glu22) on Aβ is only partially associated with the secondary nucleation processes. It has been postulated that during Aβ fibrillation, the N-terminal (3-strand extends from Glu11 to Glu22 and Ile31 to Ala41 with a turn stabilized by a salt bridge between Asp23 and Lys28. Without wishing to be bound by theory, it is postulated that the dianionic ADH-31 interacts with the positively charged (His13 to Lys16) and hydrophobic (Leu17 to Phe20) domains of Aβ and blocks the secondary nucleation processes, whereas ADH-41 only interacts with the hydrophobic domain (Leu17 to Phe20) of Aβ and, therefore, partially affects these processes.

Example 20

A Proposed Model for the Binding Mode of Oligopyridylamides to Aβ

Figure 30:
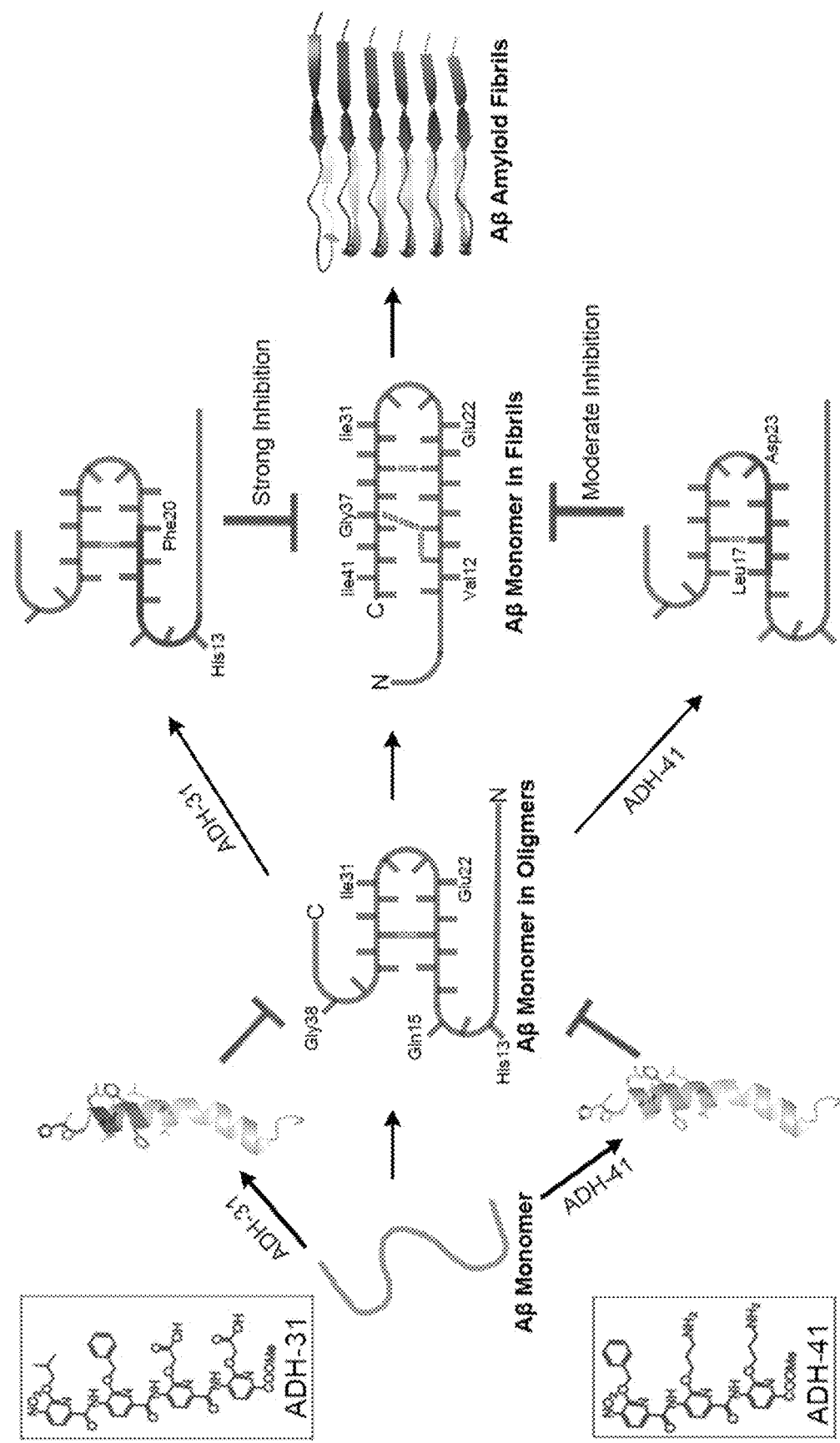
FIG. 30 illustrates a proposed model for the binding interaction between the oligopyridylamides and Aβ. The model demonstrates the interaction of oligopyridylamides with various facets of Aβ conformations. A cationic and an anionic oligopyridylamide interacts with distinct domains and thereby inhibit specific microscopic events of Aβ including primary nucleation, oligomerization, and secondary nucleation. The model provides important insights about the required chemical fingerprints for optimal interaction with which will aid in developing potent inhibitors of Aβ aggregation.

Based on the biophysical and cellular data, a model of the binding interaction of the oligopyridylamides with various facets of Aβ conformation has been proposed (FIG. 30). The model is not intended to bind any disclosure to a particular theory, and is solely presented as a hypothesis that may aid in developing a better understanding for the future generation of potent inhibitors of toxic functions of the Aβ peptide. Both oligopyridylamides, cationic (ADH-41) and anionic (ADH-31), inhibit the primary nucleation by inducing an α-helix conformation that is potentially incompetent to the oligomerization and fibrillation processes. ADH-31 is effective in disrupting the preformed toxic oligomers and inhibiting the seed catalyzed secondary nucleation. NMR suggests that ADH-31 interacts with residues span from His13 to Phe20. The conformation of Aβ monomer in Aβ oligomers demonstrate that residues from His13 to Phe20 are partially structured into β-strands and these residues are partially exposed to the solvent (FIG. 30). Therefore, ADH-31 may potentially cap these residues using salt bridge and hydrophobic interactions and may inhibit the further growth of the oligomerization of AP. ADH-41 may interact with residues from Leu17 to Asp23 which are structured into a β-strand; therefore, ADH-41 may not have the access of its binding domain when it is buried into a β-sheet structure. ADH-41 is able to inhibit Aβ oligomerization by interacting with the population of unstructured Aβ present in the solution.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

References

1. Chiti, F.; Dobson, C. M. *Annu. Rev. Biochem.* 2006, 75, 333-366.
2. Selkoe, D. J. *Nature* 2003, 426, 900-904.
3. Jakob-Roetne, R.; Jacobsen, H. *Angew. Chem. Int. Ed.* 2009, 48, 3030-3059.
4. World Alzheimer Report World Alzheimer Report. 2010, http.//www.alz.co.uk/research/worldreport/.
5. Hardy, J.; Selkoe, D. J. *Science* 2002, 297, 353-356.
6. Hardy, J. A.; Higgins, G. A. *Science* 1992, 256, 184-185.
7. Haass, C.; Selkoe, D. J. *Nat. Rev. Mol. Cell Biol.* 2007, 8, 101-112.
8. Iwatsubo, T.; Odaka, A.; Suzuki, N.; Mizusawa, H.; Nukina, N.; Ihara, Y. *Neuron* 1994, 13, 45-53.
9. Riek, R.; Güntert, P.; Döbeli, H.; Wipf, B.; Wüthrich, K. *Eur. J Biochem.* 2001, 268, 5930-5936.
10. Yan, Y.; Wang, C. *J. Mol. Biol.* 2006, 364, 853-862.
11. Jarvet, J.; Danielsson, J.; Damberg, P.; Oleszczuk, M.; GrÃslund, A. *J. Biomol. NMR* 2007, 39, 63-72.
12. Coles, M.; Bicknell, W.; Watson, A. A.; Fairlie, D. P.; Craik, D. J. *Biochemistry* 1998, 37, 11064-11077.
13. Serpell, L. C. *Biochim. Biophys. Acta* 2000, 1502, 16-30.
14. Ehrnhoefer, D. E.; Bieschke, J.; Boeddrich, A.; Herbst, M.; Masino, L.; Lurz, R.; Engemann, S.; Pastore, A.; Wanker, E. E. *Nat Struct Mot Blot* 2008, 15, 558-566.
15. Palhano, F. L.; Lee, J.; Grimster, N. P.; Kelly, J. W. *J. Am. Chem. Soc.* 2013, 135, 7503-7510.
16. Ladiwala, A. R. A.; Lin, J. C.; Bale, S. S.; Marcelino-Cruz, A. M.; Bhattacharya, M.; Dordick, J. S.; Tessier, P. M. *J. Biol. Chem.* 2010, 285, 24228-24237.
17. McLaurin, J.; Golomb, R.; Jurewicz, A.; Antel, J. P.; Fraser, P. E. *J. Biol. Chem.* 2000, 275, 18495-18502.
18. Sinha, S.; Lopes, D. H. J.; Du, Z.; Pang, E. S.; Shanmugam, A.; Lomakin, A.; Talbiersky, P.; Tennstaedt, A.; McDaniel, K.; Bakshi, R.; Kuo, P.; Ehrmann, M.; Benedek, G. B.; Loo, J. A.; KlÃrner, F.; Schrader, T.; Wang, C.; Bitan, G. *J. Am. Chem. Soc.* 2011, 133, 16958-16969.
19. Necula, M.; Breydo, L.; Milton, S.; Kayed, R.; van, d. V.; Tone, P.; Glabe, C. G. *Biochemistry* 2007, 46, 8850-8860.
20. McKoy, A. F.; Chen, J.; Schupbach, T.; Hecht, M. H. *Chem. Biol. Drug Des.* 2014, 84, 505-512.
21. McKoy, A. F.; Chen, J.; Schupbach, T.; Hecht, M. H. *J. Biol. Chem.* 2012, 287, 38992-39000.
22. Lee, H. H.; Choi, T. S.; Lee, S. J. C.; Lee, J. W.; Park, J.; Ko, Y. H.; Kim, W. J.; Kim, K.; Kim, H. I. *Angew. Chem. Int. Ed.* 2014, 53, 7461-7465.
23. WahlstrÃm, A.; Cukalevski, R.; Danielsson, J.; Jarvet, J.; Onagi, H.; Rebek, J.; Linse, S.; GrÃslund, A. *Biochemistry* 2012, 51, 4280-4289.
24. Richman, M.; Wilk, S.; Chemerovski, M.; WÃovrmlÃonder, Sebastian K. T. S.; WahlstrÃm, A.; GrÃslund, A.; Rahimipour, S. *J. Am. Chem. Soc.* 2013, 135, 3474-3484.
25. Fradinger, E. A.; Monien, B. H.; Urbane, B.; Lomakin, A.; Tan, M.; Li, H.; Spring, S. M.; Condron, M. M.; Cruz, L.; Xie, C.; Benedek, G. B.; Bitan, G. *Proc.. Natl. Acad. Sci. U.S.A.* 2008, 105, 14175-14180.
26. Arai, T.; Araya, T.; Sasaki, D.; Taniguchi, T.; Sato, T.; Sohma, Y.; Kanai, M. *Angew. Chem. Int. Ed.* 2014, 53, 8236-8239.
27. Arai, T.; Sasaki, D.; Araya, T.; Sato, T.; Sohma, Y.; Kanai, M. *ChemBioChem* 2014, 15, 2577-2583.

28. Yang, F.; Lim, G. P.; Begum, A. N.; Ubeda, O. J.; Simmons, M. R.; Ambegaokar, S. S.; Chen, P. P.; Kayed, R.; Glabe, C. G.; Frautschy, S. A.; Cole, G. M. *J. Biol. Chem.* 2005, 280, 5892-5901.
29. HochdÃrffer, K.; MÃrz-Berberich, J.; Nagel-Steger, L.; Epple, M.; Meyer-Zaika, W.; Horn, A. H. C.; Sticht, H.; Sinha, S.; Bitan, G.; Schrader, T. *J. Am. Chem. Soc.* 2011, 133, 4348-4358.
30. Hoyer, W.; Gronwall, C.; Jonsson, A.; Ståhl, S.; Härd, T. *Proc. Natl. Acad. Sci. U.S.A.* 2008, 105, 5099-5104.
31. Nerelius, C.; Sandegren, A.; Sargsyan, H.; Raunak, R.; Leijonmarck, H.; Chatterjee, U.; Fisahn, A.; Imarisio, S.; Lomas, D. A.; Crowther, D. C.; Strömberg, R.; Johansson, J. *Proc.. Natl. Acad. Sci. U.S.A.* 2009, 106, 9191-9196.
32. Cummings, C. G.; Hamilton, A. D. *Curr. Opin. Chem. Biol.* 2010, 14, 341-346.
33. Azzarito, V.; Long, K.; Murphy, N. S.; Wilson, A. J. *Nat Chem* 2013, 5, 161-173.
34. Ernst, J. T.; Kutzki, 0.; Debnath, A. K.; Jiang, S.; Lu, H.; Hamilton, A. D. *Angew. Chem. Int. Ed.* 2002, 41, 278-281.
35. Barnard, A.; Long, K.; Martin, H. L.; Miles, J. A.; Edwards, T. A.; Tomlinson, D. C.; Macdonald, A.; Wilson, A. J. *Angew. Chem. Int. Ed.* 2015, 54, 2960-2965.
36. Yin, H.; Hamilton, A. D. *Bioorg. Med. Chem. Lett.* 2004, 14, 1375-1379.
37. Ernst, J. T.; Becerril, J.; Park, H. S.; Yin, H.; Hamilton, A. D. *Angew. Chem. Int. Ed.* 2003, 42, 535-539.
38. Yin, H.; Lee, G.; Park, H. S.; Payne, G. A.; Rodriguez, J. M.; Sebti, S. M.; Hamilton, A. D. *Angew. Chem. Int. Ed.* 2005, 117, 2764-2767.
39. Prabhakaran, P.; Barnard, A.; Murphy, N. S.; Kilner, C. A.; Edwards, T. A.; Wilson, A. J. A *Eur. J. Org. Chem.* 2013, 2013, 3504-3512.
40. Lao, B. B.; Drew, K.; Guarracino, D. A.; Brewer, T. F.; Heindel, D. W.; Bonneau, R.; Arora, P. S. *J. Am. Chem. Soc.* 2014, 136, 7877-7888.
41. Lao, B. B.; Grishagin, I.; Mesallati, H.; Brewer, T. F.; Olenyuk, B. Z.; Arora, P. S. *Proc. Natl. Acad. Sci. U.S.A.* 2014, 111, 7531-7536.
42. Kumar, S.; Schlamadinger, D.; Brown, M.; Dunn, J.; Mercado, B.; Hebda, J.; Saraogi, I.; Rhoades, E.; Hamilton, A.; Miranker, A. *Chem. Biol.* 2015, 22, 369-378.
43. Hebda, J. A.; Saraogi, I.; Magzoub, M.; Hamilton, A. D.; Miranker, A. D. *Chem. Biol.* 2009, 16, 943-950.
44. Saraogi, I.; Hebda, J.; Becerril, J.; Estroff, L.; Miranker, A.; Hamilton, A. *Angew. Chem. Int. Ed.* 2010, 49, 736-739.
45. Kulikov, O. V.; Kumar, S.; Magzoub, M.; Knipe, P. C.; Saraogi, I.; Thompson, S.; Miranker, A. D.; Hamilton, A. D. *Tet. Lett.* 2015, 56, 3670-3673.
46. Kumar, S.; Birol, M.; Miranker, A. D. *Chem. Comm.* 2016, 52, 6391-6394.
47. Orner, B. P.; Ernst. J. T.; Hamilton, A. D. *J. Am. Chem. Soc.* 2001, 123, 5382-5383.
48. Yin, H.; Hamilton, A. D. *Angew. Chem. Int. Ed.* 2005, 44, 4130-4163.
49. Wolfe, L. S.; Calabrese, M. F.; Nath, A.; Blaho, D. V.; Miranker, A. D.; Xiong, Y. *Proc. Natl. Acad. Sci. U.S.A.* 2010, 107, 16863-16868.
50. Levine, H. *Protein Sci.* 1993, 2, 404-410.
51. Yan, L.; Velkova, A.; Tatarek—Nossol, M.; Andreetto, E.; Kapurniotu, A. *Angew. Chem. Int. Ed.* 2007, 46, 1246-1252.
52. Andreetto, E.; Yan, L.; Tatarek-Nossol, M.; Velkova, A.; Frank, R.; Kapurniotu, A. *Angew. Chem. Int. Ed.* 2010, 49, 3081-3085.
53. Andreetto, E.; Yan, L.; Caporale, A.; Kapurniotu, A. *ChemBioChem* 2011, 12, 1313-1322.
54. Seeliger, J.; Evers, F.; Jeworrek, C.; Kapoor, S.; Weise, K.; Andreetto, E.; Tolan, M.; Kapurniotu, A.; Winter, R. *Angew. Chem. Int. Ed.* 2012, 51, 679-683.
55. Andreetto, E.; Malideli, E.; Yan, L.; Kracklauer, M.; Farbiarz, K.; Tatarek-Nossol, M.; Rammes, G.; Prade, E.; Neumüller, T.; Caporale, A.; Spanopoulou, A.; Bakou, M.; Reif, B.; Kapurniotu, A. *Angew. Chem. Int. Ed.* 2015, 54, 13095-13100.
56. Kayed, R.; Head, E.; Thompson, J. L.; McIntire, T. M.; Milton, S. C.; Cotman, C. W.; Glabe, C. G. *Science* 2003, 300, 486-489.
57. Bitan, G. *Methods Enzymol* 2006, 413, 217-236.
58. Lindhagen-Persson, M.; Brännström, K.; Vestling, M.; Steinitz, M.; Olofsson, A. *PLoS ONE* 2010, 5, e13928.
59. Danielsson, J.; Jarvet, J.; Damberg, P.; Gräslund, A. *FEBS J.* 2005, 272, 3938-3949.
60. Gazit, E. *FASEB J.* 2002, 16, 77-83.
61. Harper, J. D.; Lansbury, P. T. *Annu. Rev. Biochem.* 1997, 66, 385-407.
62. Harper, J. D.; Lieber, C. M.; Lansbury, P. T. *Chem. Biol.* 1997, 4, 951-959.
63. Ono, K.; Condron, M. M.; Teplow, D. B. *Proc. Natl. Acad. Sci. U.S.A.* 2009, 106, 14745-14750.
64. Chen, P. S.; Toribara, T. Y.; Warner, H. *Anal. Chem.* 1956, 28, 1756-1758.
65. Wahlstrom, A.; Hugonin, L.; Peralvarez-Marin, A.; Jarvet, J.; Graslund, A. *FEBS J.* 2008, 275, 5117-5128.
66. Dobson, C. M. *Nature* 2003, 426, 884-890.
67. Wong, Y. C. & Krainc, D. *Nat. Med.* 2017, 23, 1-13.
68. Hoffner, G. & Djian, P. *Mol. Neurobiol.* 2015, 52, 1297-1314.
69. Mukherjee, A., Morales-Scheihing, D., Butler, P. C. & Soto, C. *Trends in Molecular Medicine* 2015, 21, 439-449.
70. Coelho, T. et al. *Neurology and Therapy* 2016, 5, 1-25.
71. Münch, J. et al. *Cell* 131, 1059-1071.
72. Xu, J. et al. *Nat Chem Biol* 2011, 7, 285-295.
73. Walsh, D. M. & Selkoe, D. J. *Nat. Rev. Neurosci.* 2016, 17, 251-260.
74. Glabe, C. G. Structural *Journal of Biological Chemistry* 2008, 283, 29639-29643.
75. Young, L. M., Ashcroft, A. E. & Radford, S. E. *Current Opinion in Chemical Biology* 2017, 39, 90-99 (2017).
76. Young, L. M. et al. *Methods* 2016, 95, 62-69.
77. Saunders, J. C. et al. *Nature Chemical Biology* 2015, 12, 94.
78. Kumar, S. & Hamilton, A. D. *J. Am. Chem. Soc.* 2017, 139, 5744-5755.
79. Kumar, S., Henning-Knechtel, A., Chehade, I., Magzoub, M. & Hamilton, A. D. *J. Am. Chem. Soc.* (2017).
80. Westermark, P., Andersson, A. & Westermark, G. T. *Physiol. Rev.* 2011, 91, 795.
81. Chimon, S. et al. *Nat Struct Mol Biol* 2007, 14, 1157.
82. Ahmed, M. et al. *Nat Struct Mot Blot* 2010, 17, 561-567.
83. Cohen, S. I. A. et al. *Proc Nat Acad Sci* 2013, 110, 9758-9763.
84. Lim, Y. et al. *Proteomics* 2010, 10, 1621-1633.
85. Lustbader, J. W W. et al. *Science* 2004, 304, 448.
86. Zhang, Y., McLaughlin, R., Goodyer, C. & LeBlanc, A. *J. Cell Biol.* 2002, 156, 519.
87. Bayer, T. & Wirths, O. *Frontiers in Aging Neuroscience* 2010, 2, 8.
88. Demuro, A. & Parker, I. *J. Neurosci.* 2013, 33, 3824.
89. Schindelin, J.; Arganda-Carreras, I.; Frise, E.; Kaynig, V.; Longair, M.; Pietzsch, T.; Preibisch, S.; Rueden, C.; Saalfeld, S.; Schmid, B.; Tinevez, J. Y.; White, D. J.; Hartenstein, V.; Eliceiri, K.; Tomancak, P.; Cardona, A. *Nat. Methods* 2012, 9, 676-682.

What is claimed is:
1. A compound having the following structural formula:
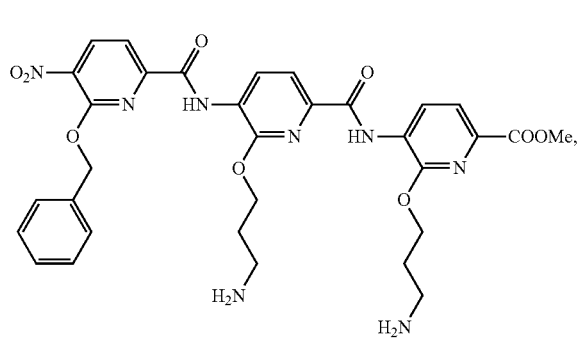 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]
or a pharmaceutically acceptable salt thereof.
2. A compound having the following structural formula:
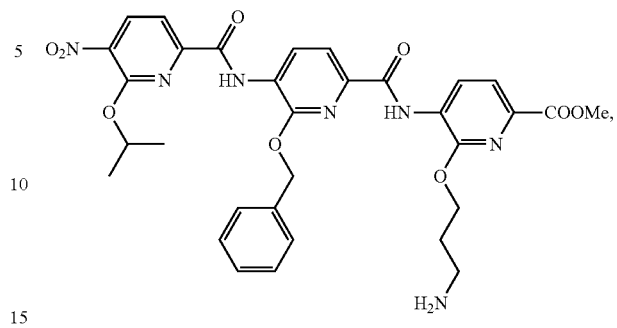
or a pharmaceutically acceptable salt thereof.
* * * * *